US012723097B2

(12) United States Patent
Boitano et al.

(10) Patent No.: US 12,723,097 B2
(45) **Date of Patent: *Sep. 1, 2026**

(54) ANTI-CD45 ANTIBODY DRUG CONJUGATES AND USES THEREOF

(71) Applicant: Regeneron Pharmaceuticals, Inc., Tarrytown, NY (US)

(72) Inventors: Anthony Boitano, Newton, MA (US); Michael Cooke, Boston, MA (US); Geoffrey O. Gillard, Harvard, MA (US); Charlotte Fenton McDonagh, Winchester, MA (US); Rahul Palchaudhuri, Somerville, MA (US); Bradley R. Pearse, Somerville, MA (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 1137 days.

This patent is subject to a terminal disclaimer.

(21) Appl. No.: 17/508,641

(22) Filed: Oct. 22, 2021

(65) Prior Publication Data

US 2022/0175951 A1 Jun. 9, 2022

Related U.S. Application Data

(63) Continuation of application No. PCT/US2020/029929, filed on Apr. 24, 2020.

(60) Provisional application No. 62/838,280, filed on Apr. 24, 2019.

(51) Int. Cl.
*C07K 16/28* (2006.01)
*A61K 47/68* (2017.01)

(52) U.S. Cl.
CPC ........ *C07K 16/289* (2013.01); *A61K 47/6803* (2017.08); *A61K 47/68035* (2023.08); *A61K 47/6849* (2017.08); *A61K 47/6867* (2017.08)

(58) Field of Classification Search
CPC .................. C07K 16/289; A61K 35/28; A61K 47/68035; A61P 37/06
See application file for complete search history.

(56) References Cited

U.S. PATENT DOCUMENTS

| | | | | |
|---|---|---|---|---|
| 9,089,617 | B2 | 7/2015 | Stull et al. | |
| 10,280,225 | B2 * | 5/2019 | Scadden | A61K 38/168 |
| 2016/0324982 | A1 * | 11/2016 | Scadden | A61P 35/00 |

FOREIGN PATENT DOCUMENTS

| | | | |
|---|---|---|---|
| WO | 2016164502 | A1 | 10/2016 |
| WO | 2017155937 | A1 | 9/2017 |
| WO | 2017219025 | A1 | 12/2017 |
| WO | 2020092654 | A1 | 5/2020 |

OTHER PUBLICATIONS

Kovtun et al., Blood advances, (Apr. 2018), 2:848-858.*
Kovtun et al., A CD123-targeting antibody-drug conjugate, IMGN632, designed to eradicate AML while sparing normal bone marrow cells. Blood Advances 2(8):848-858. Apr. 24, 2018 DOI: 10.1182/bloodadvances.2018017517.
Mantaj et al. 'From Anthramycin to Pyrrolobenzodiazepine (PBD)-Containing Antibody-Drug Conjugates (ADCs)', Angew. Chem. Int. Ed. 2017, vol. 56, pp. 462-488.
Miller et al., A New Class of Antibody-Drug Conjugates with Potent DNA Alkylating Activity. Mol Cancer Ther . Aug. 2016;15(8):1870-8. doi: 10.1158/1535-7163.MCT-16-0184. Epub May 23, 2016.
Tiberghien et al.: Design and Synthesis of Tesirine, a Clinical Antibody—Drug Conjugate Pyrrolobenzodiazepine Dimer Payload. ACS Medicinal Chemistry Letters. 7(11) 983-987. Nov. 10, 2016. doi: 10.1021/acsmedchemlett.6b00062.

* cited by examiner

*Primary Examiner* — Gyan Chandra
(74) *Attorney, Agent, or Firm* — Womble Bond Dickinson (US) LLP; Cristin Howley Cowles

(57) ABSTRACT

The invention provides anti-CD45 antibody drug conjugates (ADCs), and methods of use thereof. In one embodiment, the invention provides methods of depleting a population of CD45+ cells from a subject, by administration of an anti-CD45 ADC provided herein. In some embodiments, the ADCs include a cytotoxin containing a benzodiazepine moiety, for example. a pyrrolobenzodiazepine (PBD) or an indolinobenzodiazepine (IGN) moiety.

12 Claims, 10 Drawing Sheets

Specification includes a Sequence Listing.

ANTI-CD45 ANTIBODY DRUG CONJUGATES AND USES THEREOF

RELATED APPLICATIONS

This application is a continuation of International Application No. PCT/US2020/029929, filed on Apr. 24, 2020, which claims priority to U.S. Provisional Application No. 62/838,280, filed on Apr. 24, 2019. The entire content of the priority application is incorporated by reference herein.

SEQUENCE LISTING

The instant application contains a Sequence Listing which has been submitted electronically in ASCII format and is hereby incorporated by reference in its entirety. Said ASCII copy, created on Oct. 22, 2021, is named M103034_2100US_C1_SL.txt and is 99,312 bytes in size.

FIELD

The present invention relates to the field of anti-CD45 antibodies or antibody drug conjugates thereof. The invention further relates to the treatment of patients suffering from various pathologies, such as blood diseases, metabolic disorders, cancers, and autoimmune diseases, among others, by administration of an anti-CD45 antibody or antibody drug conjugate (ADC), wherein the antibody or ADC is capable of binding CD45 on either hematopoietic stem cells or immune cells.

BACKGROUND

Despite advances in the medicinal arts, there remains a demand for treating pathologies of the hematopoietic system, such as diseases of a particular blood cell, metabolic disorders, cancers, and autoimmune conditions, among others. While hematopoietic stem cells (HSCs) have significant therapeutic potential, a limitation that has hindered their use in the clinic has been the difficulty associated with ensuring engraftment of HSC transplants in a host. In particular, hematopoietic stem cell therapies involving antibodies that target cell surface antigens on endogenous HSCs can trigger unwanted immunostimulatory and effector functions that impede engraftment of an exogenous HSC transplant.

SUMMARY

Disclosed herein are antibody drug conjugates (ADCs) that comprise an anti-CD45 antibody, or antigen binding portion thereof, and a cytotoxin comprising a benzodiazepine moiety, e.g. a pyrrolobenzodiazepine (PBD) or an indolinobenzodiazepine (IGN). Uses of the ADC for the depletion of CD45+ cells are also provided.

Accordingly, in one aspect, the present disclosure provides an antibody-drug conjugate (ADC) comprising an anti-CD45 antibody or antigen binding portion thereof (Ab), conjugated to a cytotoxin (Cy) via a linker (L), wherein the cytotoxin comprises a pyrrolobenzodiazepine ("PBD"). In one embodiment, the cytotoxin can be a PBD dimer. For example, in one embodiment, the PBD is represented by Formula (I):

(I)

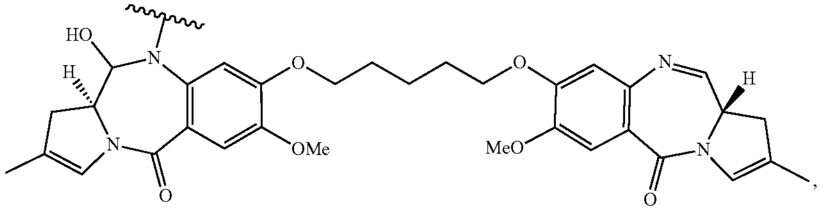

wherein the wavy line indicates the point of covalent attachment to the linker of the ADC.

In some embodiments, the linker (L) can comprise one or more of a peptide, oligosaccharide, $-(CH_2)_p-$, $-(CH_2CH_2O)_q-$, $-(C{=}O)(CH_2)_r-$, $-(C{=}O)(CH_2CH_2O)_t-$, $-(NHCH_2CH_2)_u-$, -PAB, Val-Cit-PAB, Val-Ala-PAB, Val-Lys(Ac)-PAB, Phe-Lys-PAB, Phe-Lys(Ac)-PAB, D-Val-Leu-Lys, Gly-Gly-Arg, Ala-Ala-Asn-PAB, or Ala-PAB, wherein each of p, q, r, t, and u are integers from 1-12, selected independently for each occurrence. In an exemplary embodiment, the linker has the structure of formula (II):

(II)

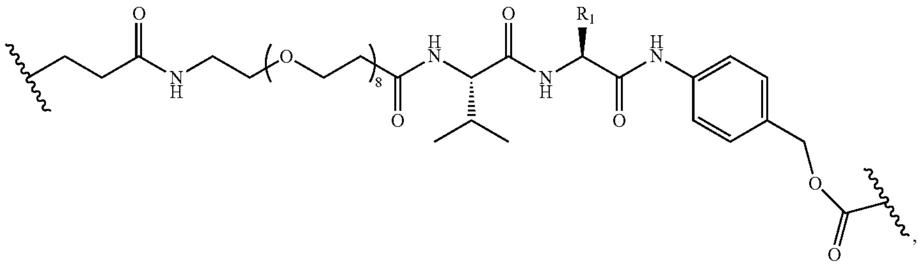

wherein $R_1$ is $CH_3$ (Ala) or $(CH_2)_3NH(CO)NH_2$ (Cit).

In one embodiment, the linker, prior to conjugation to the antibody and including the reactive substituent Z', taken together as L-Z', can have the structure:

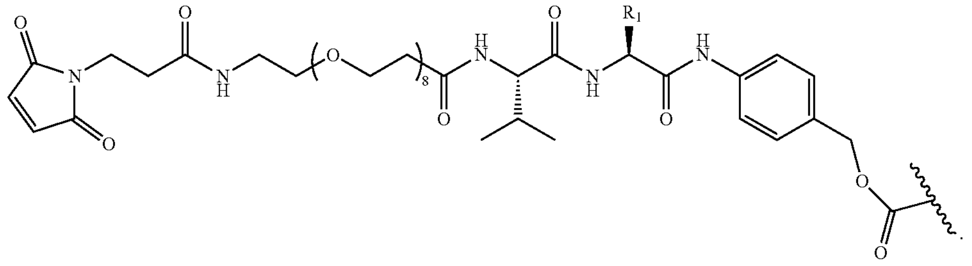
In an exemplary embodiment, $R_1$ of the previous structure can be $CH_3$.
In one embodiment, the cytotoxin-linker conjugate, prior to conjugation to the antibody and including the reactive substituent Z', taken together as Cy-L-Z', is tesirine, has the structure of formula (IV):
(IV)
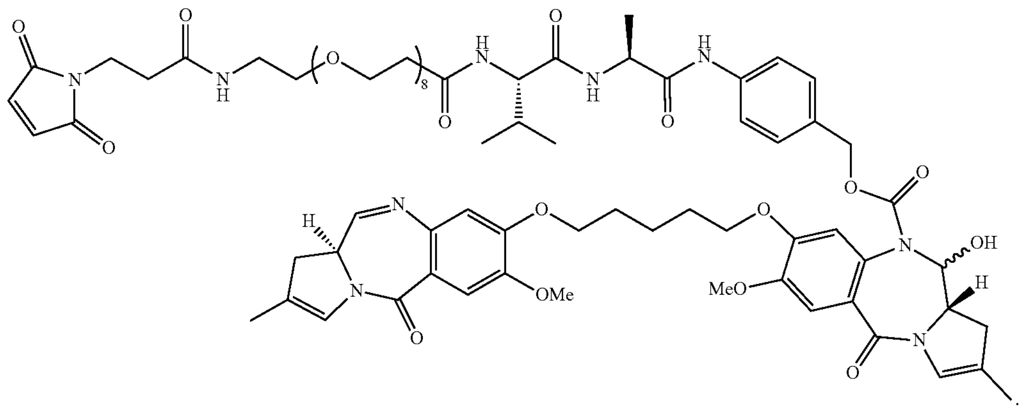
In an exemplary embodiment, the ADC can comprise the structure of formula (V):
(V)
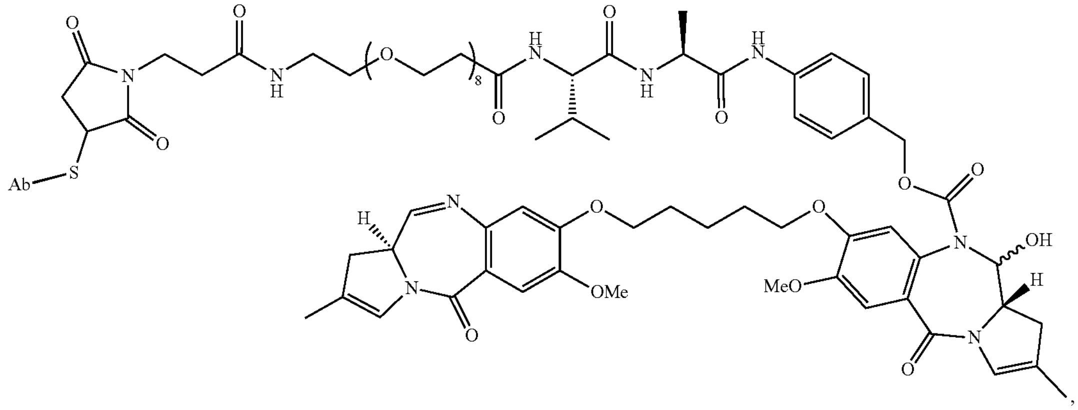

wherein Ab is the anti-CD45 antibody or antigen binding fragment thereof, and S represents a sulfur atom present in or introduced into the antibody or antigen binding fragment thereof.

In another aspect, provided herein is an antibody-drug conjugate (ADC) comprising an anti-CD45 antibody, or antigen binding portion thereof (Ab), conjugated to a cytotoxin (Cy) via a linker (L), wherein the cytotoxin comprises an indolinobenzodiazepine (IGN).

In some embodiments, the cytotoxin can be an IGN dimer or pseudodimer. For example, in some embodiments, the cytotoxin can be an IGN pseudodimer represented by Formula (VI):

(VI)

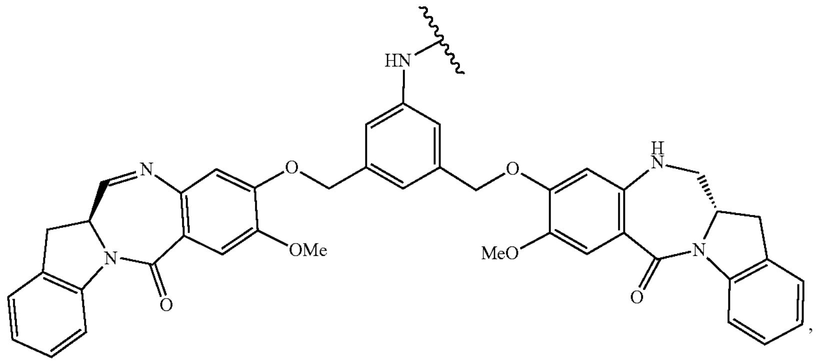

wherein the wavy line indicates the point of covalent attachment to the linker of the ADC.

In some embodiments of the foregoing aspect, the linker comprises a dipeptide, a disulfide, C1-C12 alkyl, C=O, or combinations thereof. In some embodiments, the linker comprises

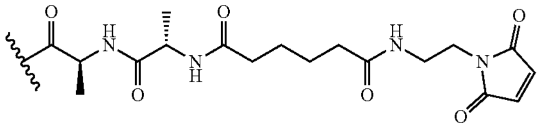

or

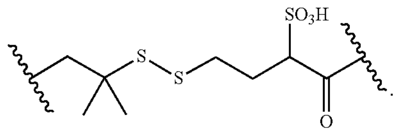

In some embodiments, the cytotoxin-linker conjugate, prior to conjugation to the antibody or antigen binding portion thereof, and including the reactive substituent Z', taken together as Cy-L-Z', has a structure of Formula (VII):

(VII)

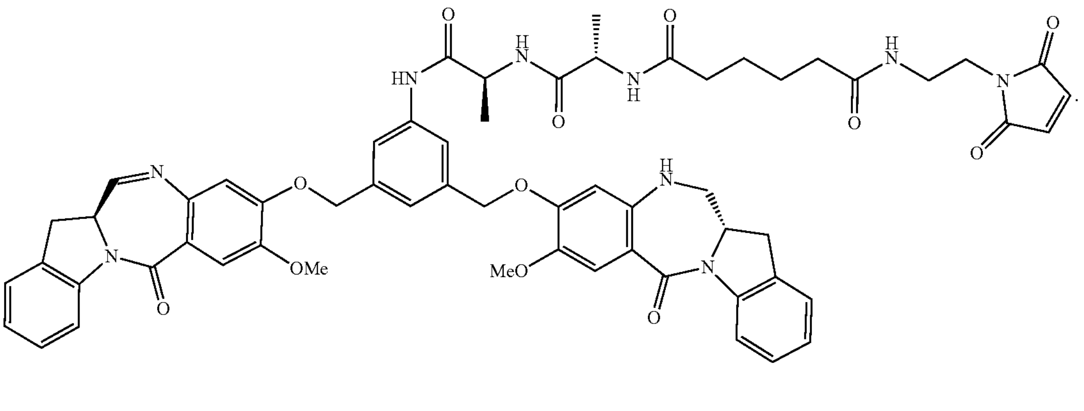

In some embodiments of the foregoing aspect, the ADC can have a drug to antibody ratio (DAR) of 1-10. For example, in one embodiment, the ADC can have a drug to antibody ratio of 1, 2, 3, 4, 5, 6, 7, 8, 9 or 10. In other embodiments, the ADC can have a DAR of 1-8. For example, in one embodiment, the ADC can have a DAR of 1, 2, 3, 4, 5, 6, 7, or 8. In other embodiments, the ADC can have a DAR of 1-4. For example, in one embodiment, the ADC can have a DAR of 1, 2, 3 or 4. In some embodiments, the ADC has a DAR of 1. In other embodiments, the ADC has a DAR of 2. In other embodiments, the ADC has a DAR of 3. In other embodiments, the ADC has a DAR of 4. In other embodiments, the ADC has a DAR of 5. In other embodiments, the ADC has a DAR of 6. In other embodiments, the ADC has a DAR of 7. In other embodiments, the ADC has a DAR of 8.

In some embodiments of the foregoing aspect, the anti-CD45 antibody can be a chimeric antibody, or antigen binding portion thereof. In other embodiments, the antibody can be a humanized antibody, or antigen binding portion thereof. In other embodiments, the antibody can be a fully human antibody, or antigen binding portion thereof.

In exemplary embodiments, the anti-CD45 antibody, or antigen-binding portion thereof, can be a monoclonal antibody or antigen-binding portion thereof, a polyclonal antibody or antigen-binding portion thereof, a bispecific antibody or antigen-binding portion thereof, a dual-variable immunoglobulin domain, a single-chain Fv molecule (scFv), a diabody, a triabody, a nanobody, an antibody-like protein scaffold, a Fv fragment, a Fab fragment, a F(ab')2 molecule, or a tandem di-scFv. The antibody can be of any isotype, including IgG, IgA, IgM, IgD, and IgE. In one embodiment, the antibody is an IgG. For example, the antibody can contain, in some embodiments, a human IgG1, IgG2, IgG3, or IgG4 isotype Fc domain.

In one embodiment, the antibody, or antigen binding portion thereof, comprises an Fc domain, and the antibody, or antigen binding portion thereof, is conjugated to the PBD by way of a cysteine residue in the Fc domain. The cysteine residue in the Fc domain can be present in the native Fc sequence. In other embodiments, the cysteine residue can be introduced by way of an amino acid substitution in the Fc domain. For example, the Fc domain can contain the substitution D265C and/or V205C (EU numbering).

In one embodiment, the ADC can comprise an anti-CD45 antibody, or antigen binding portion thereof, that is capable of specifically binding human CD45 RO.

In another aspect, the present disclosure provides a pharmaceutical composition that comprises an ADC as described herein, and a pharmaceutically acceptable carrier or excipient.

In another aspect, the present disclosure provides a method of depleting a population of CD45+ cells in a human patient, comprising administering to the patient an effective amount of an ADC or a pharmaceutical composition described herein.

In one embodiment of this aspect, the CD45+ cells are hematopoietic stem cells. In some embodiments, the hematopoietic stem cells can express CD45RO.

In other embodiments, the CD45+ cells are immune cells. In some embodiments, the immune cells express CD137, CD2, and/or CD5.

In some embodiments, the method can further comprise administering a transplant comprising hematopoietic stem cells to the patient.

In one aspect, the present disclosure provides a method comprising administering to a human patient a transplant that comprises hematopoietic stem cells, wherein the patient has previously been administered an ADC or a pharmaceutical composition described herein, in an amount sufficient to deplete a population of CD45+ cells from the patient. In one embodiment of this aspect, the CD45+ cells are hematopoietic stem cells. In some embodiments, the hematopoietic stem cells can express CD45RO.

In another aspect, the present disclosure provides a method comprising administering to a human patient a transplant that comprises hematopoietic stem cells, wherein the patient has previously been administered an ADC or a pharmaceutical composition described herein, in an amount sufficient to deplete a population of immune cells from the patient. In some embodiments, the immune cells express CD137, CD2, and/or CD5.

With respect to the foregoing aspects, the patient, in some embodiments, is a patient that has a blood disease, a metabolic disorder, a cancer, an autoimmune disease, or severe combined immunodeficiency disease (SCID).

In some embodiments, the transplant is allogeneic. For example, the transplant can be an allogeneic hematopoietic stem cell transplant. In other embodiments, the transplant can be an autologous transplant.

For example, the patient can have a hematological cancer, such as leukemia or lymphoma. In other embodiments, the patient can have an autoimmune disease, such as multiple sclerosis or scleroderma.

In another aspect, the present disclosure provides a method of depleting a population of CD45+ cells in a human patient in need of a hematopoietic stem cell (HSC) transplant, the method comprising administering to the human patient an effective amount of an antibody-drug conjugate (ADC), such that a population of CD45+ cells are depleted, wherein the ADC comprises an anti-CD45 antibody or antigen binding portion thereof conjugated to a cytotoxin via a linker, wherein the cytotoxin comprises a pyrrolobenzodiazepine ("PBD").

In another aspect, the present disclosure provides a method of conditioning a human patient for receiving a hematopoietic stem cell (HSC) transplant, the method comprising administering to the human patient an antibody-drug conjugate (ADC), wherein the ADC comprises an anti-CD45 antibody or antigen binding portion thereof conjugated to a cytotoxin via a linker, wherein the cytotoxin comprises a pyrrolobenzodiazepine ("PBD").

In some embodiments of the foregoing aspects, the cytotoxin is a PBD dimer. In an exemplary embodiment, the PBD is represented by Formula (I):

(I)

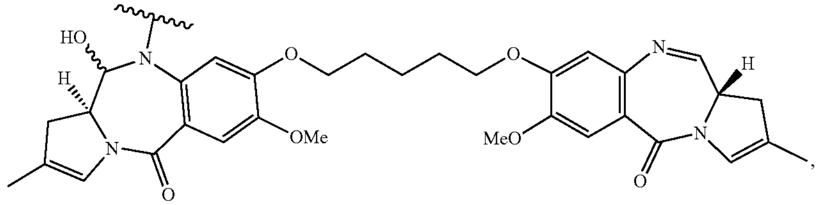

wherein the wavy line indicates the point of covalent attachment to the linker of the ADC.

In some embodiments of the foregoing aspects, the linker can comprise one or more of a peptide, oligosaccharide, $-(CH_2)_p-$, $-(CH_2CH_2O)_q-$, $-(C{=}O)(CH_2)_r-$, $-(C{=}O)(CH_2CH_2O)_t$, $-(NHCH_2CH_2)_u-$, -PAB, Val-Cit-PAB, Val-Ala-PAB, Val-Lys(Ac)-PAB, Phe-Lys-PAB, Phe-Lys(Ac)-PAB, D-Val-Leu-Lys, Gly-Gly-Arg, Ala-Ala-Asn-PAB, or Ala-PAB, wherein each of p, q, r, t, and u are integers from 1-12, selected independently for each occurrence. In an exemplary embodiment, the linker has the structure of formula (II):

(II)

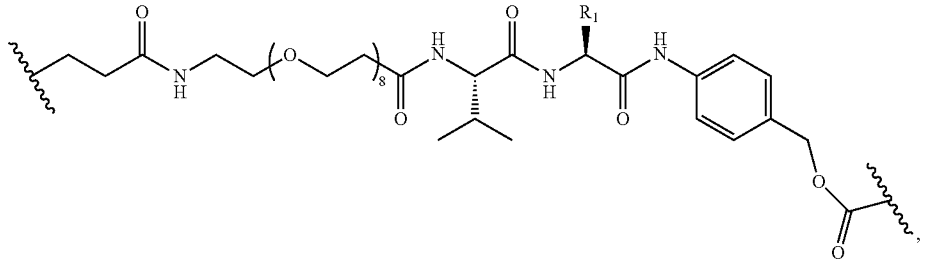

wherein $R_1$ is $CH_3$ (Ala) or $(CH_2)_3NH(CO)NH_2$ (Cit).

In one embodiment, the linker, prior to conjugation to the antibody and including the reactive substituent Z', taken together as L-Z', has the structure:

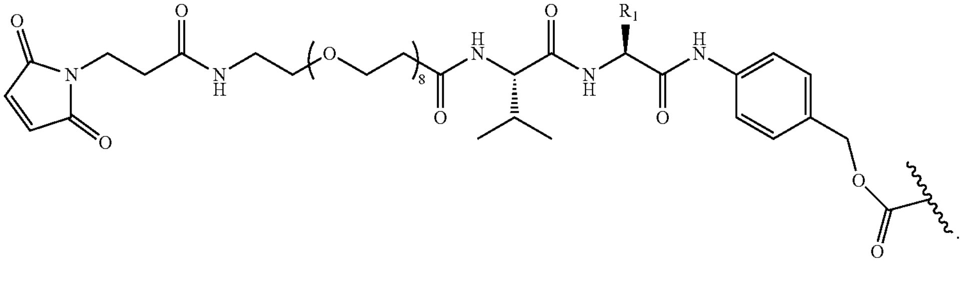

In one embodiment, $R_1$ in the foregoing structure is $CH_3$.

In another embodiment, the cytotoxin-linker conjugate, prior to conjugation to the antibody and including the reactive substituent Z', taken together as Cy-L-Z', is tesirine, having the structure of formula (IV):

(IV)

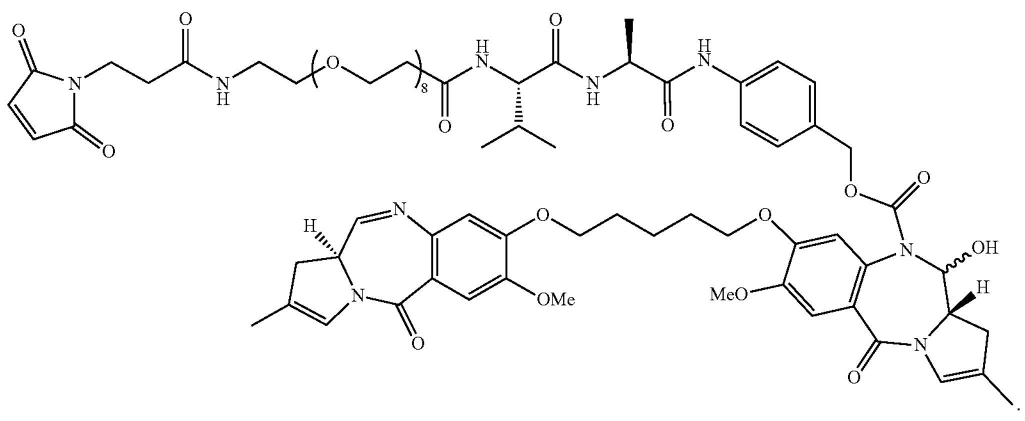

In another embodiment of the foregoing aspects, the ADC has the structure of formula (V):

(V)

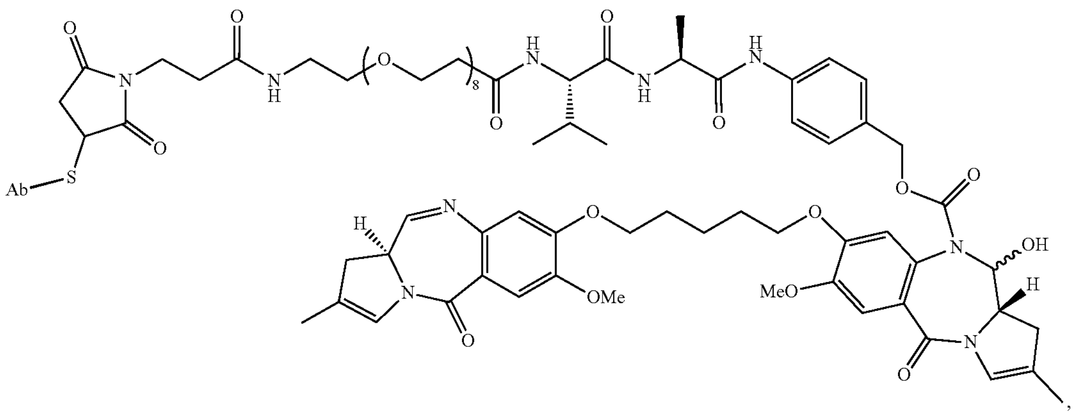

wherein Ab is the anti-CD45 antibody or antigen binding fragment thereof, and S represents a sulfur atom present in or introduced into the antibody or antigen binding fragment thereof.

In another aspect, provided herein is a method of depleting a population of CD45+ cells in a human patient in need of a hematopoietic stem cell (HSC) transplant, the method comprising administering to the human patient an effective amount of an antibody-drug conjugate (ADC), such that a population of CD45+ cells are depleted, wherein the ADC comprises an anti-CD45 antibody or antigen binding portion thereof conjugated to a cytotoxin via a linker, wherein the cytotoxin comprises an indolinobenzodiazepine (IGN).

In another aspect, provided herein is a method of conditioning a human patient for receiving a hematopoietic stem cell (HSC) transplant, the method comprising administering to the human patient an antibody-drug conjugate (ADC), wherein the ADC comprises an anti-CD45 antibody or antigen binding portion thereof conjugated to a cytotoxin via a linker, wherein the cytotoxin comprises an indolinobenzodiazepine (IGN).

In some embodiments of the foregoing aspects, the cytotoxin is an IGN dimer or pseudodimer. In some embodiments, the cytotoxin is an IGN pseudodimer represented by Formula (VI):

(VI)

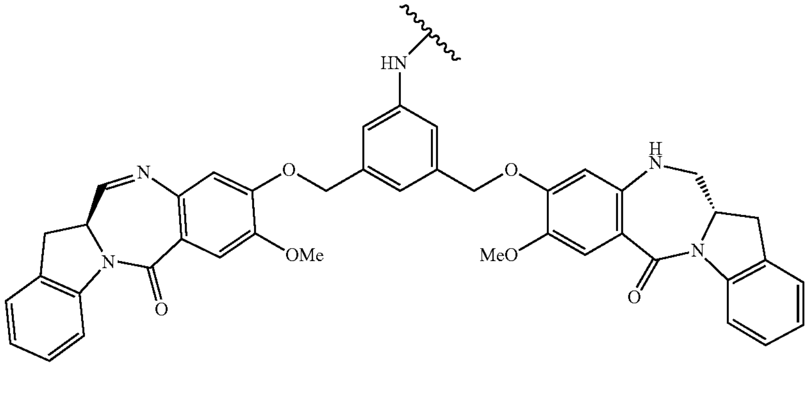

, wherein the wavy line indicates the point of covalent attachment to the linker of the ADC.

In some embodiments, the linker comprises a dipeptide, a disulfide, C1-C12 alkyl, C═O, or combinations thereof. In some embodiments, the linker comprises

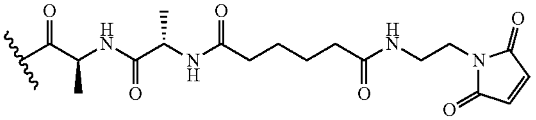

or

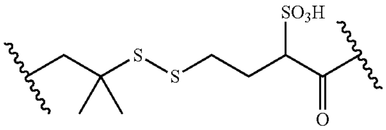

.

In some embodiments, the cytotoxin-linker conjugate, prior to conjugation to the antibody or antigen binding portion thereof, and including the reactive substituent Z', taken together as Cy-L-Z', has a structure of Formula (VII):

thereof, a polyclonal antibody or antigen-binding portion thereof, a bispecific antibody or antigen-binding portion thereof, a dual-variable immunoglobulin domain, a single-chain Fv molecule (scFv), a diabody, a triabody, a nanobody, an antibody-like protein scaffold, a Fv fragment, a Fab fragment, a F(ab')2 molecule, and a tandem di-scFv.

In some embodiments, the antibody or antigen binding portion thereof comprises an Fc domain. In some embodiments, the antibody or antigen binding portion thereof is internalized by a CD45+ cell. In some embodiments, the antibody can have one of the following isotypes: IgG, IgA, IgM, IgD, or IgE. For example, the antibody can a human IgG1, IgG2, IgG3, or IgG4 isotype Fc domain. In some embodiments in which the antibody, or antigen binding portion thereof, comprises an Fc domain, the antibody, or antigen binding portion thereof, can be conjugated to the PBD by way of a cysteine residue in the Fc domain. The cysteine residue may be naturally occurring in the Fc domain, or the cysteine residue may be introduced by way of an amino acid substitution in the Fc domain. For example, the Fc domain can contain a D265C and/or V205C substitution (EU numbering).

(VII)

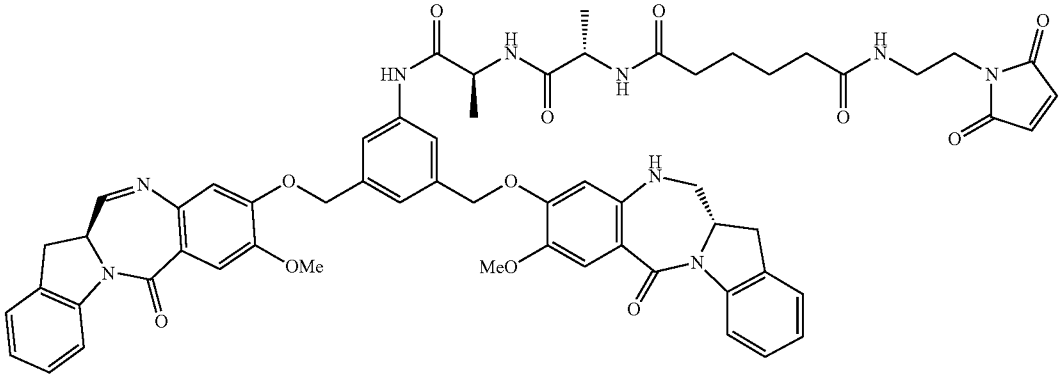

.

In one embodiment of the foregoing aspects, the ADC can have a drug to antibody ratio (DAR) of 1-10, i.e., 1, 2, 3, 4, 5, 6, 7, 8, 9 or 10, as described above.

In some embodiments, the antibody or antigen binding portion thereof can be a chimeric antibody, a humanized antibody, or a human antibody, or antigen binding portion thereof. In some embodiments, the antibody or antigen-binding portion thereof is selected from the group consisting of a monoclonal antibody or antigen-binding portion In some embodiments, the antibody, or antigen binding portion thereof, is capable of specifically binding human CD45 RO. In such embodiments, the ADC can be internalized by a CD45 RO+ cell.

In some embodiments of the foregoing aspects, the method comprises administering the ADC to the patient prior to the patient receiving a transplant comprising hematopoietic stem cells. For example, the method can comprise administering the ADC to the patient about three days prior to the patient receiving a transplant comprising hematopoietic stem cells.

In some embodiments, the patient has a blood disease, a metabolic disorder, a cancer, an autoimmune disease, a stem cell disorder, or severe combined immunodeficiency disease (SCID). In some embodiments, the patient has a stem cell disorder, such as a hematological cancer or an autoimmune disease. In an exemplary embodiment, the patient has a hematological cancer, for example, leukemia or lymphoma. In another exemplary embodiment, the patient has an autoimmune disease, such as multiple sclerosis or scleroderma.

In some embodiments of the foregoing aspects, a population of endogenous CD45+ HSCs are depleted in the human patient following administration of the ADC.

In some embodiments of the foregoing aspects, the method can further comprise administering a hematopoietic stem cell transplant to the patient. In some embodiments, the transplant is administered to the human patient after the ADC has substantially cleared from the blood of the human patient. In one embodiment, the hematopoietic stem cell transplant comprises allogeneic cells.

BRIEF DESCRIPTION OF THE DRAWINGS

FIG. 3A graphically depicts results of a flow cytometry assay assessing spleen and blood collected from anti-CD45-ADC-treated mice and gated on CD45.2+(donor) cells.

FIG. 3B graphically depict quantifications of the cell counts (total CD45.2+ cells, CD45.2+ T cells, or Ki-67+ cells) or percentage of parent cells (% T cells (total donor cells), % Ki-67+(total T cells)) in the spleen or blood of anti-CD45-ADC treated mice relative to mice treated with a control (i.e., "Iso PBD").

DETAILED DESCRIPTION

Figure 1:
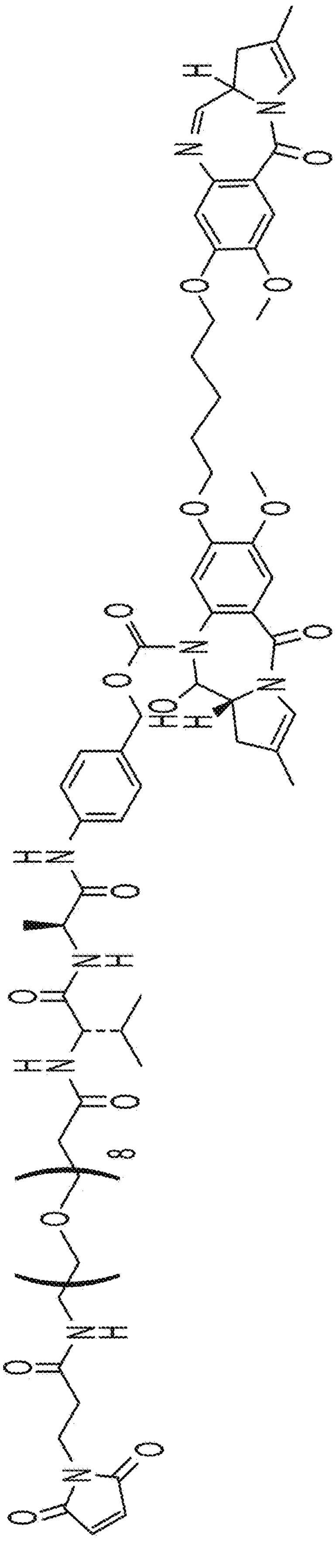
FIG. 1 depicts the chemical structure of an exemplary PBD conjugated to a linker (formula (IV); i.e., tesirine), prior to coupling with an anti-CD45 antibody, and including the reactive substituent Z', taken together as Cy-L-Z'.

The sections that follow provide a description of antibodies, antigen-binding fragments thereof, or antibody-drug conjugates (ADCs), that can be administered to a patient suffering from or at risk for developing graft versus host disease (GVHD) as well as methods of administering such therapeutics to the patient.

Definitions

Unless stated otherwise, the following terms and phrases as used herein are intended to have the following meanings.

As used herein, the term "about" refers to a value that is within 10% above or below the value being described. For example, the term "about 5 nM" indicates a range of from 4.5 nM to 5.5 nM.

As used herein, the term "antibody" refers to an immunoglobulin molecule that specifically binds to, or is immunologically reactive with, a particular antigen. An antibody includes, but is not limited to, monoclonal antibodies, polyclonal antibodies, multispecific antibodies (e.g., bispecific antibodies), genetically engineered antibodies, and otherwise modified forms of antibodies, including but not limited to de-immunized antibodies, chimeric antibodies, humanized antibodies, multispecific antibodies (e.g., bispecific antibodies), heteroconjugate antibodies (e.g., bi- tri- and quad-specific antibodies, diabodies, triabodies, and tetrabodies), and antibody fragments (i.e., antigen binding fragments of antibodies), including, for example, Fab', $F(ab')_2$, Fab, Fv, rIgG, and scFv fragments, so long as they exhibit the desired antigen-binding activity. Unless otherwise indicated, the term "monoclonal antibody" (mAb) is meant to include both intact molecules, as well as antibody fragments (including, for example, Fab and F(ab')2 fragments) that are capable of specifically binding to a target protein. As used herein, the Fab and F(ab')2 fragments refer to antibody fragments that lack the Fc fragment of an intact antibody. Examples of these antibody fragments are described herein.

The antibodies of the present disclosure are generally isolated or recombinant. "Isolated," when used herein refers to a polypeptide, e.g., an antibody, that has been identified and separated and/or recovered from a cell or cell culture from which it was expressed. Ordinarily, an isolated antibody will be prepared by at least one purification step. Thus, an "isolated antibody," refers to an antibody which is substantially free of other antibodies having different antigenic specificities. For instance, an isolated antibody that specifically binds to CD45 is substantially free of antibodies that specifically bind antigens other than CD45.

Generally, antibodies comprise heavy and light chains containing antigen binding regions. Each heavy chain is comprised of a heavy chain variable region (abbreviated herein as HCVR or VH) and a heavy chain constant region. The heavy chain constant region is comprised of three domains, CH1, CH2 and CH3. Each light chain is comprised of a light chain variable region (abbreviated herein as LCVR or VL) and a light chain constant region. The light chain constant region is comprised of one domain, CL. The VH, and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxyl-terminus in the following order: FR1, CDR1, FR2, CDR2, FR3, CDR3, FR4. The variable regions of the heavy and light chains contain a binding domain that interacts with an antigen. The constant regions of the antibodies can mediate the binding of the immunoglobulin to host tissues or factors, including various cells of the immune system (e.g., effector cells) and the first component (Clq) of the classical complement system.

The term "antigen-binding fragment," as used herein, refers to one or more fragments of an antibody that retain the ability to specifically bind to a target antigen. The antigen-binding function of an antibody can be performed by fragments of a full-length antibody. The antibody fragments can be, for example, a Fab, F(ab')2, scFv, diabody, a triabody, an affibody, a nanobody, an aptamer, or a domain antibody. Examples of binding fragments encompassed of the term "antigen-binding fragment" of an antibody include, but are not limited to: (i) a Fab fragment, a monovalent fragment consisting of the VL, VH, CL, and CH1 domains; (ii) a F(ab')2 fragment, a bivalent fragment containing two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb including VH and VL domains; (vi) a dAb fragment that consists of a VH domain (see, e.g., Ward et al., Nature 341:544-546, 1989); (vii) a dAb which consists of a VH or a VL domain; (viii) an isolated complementarity determining region (CDR); and (ix) a combination of two or more (e.g., two, three, four, five, or six) isolated CDRs which may optionally be joined by a synthetic linker. Furthermore, although the two domains of the Fv fragment, VL and VH, are coded for by separate genes, they can be joined, using recombinant methods, by a linker that enables them to be made as a single protein chain in which the VL and VH regions pair to form monovalent molecules (known as single chain Fv (scFv); see, for example, Bird et al., Science 242:423-426, 1988 and Huston et al., Proc. Natl. Acad. Sci. USA 85:5879-5883, 1988). These antibody fragments can be obtained using conventional techniques known to those of skill in the art, and the fragments can be screened for utility in the same manner as intact antibodies. Antigen-binding fragments can be produced by recombinant DNA techniques, enzymatic or chemical cleavage of intact immunoglobulins, or, in certain cases, by chemical peptide synthesis procedures known in the art.

As used herein, the term "anti-CD45 antibody" or "an antibody that binds to CD45" refers to a protein or peptide-containing molecule that includes at least a portion of an immunoglobulin molecule, such as but not limited to at least one complementarity determining region (CDR) of a heavy or light chain or a ligand binding portion thereof, a heavy chain or light chain variable region, a heavy chain or light chain constant region, a framework region, or any portion thereof, that is capable of specifically binding to CD45 with sufficient affinity such that the antibody is useful as a diagnostic and/or therapeutic agent in targeting CD45. Anti-CD45 antibodies also include antibody-like protein scaffolds, such as the tenth fibronectin type Ill domain ($^{10}$Fn3), which contains BC, DE, and FG structural loops similar in structure and solvent accessibility to antibody CDRs. The tertiary structure of the $^{10}$Fn3 domain resembles that of the variable region of the IgG heavy chain, and one of skill in the art can graft, for example, the CDRs of an anti-CD45 monoclonal antibody onto the fibronectin scaffold by replacing residues of the BC, DE, and FG loops of $^{10}$Fn3 with residues from the CDRH-1, CDRH-2, or CDRH-3 regions of an anti-CD45 monoclonal antibody. In some embodiments, an anti-CD45 antibody, or antigen-binding portion thereof, can bind the human CD45 isoform CD45RO.

As used herein, the term "bispecific antibody" refers to, for example, a monoclonal, often a human, de-immunized, humanized, or chimeric antibody that is capable of binding at least two different antigens or two different epitopes that can be on the same or different antigens. For instance, one of the binding specificities can be directed towards a hematopoietic stem cell surface antigen, e.g., CD45, and the other can specifically bind a different hematopoietic stem cell surface antigen or another cell surface protein, such as a receptor or receptor subunit involved in a signal transduction pathway that potentiates cell growth, among others. In some embodiments, the binding specificities can be directed towards unique, non-overlapping epitopes on the same target antigen (i.e., a biparatopic antibody).

As used herein, the term "complementarity determining region" (CDR) refers to a hypervariable region found both in the light chain and the heavy chain variable domains of an antibody. The more highly conserved portions of variable domains are referred to as framework regions (FRs). The amino acid positions that delineate a hypervariable region of an antibody can vary, depending on the context and the various definitions known in the art. Some positions within a variable domain may be viewed as hybrid hypervariable positions in that these positions can be deemed to be within a hypervariable region under one set of criteria while being deemed to be outside a hypervariable region under a different set of criteria. One or more of these positions can also be found in extended hypervariable regions. The antibodies described herein may contain modifications in these hybrid hypervariable positions. The variable domains of native heavy and light chains each contain four framework regions that primarily adopt a β-sheet configuration, connected by three CDRs, which form loops that connect, and in some cases form part of, the β-sheet structure. The CDRs in each chain are held together in close proximity by the framework regions in the order FR1-CDR1-FR2-CDR2-FR3-CDR3-FR4 and, with the CDRs from the other antibody chains, contribute to the formation of the target binding site of antibodies (see Kabat et al., Sequences of Proteins of Immunological Interest, National Institute of Health, Bethesda, MD, 1987). In certain embodiments, numbering of immunoglobulin amino acid residues is performed according to the immunoglobulin amino acid residue numbering system of Kabat et al., unless otherwise indicated (although any antibody numbering scheme, including, but not limited to IMGT and Chothia, can be utilized).

The terms "Fc" "Fc region," "Fc domain," and "IgG Fc domain" as used herein refer to the portion of an immunoglobulin, e.g., an IgG molecule, which correlates to a crystallizable fragment obtained by papain digestion of an IgG molecule. The Fc region comprises the C-terminal half of two heavy chains of an IgG molecule that are linked by disulfide bonds. It has no antigen binding activity but contains the carbohydrate moiety and binding sites for complement and Fc receptors, including the FcRn receptor (see below). For example, an Fc domain contains the second constant domain CH2 (e.g., residues at EU positions 231-340 of human IgG1) and the third constant domain CH3 (e.g., residues at EU positions 341-447 of human IgG1). As used herein, the Fc domain includes the "lower hinge region" (e.g., residues at EU positions 233-239 of human IgG1).

Fc can refer to this region in isolation, or this region in the context of an antibody, antibody fragment, or Fc fusion protein. Polymorphisms have been observed at a number of positions in Fc domains, including but not limited to EU positions 270, 272, 312, 315, 356, and 358, and thus slight differences between the sequences presented in the instant application and sequences known in the art can exist. Accordingly, a "wild type IgG Fc domain" or "WT IgG Fc domain" refers to any naturally occurring IgG Fc region (i.e., any allele). The sequences of the heavy chains of human IgG1, IgG2, IgG3 and IgG4 can be found in a number of sequence databases, for example, at the Uniprot database (www.uniprot.org) under accession numbers P01857 (IGHG1_HUMAN), P01859 (IGHG2_HUMAN), P01860 (IGHG3_HUMAN), and P01861 (IGHG1_HUMAN), respectively.

The terms "modified Fc region" or "variant Fc region" as used herein refers to an IgG Fc domain comprising one or more amino acid substitutions, deletions, insertions or modifications introduced at any position within the Fc domain. In certain aspects a variant IgG Fc domain comprises one or more amino acid substitutions resulting in decreased or ablated binding affinity for an Fc gamma R and/or Clq as compared to the wild type Fc domain not comprising the one or more amino acid substitutions. Further, Fc binding interactions are essential for a variety of effector functions and downstream signaling events including, but not limited to, antibody dependent cell-mediated cytotoxicity (ADCC) and complement dependent cytotoxicity (CDC). Accordingly, in certain aspects, an antibody comprising a variant Fc domain (e.g., an antibody, fusion protein or conjugate) can exhibit altered binding affinity for at least one or more Fc ligands (e.g., Fc gamma Rs) relative to a corresponding antibody otherwise having the same amino acid sequence but not comprising the one or more amino acid substitution, deletion, insertion or modifications such as, for example, an unmodified Fc region containing naturally occurring amino acid residues at the corresponding position in the Fc region.

Variant Fc domains are defined according to the amino acid modifications that compose them. For all amino acid substitutions discussed herein in regard to the Fc region, numbering is always according to the EU index as in Kabat. Thus, for example, D265C is an Fc variant with the aspartic acid (D) at EU position 265 substituted with cysteine (C) relative to the parent Fc domain. Likewise, e.g., D265C/L234A/L235A defines a variant Fc variant with substitutions at EU positions 265 (D to C), 234 (L to A), and 235 (L to A) relative to the parent Fc domain. A variant can also be designated according to its final amino acid composition in the mutated EU amino acid positions. For example, the L234A/L235A mutant can be referred to as "LALA". As a further example, the E233P.L234V.L235A.delG236 (deletion of 236) mutant can be referred to as "EPLVLAdeIG". As yet another example, the I253A.H310A.H435A mutant can be referred to as "IHH". It is noted that the order in which substitutions are provided is arbitrary.

The terms "Fc gamma receptor" or "Fc gamma R" as used herein refer to any member of the family of proteins that bind the IgG antibody Fc region and are encoded by the Fc gamma R genes. In humans this family includes but is not limited to Fc-gamma RI (CD64), including isoforms Fc gamma RIa, Fc gamma RIb, and Fc gamma RIc; Fc gamma RII (CD32), including isoforms Fc gamma RIIa (including allotypes H131 and R131), Fc gamma RIIb (including Fc gamma RIIb-1 and Fc gamma RIIb-2), and Fc gamma RIIc; and Fc gamma RIII (CD16), including isoforms Fc gamma RIIIa (including allotypes V158 and F158) and Fc gamma RIIIb (including allotypes Fc gamma RIIIb-NA1 and Fc gamma RIIIb-NA2), as well as any undiscovered human Fc gamma Rs or Fc gamma R isoforms or allotypes. An Fc gamma R can be from any organism, including but not limited to humans, mice, rats, rabbits, and monkeys. Mouse Fc gamma Rs include but are not limited to Fc gamma RI (CD64), Fc gamma RII (CD32), Fc gamma RIII (CD16), and Fc gamma RIII-2 (CD16-2), as well as any undiscovered mouse Fc gamma Rs or Fc gamma R isoforms or allotypes.

The term "effector function" as used herein refers to a biochemical event that results from the interaction of an Fc domain with an Fc receptor. Effector functions include but are not limited to ADCC, ADCP, and CDC. By "effector cell" as used herein is meant a cell of the immune system that expresses or one or more Fc receptors and mediates one or more effector functions. Effector cells include but are not limited to monocytes, macrophages, neutrophils, dendritic cells, eosinophils, mast cells, platelets, B cells, large granular lymphocytes, Langerhans' cells, natural killer (NK) cells, and gamma delta T cells, and can be from any organism included but not limited to humans, mice, rats, rabbits, and monkeys.

The term "silent", "silenced", or "silencing" as used herein refers to an antibody having a modified Fc region described herein that has decreased binding to an Fc gamma receptor (FcγR) relative to binding of an identical antibody comprising an unmodified Fc region to the FcγR (e.g., a decrease in binding to a FcγR by at least 70%, at least 80%, at least 90%, at least 95%, at least 98%, at least 99%, or 100% relative to binding of the identical antibody comprising an unmodified Fc region to the FcγR as measured by, e.g., BLI). In some embodiments, the Fc silenced antibody has no detectable binding to an FcγR. Binding of an antibody having a modified Fc region to an FcγR can be determined using a variety of techniques known in the art, for example but not limited to, equilibrium methods (e.g., enzyme-linked immunoabsorbent assay (ELISA); KinExA, Rathanaswami et al. Analytical Biochemistry, Vol. 373:52-60, 2008; or radioimmunoassay (RIA)), or by a surface plasmon resonance assay or other mechanism of kinetics-based assay (e.g., BIACORE™ analysis or Octet™ analysis (forteBIO)), and other methods such as indirect binding assays, competitive binding assays fluorescence resonance energy transfer (FRET), gel electrophoresis and chromatography (e.g., gel filtration). These and other methods may utilize a label on one or more of the components being examined and/or employ a variety of detection methods including but not limited to chromogenic, fluorescent, luminescent, or isotopic labels. A detailed description of binding affinities and kinetics can be found in Paul, W. E., ed., Fundamental Immunology, 4th Ed., Lippincott-Raven, Philadelphia (1999), which focuses on antibody-immunogen interactions. One example of a competitive binding assay is a radioimmunoassay comprising the incubation of labeled antigen with the antibody of interest in the presence of increasing amounts of unlabeled antigen, and the detection of the antibody bound to the labeled antigen. The affinity of the antibody of interest for a particular antigen and the binding off-rates can be determined from the data by scatchard plot analysis. Competition with a second antibody can also be determined using radioimmunoassays. In this case, the antigen is incubated with antibody of interest conjugated to a labeled compound in the presence of increasing amounts of an unlabeled second antibody.

As used herein, the term "identical antibody comprising an unmodified Fc region" refers to an antibody that lacks the recited amino acid substitutions (e.g., D265C, H435A, L234A, and/or L235A), but otherwise has the same amino acid sequence as the Fc modified antibody to which it is being compared.

As used herein, the terms "condition" and "conditioning" refer to processes by which a patient is prepared for receipt of a transplant containing hematopoietic stem cells. Such procedures promote the engraftment of a hematopoietic stem cell transplant (for instance, as inferred from a sustained increase in the quantity of viable hematopoietic stem cells within a blood sample isolated from a patient following a conditioning procedure and subsequent hematopoietic stem cell transplantation. According to the methods described herein, a patient may be conditioned for hematopoietic stem cell transplant therapy by administration to the patient of an ADC, antibody or antigen-binding fragment thereof capable of binding an antigen expressed by hematopoietic stem cells, such as CD45 (e.g., GNNK+CD45). As described herein, the antibody may be covalently conjugated to a cytotoxin so as to form a drug-antibody conjugate. Administration of an ADC, antibody, antigen-binding fragment thereof, or drug-antibody conjugate capable of binding one or more of the foregoing antigens to a patient in need of hematopoietic stem cell transplant therapy can promote the engraftment of a hematopoietic stem cell graft, for example, by selectively depleting endogenous hematopoietic stem cells, thereby creating a vacancy filled by an exogenous hematopoietic stem cell transplant.

The term "deplete," in the context of the effect of an anti-CD45 antibody or ADC on CD45-expressing cells, refers to a reduction in the number of or elimination of CD45-expressing cells.

The phrase "therapeutically effective amount" or "therapeutically effective dose", used interchangeably herein, refers to the amount or dose of a therapeutic agent, e.g., an anti-CD45 ADC, which, upon single or multiple dose administration to a patient, provides the desired treatment. A "therapeutically effective amount" of a therapeutic agent may vary according to factors such as the disease state, age, sex, and weight of the individual, such that the amount is able to elicit a desired response in the individual. The term "therapeutically effective amount" includes an amount that is effective to "treat" a subject (e.g., a patient). When a therapeutic amount is indicated, the precise amount of the compositions of the present invention to be administered can be determined by a physician with consideration of individual differences in age, weight, tumor size, extent of infection or metastasis, and condition of the patient (subject).

As used herein, the term "half-life" refers to the time it takes for the plasma concentration of the antibody drug in the body to be reduced by one half or 50% in a subject, e.g., a human subject. This 50% reduction in serum concentration reflects the amount of drug circulating.

As used herein, the term "conjugate" refers to a compound formed by the chemical bonding of a reactive functional group of one molecule, such as an antibody or antigen-binding fragment thereof, with an appropriately reactive functional group of another molecule, such as a cytotoxin described herein. Conjugates may include a linker between the two molecules bound to one another. Examples of linkers that can be used for the formation of a conjugate include peptide-containing linkers, such as those that contain naturally occurring or non-naturally occurring amino acids, such as D-amino acids. Linkers can be prepared using a variety of strategies described herein and known in the art. Depending on the reactive components therein, a linker may be cleaved, for example, by enzymatic hydrolysis, photolysis, hydrolysis under acidic conditions, hydrolysis under basic conditions, oxidation, disulfide reduction, nucleophilic cleavage, or organometallic cleavage (see, for example, Leriche et al., Bioorg. Med. Chem., 20:571-582, 2012).

As used herein, the term "coupling reaction" refers to a chemical reaction in which two or more substituents suitable for reaction with one another react so as to form a chemical moiety that joins (e.g., covalently) the molecular fragments bound to each substituent. Coupling reactions include those in which a reactive substituent bound to a fragment that is a cytotoxin, such as a cytotoxin known in the art or described herein, reacts with a suitably reactive substituent bound to a fragment that is an antibody, or antigen-binding fragment thereof, such as an antibody, antigen-binding fragment thereof, or specific anti-CD45 antibody that binds CD45 known in the art or described herein. Examples of suitably reactive substituents include a nucleophile/electrophile pair (e.g., a thiol/haloalkyl pair, an amine/carbonyl pair, or a thiol/α,β-unsaturated carbonyl pair, among others), a diene/dienophile pair (e.g., an azide/alkyne pair, among others), and the like. Coupling reactions include, without limitation, thiol alkylation, hydroxyl alkylation, amine alkylation, amine condensation, amidation, esterification, disulfide formation, cycloaddition (e.g., [4+2] Diels-Alder cycloaddition, [3+2] Huisgen cycloaddition, among others), nucleophilic aromatic substitution, electrophilic aromatic substitution, and other reactive modalities known in the art or described herein.

As used herein, "CRU (competitive repopulating unit)" refers to a unit of measure of long-term engrafting stem cells, which can be detected after in-vivo transplantation.

As used herein, the term "donor" refers to a human or animal from which one or more cells are isolated prior to administration of the cells, or progeny thereof, into a recipient. The one or more cells may be, for example, a population of hematopoietic stem cells.

As used herein, the term "diabody" refers to a bivalent antibody containing two polypeptide chains, in which each polypeptide chain includes $V_H$ and $V_L$ domains joined by a linker that is too short (e.g., a linker composed of five amino acids) to allow for intramolecular association of $V_H$ and $V_L$ domains on the same peptide chain. This configuration forces each domain to pair with a complementary domain on another polypeptide chain so as to form a homodimeric structure. Accordingly, the term "triabody" refers to trivalent antibodies containing three peptide chains, each of which contains one $V_H$ domain and one $V_L$ domain joined by a linker that is exceedingly short (e.g., a linker composed of 1-2 amino acids) to permit intramolecular association of $V_H$ and $V_L$ domains within the same peptide chain. In order to fold into their native structures, peptides configured in this way typically trimerize so as to position the $V_H$ and $V_L$ domains of neighboring peptide chains spatially proximal to one another (see, for example, Holliger et al., Proc. Natl. Acad. Sci. USA 90:6444-48, 1993).

As used herein, a "dual variable domain immunoglobulin" ("DVD-Ig") refers to an antibody that combines the target-binding variable domains of two monoclonal antibodies via linkers to create a tetravalent, dual-targeting single agent (see, for example, Gu et al., Meth. Enzymol., 502:25-41, 2012).

As used herein, the term "endogenous" describes a substance, such as a molecule, cell, tissue, or organ (e.g., a hematopoietic stem cell or a cell of hematopoietic lineage, such as a megakaryocyte, thrombocyte, platelet, erythrocyte, mast cell, myeoblast, basophil, neutrophil, eosinophil, microglial cell, granulocyte, monocyte, osteoclast, antigen-presenting cell, macrophage, dendritic cell, natural killer cell, T-lymphocyte, or B-lymphocyte) that is found naturally in a particular organism, such as a human patient.

As used herein, the term "engraftment potential" is used to refer to the ability of hematopoietic stem and progenitor cells to repopulate a tissue, whether such cells are naturally circulating or are provided by transplantation. The term encompasses all events surrounding or leading up to engraftment, such as tissue homing of cells and colonization of cells within the tissue of interest. The engraftment efficiency or rate of engraftment can be evaluated or quantified using any clinically acceptable parameter as known to those of skill in the art and can include, for example, assessment of competitive repopulating units (CRU); incorporation or expression of a marker in tissue(s) into which stem cells have homed, colonized, or become engrafted; or by evaluation of the progress of a subject through disease progression, survival of hematopoietic stem and progenitor cells, or survival of a recipient. Engraftment can also be determined by measuring white blood cell counts in peripheral blood during a post-transplant period. Engraftment can also be assessed by measuring recovery of marrow cells by donor cells in a bone marrow aspirate sample.

As used herein, the term "exogenous" describes a substance, such as a molecule, cell, tissue, or organ (e.g., a hematopoietic stem cell or a cell of hematopoietic lineage, such as a megakaryocyte, thrombocyte, platelet, erythrocyte, mast cell, myeoblast, basophil, neutrophil, eosinophil, microglial cell, granulocyte, monocyte, osteoclast, antigen-presenting cell, macrophage, dendritic cell, natural killer cell, T-lymphocyte, or B-lymphocyte) that is not naturally found in a particular organism, such as a human patient. A substance that is exogenous to a recipient organism, e.g., a recipient patient, may be naturally present in a donor organism, e.g., a donor subject, from which the substance is derived. For example, an allogeneic cell transplant contains cells that are exogenous to the recipient, but native to the donor. Exogenous substances include those that are provided from an external source to an organism, or to cultured matter extracted therefrom.

The terms "full length antibody" and "intact antibody" are used herein interchangeably to refer to an antibody in its substantially intact form, and not an antibody fragment as defined herein. Thus, for an IgG antibody, an intact antibody comprises two heavy chains each comprising a variable region, a constant region and an Fc region, and two light chains each comprising a variable region and a constant region. More specifically, an intact IgG comprises two light chains each comprising a light chain variable region (VL) and a light chain constant region (CL), and comprises two heavy chains each comprising a heavy chain variable region (VH) and three heavy chain constant regions (CH1, CH2, and CH3). CH2 and CH3 represent the Fc region of the heavy chain.

As used herein, the term "framework region" or "FW region" includes amino acid residues that are adjacent to the CDRs of an antibody or antigen-binding fragment thereof. FW region residues may be present in, for example, human antibodies, humanized antibodies, monoclonal antibodies, antibody fragments, Fab fragments, single chain antibody fragments, scFv fragments, antibody domains, and bispecific antibodies, among others.

As used herein, the term "immune cell" is intended to include, but is not limited to, a cell that is of hematopoietic origin and that plays a role in the immune response. Immune cells include, but are not limited to, T cells and natural killer (NK) cells. Natural killer cells are well known in the art. In one embodiment, natural killer cells include cell lines, such as NK-92 cells. Further examples of NK cell lines include NKG, YT, NK-YS, HANK-1, YTS cells, and NKL cells. An immune cell can be allogeneic or autologous. In one embodiment, an immune cell is a T cell.

As used herein, the term "hematopoietic stem cells" ("HSCs") refers to immature blood cells having the capacity to self-renew and to differentiate into mature blood cells containing diverse lineages including but not limited to granulocytes (e.g., promyelocytes, neutrophils, eosinophils, basophils), erythrocytes (e.g., reticulocytes, erythrocytes), thrombocytes (e.g., megakaryoblasts, platelet producing megakaryocytes, platelets), monocytes (e.g., monocytes, macrophages), dendritic cells, microglia, osteoclasts, and lymphocytes (e.g., NK cells, B-cells and T-cells). Such cells may include $CD34^+$ cells. $CD34^+$ cells are immature cells that express the CD34 cell surface marker. In humans, CD34+ cells are believed to include a subpopulation of cells with the stem cell properties defined above, whereas in mice, HSCs are CD34−. In addition, HSCs also refer to long term repopulating HSCs (LT-HSC) and short term repopulating HSCs (ST-HSC). LT-HSCs and ST-HSCs are differentiated, based on functional potential and on cell surface marker expression. For example, human HSCs are CD34+, CD38−, CD45RA−, CD90+, CD49F+, and lin− (negative for mature lineage markers including CD2, CD3, CD4, CD7, CD8, CD10, CD11B, CD19, CD20, CD56, CD235A). In mice, bone marrow LT-HSCs are CD34−, SCA-1+, C-kit+, CD135−, Slamfl/CD150+, CD48−, and lin− (negative for mature lineage markers including Ter119, CD11b, Gr1, CD3, CD4, CD8, B220, IL7ra), whereas ST-HSCs are CD34+, SCA-1+, C-kit+, CD135−, Slamfl/CD150+, and lin− (negative for mature lineage markers including Ter119, CD11b, Gr1, CD3, CD4, CD8, B220, IL7ra). In addition, ST-HSCs are less quiescent and more proliferative than LT-HSCs under homeostatic conditions. However, LT-HSC have greater self-renewal potential (i.e., they survive throughout adulthood, and can be serially transplanted through successive recipients), whereas ST-HSCs have limited self-renewal (i.e., they survive for only a limited period of time, and do not possess serial transplantation potential). Any of these HSCs can be used in the methods described herein. ST-HSCs are particularly useful because they are highly proliferative and thus, can more quickly give rise to differentiated progeny.

As used herein, the term "hematopoietic stem cell functional potential" refers to the functional properties of hematopoietic stem cells which include 1) multi-potency (which refers to the ability to differentiate into multiple different blood lineages including, but not limited to, granulocytes (e.g., promyelocytes, neutrophils, eosinophils, basophils), erythrocytes (e.g., reticulocytes, erythrocytes), thrombocytes (e.g., megakaryoblasts, platelet producing megakaryocytes, platelets), monocytes (e.g., monocytes, macrophages), dendritic cells, microglia, osteoclasts, and lymphocytes (e.g., NK cells, B-cells and T-cells), 2) self-renewal (which refers to the ability of hematopoietic stem cells to give rise to daughter cells that have equivalent potential as the mother cell, and further that this ability can repeatedly occur throughout the lifetime of an individual without exhaustion), and 3) the ability of hematopoietic stem cells or progeny thereof to be reintroduced into a transplant recipient whereupon they home to the hematopoietic stem cell niche and re-establish productive and sustained hematopoiesis.

As used herein, the term "human antibody" is intended to include antibodies having variable and constant regions derived from human germline immunoglobulin sequences. A human antibody may include amino acid residues not encoded by human germline immunoglobulin sequences (e.g., mutations introduced by random or site-specific mutagenesis in vitro or during gene rearrangement or by somatic mutation in vivo). However, the term "human antibody", as used herein, is not intended to include antibodies in which CDR sequences derived from the germline of another mammalian species, such as a mouse, have been grafted onto human framework sequences. A human antibody can be produced in a human cell (for example, by recombinant expression) or by a non-human animal or a prokaryotic or eukaryotic cell that is capable of expressing functionally rearranged human immunoglobulin (such as heavy chain and/or light chain) genes. When a human antibody is a single chain antibody, it can include a linker peptide that is not found in native human antibodies. For example, an Fv can contain a linker peptide, such as two to about eight glycine or other amino acid residues, which connects the variable region of the heavy chain and the variable region of the light chain. Such linker peptides are considered to be of human origin. Human antibodies can be made by a variety of methods known in the art including phage display methods using antibody libraries derived from human immunoglobulin sequences. Human antibodies can also be produced using transgenic mice that are incapable of expressing functional endogenous immunoglobulins, but which can express human immunoglobulin genes (see, for example, PCT Publication Nos. WO 1998/24893; WO 1992/01047; WO 1996/34096; WO 1996/33735; U.S. Pat. Nos. 5,413,923; 5,625,126; 5,633,425; 5,569,825; 5,661,016; 5,545,806; 5,814,318; 5,885,793; 5,916,771; and 5,939,598).

A "humanized" antibody refers to an antibody that contains minimal sequences derived from non-human immunoglobulin. Thus, "humanized" forms of non-human (e.g., murine) antibodies are antibodies that contain minimal sequence derived from the non-human antibody. All or substantially all of the FW regions may also be those of a human immunoglobulin sequence. A humanized antibody can also contain at least a portion of an immunoglobulin constant region (Fc), typically that of a human immunoglobulin consensus sequence. Methods of antibody humanization are known in the art and have been described, for example, in Riechmann et al., Nature 332:323-7, 1988; U.S. Pat. Nos. 5,530,101; 5,585,089; 5,693,761; 5,693,762; and 6,180,370.

The term "chimeric" antibody as used herein refers to an antibody having variable sequences derived from a non-human immunoglobulin, such as a rat or a mouse antibody, and human immunoglobulin constant regions, typically chosen from a human immunoglobulin template. Methods for producing chimeric antibodies are known in the art. See, e.g., Morrison, 1985, Science 229(4719):1202-7; Oi et al., 1986, BioTechniques 4:214-221; Gillies et al., 1985, J. Immunol. Methods 125:191-202; U.S. Pat. Nos. 5,807,715; 4,816,567; and 4,816,397.

The term "de-immunized" or "de-immunization", as used herein, relates to modification of an original wild type construct (or parent antibody) by rendering said wild type construct non-immunogenic or less immunogenic in humans. De-immunized antibodies contain part(s), e.g., a framework region(s) and/or a CDR(s), of non-human origin. As used herein, the term "deimmunized antibody" refers to an antibody that is de-immunized by mutation not to activate the immune system of a subject (for example, Nanus et al., J. Urology 170:S84-S89, 2003; WO98/52976; WO00/34317).

As used herein, "drug-to-antibody ratio" or "DAR" refers to the average number of cytotoxins, e.g., amatoxin, conjugated to an antibody. Generally, the DAR of an ADC ranges from about 1 to about 8, although higher loads are also possible depending on the number of linkage sites on an antibody. Thus, in certain embodiments, an anti-CD45 ADC described herein has a DAR of 1, 2, 3, 4, 5, 6, 7, or 8.

As used herein, patients that are "in need of" a hematopoietic stem cell transplant include patients that exhibit a defect or deficiency in one or more blood cell types, as well as patients having a stem cell disorder, autoimmune disease, cancer, or other pathology described herein. Hematopoietic stem cells generally exhibit 1) multi-potency, and can thus differentiate into multiple different blood lineages including, but not limited to, granulocytes (e.g., promyelocytes, neutrophils, eosinophils, basophils), erythrocytes (e.g., reticulocytes, erythrocytes), thrombocytes (e.g., megakaryoblasts, platelet producing megakaryocytes, platelets), monocytes (e.g., monocytes, macrophages), dendritic cells, microglia, osteoclasts, and lymphocytes (e.g., NK cells, B-cells and T-cells), 2) self-renewal, and can thus give rise to daughter cells that have equivalent potential as the mother cell, and 3) the ability to be reintroduced into a transplant recipient whereupon they home to the hematopoietic stem cell niche and re-establish productive and sustained hematopoiesis. Hematopoietic stem cells can thus be administered to a patient defective or deficient in one or more cell types of the hematopoietic lineage in order to re-constitute the defective or deficient population of cells in vivo. For example, the patient may be suffering from cancer, and the deficiency may be caused by administration of a chemotherapeutic agent or other medicament that depletes, either selectively or non-specifically, the cancerous cell population. Additionally or alternatively, the patient may be suffering from a hemoglobinopathy (e.g., a non-malignant hemoglobinopathy), such as sickle cell anemia, thalassemia, Fanconi anemia, aplastic anemia, and Wiskott-Aldrich syndrome. The subject may be one that is suffering from adenosine deaminase severe combined immunodeficiency (ADA SCID), HIV/AIDS, metachromatic leukodystrophy, Diamond-Blackfan anemia, and Schwachman-Diamond syndrome. The subject may have or be affected by an inherited blood disorder (e.g., sickle cell anemia) or an autoimmune disorder. Additionally or alternatively, the subject may have or be affected by a malignancy, such as neuroblastoma or a hematologic cancer. For instance, the subject may have a leukemia, lymphoma, or myeloma. In some embodiments, the subject has acute myeloid leukemia, acute lymphoid leukemia, chronic myeloid leukemia, chronic lymphoid leukemia, multiple myeloma, diffuse large B-cell lymphoma, or non-Hodgkin's lymphoma. In some embodiments, the subject has myelodysplastic syndrome. In some embodiments, the subject has an autoimmune disease, such as scleroderma, multiple sclerosis, ulcerative colitis, Crohn's disease, Type 1 diabetes, or another autoimmune pathology described herein. In some embodiments, the subject is in need of chimeric antigen receptor T-cell (CART) therapy. In some embodiments, the subject has or is otherwise affected by a metabolic storage disorder. The subject may suffer or otherwise be affected by a metabolic disorder selected from the group consisting of glycogen storage diseases, mucopolysaccharidoses, Gaucher's Disease, Hurlers Disease, sphingolipidoses, metachromatic leukodystrophy, or any other diseases or disorders which may benefit from the treatments and therapies disclosed herein and including, without limitation, severe combined immunodeficiency, Wiscott-Aldrich syndrome, hyper immunoglobulin M (IgM) syndrome, Chediak-Higashi disease, hereditary lymphohistiocytosis, osteopetrosis, osteogenesis imperfecta, storage diseases, thalassemia major, sickle cell disease, systemic sclerosis, systemic lupus erythematosus, multiple sclerosis, juvenile rheumatoid arthritis and those diseases, or disorders described in "Bone Marrow Transplantation for Non-Malignant Disease," ASH Education Book, 1:319-338 (2000), the disclosure of which is incorporated herein by reference in its entirety as it pertains to pathologies that may be treated by administration of hematopoietic stem cell transplant therapy. Additionally or alternatively, a patient "in need of" a hematopoietic stem cell transplant may one that is or is not suffering from one of the foregoing pathologies, but nonetheless exhibits a reduced level (e.g., as compared to that of an otherwise healthy subject) of one or more endogenous cell types within the hematopoietic lineage, such as megakaryocytes, thrombocytes, platelets, erythrocytes, mast cells, myeoblasts, basophils, neutrophils, eosinophils, microglia, granulocytes, monocytes, osteoclasts, antigen-presenting cells, macrophages, dendritic cells, natural killer cells, T-lymphocytes, and B-lymphocytes. One of skill in the art can readily determine whether one's level of one or more of the foregoing cell types, or other blood cell type, is reduced with respect to an otherwise healthy subject, for instance, by way of flow cytometry and fluorescence activated cell sorting (FACS) methods, among other procedures, known in the art.

As used herein, the term "monoclonal antibody" refers to an antibody that is derived from a single clone, including any eukaryotic, prokaryotic, or phage clone, and not the method by which it is produced. Monoclonal antibodies useful with the present disclosure can be prepared using a wide variety of techniques known in the art including the use of hybridoma, recombinant, and phage display technologies, or a combination thereof. Unless otherwise indicated, the term "monoclonal antibody" (mAb) is meant to include both intact molecules, as well as antibody fragments (including, for example, Fab and $F(ab')_2$ fragments) that are capable of specifically binding to a target protein. As used herein, the Fab and $F(ab')_2$ fragments refer to antibody fragments that lack the Fc fragment of an intact antibody. In one embodiment, an antibody fragment comprises an Fc region.

As used herein a "neutral antibody" refers to an antibody, or an antigen binding fragment thereof, that is not capable of significantly neutralizing, blocking, inhibiting, abrogating, reducing or interfering with the activities of a particular or specified target (e.g., CD45), including the binding of receptors to ligands or the interactions of enzymes with substrates.

As used herein, the term "recipient" refers to a patient that receives a transplant, such as a transplant containing a population of hematopoietic stem cells. The transplanted cells administered to a recipient may be, e.g., autologous, syngeneic, or allogeneic cells.

As used herein, the term "sample" refers to a specimen (e.g., blood, blood component (e.g., serum or plasma), urine, saliva, amniotic fluid, cerebrospinal fluid, tissue (e.g., placental or dermal), pancreatic fluid, chorionic villus sample, and cells) taken from a subject.

As used herein, the term "scFv" refers to a single chain Fv antibody in which the variable domains of the heavy chain and the light chain from an antibody have been joined to form one chain. scFv fragments contain a single polypeptide chain that includes the variable region of an antibody light chain ($V_L$) (e.g., CDR-L1, CDR-L2, and/or CDR-L3) and the variable region of an antibody heavy chain ($V_H$) (e.g., CDR-H1, CDR-H2, and/or CDR-H3) separated by a linker. The linker that joins the $V_L$ and $V_H$ regions of a scFv fragment can be a peptide linker composed of proteinogenic amino acids. Alternative linkers can be used to so as to increase the resistance of the scFv fragment to proteolytic degradation (for example, linkers containing D-amino acids), in order to enhance the solubility of the scFv fragment (for example, hydrophilic linkers such as polyethylene glycol-containing linkers or polypeptides containing repeating glycine and serine residues), to improve the biophysical stability of the molecule (for example, a linker containing cysteine residues that form intramolecular or intermolecular disulfide bonds), or to attenuate the immunogenicity of the scFv fragment (for example, linkers containing glycosylation sites). It will also be understood by one of ordinary skill in the art that the variable regions of the scFv molecules described herein can be modified such that they vary in amino acid sequence from the antibody molecule from which they were derived. For example, nucleotide or amino acid substitutions leading to conservative substitutions or changes at amino acid residues can be made (e.g., in CDR and/or framework residues) so as to preserve or enhance the ability of the scFv to bind to the antigen recognized by the corresponding antibody.

The terms "specific binding" or "specifically binding", as used herein, refers to the ability of an antibody to recognize and bind to a specific protein structure (epitope) rather than to proteins generally. If an antibody is specific for epitope "A", the presence of a molecule containing epitope A (or free, unlabeled A), in a reaction containing labeled "A" and the antibody, will reduce the amount of labeled A bound to the antibody. By way of example, an antibody "binds specifically" to a target if the antibody, when labeled, can be competed away from its target by the corresponding non-labeled antibody. In one embodiment, an antibody specifically binds to a target, e.g., CD45, if the antibody has a $K_D$ for the target of at least about $10^{-4}$ M, about $10^{-5}$ M, about $10^{-6}$ M, about $10^{-7}$ M, about $10^{-8}$ M, about $10^{-9}$ M, about $10^{-10}$ M, about $10^{-11}$ M, about $10^{-12}$ M, or less (less meaning a number that is less than $10^{-12}$, e.g. $10^{-13}$). In one embodiment, the term "specific binding to CD45" or "specifically binds to CD45," as used herein, refers to an antibody or that binds to CD45 and has a dissociation constant ($K_D$) of $1.0\times10^{-7}$ M or less, as determined by surface plasmon resonance. In one embodiment, $K_D$ is determined according to standard bio-layer interferometery (BLI). It shall be understood, however, that the antibody may be capable of specifically binding to two or more antigens which are related in sequence. For example, in one embodiment, an antibody can specifically bind to both human and a non-human (e.g., mouse or non-human primate) orthologs of CD45. Thus, as used herein, an antibody that "specifically binds to human CD45" is intended to refer to an antibody that binds to human CD45 (and possibly CD45 from one or more non-human species) but does not substantially bind to non-CD45 proteins. Preferably, the antibody binds to human CD45 with a $K_D$ of $1\times10^{-7}$ M or less, a $K_D$ of $5\times10^{-8}$ M or less, a $K_D$ of $3\times10^{-8}$ M or less, a $K_D$ of $1\times10^{-8}$ M or less, or a $K_D$ of $5\times10^{-9}$ M or less. In some embodiments, the anti-CD45 antibody is able to specifically bind the extracellular domain of each one of the various isoforms of human CD45 (e.g., CD45RA (Uniprot Accession No: P08575-8; SEQ ID NO: 2), CD45RO (NCBI Accession No: NP_563578.2; SEQ ID NO: 1), CD45RB (NCBI Accession No: XP_006711537.1; SEQ ID NO: 3), CD45RC (Uniprot Accession No. P08575-10; SEQ ID NO: 4), CD45RAB (NCBI Accession No: XP_006711535.1; SEQ ID NO: 5), CD45RBC (NCBI Accession No: XP_006711536.1; SEQ ID NO: 6) and CD45RABC (NCBI Accession No. NP_002829.3; SEQ ID NO: 7)). Accordingly, in certain embodiments, the antibody herein is a pan-specific anti-CD45 antibody (i.e., an antibody that specifically binds to the extracellular region of all human CD45 isoforms).

As used herein, the phrase "stem cell disorder" broadly refers to any disease, disorder, or condition that may be treated or cured by conditioning a subject's target tissues, and/or by ablating an endogenous stem cell population in a target tissue (e.g., ablating an endogenous hematopoietic stem or progenitor cell population from a subject's bone marrow tissue) and/or by engrafting or transplanting stem cells in a subject's target tissues. For example, Type I diabetes has been shown to be cured by hematopoietic stem cell transplant and may benefit from conditioning in accordance with the compositions and methods described herein. Additional disorders that can be treated using the compositions and methods described herein include, without limitation, sickle cell anemia, thalassemias, Fanconi anemia, aplastic anemia, Wiskott-Aldrich syndrome, ADA SCID, HIV/AIDS, metachromatic leukodystrophy, Diamond-Blackfan anemia, and Schwachman-Diamond syndrome. Additional diseases that may be treated using the patient conditioning and/or hematopoietic stem cell transplant methods described herein include inherited blood disorders (e.g., sickle cell anemia) and autoimmune disorders, such as scleroderma, multiple sclerosis, ulcerative colitis, and Chrohn's disease. Additional diseases that may be treated using the conditioning and/or transplantation methods described herein include a malignancy, such as a neuroblastoma or a hematologic cancer, such as leukemia, lymphoma, and myeloma. For instance, the cancer may be acute myeloid leukemia, acute lymphoid leukemia, chronic myeloid leukemia, chronic lymphoid leukemia, multiple myeloma, diffuse large B-cell lymphoma, or non-Hodgkin's lymphoma. Additional diseases treatable using the conditioning and/or transplantation methods described herein include myelodysplastic syndrome. In some embodiments, the subject has or is otherwise affected by a metabolic storage disorder. For example, the subject may suffer or otherwise be affected by a metabolic disorder selected from the group consisting of glycogen storage diseases, mucopolysaccharidoses, Gaucher's Disease, Hurlers Disease, sphingolipidoses, metachromatic leukodystrophy, or any other diseases or disorders which may benefit from the treatments and therapies disclosed herein and including, without limitation, severe combined immunodeficiency, Wiscott-Aldrich syndrome, hyper immunoglobulin M (IgM) syndrome, Chediak-Higashi disease, hereditary lymphohistiocytosis, osteopetrosis, osteogenesis imperfecta, storage diseases, thalassemia major, sickle cell disease, systemic sclerosis, systemic lupus erythematosus, multiple sclerosis, juvenile rheumatoid arthritis and those diseases, or disorders described in "Bone Marrow Transplantation for Non-Malignant Disease," ASH Education Book, 1:319-338 (2000), the disclosure of which is incorporated herein by reference in its entirety as it pertains to pathologies that may be treated by administration of hematopoietic stem cell transplant therapy.

As used herein, the terms "subject" and "patient" refer to an organism, such as a human, that receives treatment for a particular disease or condition as described herein. For instance, a patient, such as a human patient, may receive treatment prior to hematopoietic stem cell transplant therapy in order to promote the engraftment of exogenous hematopoietic stem cells.

As used herein, the phrase "substantially cleared from the blood" refers to a point in time following administration of a therapeutic agent (such as an anti-CD45 antibody, or antigen-binding fragment thereof) to a patient when the concentration of the therapeutic agent in a blood sample isolated from the patient is such that the therapeutic agent is not detectable by conventional means (for instance, such that the therapeutic agent is not detectable above the noise threshold of the device or assay used to detect the therapeutic agent). A variety of techniques known in the art can be used to detect antibodies, or antibody fragments, such as ELISA-based detection assays known in the art or described herein. Additional assays that can be used to detect antibodies, or antibody fragments, include immunoprecipitation techniques and immunoblot assays, among others known in the art.

As used herein, the term "transfection" refers to any of a wide variety of techniques commonly used for the introduction of exogenous DNA into a prokaryotic or eukaryotic host cell, such as electroporation, lipofection, calcium-phosphate precipitation, DEAE-dextran transfection and the like.

As used herein, the terms "treat" or "treatment" refers to reducing the severity and/or frequency of disease symptoms, eliminating disease symptoms and/or the underlying cause of said symptoms, reducing the frequency or likelihood of disease symptoms and/or their underlying cause, and improving or remediating damage caused, directly or indirectly, by disease. Beneficial or desired clinical results include, but are not limited to, promoting the engraftment of exogenous hematopoietic cells in a patient following antibody conditioning therapy as described herein and subsequent hematopoietic stem cell transplant therapy. Additional beneficial results include an increase in the cell count or relative concentration of hematopoietic stem cells in a patient in need of a hematopoietic stem cell transplant following conditioning therapy and subsequent administration of an exogenous hematopoietic stem cell graft to the patient. Beneficial results of therapy described herein may also include an increase in the cell count or relative concentration of one or more cells of hematopoietic lineage, such as a megakaryocyte, thrombocyte, platelet, erythrocyte, mast cell, myeoblast, basophil, neutrophil, eosinophil, microglial cell, granulocyte, monocyte, osteoclast, antigen-presenting cell, macrophage, dendritic cell, natural killer cell, T-lymphocyte, or B-lymphocyte, following conditioning therapy and subsequent hematopoietic stem cell transplant therapy. Additional beneficial results may include the reduction in quantity of a disease-causing cell population, such as a population of cancer cells (e.g., CD45+ leukemic cells) or autoimmune cells (e.g., CD45+ autoimmune lymphocytes, such as a CD45+ T-cell that expresses a T-cell receptor that cross-reacts with a self antigen). Insofar as the methods of the present disclosure are directed to preventing disorders, it is understood that the term "prevent" does not require that the disease state be completely thwarted. Rather, as used herein, the term preventing refers to the ability of the skilled artisan to identify a population that is susceptible to disorders, such that administration of the compounds of the present disclosure may occur prior to onset of a disease. The term does not imply that the disease state is completely avoided.

As used herein, the terms "variant" and "derivative" are used interchangeably and refer to naturally-occurring, synthetic, and semi-synthetic analogues of a compound, peptide, protein, or other substance described herein. A variant or derivative of a compound, peptide, protein, or other substance described herein may retain or improve upon the biological activity of the original material.

As used herein, the term "vector" includes a nucleic acid vector, such as a plasmid, a DNA vector, a plasmid, a RNA vector, virus, or other suitable replicon. Expression vectors described herein may contain a polynucleotide sequence as well as, for example, additional sequence elements used for the expression of proteins and/or the integration of these polynucleotide sequences into the genome of a mammalian cell. Certain vectors that can be used for the expression of antibodies and antibody fragments of the disclosure include plasmids that contain regulatory sequences, such as promoter and enhancer regions, which direct gene transcription. Other useful vectors for expression of antibodies and antibody fragments contain polynucleotide sequences that enhance the rate of translation of these genes or improve the stability or nuclear export of the mRNA that results from gene transcription. These sequence elements may include, for example, 5' and 3' untranslated regions and a polyadenylation signal site in order to direct efficient transcription of the gene carried on the expression vector. The expression vectors described herein may also contain a polynucleotide encoding a marker for selection of cells that contain such a vector. Examples of a suitable marker include genes that encode resistance to antibiotics, such as ampicillin, chloramphenicol, kanamycin, and nourseothricin.

The term "acyl" as used herein refers to —C(═O)R, wherein R is hydrogen ("aldehyde"), $C_1$-$C_{12}$ alkyl, $C_2$-$C_{12}$ alkenyl, $C_2$-$C_{12}$ alkynyl, $C_3$-$C_7$ carbocyclyl, $C_6$-$C_{20}$ aryl, 5-10 membered heteroaryl, or 5-10 membered heterocyclyl, as defined herein. Non-limiting examples include formyl, acetyl, propanoyl, benzoyl, and acryloyl.

The term "$C_1$-$C_{12}$ alkyl" as used herein refers to a straight chain or branched, saturated hydrocarbon having from 1 to 12 carbon atoms. Representative $C_1$-$C_{12}$ alkyl groups include, but are not limited to, -methyl, -ethyl, -n-propyl, -n-butyl, -n-pentyl, and -n-hexyl; while branched $C_1$-$C_{12}$ alkyls include, but are not limited to, -isopropyl, -sec-butyl, -isobutyl, -tert-butyl, -isopentyl, and 2-methylbutyl. A $C_1$-$C_{12}$ alkyl group can be unsubstituted or substituted.

The term "alkenyl" as used herein refers to $C_2$-$C_{12}$ hydrocarbon containing normal, secondary, or tertiary carbon atoms with at least one site of unsaturation, i.e., a carbon-carbon, $sp^2$ double bond. Examples include, but are not limited to: ethylene or vinyl, -allyl, -1-butenyl, -2-butenyl, -isobutylenyl, -1-pentenyl, -2-pentenyl, -3-methyl-1-butenyl, -2-methyl-2-butenyl, -2,3-dimethyl-2-butenyl, and the like. An alkenyl group can be unsubstituted or substituted.

"Alkynyl" as used herein refers to a $C_2$-$C_{12}$ hydrocarbon containing normal, secondary, or tertiary carbon atoms with at least one site of unsaturation, i.e., a carbon-carbon, sp triple bond. Examples include, but are not limited to acetylenic and propargyl. An alkynyl group can be unsubstituted or substituted.

"Aryl" as used herein refers to a $C_6$-$C_{20}$ carbocyclic aromatic group. Examples of aryl groups include, but are not limited to, phenyl, naphthyl and anthracenyl. An aryl group can be unsubstituted or substituted.

"Arylalkyl" as used herein refers to an acyclic alkyl radical in which one of the hydrogen atoms bonded to a carbon atom, typically a terminal or $sp^3$ carbon atom, is replaced with an aryl radical. Typical arylalkyl groups include, but are not limited to, benzyl, 2-phenylethan-1-yl, 2-phenylethen-1-yl, naphthylmethyl, 2-naphthylethan-1-yl, 2-naphthylethen-1-yl, naphthobenzyl, 2-naphthophenylethan-1-yl and the like. The arylalkyl group comprises 6 to 20 carbon atoms, e.g. the alkyl moiety, including alkanyl, alkenyl or alkynyl groups, of the arylalkyl group is 1 to 6 carbon atoms and the aryl moiety is 5 to 14 carbon atoms. An alkaryl group can be unsubstituted or substituted.

"Cycloalkyl" as used herein refers to a saturated carbocyclic radical, which may be mono- or bicyclic. Cycloalkyl groups include a ring having 3 to 7 carbon atoms as a monocycle or 7 to 12 carbon atoms as a bicycle. Examples of monocyclic cycloalkyl groups include cyclopropyl, cyclobutyl, cyclopentyl, cyclohexyl, cycloheptyl, and cyclooctyl. A cycloalkyl group can be unsubstituted or substituted.

"Cycloalkenyl" as used herein refers to an unsaturated carbocyclic radical, which may be mono- or bicyclic. Cycloalkenyl groups include a ring having 3 to 6 carbon atoms as a monocycle or 7 to 12 carbon atoms as a bicycle. Examples of monocyclic cycloalkenyl groups include 1-cyclopent-1-enyl, 1-cyclopent-2-enyl, 1-cyclopent-3-enyl, 1-cyclohex-1-enyl, 1-cyclohex-2-enyl, and 1-cyclohex-3-enyl. A cycloalkenyl group can be unsubstituted or substituted.

"Heteroaralkyl" as used herein refers to an acyclic alkyl radical in which one of the hydrogen atoms bonded to a carbon atom, typically a terminal or $sp^3$ carbon atom, is replaced with a heteroaryl radical. Typical heteroarylalkyl groups include, but are not limited to, 2-benzimidazolylmethyl, 2-furylethyl, and the like. The heteroarylalkyl group comprises 6 to 20 carbon atoms, e.g. the alkyl moiety, including alkanyl, alkenyl or alkynyl groups, of the heteroarylalkyl group is 1 to 6 carbon atoms and the heteroaryl moiety is 5 to 14 carbon atoms and 1 to 3 heteroatoms selected from N, O, P, and S. The heteroaryl moiety of the heteroarylalkyl group may be a monocycle having 3 to 7 ring members (2 to 6 carbon atoms or a bicycle having 7 to 10 ring members (4 to 9 carbon atoms and 1 to 3 heteroatoms selected from N, O, P, and S), for example: a bicyclo[4,5], [5,5], [5,6], or [6,6] system.

"Heteroaryl" and "heterocycloalkyl" as used herein refer to an aromatic or non-aromatic ring system, respectively, in which one or more ring atoms is a heteroatom, e.g. nitrogen, oxygen, and sulfur. The heteroaryl or heterocycloalkyl radical comprises 2 to 20 carbon atoms and 1 to 3 heteroatoms selected from N, O, P, and S. A heteroaryl or heterocycloalkyl may be a monocycle having 3 to 7 ring members (2 to 6 carbon atoms and 1 to 3 heteroatoms selected from N, O, P, and S) or a bicycle having 7 to 10 ring members (4 to 9 carbon atoms and 1 to 3 heteroatoms selected from N, O, P, and S), for example: a bicyclo[4,5], [5,5], [5,6], or [6,6] system. Heteroaryl and heterocycloalkyl can be unsubstituted or substituted.

Heteroaryl and heterocycloalkyl groups are described in Paquette, Leo A.; "Principles of Modern Heterocyclic Chemistry" (W. A. Benjamin, New York, 1968), particularly Chapters 1, 3, 4, 6, 7, and 9; "The Chemistry of Heterocyclic Compounds, A series of Monographs" (John Wiley & Sons, New York, 1950 to present), in particular Volumes 13, 14, 16, 19, and 28; and J. Am. Chem. Soc. (1960) 82:5566.

Examples of heteroaryl groups include by way of example and not limitation pyridyl, thiazolyl, tetrahydrothiophenyl, pyrimidinyl, furanyl, thienyl, pyrrolyl, pyrazolyl, imidazolyl, tetrazolyl, benzofuranyl, thianaphthalenyl, indolyl, indolenyl, quinolinyl, isoquinolinyl, benzimidazolyl, isoxazolyl, pyrazinyl, pyridazinyl, indolizinyl, isoindolyl, 3H-indolyl, 1H-indazolyl, purinyl, 4H-quinolizinyl, phthalazinyl, naphthyridinyl, quinoxalinyl, quinazolinyl, cinnolinyl, pteridinyl, 4aH-carbazolyl, carbazolyl, phenanthridinyl, acridinyl, pyrimidinyl, phenanthrolinyl, phenazinyl, phenothiazinyl, furazanyl, phenoxazinyl, isochromanyl, chromanyl, imidazolidinyl, imidazolinyl, pyrazolidinyl, pyrazolinyl, benzotriazolyl, benzisoxazolyl, and isatinoyl.

Examples of heterocycloalkyls include by way of example and not limitation dihydroypyridyl, tetrahydropyridyl (piperidyl), tetrahydrothiophenyl, piperidinyl, 4-piperidonyl, pyrrolidinyl, 2-pyrrolidonyl, tetrahydrofuranyl, tetrahydropyranyl, bis-tetrahydropyranyl, tetrahydroquinolinyl, tetrahydroisoquinolinyl, decahydroquinolinyl, octahydroisoquinolinyl, piperazinyl, quinuclidinyl, and morpholinyl.

By way of example and not limitation, carbon bonded heteroaryls and heterocycloalkyls are bonded at position 2, 3, 4, 5, or 6 of a pyridine, position 3, 4, 5, or 6 of a pyridazine, position 2, 4, 5, or 6 of a pyrimidine, position 2, 3, 5, or 6 of a pyrazine, position 2, 3, 4, or 5 of a furan, tetrahydrofuran, thiofuran, thiophene, pyrrole or tetrahydropyrrole, position 2, 4, or 5 of an oxazole, imidazole or thiazole, position 3, 4, or 5 of an isoxazole, pyrazole, or isothiazole, position 2 or 3 of an aziridine, position 2, 3, or 4 of an azetidine, position 2, 3, 4, 5, 6, 7, or 8 of a quinoline or position 1, 3, 4, 5, 6, 7, or 8 of an isoquinoline. Still more typically, carbon bonded heterocycles include 2-pyridyl, 3-pyridyl, 4-pyridyl, 5-pyridyl, 6-pyridyl, 3-pyridazinyl, 4-pyridazinyl, 5-pyridazinyl, 6-pyridazinyl, 2-pyrimidinyl, 4-pyrimidinyl, 5-pyrimidinyl, 6-pyrimidinyl, 2-pyrazinyl, 3-pyrazinyl, 5-pyrazinyl, 6-pyrazinyl, 2-thiazolyl, 4-thiazolyl, or 5-thiazolyl.

By way of example and not limitation, nitrogen bonded heteroaryls and heterocycloalkyls are bonded at position 1 of an aziridine, azetidine, pyrrole, pyrrolidine, 2-pyrroline, 3-pyrroline, imidazole, imidazolidine, 2-imidazoline, 3-imidazoline, pyrazole, pyrazoline, 2-pyrazoline, 3-pyrazoline, piperidine, piperazine, indole, indoline, 1H-indazole, position 2 of a isoindole, or isoindoline, position 4 of a morpholine, and position 9 of a carbazole, or beta-carboline. Still more typically, nitrogen bonded heterocycles include 1-aziridyl, 1-azetedyl, 1-pyrrolyl, 1-imidazolyl, 1-pyrazolyl, and 1-piperidinyl.

"Substituted" as used herein and as applied to any of the above alkyl, alkenyl, alkynyl, aryl, arylalkyl, cycloalkyl, heteroaryl, heterocyclyl, and the like, means that one or more hydrogen atoms are each independently replaced with a substituent. Unless otherwise constrained by the definition of the individual substituent, the foregoing chemical moieties, such as "alkyl", "alkylene", "heteroalkyl", "heteroalkylene", "alkenyl", "alkenylene", "heteroalkenyl", "heteroalkenylene", "alkynyl", "alkynylene", "heteroalkynyl", "heteroalkynylene", "cycloalkyl", "cycloalkylene", "heterocyclolalkyl", heterocycloalkylene", "aryl," "arylene", "heteroaryl", and "heteroarylene" groups can optionally be substituted. Typical substituents include, but are not limited to, —X, —R, —OH, —OR, —SH, —SR, $NH_2$, —NHR, $—N(R)_2$, $—N^+(R)_3$, $—CX_3$, —CN, —OCN, —SCN, —NCO, —NCS, —NO, $—NO_2$, $—N_3$, —NC(═O)H, —NC(═O)R, —C(═O)H, —C(═O)R, $—C(═O)NH_2$, $—C(═O)N(R)_2$, $—SO_3—$, $—SO_3H$, $—S(═O)_2R$, $—OS(═O)_2OR$, $—S(═O)_2NH_2$, $—S(═O)_2N(R)_2$, —S(═O)R, $—OP(═O)(OH)_2$, $—OP(═O)(OR)_2$, $—P(═O)(OR)_2$, $—PO_3$, $—PO_3H_2$, —C(═O)X, —C(═S)R, $—CO_2H$, $—CO_2R$, $—CO_2—$, —C(═S)OR, —C(═O)SR, —C(═S)SR, $—C(═O)NH_2$, $—C(═O)N(R)_2$, $—C(═S)NH_2$, $—C(═S)N(R)_2$, $—C(═NH)NH_2$, and $—C(═NR)N(R)_2$; wherein each X is independently selected for each occasion from F, Cl, Br, and I; and each R is independently selected for each occasion from $C_1$-$C_{12}$ alkyl, $C_6$-$C_{20}$ aryl, $C_3$-$C_{14}$ heterocycloalkyl or heteroaryl, protecting group and prodrug moiety. Wherever a group is described as "optionally substituted," that group can be substituted with one or more of the above substituents, independently for each occasion. The substitution may include situations in which neighboring substituents have undergone ring closure, such as ring closure of vicinal functional substituents, to form, for instance, lactams, lactones, cyclic anhydrides, acetals, hemiacetals, thioacetals, aminals, and hemiaminals, formed by ring closure, for example, to furnish a protecting group.

It is to be understood that certain radical naming conventions can include either a mono-radical or a di-radical, depending on the context. For example, where a substituent requires two points of attachment to the rest of the molecule, it is understood that the substituent is a di-radical. For example, a substituent identified as alkyl that requires two points of attachment includes di-radicals such as $—CH_2—$, $—CH_2CH_2—$, $—CH_2CH(CH_3)CH_2—$, and the like. Other radical naming conventions clearly indicate that the radical is a di-radical such as "alkylene," "alkenylene," "arylene," "heterocycloalkylene," and the like.

Wherever a substituent is depicted as a di-radical (i.e., has two points of attachment to the rest of the molecule), it is to be understood that the substituent can be attached in any directional configuration unless otherwise indicated.

"Isomerism" means compounds that have identical molecular formulae but differ in the sequence of bonding of their atoms or in the arrangement of their atoms in space. Isomers that differ in the arrangement of their atoms in space are termed "stereoisomers." Stereoisomers that are not mirror images of one another are termed "diastereoisomers," and stereoisomers that are non-superimposable mirror images of each other are termed "enantiomers," or sometimes "optical isomers."

A carbon atom bonded to four non-identical substituents is termed a "chiral center." "Chiral isomer" means a compound with at least one chiral center. Compounds with more than one chiral center may exist either as an individual diastereomer or as a mixture of diastereomers, termed "diastereomeric mixture." When one chiral center is present, a stereoisomer may be characterized by the absolute configuration (R or S) of that chiral center. Absolute configuration refers to the arrangement in space of the substituents attached to the chiral center. The substituents attached to the chiral center under consideration are ranked in accordance with the Sequence Rule of Cahn, Ingold and Prelog. (Cahn et al., *Angew. Chem. Inter. Edit.* 1966, 5, 385; errata 511; Cahn et al., *Angew. Chem.* 1966, 78, 413; Cahn and Ingold, *J. Chem. Soc.* 1951 (London), 612; Cahn et al., *Experientia* 1956, 12, 81; Cahn, *J. Chem. Educ.* 1964, 41, 116). A mixture containing equal amounts of individual enantiomeric forms of opposite chirality is termed a "racemic mixture."

The compounds disclosed in this description and in the claims may comprise one or more asymmetric centers, and different diastereomers and/or enantiomers of each of the compounds may exist. The description of any compound in this description and in the claims is meant to include all enantiomers, diastereomers, and mixtures thereof, unless stated otherwise. In addition, the description of any compound in this description and in the claims is meant to include both the individual enantiomers, as well as any mixture, racemic or otherwise, of the enantiomers, unless stated otherwise. When the structure of a compound is depicted as a specific enantiomer, it is to be understood that the disclosure of the present application is not limited to that specific enantiomer. Accordingly, enantiomers, optical isomers, and diastereomers of each of the structural formulae of the present disclosure are contemplated herein. In the present specification, the structural formula of the compound represents a certain isomer for convenience in some cases, but the present disclosure includes all isomers, such as geometrical isomers, optical isomers based on an asymmetrical carbon, stereoisomers, tautomers, and the like, it being understood that not all isomers may have the same level of activity. The compounds may occur in different tautomeric forms. The compounds according to the disclosure are meant to include all tautomeric forms, unless stated otherwise. When the structure of a compound is depicted as a specific tautomer, it is to be understood that the disclosure of the present application is not limited to that specific tautomer.

The compounds of any formula described herein include the compounds themselves, as well as their salts, and their solvates, if applicable. A salt, for example, can be formed between an anion and a positively charged group (e.g., amino) on a compound of the disclosure. Suitable anions include chloride, bromide, iodide, sulfate, bisulfate, sulfamate, nitrate, phosphate, citrate, methanesulfonate, trifluoroacetate, glutamate, glucuronate, glutarate, malate, maleate, succinate, fumarate, tartrate, tosylate, salicylate, lactate, naphthalenesulfonate, and acetate (e.g., trifluoroacetate). The term "pharmaceutically acceptable anion" refers to an anion suitable for forming a pharmaceutically acceptable salt. Likewise, a salt can also be formed between a cation and a negatively charged group (e.g., carboxylate) on a compound of the disclosure. Suitable cations include sodium ion, potassium ion, magnesium ion, calcium ion, and an ammonium cation such as tetramethylammonium ion. Examples of some suitable substituted ammonium ions are those derived from: ethylamine, diethylamine, dicyclohexylamine, triethylamine, butylamine, ethylenediamine, ethanolamine, diethanolamine, piperazine, benzylamine, phenylbenzylamine, choline, meglumine, and tromethamine, as well as amino acids, such as lysine and arginine. The compounds of the disclosure also include those salts containing quaternary nitrogen atoms.

Examples of suitable inorganic anions include, but are not limited to, those derived from the following inorganic acids: hydrochloric, hydrobromic, hydroiodic, sulfuric, sulfurous, nitric, nitrous, phosphoric, and phosphorous. Examples of suitable organic anions include, but are not limited to, those derived from the following organic acids: 2-acetyoxybenzoic, acetic, ascorbic, aspartic, benzoic, camphorsulfonic, cinnamic, citric, edetic, ethanedisulfonic, ethanesulfonic, fumaric, glucheptonic, gluconic, glutamic, glycolic, hydroxymaleic, hydroxynaphthalene carboxylic, isethionic, lactic, lactobionic, lauric, maleic, malic, methanesulfonic, mucic, oleic, oxalic, palmitic, pamoic, pantothenic, phenylacetic, phenylsulfonic, propionic, pyruvic, salicylic, stearic, succinic, sulfanilic, tartaric, toluenesulfonic, and valeric. Examples of suitable polymeric organic anions include, but are not limited to, those derived from the following polymeric acids: tannic acid, carboxymethyl cellulose.

Additionally, the compounds of the present disclosure, for example, the salts of the compounds, can exist in either hydrated or unhydrated (the anhydrous) form or as solvates with other solvent molecules. Non-limiting examples of hydrates include monohydrates, dihydrates, etc. Non-limiting examples of solvates include ethanol solvates, acetone solvates, etc. "Solvate" means solvent addition forms that contain either stoichiometric or non-stoichiometric amounts of solvent. Some compounds have a tendency to trap a fixed molar ratio of solvent molecules in the crystalline solid state, thus forming a solvate. If the solvent is water the solvate formed is a hydrate; and if the solvent is alcohol, the solvate formed is an alcoholate. Hydrates are formed by the combination of one or more molecules of water with one molecule of the substance in which the water retains its molecular state as $H_2O$. A hydrate refers to, for example, a mono-hydrate, a di-hydrate, a tri-hydrate, etc.

In addition, a crystal polymorphism may be present for the compounds or salts thereof represented by the formulae disclosed herein. It is noted that any crystal form, crystal form mixture, or anhydride or hydrate thereof, is included in the scope of the present disclosure.

Antibody-Drug Conjugates (ADCs)

Antibodies, and antigen-binding fragments thereof that bind CD45 as described herein can be conjugated (linked) to a cytotoxic molecule (i.e., a cytotoxin), thus forming an antibody-drug conjugate (ADC). As used herein, the terms "cytotoxin", "cytotoxic moiety", and "drug" are used interchangeably.

In particular, the ADCs as disclosed herein include an antibody that binds CD45 (including an antigen-binding fragment thereof) conjugated (i.e., covalently attached by a linker) to a cytotoxic moiety, such as a cytotoxin comprising a benzodiazepine moiety (e.g., a pyrrolobenzodiazepine (PBD), or an indolinobenzodiazepine (IGN)), wherein the cytotoxic moiety, when not conjugated to an antibody moiety, has a cytotoxic or cytostatic effect. In various embodiments, the cytotoxic moiety exhibits reduced or no cytotoxicity when bound in a conjugate, but resumes cytotoxicity after cleavage from the linker. In various embodiments, the cytotoxic moiety maintains cytotoxicity without cleavage from the linker. In some embodiments, the cytotoxic molecule is conjugated to a cell internalizing antibody, or antigen-binding fragment thereof as disclosed herein, such that following the cellular uptake of the antibody, or fragment thereof, the cytotoxin may access its intracellular target and, e.g., mediate hematopoietic cell death. ADCs of the present disclosure therefore may be of the general formula Ab-(Z-L-Cy)$_n$, wherein an antibody or antigen-binding fragment thereof (Ab) is conjugated (covalently linked) to a linker (L), through a chemical moiety (Z), to a cytotoxic moiety (Cy).

Accordingly, the antibody or antigen-binding fragment thereof may be conjugated to a number of drug moieties as indicated by integer n, which represents the average number of cytotoxins per antibody, which may range, e.g., from about 1 to about 20. Any number of cytotoxins can be conjugated to the anti-CD45 antibody, e.g., 1, 2, 3, 4, 5, 6, 7, or 8. In some embodiments, n is from about 1 to about 5, about 1 to about 4, about 1 to about 3, or about 2 to about 5, or about 3 to about 5. In some embodiments, n is about 1, about 2, about 3, or about 4. The average number of drug moieties per antibody in preparations of ADC from conjugation reactions may be characterized by conventional means such as mass spectroscopy, ELISA assay, and HPLC. The quantitative distribution of ADC in terms of n may also be determined. In some instances, separation, purification, and characterization of homogeneous ADC where n is a certain value from ADC with other drug loadings may be achieved by means such as reverse phase HPLC or electrophoresis.

For some antibody-drug conjugates, n may be limited by the number of attachment sites on the antibody. For example, where the attachment is a cysteine thiol, an antibody may have only one or several cysteine thiol groups, or may have only one or several sufficiently reactive thiol groups through which a linker may be attached. Generally, antibodies do not contain many free and reactive cysteine thiol groups which may be linked to a drug moiety; primarily, cysteine thiol residues in antibodies exist as disulfide bridges. In certain embodiments, an antibody may be reduced with a reducing agent such as dithiothreitol (DTT) or tricarbonylethylphosphine (TCEP), under partial or total reducing conditions, to generate reactive cysteine thiol groups. In certain embodiments, higher drug loading, e.g. n>5, may cause aggregation, insolubility, toxicity, or loss of cellular permeability of certain antibody-drug conjugates.

In certain embodiments, fewer than the theoretical maximum of drug moieties are conjugated to an antibody during a conjugation reaction. An antibody may contain, for example, lysine residues that do not react with the drug-linker intermediate or linker reagent, as discussed below. Only the most reactive lysine groups may react with an amine-reactive linker reagent. In certain embodiments, an antibody is subjected to denaturing conditions to reveal reactive nucleophilic groups such as lysine or cysteine.

The loading (drug/antibody ratio) of an ADC may be controlled in different ways, e.g., by: (i) limiting the molar excess of drug-linker intermediate or linker reagent relative to antibody, (ii) limiting the conjugation reaction time or temperature, (iii) partial or limiting reductive conditions for cysteine thiol modification, (iv) engineering by recombinant techniques the amino acid sequence of the antibody such that the number and position of cysteine residues is modified for control of the number and/or position of linker-drug attachments.

Anti-CD45 Antibodies

The present disclosure is based in part on the discovery that antibodies, antigen-binding fragments thereof, and ligands capable of binding CD45 can be used as therapeutic agents to (i) directly treat cancers and autoimmune diseases characterized by cells that express one or more of these antigens and (ii) promote the engraftment of transplanted hematopoietic stem cells in a patient in need of transplant therapy. These therapeutic activities can be caused, for instance, by the binding of antibodies, antigen-binding fragments thereof, and/or ligands to CD45 expressed on the surface of a cell, such as a cancer cell, autoimmune cell, or hematopoietic stem cell and subsequently inducing cell death. The depletion of endogenous hematopoietic stem cells can provide a niche toward which transplanted hematopoietic stem cells can home, and subsequently establish productive hematopoiesis. In this way, transplanted hematopoietic stem cells may successfully engraft in a patient, such as human patient suffering from a stem cell disorder described herein.

Antibodies and antigen-binding fragments capable of binding human CD45 (mRNA NCBI Reference Sequence: NM_080921.3, Protein NCBI Reference Sequence: NP_563578.2), can be used in conjunction with the compositions and methods disclosed herein, such as to promote engraftment of hematopoietic stem cell grafts in a patient in need of hematopoietic stem cell transplant therapy. In some embodiments, the anti-CD45 antibody, or antigen binding portion thereof, is a de-immunized anti-CD45 antibody, or antigen binding portion thereof. In some embodiments, the anti-CD45 antibody, or antigen binding portion thereof, is a chimeric anti-CD45 antibody, or antigen binding portion thereof. In other embodiments, the anti-CD45 antibody, or antigen binding portion thereof, is a humanized anti-CD45 antibody, or antigen binding portion thereof. In other embodiments, the anti-CD45 antibody, or antigen binding portion thereof, is a fully human anti-CD45 antibody, or antigen binding portion thereof.

CD45 is a hematopoietic cell-specific transmembrane protein tyrosine phosphatase essential for T and B cell antigen receptor-mediated signaling. CD45 includes a large extracellular domain, and a phosphatase containing cytosolic domain. Multiple isoforms of CD45 arise from the alternative splicing of 34 exons in the primary transcript. Splicing of exons 4, 5, 6, and potentially 7 give rise to multiple CD45 variations. Although there are a large number of permutations possible in the CD45 gene, six isoforms are most commonly identified in humans. The isoforms are RA (Uniprot Accession No: P08575-8; SEQ ID NO: 31), RO (NCBI Accession No: NP_563578.2; SEQ ID NO: 32), RB (NCBI Accession No: XP_006711537.1; SEQ ID NO: 33), RAB (NCBI Accession No: XP_006711535.1; SEQ ID NO: 34), RBC (NCBI Accession No: XP_006711536.1; SEQ ID NO: 35) and RABC (NCBI Accession No. NP_002829.3; SEQ ID NO: 36) (Hermiston et al. 2003 "CD45: a critical regulator of signaling thresholds in immune cells." *Annu Rev Immunol.* 2:107-137). CD45RA is expressed on naïve T cells, and CD45RO is expressed on activated and memory T cells, some B cell subsets, activated monocytes/macrophages, and granulocytes. CD45RB is expressed on peripheral B cells, naïve T cells, thymocytes, weakly on macrophages, and dendritic cells. Selective exon expression is observed in the CD45 isoforms described in Table 1, below.

TABLE 1

Exon expression in various CD45 isoforms

| CD45 Isoform | Exon Expression Pattern |
|---|---|
| CD45RA (SEQ ID NO: 2) | Expresses exon 4 only |
| CD45RB (SEQ ID NO: 3) | Expresses exon 5 only |

TABLE 1-continued

| Exon expression in various CD45 isoforms | |
|---|---|
| CD45 Isoform | Exon Expression Pattern |
| CD45RC (SEQ ID NO: 4) | Expresses exon 6 only |
| CD45RO (SEQ ID NO: 1) | Does not express exons 4-6 |

Alternative splicing can result in individual exons or combinations of exons expressed in various isoforms of the CD45 protein (for example, CD45RA, CD45RAB, CD45RABC). In contrast, CD45RO lacks expression of exons 4-6 and is generated from a combination of exons 1-3 and 7-34. There is evidence that exon 7 can also be excluded from the protein, resulting in splicing together of exons 1-3 and 8-34. This protein, designated E3-8, has been detected at the mRNA level but has not been currently identified by flow cytometry.

CD45RO is currently the only known CD45 isoform expressed on hematopoietic stem cells. CD45RA and CD45RABC have not been detected or are excluded from the phenotype of hematopoietic stem cells. There is evidence from studies conducted in mice that CD45RB is expressed on fetal hematopoietic stem cells, but it is not present on adult bone marrow hematopoietic stem cells. Notably, CD45RC has a high rate of polymorphism in exon 6 found within Asian populations (a polymorphism at exon 6 in CD45RC is found in approximately 25% of the Japanese population). This polymorphism leads to high expression of CD45RO and decreased levels of CD45RA, CD45RB, and CD45RC. Additionally, CD45RA variants (such as CD45RAB and CD45RAC) exhibit a polymorphism in exon 4 that has been associated with autoimmune disease.

The presence of CD45RO on hematopoietic stem cells and its comparatively limited expression on other immune cells (such as T and B lymphocyte subsets and various myeloid cells) renders CD45RO a particularly well-suited target for conditioning therapy for patients in need of a hematopoietic stem cell transplant. As CD45RO only lacks expression of exons 4, 5, and 6, its use as an immunogen enables the screening of pan CD45 Abs and CD45RO-specific antibodies.

In some embodiments, the anti-CD45 antibody, or antigen binding portion thereof, used in the ADCs, compositions, and methods described herein, is a pan-CD45 antibody, or antigen binding portion thereof, which binds all isoforms of CD45. In other embodiments, the anti-CD45 antibody, or antigen binding portion thereof, used in the ADCs, compositions, and methods described herein, is an isoform specific anti-CD45 antibody, which specifically binds to one or more of the foregoing isoforms of human CD45, e.g., one or more of CD45RA, CD45RB, CD45RC, CD45RO, CD45RAB, CD45RBC, and CD45 RABC.

Anti-CD45 antibodies that can be used in conjunction with the patient conditioning methods described herein include anti-CD45 antibodies, and antigen-binding portions thereof. Antigen-binding portions of antibodies are well known in the art, and can readily be constructed based on the antigen-binding region of the antibody. In exemplary embodiments, the anti-CD45 antibody used in conjunction with the conditioning methods described herein can be a monoclonal antibody or antigen-binding fragment thereof, a polyclonal antibody or antigen-binding fragment thereof, a humanized antibody or antigen-binding fragment thereof, a fully human antibody or antigen-binding fragment thereof, a chimeric antibody or antigen-binding fragment thereof, a bispecific antibody or antigen-binding fragment thereof, a dual-variable immunoglobulin domain, a single-chain Fv molecule (scFv), a diabody, a triabody, a nanobody, an antibody-like protein scaffold, a Fv fragment, a Fab fragment, a F(ab')2 molecule, or a tandem di-scFv. Exemplary anti-CD45 antibodies which may be used in whole or in part in the ADCs or methods described herein are provided below.

In one embodiment, the anti-CD45 antibody is or is derived from clone HI30, which is commercially available from BIOLEGEND® (San Diego, CA), or a humanized variant thereof. Humanization of antibodies can be performed by replacing framework residues and constant region residues of a non-human antibody with those of a germline human antibody according to procedures known in the art (as described, for instance, in Example 7, below). Additional anti-CD45 antibodies that can be used in conjunction with the methods described herein include the anti-CD45 antibodies ab10558, EP322Y, MEM-28, ab10559, 0.N.125, F10-89-4, Hle-1, 2B111, YTH24.5, PD7/26/16, F10-89-4, 1B7, ab154885, B-A11, phosphor S1007, ab170444, EP350, Y321, GA90, D3/9, X1 6/99, and LT45, which are commercially available from ABCAM® (Cambridge, MA), as well as humanized variants thereof. Further anti-CD45 antibodies that may be used in conjunction with the patient conditioning procedures described herein include anti-CD45 antibody HPA000440, which is commercially available from SIGMA-ALDRICH® (St. Louis, MO), and humanized variants thereof. Additional anti-CD45 antibodies that can be used in conjunction with the patient conditioning methods described herein include murine monoclonal antibody BC8, which is described, for instance, in Matthews et al., Blood 78:1864-1874, 1991, the disclosure of which is incorporated herein by reference as it pertains to anti-CD45 antibodies, as well as humanized variants thereof. Further anti-CD45 antibodies that can be used in conjunction with the methods described herein include monoclonal antibody YAML568, which is described, for instance, in Glatting et al., J. Nucl. Med. 8:1335-1341, 2006, the disclosure of which is incorporated herein by reference as it pertains to anti-CD45 antibodies, as well as humanized variants thereof. Additional anti-CD45 antibodies that can be used in conjunction with the patient conditioning procedures described herein include monoclonal antibodies YTH54.12 and YTH25.4, which are described, for instance, in Brenner et al., Ann. N.Y. Acad. Sci. 996:80-88, 2003, the disclosure of which is incorporated herein by reference as it pertains to anti-CD45 antibodies, as well as humanized variants thereof. Additional anti-CD45 antibodies for use with the patient conditioning methods described herein include UCHL1, 2H4, SN130, MD4.3, MBI, and MT2, which are described, for instance, in Brown et al., Immunology 64:331-336, 1998, the disclosure of which is incorporated herein by reference as it pertains to anti-CD45 antibodies, as well as humanized variants thereof. Additional anti-CD45 antibodies that can be used in conjunction with the methods described herein include those produced and released from American Type Culture Collection (ATCC) Accession Nos. RA3-6132, RA3-2C2, and TIB122, as well as monoclonal antibodies C363.16A, and 13/2, which are described, for instance, in Johnson et al., J. Exp. Med. 169:1179-1184, 1989, the disclosure of which is incorporated herein by reference as it pertains to anti-CD45 antibodies, as well as humanized variants thereof. Further anti-CD45 antibodies that can be used in conjunction with the patient conditioning methods described herein include the monoclonal antibodies AHN-12.1, AHN-12, AHN-12.2, AHN-12.3, AHN-12.4, HLe-1, and KC56(T200), which are described, for instance, in Harvath et al., J. Immunol. 146:949-957, 1991, the disclosure of which is incorporated herein by reference as it pertains to anti-CD45 antibodies, as well as humanized variants thereof.

Additional anti-CD45 antibodies that can be used in conjunction with the patient conditioning methods described herein include those described, for example, in U.S. Pat. No. 7,265,212 (which describes, e.g., anti-CD45 antibodies 39E11, 16C9, and 1G10, among other clones); 7,160,987 (which describe, e.g., anti-CD45 antibodies produced and released by ATCC Accession No. HB-11873, such as monoclonal antibody 6G3); and 6,099,838 (which describes, e.g., anti-CD45 antibody MT3, as well as antibodies produced and released by ATCC Accession Nos. HB220 (also designated MB23G2) and HB223), as well as US 2004/0096901 and US 2008/0003224 (which describes, e.g., anti-CD45 antibodies produced and released by ATCC Accession No. PTA-7339, such as monoclonal antibody 17.1), the disclosures of each of which are incorporated herein by reference as they pertain to anti-CD45 antibodies.

Further anti-CD45 antibodies that can be used in conjunction with the patient conditioning methods described herein include antibodies produced and released from ATCC Accession Nos. MB4B4, MB23G2, 14.8, GAP 8.3, 74-9-3, I/24.D6, 9.4, 4B2, M1/9.3.4.HL.2, as well as humanized and/or affinity-matured variants thereof. Affinity maturation can be performed, for instance, using in vitro display techniques described herein or known in the art, such as phage display, as described in Example 6, below.

Additional anti-CD45 antibodies that can be used in conjunction with the patient conditioning methods described herein include anti-CD45 antibody T29/33, which is described, for instance, in Morikawa et al., Int. J. Hematol. 54:495-504, 1991, the disclosure of which is incorporated herein by reference as it pertains to anti-CD45 antibodies.

In certain embodiments, the anti-CD45 antibody is selected from apamistamab (also known 90Y-BC8, lomab-B, BC8; as described in, e.g., US20170326259, WO2017155937, and Orozco et al. Blood. 127.3 (2016): 352-359.) or BC8-B10 (as described, e.g., in Li et al. *PloS one* 13.10 (2018): e0205135.), each of which is incorporated by reference. Other anti-CD45 antibodies have been described, for example, in WO2003/048327, WO2016/016442, US2017/0226209, US2016/0152733, U.S. Pat. No. 9,701,756; US2011/0076270, or U.S. Pat. No. 7,825,222, each of which is incorporated by reference in its entirety.

For example, in one embodiment, the anti-CD45 antibody, or antigen-binding fragment thereof, comprises binding regions, e.g., CDRs, variable regions, corresponding to those of apamistamab. The heavy chain variable region (VH) amino acid sequence of apamistamab is set forth in SEQ ID NO: 10 (see Table 5). The light chain variable region (VL) amino acid sequence of apamistamab is described in SEQ ID NO: 11 (see Table 5). In some embodiments, an anti-CD45 antibody, or antigen-binding portion thereof, comprises a variable heavy chain comprising the amino acid residues set forth in SEQ ID NO: 10, and a light chain variable region as set forth in SEQ ID NO: 11. In one embodiment, the anti-CD45 antibody comprises a heavy chain comprising a CDR1, CDR2 and CDR3 of apamistamab, and a light chain variable region comprising a CDR1, CDR2 and CDR3 of apamistamab.

In one embodiment, the anti-CD45 antibody comprises the variable regions of monoclonal antibody 104. 104 is a commercially available anti-CD45 antibody that binds the mouse CD45.2 isoform (BioLegend, San Diego, CA), and is also known as mAb Ly-5.2. In some embodiments, the variable regions of 104 are coupled to a human IgG constant region comprising one or more amino acid substitutions in the Fc domain. For example, in some embodiments, the variable regions of 104 are coupled to a human IgG constant region comprising S239C and N297A substitutions in the Fc domain. In some embodiments, the variable regions of 104 are coupled to a human IgG constant region comprising S239C and IHH (i.e., I253A, H310A, and H435A) substitutions in the Fc domain.

For example, in one embodiment, the anti-CD45 antibody, or antigen-binding fragment thereof, comprises binding regions, e.g., CDRs, variable regions, corresponding to those of 104 S239C/IHH. The heavy chain amino acid sequence of 104 S239C/IHH is described in SEQ ID NO: 12 (see Table 5). The light chain amino acid sequence of 104 S239C/IHH is described in SEQ ID NO: 13 (see Table 5). In some embodiments, an anti-CD45 antibody, or antigen-binding portion thereof, comprises a heavy chain comprising the amino acid residues set forth in SEQ ID NO: 12, and a light chain comprising the amino acid residues set forth in SEQ ID NO: 13.

In one embodiment, the anti-CD45 antibody comprises the CDR regions and/or variable regions of monoclonal antibody AbA. The heavy chain variable region (VH) amino acid sequence of AbA is set forth in SEQ ID NO: 14 (see Table 5). The VH CDR domain amino acid sequences of AbA are set forth in SEQ ID NO: 15 (VH CDR1); SEQ ID NO: 16 (VH CDR2), and SEQ ID NO: 17 (VH CDR3). The light chain variable region (VL) amino acid sequence of AbA is described in SEQ ID NO: 18. The VL CDR domain amino acid sequences of AbA are set forth in SEQ ID NO: 19 (VL CDR1); SEQ ID NO: 20 (VL CDR2), and SEQ ID NO: 21 (VL CDR3). Accordingly, in certain embodiments, the anti-CD45 antibody, or antigen-binding fragment thereof, provided herein comprises a heavy chain variable region comprising the amino acid sequence set forth in SEQ ID NO: 14, and a light chain variable region comprising the amino acid sequence as set forth in SEQ ID NO: 18. In one embodiment, the anti-CD45 antibody, or antigen binding fragment thereof, comprises a heavy chain comprising a CDR1, CDR2 and CDR3 comprising the amino acid sequences set forth in SEQ ID NOs: 15, 16, and 17, and a light chain variable region comprising a CDR1, CDR2 and CDR3 comprising the amino acid sequences set forth in SEQ ID NOs: 19, 20, and 21.

In one embodiment, the anti-CD45 antibody comprises the CDR regions and/or variable regions of monoclonal antibody AbB. The heavy chain variable region (VH) amino acid sequence of AbB is set forth in SEQ ID NO: 22 (see Table 5). The VH CDR domain amino acid sequences of AbB are set forth in SEQ ID NO: 23 (VH CDR1); SEQ ID NO: 24 (VH CDR2), and SEQ ID NO: 25 (VH CDR3). The light chain variable region (VL) amino acid sequence of AbB is described in SEQ ID NO: 26. The VL CDR domain amino acid sequences of AbB are set forth in SEQ ID NO: 27 (VL CDR1); SEQ ID NO: 28 (VL CDR2), and SEQ ID NO: 29 (VL CDR3). Accordingly, in certain embodiments, the anti-CD45 antibody, or antigen-binding fragment thereof, provided herein comprises a heavy chain variable region comprising the amino acid sequence set forth in SEQ ID NO: 22, and a light chain variable region comprising the amino acid sequence as set forth in SEQ ID NO: 26. In one embodiment, the anti-CD45 antibody, or antigen binding fragment thereof, comprises a heavy chain comprising a CDR1, CDR2 and CDR3 comprising the amino acid sequences set forth in SEQ ID NOs: 23, 24, and 25, and a light chain variable region comprising a CDR1, CDR2 and CDR3 comprising the amino acid sequences set forth in SEQ ID NOs: 27, 28, and 29.

In one embodiment, the anti-CD45 antibody comprises the CDR regions and/or variable regions of monoclonal antibody AbC. The heavy chain variable region (VH) amino acid sequence of AbC is set forth in SEQ ID NO: 30 (see Table 5). The VH CDR domain amino acid sequences of AbC are set forth in SEQ ID NO: 31 (VH CDR1); SEQ ID NO: 32 (VH CDR2), and SEQ ID NO: 33 (VH CDR3). The light chain variable region (VL) amino acid sequence of AbC is described in SEQ ID NO: 34. The VL CDR domain amino acid sequences of AbC are set forth in SEQ ID NO: 35 (VL CDR1); SEQ ID NO: 36 (VL CDR2), and SEQ ID NO: 37 (VL CDR3). Accordingly, in certain embodiments, the anti-CD45 antibody, or antigen-binding fragment thereof, provided herein comprises a heavy chain variable region comprising the amino acid sequence set forth in SEQ ID NO: 30, and a light chain variable region comprising the amino acid sequence as set forth in SEQ ID NO: 34. In one embodiment, the anti-CD45 antibody comprises a heavy chain comprising a CDR1, CDR2 and CDR3 comprising the amino acid sequences set forth in SEQ ID NOs: 31, 32, and 33, and a light chain variable region comprising a CDR1, CDR2 and CDR3 comprising the amino acid sequences set forth in SEQ ID NOs: 35, 36, and 37. In one embodiment, the anti-CD45 antibody comprises a heavy chain of an anti-CD45 antibody described herein, and a light chain variable region of anti-CD45 antibody described herein. In one embodiment, the anti-CD45 antibody comprises a heavy chain comprising a CDR1, CDR2 and CDR3 of an anti-CD45 antibody described herein, and a light chain variable region comprising a CDR1, CDR2 and CDR3 of an anti-CD45 antibody described herein.

In another embodiment, the antibody, or antigen-binding fragment thereof, comprises a heavy chain variable region that comprises an amino acid sequence having at least 95% identity to an anti-CD45 antibody herein, e.g., at least 95%, 96%, 97%, 98%, 99%, or 100% identity to an anti-CD45 antibody herein. In certain embodiments, an antibody comprises a modified heavy chain (HC) variable region comprising an HC variable domain of an anti-CD45 antibody herein, or a variant thereof, which variant (i) differs from the anti-CD45 antibody in 1, 2, 3, 4 or 5 amino acids substitutions, additions or deletions; (ii) differs from the anti-CD45 antibody in at most 5, 4, 3, 2, or 1 amino acids substitutions, additions or deletions; (iii) differs from the anti-CD45 antibody in 1-5, 1-3, 1-2, 2-5 or 3-5 amino acids substitutions, additions or deletions and/or (iv) comprises an amino acid sequence that is at least about 75%, 80%, 85%, 90%, 95%, 96%, 97%, 98% or 99% identical to the anti-CD45 antibody, wherein in any of (i)-(iv), an amino acid substitution may be a conservative amino acid substitution or a non-conservative amino acid substitution; and wherein the modified heavy chain variable region can have an enhanced biological activity relative to the heavy chain variable region of the anti-CD45 antibody, while retaining the CD45 binding specificity of the antibody.

Additional anti-CD45 antibodies are provided in International Patent Application Nos. PCT/US2019/058973 and PCT/US2019/058971, the entire contents of each of which are incorporated herein by reference.

Additional anti-CD45 antibodies, and antigen-binding portions thereof, can be generated using art recognized methods, including but not limited to the methods of identifying antibodies described herein (e.g., high throughput screening of antibody libraries, phage display, computational modeling, etc.).

The disclosures of each of the foregoing publications are incorporated herein by reference in their entirety. Antibodies and antigen-binding fragments that may be used in conjunction with the compositions and methods described herein include the above-described antibodies and antigen-binding fragments thereof, as well as humanized variants of those non-human antibodies and antigen-binding fragments described above and antibodies or antigen-binding fragments that bind the same epitope as those described above, as assessed, for instance, by way of a competitive CD45 binding assay.

Fc-Modified Antibodies

In some embodiments, the anti-CD45 antibody or antigen binding portion thereof provided herein lacks an antibody constant region, e.g., an Fc region (e.g., tandem scFv, (scFv)2, diabodies, etc.). In other embodiments, the anti-CD45 antibody or antigen binding portion thereof provided herein comprises one or more antibody constant regions (e.g., one or more of CH1, CH2, or CH3). In some embodiments, the anti-CD45 antibody or antigen binding portion thereof provided herein comprises one or more Fc regions.

In some embodiments, the anti-CD45 antibody or antigen binding portion thereof provided herein comprises a native or wild-type Fc region. In other embodiments, the antibodies or binding fragments described herein may include modifications and/or mutations in the Fc region that alter the properties of the antibodies and/or fragments, such as those that increase half-life, or increase or decrease ADCC. The Fc-modified antibodies and ADCs provided herein not only allow for selective depletion of endogenous hematopoietic stem cells but also have reduced cytotoxic effects on the exogenous hematopoietic stem cell transplant, thereby further promoting engraftment of the hematopoietic stem cell graft.

The antibodies or binding fragments described herein may also include modifications and/or mutations that alter the properties of the antibodies and/or fragments, such as those that increase half-life, or increase or decrease ADCC.

In one embodiment, antibodies comprising one or more radiolabeled amino acids are provided. A radiolabeled antibody may be used for both diagnostic and therapeutic purposes (conjugation to radiolabeled molecules is another possible feature). Non-limiting examples of labels for polypeptides include, but are not limited to 3H, 14C, 15N, 35S, 90Y, 99Tc, and 125I, 131I, and 186Re. Methods for preparing radiolabeled amino acids and related peptide derivatives are known in the art (see for instance Junghans et al., in Cancer Chemotherapy and Biotherapy 655-686 (2d edition, Chafner and Longo, eds., Lippincott Raven (1996)) and U.S. Pat. Nos. 4,681,581, 4,735,210, 5,101,827, 5,102,990 (U.S. RE35,500), U.S. Pat. Nos. 5,648,471 and 5,697,902. For example, a radioisotope may be conjugated by a chloramine T method.

In one embodiment, the anti-CD45 antibody, or binding fragment thereof, comprises a modified Fc region, wherein said modified Fc region comprises at least one amino acid modification relative to a wild-type Fc region, such that said molecule has an altered affinity for or binding to an FcgammaR (FcγR). Certain amino acid positions within the Fc region are known through crystallography studies to make a direct contact with FcγR. Specifically, amino acids 234-239 (hinge region), amino acids 265-269 (B/C loop), amino acids 297-299 (C'/E loop), and amino acids 327-332 (F/G) loop. (see Sondermann et al., 2000 Nature, 406: 267-273). In some embodiments, the antibodies described herein may comprise variant Fc regions comprising modification of at least one residue that makes a direct contact with an FcγR based on structural and crystallographic analysis. In one embodiment, the Fc region of the anti-CD45 antibody (or fragment thereof) comprises an amino acid substitution at amino acid 265 according to the EU index as in Kabat et al., Sequences of Proteins of Immunological Interest, 5th Ed. Public Health Service, NH1, MD (1991), expressly incorporated herein by references. The "EU index as in Kabat" refers to the numbering of the human IgG1 EU antibody. In one embodiment, the Fc region comprises a D265A mutation. In one embodiment, the Fc region comprises a D265C mutation. In some embodiments, the Fc region of the antibody (or fragment thereof) comprises an amino acid substitution at amino acid 234 according to the EU index as in Kabat.

In one embodiment, the Fc region comprises a mutation at an amino acid position of D265, V205, H435, 1253, and/or H310. For example, specific mutations at these positions include D265C, V205C, H435A, I253A, and/or H310A.

In one embodiment, the Fc region comprises a L234A mutation. In some embodiments, the Fc region of the anti-CD45 antibody (or fragment thereof) comprises an amino acid substitution at amino acid 235 according to the EU index as in Kabat. In one embodiment, the Fc region comprises a L235A mutation. In yet another embodiment, the Fc region comprises a L234A and L235A mutation. In a further embodiment, the Fc region comprises a D265C, L234A, and L235A mutation. In yet a further embodiment, the Fc region comprises a D265C, L234A, L235A, and H435A mutation. In a further embodiment, the Fc region comprises a D265C and H435A mutation.

In one embodiment, the Fc region comprises a mutation at S239, alone or in addition to other Fc mutations described herein. In an exemplary embodiment, the Fc region comprises a S239C mutation.

In yet another embodiment, the Fc region comprises a L234A and L235A mutation (also referred to herein as "L234A.L235A" or as "LALA"). In another embodiment, the Fc region comprises a L234A and L235A mutation, wherein the Fc region does not include a P329G mutation. In a further embodiment, the Fc region comprises a D265C, L234A, and L235A mutation (also referred to herein as "D265C.L234A.L235A"). In another embodiment, the Fc region comprises a D265C, L234A, and L235A mutation, wherein the Fc region does not include a P329G mutation. In yet a further embodiment, the Fc region comprises a D265C, L234A, L235A, and H435A mutation (also referred to herein as "D265C.L234A.L235A.H435A"). In another embodiment, the Fc region comprises a D265C, L234A, L235A, and H435A mutation, wherein the Fc region does not include a P329G mutation. In a further embodiment, the Fc region comprises a D265C and H435A mutation (also referred to herein as "D265C.H435A"). In yet another embodiment, the Fc region comprises a D265A, S239C, L234A, and L235A mutation (also referred to herein as "D265A.S239C.L234A.L235A"). In yet another embodiment, the Fc region comprises a D265A, S239C, L234A, and L235A mutation, wherein the Fc region does not include a P329G mutation. In another embodiment, the Fc region comprises a D265C, N297G, and H435A mutation (also referred to herein as "D265C.N297G.H435A"). In another embodiment, the Fc region comprises a D265C, N297Q, and H435A mutation (also referred to herein as "D265C.N297Q.H435A"). In another embodiment, the Fc region comprises a E233P, L234V, L235A and delG236 (deletion of 236) mutation (also referred to herein as "E233P.L234V.L235A.delG236" or as "EPLVLAdeIG"). In another embodiment, the Fc region comprises a E233P, L234V, L235A and delG236 (deletion of 236) mutation, wherein the Fc region does not include a P329G mutation. In another embodiment, the Fc region comprises a E233P, L234V, L235A, delG236 (deletion of 236) and H435A mutation (also referred to herein as "E233P.L234V.L235A.delG236.H435A" or as "EPLVLAdeIG.H435A"). In another embodiment, the Fc region comprises a E233P, L234V, L235A, delG236 (deletion of 236) and H435A mutation, wherein the Fc region does not include a P329G mutation. In another embodiment, the Fc region comprises a L234A, L235A, S239C and D265A mutation. In another embodiment, the Fc region comprises a L234A, L235A, S239C and D265A mutation, wherein the Fc region does not include a P329G mutation. In another embodiment, the Fc region comprises a H435A, L234A, L235A, and D265C mutation. In another embodiment, the Fc region comprises a H435A, L234A, L235A, and D265C mutation, wherein the Fc region does not include a P329G mutation.

In some embodiments, the antibody has a modified Fc region such that, the antibody decreases an effector function in an in vitro effector function assay with a decrease in binding to an Fc receptor (Fc R) relative to binding of an identical antibody comprising an unmodified Fc region to the FcR. In some embodiments, the antibody has a modified Fc region such that, the antibody decreases an effector function in an in vitro effector function assay with a decrease in binding to an Fc gamma receptor (FcγR) relative to binding of an identical antibody comprising an unmodified Fc region to the FcγR. In some embodiments, the FcγR is FcγR1. In some embodiments, the FcγR is FcγR2A. In some embodiments, the FcγR is FcγR2B. In other embodiments, the FcγR is FcγR2C. In some embodiments, the FcγR is FcγR3A. In some embodiments, the FcγR is FcγR3B. In other embodiments, the decrease in binding is at least a 70% decrease, at least a 80% decrease, at least a 90% decrease, at least a 95% decrease, at least a 98% decrease, at least a 99% decrease, or a 100% decrease in antibody binding to a FcγR relative to binding of the identical antibody comprising an unmodified Fc region to the FcγR. In other embodiments, the decrease in binding is at least a 70% to a 100% decrease, at least a 80% to a 100% decrease, at least a 90% to a 100% decrease, at least a 95% to a 100% decrease, or at least a 98% to a 100% decrease, in antibody binding to a FcγR relative to binding of the identical antibody comprising an unmodified Fc region to the FcγR.

In some embodiments, the antibody has a modified Fc region such that, the antibody decreases cytokine release in an in vitro cytokine release assay with a decrease in cytokine release of at least 50% relative to cytokine release of an identical antibody comprising an unmodified Fc region. In some embodiments, the decrease in cytokine release is at least a 70% decrease, at least a 80% decrease, at least a 90% decrease, at least a 95% decrease, at least a 98% decrease, at least a 99% decrease, or a 100% decrease in cytokine release relative to cytokine release of the identical antibody comprising an unmodified Fc region. In some embodiments, the decrease in cytokine release is at least a 70% to a 100% decrease, at least an 80% to a 100% decrease, at least a 90% to a 100% decrease, at least a 95% to a 100% decrease in cytokine release relative to cytokine release of the identical antibody comprising an unmodified Fc region. In certain embodiments, cytokine release is by immune cells.

In some embodiments, the antibody has a modified Fc region such that, the antibody decreases mast cell degranulation in an in vitro mast cell degranulation assay with a decrease in mast cell degranulation of at least 50% relative to mast cell degranulation of an identical antibody comprising an unmodified Fc region. In some embodiments, the decrease in mast cell degranulation is at least a 70% decrease, at least a 80% decrease, at least a 90% decrease, at least a 95% decrease, at least a 98% decrease, at least a 99% decrease, or a 100% decrease in mast cell degranulation relative to mast cell degranulation of the identical antibody comprising an unmodified Fc region. In some embodiments, the decrease in mast cell degranulation is at least a 70% to a 100% decrease, at least a 80% to a 100% decrease, at least a 90% to a 100% decrease, or at least a 95% to a 100% decrease, in mast cell degranulation relative to mast cell degranulation of the identical antibody comprising an unmodified Fc region.

In some embodiments, the antibody has a modified Fc region such that, the antibody decreases or prevents antibody dependent cell phagocytosis (ADCP) in an in vitro antibody dependent cell phagocytosis assay, with a decrease in ADCP of at least 50% relative to ADCP of an identical antibody comprising an unmodified Fc region. In some embodiments, the decrease in ADCP is at least a 70% decrease, at least a 80% decrease, at least a 90% decrease, at least a 95% decrease, at least a 98% decrease, at least a 99% decrease, or a 100% decrease in cytokine release relative to cytokine release of the identical antibody comprising an unmodified Fc region.

In some embodiments, the anti-HC antibody (e.g., anti-CD45 antibody) described herein comprises an Fc region comprising one of the following modifications or combinations of modifications: D265A, D265C, D265C/H435A, D265C/LALA, D265C/LALA/H435A, D265A/S239C/L234A/L235A/H435A, D265A/S239C/L234A/L235A, D265C/N297G, D265C/N297G/H435A, D265C (EPLVLAdeIG*), D265C (EPLVLAdeIG)/H435A, D265C/N297Q/H435A, D265C/N297Q, EPLVLAdeIG/H435A, EPLVLAdeIG/D265C, EPLVLAdeIG/D265A, N297A, N297G, or N297Q.

In some embodiments, the anti-CD45 antibody herein comprises an Fc region comprising one of the following modifications or combinations of modifications: D265A, D265C, D265C/H435A, D265C/LALA, D265C/LALA/H435A, D265C/N297G, D265C/N297G/H435A, D265C (IgG2*), D265C (IgG2)/H435A, D265C/N297Q/H435A, D265C/N297Q, EPLVLAdeIG/H435A, N297A, N297G, or N297Q.

Binding or affinity between a modified Fc region and a Fc gamma receptor can be determined using a variety of techniques known in the art, for example but not limited to, equilibrium methods (e.g., enzyme-linked immunoabsorbent assay (ELISA); KinExA, Rathanaswami et al. Analytical Biochemistry, Vol. 373:52-60, 2008; or radioimmunoassay (RIA)), or by a surface plasmon resonance assay or other mechanism of kinetics-based assay (e.g., BIACORE® analysis or Octet™ analysis (forteBIO)), and other methods such as indirect binding assays, competitive binding assays fluorescence resonance energy transfer (FRET), gel electrophoresis and chromatography (e.g., gel filtration). These and other methods may utilize a label on one or more of the components being examined and/or employ a variety of detection methods including but not limited to chromogenic, fluorescent, luminescent, or isotopic labels. A detailed description of binding affinities and kinetics can be found in Paul, W. E., ed., Fundamental Immunology, 4th Ed., Lippincott-Raven, Philadelphia (1999), which focuses on antibody-immunogen interactions. One example of a competitive binding assay is a radioimmunoassay comprising the incubation of labeled antigen with the antibody of interest in the presence of increasing amounts of unlabeled antigen, and the detection of the antibody bound to the labeled antigen. The affinity of the antibody of interest for a particular antigen and the binding off-rates can be determined from the data by scatchard plot analysis. Competition with a second antibody can also be determined using radioimmunoassays. In this case, the antigen is incubated with antibody of interest conjugated to a labeled compound in the presence of increasing amounts of an unlabeled second antibody.

In one embodiment, an antibody having the Fc modifications described herein (e.g., D265C, L234A, L235A, and/or H435A) has at least a 70% decrease, at least a 80% decrease, at least a 90% decrease, at least a 95% decrease, at least a 98% decrease, at least a 99% decrease, or a 100% decrease in binding to a Fc gamma receptor relative to binding of the identical antibody comprising an unmodified Fc region to the Fc gamma receptor (e.g., as assessed by biolayer interferometry (BLI)).

Without wishing to be bound by any theory, it is believed that Fc region binding interactions with a Fc gamma receptor are essential for a variety of effector functions and downstream signaling events including, but not limited to, antibody dependent cell-mediated cytotoxicity (ADCC) and complement dependent cytotoxicity (CDC). Accordingly, in certain aspects, an antibody comprising a modified Fc region (e.g., comprising a L234A, L235A, and/or a D265C mutation) has substantially reduced or abolished effector functions. Effector functions can be assayed using a variety of methods known in the art, e.g., by measuring cellular responses (e.g., mast cell degranulation or cytokine release) in response to the antibody of interest. For example, using standard methods in the art, the Fc-modified antibodies can be assayed for their ability to trigger mast cell degranulation in or for their ability to trigger cytokine release, e.g. by human peripheral blood mononuclear cells.

Thus, in one embodiment, the Fc region comprises a mutation resulting in a decrease in half-life (e.g., relative to an antibody having an unmodified Fc region). An antibody having a short half-life may be advantageous in certain instances where the antibody is expected to function as a short-lived therapeutic, e.g., the conditioning step described herein where the antibody is administered followed by HSCs. Ideally, the antibody would be substantially cleared prior to delivery of the HSCs, which also generally express a target antigen (e.g., CD45) but are not the target of the anti-CD45 antibody unlike the endogenous stem cells. In one embodiment, the Fc regions comprises a mutation at position 435 (EU index according to Kabat). In one embodiment, the mutation is an H435A mutation.

In one embodiment, the anti-CD45 described herein has a half-life (e.g., in humans) equal to or less than about 24 hours, equal to or less than about 23 hours, equal to or less than about 22 hours, equal to or less than about 21 hours, equal to or less than about 20 hours, equal to or less than about 19 hours, equal to or less than about 18 hours, equal to or less than about 17 hours, equal to or less than about 16 hours, equal to or less than about 15 hours, equal to or less than about 14 hours, equal to or less than about 13 hours, equal to or less than about 12 hours, or equal to or less than about 11 hours.

In one embodiment, the anti-CD45 antibody described herein has a half-life (e.g., in humans) of 1-5 hours, 5-10 hours, 10-15 hours, 15-20 hours, or 20 to 25 hours. In one embodiment, the half-life of the anti-CD45 antibody is about 5-7 hours; about 5-9 hours; about 5-11 hours; about 5-13 hours; about 5-15 hours; about 5-20 hours; about 5-24 hours; about 7-24 hours; about 9-24 hours; about 11-24 hours; about 12-22 hours; about 10-20 hours; about 8-18 hours; or about 14-24 hours.

In some aspects, the Fc region comprises two or more mutations that confer reduced half-life and reduce an effector function of the antibody. In some embodiments, the Fc region comprises a mutation resulting in a decrease in half-life and a mutation of at least one residue that can make direct contact with an FcγR (e.g., as based on structural and crystallographic analysis). In one embodiment, the Fc region comprises a H435A mutation, a L234A mutation, and a L235A mutation. In one embodiment, the Fc region comprises a H435A mutation and a D265C mutation. In one embodiment, the Fc region comprises a H435A mutation, a L234A mutation, a L235A mutation, and a D265C mutation.

In some embodiments, the antibody or antigen-binding fragment thereof is conjugated to a cytotoxin (e.g., PBD) by way of a cysteine residue in the Fc domain of the antibody or antigen-binding fragment thereof. In some embodiments, the cysteine residue is introduced by way of a mutation in the Fc domain of the antibody or antigen-binding fragment thereof. For instance, the cysteine residue may be selected from the group consisting of Cys118, Cys239, and Cys265. In one embodiment, the Fc region of the anti-CD45 antibody (or fragment thereof) comprises an amino acid substitution at amino acid 265 according to the EU index as in Kabat. In one embodiment, the Fc region comprises a D265C mutation. In one embodiment, the Fc region comprises a D265C and H435A mutation. In one embodiment, the Fc region comprises a D265C, a L234A, and a L235A mutation. In one embodiment, the Fc region comprises a D265C, a L234A, a L235A, and a H435A mutation. In addition, or alternatively, to the forgoing mutations, in some embodiments, the Fc region comprises a S239C mutation. In one embodiment, the Fc region comprises a L234A mutation, a L235A mutation, a S239C mutation and a D265A mutation. In another embodiment, the Fc region comprises a S239C and H435A mutation. In another embodiment, the Fc region comprises a L234A mutation, a L235A mutation, and S239C mutation. In yet another embodiment, the Fc region comprises a H435A mutation, a L234A mutation, a L235A mutation, and S239C mutation. In yet another embodiment, the Fc region comprises a H435A mutation, a L234A mutation, a L235A mutation, a S239C mutation and D265A mutation.

Notably, Fc amino acid positions are in reference to the EU numbering index unless otherwise indicated.

Antibodies and antigen-binding fragments that may be used in conjunction with the compositions and methods described herein include the above-described antibodies and antigen-binding fragments thereof, as well as variants of those non-human antibodies and antigen-binding fragments described above and antibodies or antigen-binding fragments that bind the same epitope as those described above, as assessed, for instance, by way of a competitive antigen binding assay.

The antibodies of the present disclosure may be further engineered to further modulate antibody half-life by introducing additional Fc mutations, such as those described for example in (Dall'Acqua et al. (2006) J Biol Chem 281: 23514-24), (Zalevsky et al. (2010) Nat Biotechnol 28: 157-9), (Hinton et al. (2004) J Biol Chem 279: 6213-6), (Hinton et al. (2006) J Immunol 176: 346-56), (Shields et al. (2001) J Biol Chem 276: 6591-604), (Petkova et al. (2006) Int Immunol 18: 1759-69), (Datta-Mannan et al. (2007) Drug Metab Dispos 35: 86-94), (Vaccaro et al. (2005) Nat Biotechnol 23: 1283-8), (Yeung et al. (2010) Cancer Res 70: 3269-77) and (Kim et al. (1999) Eur J Immunol 29: 2819-25), and include positions 250, 252, 253, 254, 256, 257, 307, 376, 380, 428, 434 and 435. Exemplary mutations that may be made singularly or in combination are T250Q, M252Y, I253A, S254T, T256E, P2571, T307A, D376V, E380A, M428L, H433K, N434S, N434A, N434H, N434F, H435A and H435R mutations.

Methods of engineering antibodies to include any of the Fc modifications herein are well known in the art. These methods include, but are not limited to, preparation by site-directed (or oligonucleotide-mediated) mutagenesis, PCR mutagenesis, and cassette mutagenesis of a prepared DNA molecule encoding the antibody or at least the constant region of the antibody. Site-directed mutagenesis is well known in the art (see, e.g., Carter et al., Nucleic Acids Res., 13:4431-4443 (1985) and Kunkel et al., Proc. Natl. Acad. Sci. USA, 82:488 (1987)). PCR mutagenesis is also suitable for making amino acid sequence variants of the starting polypeptide. See Higuchi, in PCR Protocols, pp. 177-183 (Academic Press, 1990); and Vallette et al., Nuc. Acids Res. 17:723-733 (1989). Another method for preparing sequence variants, cassette mutagenesis, is based on the technique described by Wells et al., Gene, 34:315-323 (1985).

Methods of Identifying Antibodies

Methods for high throughput screening of antibody, or antibody fragment libraries capable of binding CD45 expressed by hematopoietic stem can be used to identify anti-CD45 antibodies useful for treating cancers, autoimmune diseases, and conditioning a patient (e.g., a human patient) in need of hematopoietic stem cell therapy as described herein. Such methods can be used to identify improved versions of Ab1 described herein. Such methods include in vitro display techniques known in the art, such as phage display, bacterial display, yeast display, mammalian cell display, ribosome display, mRNA display, and cDNA display, among others.

The use of phage display to isolate antibodies, or antigen-binding fragments, that bind biologically relevant molecules has been reviewed, for example, in Felici et al., Biotechnol. Annual Rev. 1:149-183, 1995; Katz, Annual Rev. Biophys. Biomol. Struct. 26:27-45, 1997; and Hoogenboom et al., Immunotechnology 4:1-20, 1998, the disclosures of each of which are incorporated herein by reference as they pertain to in vitro display techniques. Randomized combinatorial peptide libraries have been constructed to select for polypeptides that bind cell surface antigens as described in Kay, Perspect. Drug Discovery Des. 2:251-268, 1995 and Kay et al., Mol. Divers. 1:139-140, 1996, the disclosures of each of which are incorporated herein by reference as they pertain to the discovery of antigen-binding molecules. Proteins, such as multimeric proteins, have been successfully phage-displayed as functional molecules (see, for example, EP 0349578; EP 4527839; and EP 0589877, as well as Chiswell and McCafferty, Trends Biotechnol. 10:80-84 1992, the disclosures of each of which are incorporated herein by reference as they pertain to the use of in vitro display techniques for the discovery of antigen-binding molecules. In addition, functional antibody fragments, such as Fab and scFv fragments, have been expressed in in vitro display formats (see, for example, McCafferty et al., Nature 348: 552-554, 1990; Barbas et al., Proc. Natl. Acad. Sci. USA 88:7978-7982, 1991; and Clackson et al., Nature 352:624-628, 1991, the disclosures of each of which are incorporated herein by reference as they pertain to in vitro display platforms for the discovery of antigen-binding molecules). Human anti-CD45 antibodies can also be generated, for example, in the HuMAb-Mouse® or XenoMouse™. These techniques, among others, can be used to identify and improve the affinity of antibodies, antibody or fragments, capable of binding CD45 expressed by hematopoietic stem cells in turn be used to deplete endogenous hematopoietic stem cells in a patient (e.g., a human patient) in need of hematopoietic stem cell transplant therapy.

In addition to in vitro display techniques, computational modeling techniques can be used to design and identify antibodies capable of binding an antigen (e.g., CD45) expressed by hematopoietic stem cells. For example, using computational modeling techniques, one of skill in the art can screen libraries of antibodies, or antibody fragments, in silico for molecules capable of binding specific epitopes on an antigen expressed by hematopoietic stem cells (e.g., CD45), such as extracellular epitopes of the antigen.

Additional techniques can be used to identify antibodies, or antibody fragments, capable of binding CD45 expressed by hematopoietic stem cells and that are internalized by the cell, for instance, by receptor-mediated endocytosis. For example, the in vitro display techniques described above can be adapted to screen for antibodies, or antibody fragments, that bind CD45 and that are subsequently internalized. Phage display represents one such technique that can be used in conjunction with this screening paradigm. To identify an anti-CD45 antibody, or antibody fragment, that can be internalized by hematopoietic stem cells, one of skill in the art can use the phage display techniques described in Williams et al., Leukemia 19:1432-1438, 2005, the disclosure of which is incorporated herein by reference in its entirety. For example, using mutagenesis methods known in the art, recombinant phage libraries can be produced that encode antibodies, antibody fragments, such as scFv fragments, Fab fragments, diabodies, triabodies, and $^{10}$Fn3 domains, among others, or ligands that contain randomized amino acid cassettes (e.g., in one or more, or all, of the CDRs or equivalent regions thereof or an antibody or antibody fragment). The framework regions, hinge, Fc domain, and other regions of the antibodies or antibody fragments may be designed such that they are non-immunogenic in humans, for instance, by virtue of having human germline antibody sequences or sequences that exhibit only minor variations relative to human germline antibodies.

Using phage display techniques described herein or known in the art, phage libraries containing randomized antibodies, or antibody fragments, covalently bound to the phage particles can be incubated with CD45 for instance, by first incubating the phage library with blocking agents (such as, for instance, milk protein, bovine serum albumin, and/or IgG so as to remove phage encoding antibodies, or antibody fragments, that exhibit non-specific protein binding and phage that encode antibodies or fragments thereof that bind Fc domains, and then incubating the phage library with a population of cells, e.g., hematopoietic stem cells, which express CD45. The phage library can be incubated with the hematopoietic stem cells for a time sufficient to allow anti-CD45 antibodies, or antibody fragments, to bind the cognate cell-surface antigen and to subsequently be internalized by the hematopoietic stem cells (e.g., from 30 minutes to 6 hours at 4° C., such as 1 hour at 4° C.). Phage containing antibodies, or antibody fragments, that do not exhibit sufficient affinity for the CD45 so as to permit binding to, and internalization by, hematopoietic stem cells can subsequently be removed by washing the cells, for instance, with cold (4° C.) 0.1 M glycine buffer at pH 2.8. Phage bound to antibodies, or antibody fragments, that have been internalized by the hematopoietic stem cells can be identified, for instance, by lysing the cells and recovering internalized phage from the cell culture medium. The phage can then be amplified in bacterial cells, for example, by incubating bacterial cells with recovered phage in 2×YT medium using methods known in the art. Phage recovered from this medium can then be characterized, for instance, by determining the nucleic acid sequence of the gene(s) encoding the antibodies, or antibody fragments, inserted within the phage genome. The encoded antibodies, or antibody fragments, can subsequently be prepared de novo by chemical synthesis (for instance, of antibody fragments, such as scFv fragments) or by recombinant expression (for instance, of full-length antibodies).

The internalizing capacity of the prepared antibodies, or antibody fragments, can be assessed, for instance, using radionuclide internalization assays known in the art. For example, anti-CD45 antibodies, or antibody fragments, identified using in vitro display techniques described herein or known in the art can be functionalized by incorporation of a radioactive isotope, such as $^{18}$F, $^{75}$Br, $^{77}$Br, $^{122}$I, $^{123}$I, $^{124}$I, $^{125}$I, $^{129}$I, $^{131}$I, $^{211}$At, $^{67}$Ga, $^{111}$In, $^{99}$Tc, $^{169}$Yb, $^{186}$Re, $^{64}$Cu, $^{67}$Cu, $^{177}$Lu, $^{77}$As, $^{72}$As, $^{86}$Y, $^{90}$Y, $^{89}$Zr, $^{212}$Bi, $^{213}$Bi, or $^{225}$Ac. For instance, radioactive halogens, such as $^{18}$F, $^{75}$Br, $^{77}$Br, $^{122}$I, $^{123}$I, $^{124}$I, $^{125}$I, $^{129}$I, $^{131}$I, $^{211}$At, can be incorporated into antibodies, or antibody fragments, using beads, such as polystyrene beads, containing electrophilic halogen reagents (e.g., lodination Beads, Thermo Fisher Scientific, Inc., Cambridge, MA). Radiolabeled antibodies, fragments thereof, or ADCs, can be incubated with hematopoietic stem cells for a time sufficient to permit internalization (e.g., from 30 minutes to 6 hours at 4° C., such as 1 hour at 4° C.). The cells can then be washed to remove non-internalized antibodies or fragments thereof, (e.g., using cold (4° C.) 0.1 M glycine buffer at pH 2.8). Internalized antibodies, or antibody fragments, can be identified by detecting the emitted radiation (e.g., γ-radiation) of the resulting hematopoietic stem cells in comparison with the emitted radiation (e.g., γ-radiation) of the recovered wash buffer. The foregoing internalization assays can also be used to characterize ADCs.

Antibodies may be produced using recombinant methods and compositions, e.g., as described in U.S. Pat. No. 4,816,567. In one embodiment, isolated nucleic acid encoding an anti-CD45 antibody described herein is provided. Such nucleic acid may encode an amino acid sequence comprising the VL and/or an amino acid sequence comprising the VH of the antibody (e.g., the light and/or heavy chains of the antibody). In a further embodiment, one or more vectors (e.g., expression vectors) comprising such nucleic acid are provided. In a further embodiment, a host cell comprising such nucleic acid is provided. In one such embodiment, a host cell comprises (e.g., has been transformed with): (1) a vector comprising a nucleic acid that encodes an amino acid sequence comprising the VL of the antibody and an amino acid sequence comprising the VH of the antibody, or (2) a first vector comprising a nucleic acid that encodes an amino acid sequence comprising the VL of the antibody and a second vector comprising a nucleic acid that encodes an amino acid sequence comprising the VH of the antibody. In one embodiment, the host cell is eukaryotic, e.g. a Chinese Hamster Ovary (CHO) cell or lymphoid cell (e.g., Y0, NS0, Sp20 cell). In one embodiment, a method of making an anti-CLL-1 antibody is provided, wherein the method comprises culturing a host cell comprising a nucleic acid encoding the antibody, as provided above, under conditions suitable for expression of the antibody, and optionally recovering the antibody from the host cell (or host cell culture medium).

For recombinant production of an anti-CD45 antibody, a nucleic acid encoding an antibody, e.g., as described above, is isolated and inserted into one or more vectors for further cloning and/or expression in a host cell. Such nucleic acid may be readily isolated and sequenced using conventional procedures (e.g., by using oligonucleotide probes that are capable of binding specifically to genes encoding the heavy and light chains of the antibody).

Suitable host cells for cloning or expression of antibody-encoding vectors include prokaryotic or eukaryotic cells described herein. For example, antibodies may be produced in bacteria, in particular when glycosylation and Fc effector function are not needed. For expression of antibody fragments and polypeptides in bacteria, see, e.g., U.S. Pat. Nos. 5,648,237, 5,789,199, and 5,840,523. (See also Charlton, Methods in Molecular Biology, Vol. 248 (B.K.C. Lo, ed., Humana Press, Totowa, N.J., 2003), pp. 245-254, describing expression of antibody fragments in *E. coli.*) After expression, the antibody may be isolated from the bacterial cell paste in a soluble fraction and can be further purified.

Vertebrate cells may also be used as hosts. For example, mammalian cell lines that are adapted to grow in suspension may be useful. Other examples of useful mammalian host cell lines are monkey kidney CV1 line transformed by SV40 (COS-7); human embryonic kidney line (293 or 293 cells as described, e.g., in Graham et al., J. Gen Virol. 36:59 (1977)); baby hamster kidney cells (BHK); mouse sertoli cells (TM4 cells as described, e.g., in Mather, Biol. Reprod. 23:243-251 (1980)); monkey kidney cells (CV1); African green monkey kidney cells (VERO-76); human cervical carcinoma cells (HELA); canine kidney cells (MDCK; buffalo rat liver cells (BRL 3A); human lung cells (W138); human liver cells (Hep G2); mouse mammary tumor (MMT 060562); TRI cells, as described, e.g., in Mather et al., Annals N.Y. Acad. Sci. 383:44-68 (1982); MRC 5 cells; and FS4 cells. Other useful mammalian host cell lines include Chinese hamster ovary (CHO) cells, including DHFR-CHO cells (Urlaub et al., Proc. Natl. Acad. Sci. USA 77:4216 (1980)); and myeloma cell lines such as Y0, NS0 and Sp2/0. For a review of certain mammalian host cell lines suitable for antibody production, see, e.g., Yazaki and Wu, Methods in Molecular Biology, Vol. 248 (B. K. C. Lo, ed., Humana Press, Totowa, N.J.), pp. 255-268 (2003). In one embodiment, the host cell is eukaryotic, e.g. a Chinese Hamster Ovary (CHO) cell or lymphoid cell (e.g., Y0, NS0, Sp20 cell).

Cytotoxins

Anti-CD45 antibodies, and antigen-binding fragments thereof, as described herein can be conjugated (linked) to a cytotoxin, for example, a cytotoxin comprising a benzodiazepine moiety, such as a PBD or an IGN, as described herein.

Pyrrolobenzodiazepines (PBDs)

In some embodiments, the antibodies, or antigen-binding fragments thereof, that bind CD45 as described herein can be conjugated to a cytotoxin that is a pyrrolobenzodiazepine ("PBD") or a cytotoxin that comprises a PBD. PBDs are natural products produced by certain actinomycetes and have been shown to be sequence selective DNA alkylating compounds. PBD cytotoxins include, but are not limited to, anthramycin, dimeric PBDs, and those disclosed in, for example, Hartley, J A (2011). The development of pyrrolobenzodiazepines as antitumor agents. Expert Opin Inv Drug, 20(6), 733-744 and Antonow D, Thurston D E (2011) Synthesis of DNA-interactive pyrrolo[2,1-c][1,4]benzodiazepines (PBDs). Chem Rev 111: 2815-2864.

PBDs are of the general structure:

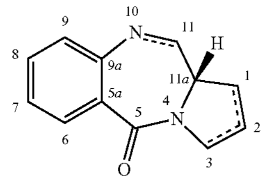

They differ in the number, type and position of substituents, in both their aromatic ("A") rings and pyrrolo ("C") rings, and in the degree of saturation of the C ring. In the diazepine B-ring there is either an imine (N═C), a carbinolamine (NH—CH(OH)), or a carbinolamine methyl ether (NH—CH(OMe)) at the N10-C11 position. This position is the electrophilic moiety responsible for DNA alkylation. All of the known natural product PBDs have an (S)-configuration at the chiral C11a position which provides them with a right-handed twist when viewed from the C ring towards the A ring. This provides the appropriate three-dimensional shape for isohelicity with the minor groove of B-form DNA, leading to a tight fit at the binding site (Kohn, In *Antibiotics III*. Springer-Verlag, New York, pp. 3-11 (1975); Hurley and Needham-VanDevanter, *Acc. Chem. Res.,* 19, 230-237 (1986)). The ability of PBDs to form adducts in the minor groove enables them to interfere with DNA processing, resulting in anti-tumor activity.

It has been previously disclosed that the biological activity of these molecules can be potentiated by joining two PBD units together through their C8-hydroxyl functionalities via a flexible alkylene linker (Bose, D. S., et al., *J. Am. Chem. Soc.,* 114, 4939-4941 (1992); Thurston, D. E., et al., *J. Org. Chem.,* 61, 8141-8147 (1996)). The PBD dimers are thought to form sequence-selective DNA lesions, such as the palindromic 5'-Pu-GATC-Py-3' inter-strand cross-link (Smellie, M., et al., *Biochemistry,* 42, 8232-8239 (2003); Martin, C., et al., *Biochemistry,* 44, 4135-4147) which is thought to be mainly responsible for their biological activity. An advantageous dimeric pyrrolobenzodiazepine compound has been described by Gregson et al. (*Chem. Commun.* 1999, 797-798; "compound 1", and by Gregson et al. (*J. Med. Chem.* 2001, 44, 1161-1174; "compound 4a"). This compound, also known as SG2000, is of the structural formula:

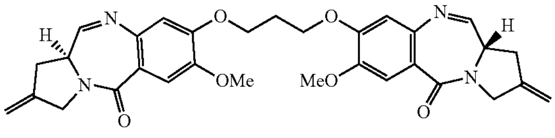
.

Generally, modifications to the pyrrolidine alkene moiety provide the handle with which to covalently bond the linking moiety and, hence the antibodies or antigen-binding fragments thereof (-L-Z' and -L-Z-Ab, respectively, as described herein). Alternatively, a linker may be attached at position N10.

In some embodiments, the cytotoxin is a pyrrolobenzodiazepine dimer represented by the structural formula:

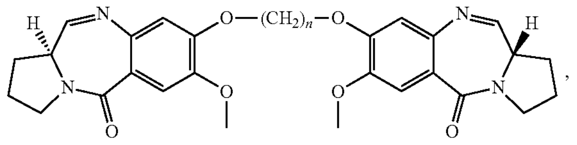

wherein n is an integer from 2 to 5. The compound of this formula wherein n is 3 is known as DSB-120 (Bose et al., J. Am. Chem. Soc. 1992, 114, 4939-4941).

In some embodiments, the cytotoxin is a pyrrolobenzodiazepine dimer represented by the structural formula:

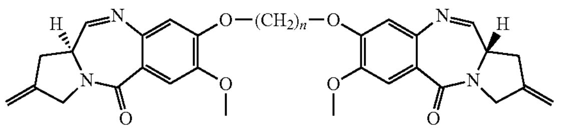

wherein n is an integer from 2 to 5. The compound of this formula wherein n is 3 is known as SJG-136 (Gregson et al., J. Med. Chem. 2001, 44, 737-748). The compound of this formula wherein n is 5 is known as DRG-16 (Gregson et al., Med. Chem. 2004; 47:1161-1174).

In some embodiments, the cytotoxin is a pyrrolobenzodiazepine dimer represented by the structural formula:

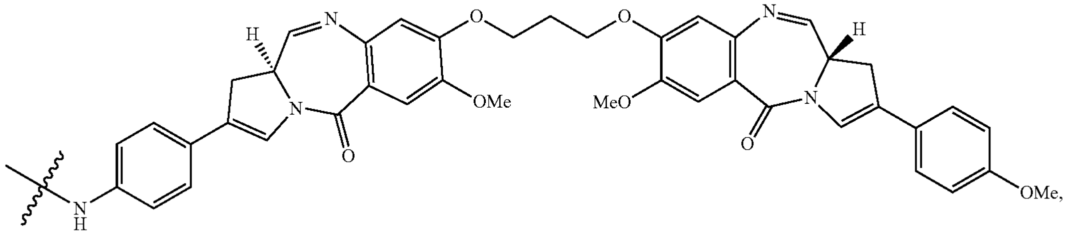 [SMILES: *Nc1ccc(C2=CN3C(=O)c4cc(OC)c(OCCCOc5cc6c(cc5OC)C(=O)N5C=C(c7ccc(OC)cc7)C[C@H]5C=N6)cc4N=C[C@@H]3C2)cc1]

wherein the wavy line indicates the point of covalent attachment to the linker of the ADC as described herein. ADCs based on this PBD are disclosed in, for example, Sutherland et al., Blood 2013 122:1455-1463, which is incorporated by reference herein in its entirety.

In some embodiments, the cytotoxin is a PBD dimer represented by the structural formula:

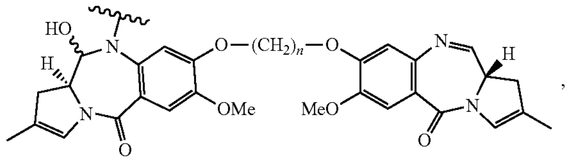

wherein n is 3 or 5, and wherein the wavy line indicates the point of covalent attachment to the linker of the ADC as described herein.

In some embodiments, the cytotoxin is a PBD dimer represented by the structural formula (I):

(I)

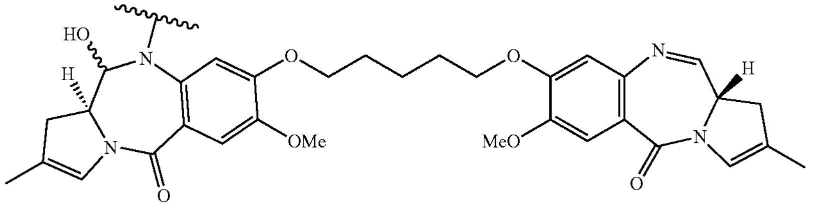

wherein the wavy line indicates the point of covalent attachment to the linker of the ADC as described herein.

Indolinobenzodiazepines (IGNs)

In some embodiments, the antibodies, or antigen-binding fragments thereof, that bind CD45 as described herein can be conjugated to a cytotoxin that is an indolinobenzodiazepine ("IGN") or a cytotoxin that comprises an IGN. In some embodiments, the IGN cytotoxin is an indolinobenzodiazepine dimer or an indolinobenzodiazepine pseudodimer.

Indolinobenzodiazepine dimers represent a relatively new chemical class of cytotoxins with high in vitro potency (low pM range $IC_{50}$ values) towards cancer cells. Similar to the PBD dimer SJG-136, IGN dimers bind to the minor groove of DNA, and covalently bind to guanine residues via the two imine functionalities in the dimer, resulting in crosslinking of the DNA. An IGN dimer (IGN 6; replacing the methylene groups of the PBD moiety with phenyl rings) demonstrated ~10-fold higher potency in vitro as compared to SJG-136, possibly due to faster rate of adduct formation with DNA IGN (see, e.g., Miller et al., "A New Class of Antibody-Drug Conjugates with Potent DNA Alkylating Activity" Mol. Cancer Ther. 2016, 15(8), 1870-1878). In contrast, IGN pseudodimers comprise a single reactive indolinobenzodiazepine imine; the second indolinobenzodiazepine in the dimeric cytotoxin is present in reduced (amine) form. Accordingly, IGN pseudodimers alkylate DNA through the single imine moiety present in the dimer, and do not cross-link DNA.

In some embodiments, the cytotoxin is an IGN pseudodimer having a structure of formula:

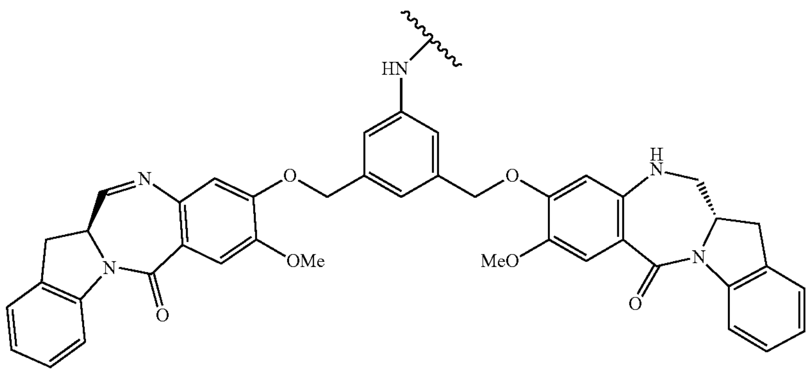

, wherein the wavy line indicates the attachment point of the linker.

In some embodiments, the cytotoxin-linker conjugate, prior to conjugation to the antibody and including the reactive substituent Z', taken together as Cy-L-Z', has the structure:

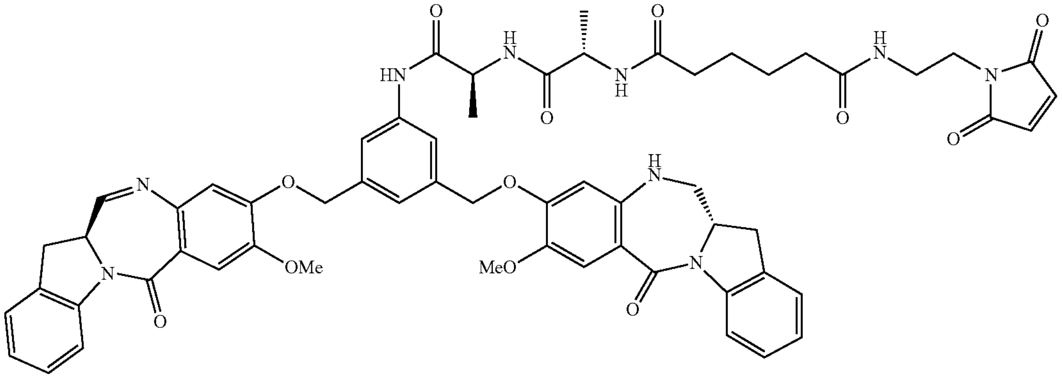

,

This cytotoxin-linker conjugate is referred to herein as DGN549, and is present in the ADC IMGN632, both of which are disclosed in, for example, International Patent Application Publication No. WO2017004026, which is incorporated by reference herein.

In some embodiments, the cytotoxin is an indolinobenzodiazepine pseudodimer having a structure of formula:

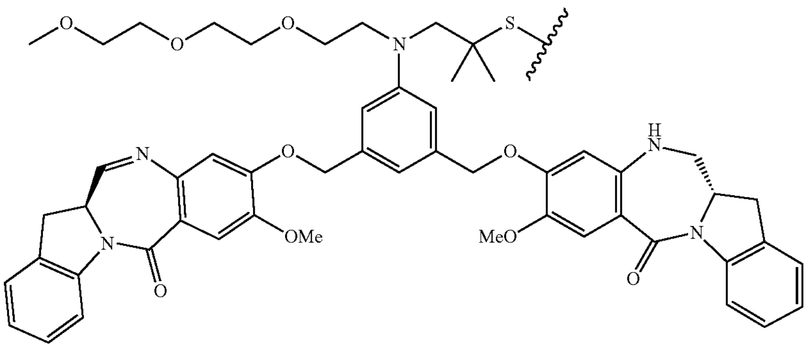 [SMILES: *SC(C)(C)CN(CCOCCOCCOC)c1cc(COc2cc3c(cc2OC)C(=O)N2c4ccccc4C[C@H]2C=N3)cc(COc2cc3c(cc2OC)C(=O)N2c4ccccc4C[C@H]2CN3)c1]

wherein the wavy line indicates the attachment point of the linker. This IGN pseudodimer cytotoxin is referred to herein as DGN462, disclosed in, for example, U.S. Patent Application Publication No. 20170080102, which is incorporated by reference herein.

In some embodiments, the cytotoxin-linker conjugate, prior to conjugation to the antibody and including the chemical moiety Z, taken together as Cy-L-Z, has the structure:

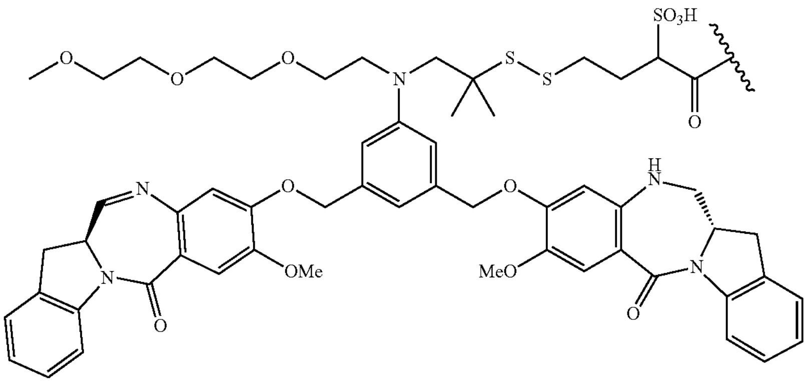 [SMILES: *C(=O)C(CCSSC(C)(C)CN(CCOCCOCCOC)c1cc(COc2cc3c(cc2OC)C(=O)N2c4ccccc4C[C@H]2C=N3)cc(COc2cc3c(cc2OC)C(=O)N2c4ccccc4C[C@H]2CN3)c1)S(=O)(=O)O]

wherein the wavy line indicates the point of attachment to the antibody (e.g., an anti-CD45 antibody or fragment thereof). This cytotoxin-linker conjugate is present in the ADC IMGN779, disclosed in, for example, U.S. Patent Application Publication No. 20170080102, previously incorporated by reference herein.

Linkers

The term "Linker" as used herein means a divalent chemical moiety comprising a covalent bond or a chain of atoms that covalently attaches an anti-CD45 antibody or fragment thereof (Ab) to a cytotoxin (e.g., a PBD) to form an antibody-drug conjugate (ADC).

Covalent attachment of the antibody and the drug moiety requires the linker to have two reactive functional groups, i.e. bivalency in a reactive sense. Bivalent linker reagents which are useful to attach two or more functional or biologically active moieties, such as peptides, nucleic acids, drugs, toxins, antibodies, haptens, and reporter groups are known, and methods have been described their resulting conjugates (Hermanson, G. T. (1996) Bioconjugate Techniques; Academic Press: New York, p. 234-242).

Accordingly, present linkers have two reactive termini, one for conjugation to an antibody and the other for conjugation to a cytotoxin. The antibody conjugation reactive terminus of the linker (reactive moiety, defined herein as Z') is typically a chemical moiety that is capable of conjugation to the antibody through, e.g., a cysteine thiol or lysine amine group on the antibody, and so is typically a thiol-reactive group such as a Michael acceptor (as in maleimide), a leaving group, such as a chloro, bromo, iodo, or an R-sulfanyl group, or an amine-reactive group such as a carboxyl group. Conjugation of the linker to the antibody is described more fully herein below.

The cytotoxin conjugation reactive terminus of the linker is typically a chemical moiety that is capable of conjugation to the cytotoxin through formation of a bond with a reactive substituent within the cytotoxin molecule. Non-limiting examples include, for example, formation of an amide bond with a basic amine or carboxyl group on the cytotoxin, via a carboxyl or basic amine group on the linker, respectively, or formation of an ether, a sulfide, or the like, via alkylation of an OH or SH group, respectively, on the cytotoxin.

When the term "linker" is used in describing the linker in conjugated form, one or both of the reactive termini will be absent (such as reactive moiety Z', having been converted to chemical moiety Z, as described herein below) or incomplete (such as being only the carbonyl of the carboxylic acid) because of the formation of the bonds between the linker and/or the cytotoxin, and between the linker and/or the antibody or antigen-binding fragment thereof. Such conjugation reactions are described further herein below.

A variety of linkers can be used to conjugate the antibodies, antigen-binding fragments, and ligands described to a cytotoxic molecule. Generally, linkers suitable for the present disclosure may be substantially stable in circulation, but allow for release of the cytotoxin within or in close proximity to the target cells. In some embodiments, certain linkers suitable for the present disclosure may be categorized as "cleavable" or "non-cleavable". Generally, cleavable linkers contain one or more functional groups that are cleaved in response to a physiological environment. For example, a cleavable linker may contain an enzymatic substrate (e.g., valine-alanine) that degrades in the presence of an intracellular enzyme (e.g., cathepsin B), an acid-cleavable group (e.g., a hydrozone) that degrades in the acidic environment of a cellular compartment, or a reducible group (e.g., a disulfide) that degrades in an intracellular reducing environment. By contrast, generally, non-cleavable linkers are released from the ADC during degradation (e.g., lysosomal degradation) of the antibody moiety of the ADC inside the target cell.

Non-Cleavable Linkers Non-cleavable linkers suitable for use herein further may include one or more groups selected from a bond, —(C═O)—, $C_1$-$C_{12}$ alkylene, $C_1$-$C_{12}$ heteroalkylene, $C_2$-$C_{12}$ alkenylene, $C_2$-$C_{12}$ heteroalkenylene, $C_2$-$C_{12}$ alkynylene, $C_2$-$C_{12}$ heteroalkynylene, $C_3$-$C_{12}$ cycloalkylene, heterocycloalkylene, arylene, heteroarylene, and combinations thereof, each of which may be optionally substituted, and/or may include one or more heteroatoms (e.g., S, N, or O) in place of one or more carbon atoms. Non-limiting examples of such groups include alkylene $(CH_2)_p$, $(C{=}O)(CH_2)_r$, and polyethyleneglycol (PEG; $(CH_2CH_2O)_q$), units, $—(NHCH_2CH_2)_u—$, wherein each of p, q, r, t, and u are integers from 1-12, selected independently for each occurrence.

In some embodiments, the linker L comprises one or more of a bond, —(C═O)—, a —C(O)NH— group, an —OC(O)NH— group, $C_1$-$C_{12}$ alkylene, $C_1$-$C_{12}$ heteroalkylene, $C_2$-$C_{12}$ alkenylene, $C_2$-$C_{12}$ heteroalkenylene, $C_2$-$C_{12}$ alkynylene, $C_2$-$C_{12}$ heteroalkynylene, $C_3$-$C_{12}$ cycloalkylene, heterocycloalkylene, arylene, heteroarylene, a $—(CH_2CH_2O)_q—$ group where q is an integer from 1-12, or a solubility enhancing group;

wherein each $C_1$-$C_{12}$ alkylene, $C_1$-$C_{12}$ heteroalkylene, $C_2$-$C_{12}$ alkenylene, $C_2$-$C_{12}$ heteroalkenylene, $C_2$-$C_{12}$ alkynylene, $C_2$-$C_{12}$ heteroalkynylene, $C_3$-$C_{12}$ cycloalkylene, heterocycloalkylene, arylene, or heteroarylene may optionally be substituted with from 1 to 5 substituents independently selected for each occasion from the group consisting of alkyl, alkenyl, alkynyl, cycloalkyl, heterocycloalkyl, alkaryl, alkyl heteroaryl, amino, ammonium, acyl, acyloxy, acylamino, aminocarbonyl, alkoxycarbonyl, ureido, carbamate, aryl, heteroaryl, sulfinyl, sulfonyl, hydroxyl, alkoxy, sulfanyl, halogen, carboxy, trihalomethyl, cyano, hydroxy, mercapto, and nitro.

In some embodiments, each $C_1$-$C_{12}$ alkylene, $C_1$-$C_{12}$ heteroalkylene, $C_2$-$C_{12}$ alkenylene, $C_2$-$C_{12}$ heteroalkenylene, $C_2$-$C_{12}$ alkynylene, $C_2$-$C_{12}$ heteroalkynylene, $C_3$-$C_{12}$ cycloalkylene, heterocycloalkylene, arylene, or heteroarylene may optionally be interrupted by one or more heteroatoms selected from O, S and N.

In some embodiments, each $C_1$-$C_6$ alkylene, $C_1$-$C_{12}$ heteroalkylene, $C_2$-$C_{12}$ alkenylene, $C_2$-$C_{12}$ heteroalkenylene, $C_2$-$C_{12}$ alkynylene, $C_2$-$C_{12}$ heteroalkynylene, $C_3$-$C_{12}$ cycloalkylene, heterocycloalkylene, arylene, or heteroarylene may optionally be interrupted by one or more heteroatoms selected from O, S and N and may be optionally substituted with from 1 to 5 substituents independently selected for each occasion from the group consisting of alkyl, alkenyl, alkynyl, cycloalkyl, heterocycloalkyl, alkaryl, alkyl heteroaryl, amino, ammonium, acyl, acyloxy, acylamino, aminocarbonyl, alkoxycarbonyl, ureido, carbamate, aryl, heteroaryl, sulfinyl, sulfonyl, hydroxyl, alkoxy, sulfanyl, halogen, carboxy, trihalomethyl, cyano, hydroxy, mercapto, and nitro.

In some embodiments, the non-cleavable linker comprises a $—(CH_2)_n—$ unit, where n is an integer from, 2-12, e.g., 2-6. In some embodiments, the non-cleavable linker comprises a $—(CH_2)_n—$ where n is 1, 2, 3, 4, 5, or 6. In some embodiments, the non-cleavable linker is $—(CH_2)_n—$ where n is 6, represented by the formula:

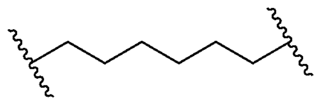

.

Cleavable Linkers

In some embodiments, the linker conjugating the anti-CD45 antibody or antigen binding fragment thereof and the cytotoxin (e.g., a PBD) is cleavable under intracellular conditions, such that cleavage of the linker releases the cytotoxin unit from the antibody in the intracellular environment. Cleavable linkers are designed to exploit the differences in local environments, e.g., extracellular and intracellular environments, including, for example, pH, reduction potential or enzyme concentration, to trigger the release of the cytotoxin in the target cell. Generally, cleavable linkers are relatively stable in circulation, but are particularly susceptible to cleavage in the intracellular environment through one or more mechanisms (e.g., including, but not limited to, activity of proteases, peptidases, and glucuronidases). Cleavable linkers used herein are substantially stable in circulating plasma and/or outside the target cell and may be cleaved at some efficacious rate inside the target cell or in close proximity to the target cell.

Suitable cleavable linkers include those that may be cleaved, for instance, by enzymatic hydrolysis, photolysis, hydrolysis under acidic conditions, hydrolysis under basic conditions, oxidation, disulfide reduction, nucleophilic cleavage, or organometallic cleavage (see, for example, Leriche et al., Bioorg. Med. Chem., 20:571-582, 2012, the disclosure of which is incorporated herein by reference as it pertains to linkers suitable for covalent conjugation). Suitable cleavable linkers may include, for example, chemical moieties such as a hydrazine, a disulfide, a thioether or a dipeptide.

Linkers hydrolyzable under acidic conditions include, for example, hydrazones, semicarbazones, thiosemicarbazones, cis-aconitic amides, orthoesters, acetals, ketals, or the like. (See, e.g., U.S. Pat. Nos. 5,122,368; 5,824,805; 5,622,929; Dubowchik and Walker, 1999, Pharm. Therapeutics 83:67-123; Neville et al., 1989, Biol. Chem. 264:14653-14661, the disclosure of each of which is incorporated herein by reference in its entirety as it pertains to linkers suitable for covalent conjugation. Such linkers are relatively stable under neutral pH conditions, such as those in the blood, but are unstable at below pH 5.5 or 5.0, the approximate pH of the lysosome.

Linkers cleavable under reducing conditions include, for example, a disulfide. A variety of disulfide linkers are known in the art, including, for example, those that can be formed using SATA (N-succinimidyl-S-acetylthioacetate), SPDP (N-succinimidyl-3-(2-pyridyldithio)propionate), SPDB (N-succinimidyl-3-(2-pyridyldithio)butyrate) and SMPT (N-succinimidyl-oxycarbonyl-alpha-methyl-alpha-(2-pyridyl-dithio)toluene), SPDB and SMPT (See, e.g., Thorpe et al., 1987, Cancer Res. 47:5924-5931; Wawrzynczak et al., In Immunoconjugates: Antibody Conjugates in Radioimagery and Therapy of Cancer (C. W. Vogel ed., Oxford U. Press, 1987. See also U.S. Pat. No. 4,880,935, the disclosure of each of which is incorporated herein by reference in its entirety as it pertains to linkers suitable for covalent conjugation.

Linkers susceptible to enzymatic hydrolysis can be, e.g., a peptide-containing linker that is cleaved by an intracellular peptidase or protease enzyme, including, but not limited to, a lysosomal or endosomal protease. One advantage of using intracellular proteolytic release of the therapeutic agent is that the agent is typically attenuated when conjugated and the serum stabilities of the conjugates are typically high. In some embodiments, the peptidyl linker is at least two amino acids long or at least three amino acids long. Exemplary amino acid linkers include a dipeptide, a tripeptide, a tetrapeptide or a pentapeptide. Examples of suitable peptides include those containing amino acids such as Valine, Alanine, Citrulline (Cit), Phenylalanine, Lysine, Leucine, and Glycine. Amino acid residues which comprise an amino acid linker component include those occurring naturally, as well as minor amino acids and non-naturally occurring amino acid analogs, such as citrulline. Exemplary dipeptides include valine-citrulline (vc or val-cit) and alanine-phenylalanine (af or ala-phe). Exemplary tripeptides include glycine-valine-citrulline (gly-val-cit) and glycine-glycine-glycine (gly-gly-gly). In some embodiments, the linker includes a dipeptide such as Val-Cit, Ala-Val, or Phe-Lys, Val-Lys, Ala-Lys, Phe-Cit, Leu-Cit, Ile-Cit, Phe-Arg, or Trp-Cit. Linkers containing dipeptides such as Val-Cit or Phe-Lys are disclosed in, for example, U.S. Pat. No. 6,214,345, the disclosure of which is incorporated herein by reference in its entirety as it pertains to linkers suitable for covalent conjugation. In some embodiments, the linker comprises a dipeptide selected from Val-Ala and Val-Cit.

Linkers suitable for conjugating the antibodies, antigen-binding fragments, and ligands described herein to a cytotoxic molecule include those capable of releasing a cytotoxin by a 1,6-elimination process. Chemical moieties capable of this elimination process include the p-aminobenzyl (PAB) group, 6-maleimidohexanoic acid, pH-sensitive carbonates, and other reagents as described in Jain et al., Pharm. Res. 32:3526-3540, 2015, the disclosure of which is incorporated herein by reference in its entirety as it pertains to linkers suitable for covalent conjugation.

In some embodiments, the linker includes a "self-immolative" group such as the afore-mentioned PAB or PABC (para-aminobenzyloxycarbonyl), which are disclosed in, for example, Carl et al., J. Med. Chem. (1981) 24:479-480; Chakravarty et al (1983) J. Med. Chem. 26:638-644; U.S. Pat. No. 6,214,345; US20030130189; US20030096743; U.S. Pat. No. 6,759,509; US20040052793; U.S. Pat. Nos. 6,218,519; 6,835,807; 6,268,488; US20040018194; WO98/13059; US20040052793; U.S. Pat. Nos. 6,677,435; 5,621,002; US20040121940; WO2004/032828). Other such chemical moieties capable of this process ("self-immolative linkers") include methylene carbamates and heteroaryl groups such as aminothiazoles, aminoimidazoles, aminopyrimidines, and the like. Linkers containing such heterocyclic self-immolative groups are disclosed in, for example, U.S. Patent Publication Nos. 20160303254 and 20150079114, and U.S. Pat. No. 7,754,681; Hay et al. (1999) Bioorg. Med. Chem. Lett. 9:2237; US 2005/0256030; de Groot et al (2001) J. Org. Chem. 66:8815-8830; and U.S. Pat. No. 7,223,837. In some embodiments, a dipeptide is used in combination with a self-immolative linker.

In some embodiments, the linker L comprises one or more of a hydrazine, a disulfide, a thioether, an amino acid, a peptide consisting of up to 10 amino acids, a p-aminobenzyl (PAB) group, a heterocyclic self-immolative group, $C_1$-$C_{12}$ alkyl, $C_1$-$C_{12}$ heteroalkyl, $C_2$-$C_{12}$ alkenyl, $C_2$-$C_{12}$ heteroalkenyl, $C_2$-$C_{12}$ alkynyl, $C_2$-$C_{12}$ heteroalkynyl, $C_3$-$C_{12}$ cycloalkyl, heterocycloalkyl, aryl, heteroaryl, a —(C═O)— group, a —C(O)NH— group, an —OC(O)NH— group, or a $—(CH_2CH_2O)_q—$ group where p is an integer from 1-12;

wherein each $C_1$-$C_{12}$ alkyl, $C_1$-$C_{12}$ heteroalkyl, $C_2$-$C_{12}$ alkenyl, $C_2$-$C_{12}$ heteroalkenyl, $C_2$-$C_{12}$ alkynyl, $C_2$-$C_{12}$ heteroalkynyl, $C_3$-$C_{12}$ cycloalkyl, heterocycloalkyl, aryl, or heteroaryl group may be optionally substituted with from 1 to 5 substituents independently selected for each occasion from the group consisting of alkyl, alkenyl, alkynyl, cycloalkyl, heterocycloalkyl, alkaryl, alkyl heteroaryl, amino, ammonium, acyl, acyloxy, acylamino, aminocarbonyl, alkoxycarbonyl, ureido, carbamate, aryl, heteroaryl, sulfinyl, sulfonyl, hydroxyl, alkoxy, sulfanyl, halogen, carboxy, trihalomethyl, cyano, hydroxy, mercapto, and nitro.

In some embodiments, each $C_1$-$C_{12}$ alkyl, $C_1$-$C_{12}$ heteroalkyl, $C_2$-$C_{12}$ alkenyl, $C_2$-$C_{12}$ heteroalkenyl, $C_2$-$C_{12}$ alkynyl, $C_2$-$C_{12}$ heteroalkynyl, $C_3$-$C_{12}$ cycloalkyl, heterocycloalkyl, aryl, or heteroaryl group may optionally be interrupted by one or more heteroatoms selected from O, S and N.

In some embodiments, each $C_1$-$C_{12}$ alkyl, $C_1$-$C_{12}$ heteroalkyl, $C_2$-$C_{12}$ alkenyl, $C_2$-$C_{12}$ heteroalkenyl, $C_2$-$C_{12}$ alkynyl, $C_2$-$C_{12}$ heteroalkynyl, $C_3$-$C_{12}$ cycloalkyl, heterocycloalkyl, aryl, or heteroaryl group may optionally be interrupted by one or more heteroatoms selected from O, S and N and may be optionally substituted with from 1 to 5 substituents independently selected for each occasion from the group consisting of alkyl, alkenyl, alkynyl, cycloalkyl, heterocycloalkyl, alkaryl, alkyl heteroaryl, amino, ammonium, acyl, acyloxy, acylamino, aminocarbonyl, alkoxycarbonyl, ureido, carbamate, aryl, heteroaryl, sulfinyl, sulfonyl, hydroxyl, alkoxy, sulfanyl, halogen, carboxy, trihalomethyl, cyano, hydroxy, mercapto, and nitro.

One of skill in the art will recognize that one or more of the groups listed may be present in the form of a bivalent (diradical) species, e.g., $C_1$-$C_{12}$ alkylene and the like.

In some embodiments, the linker L comprises the moiety *-$L_1L_2$-**, wherein:

$L_1$ is absent or is $—(CH_2)_mNR^1C(═O)—$, $—(CH_2)_mNR^1—$, $—(CH_2)_mX_3(CH_2)_m—$,

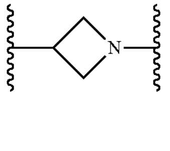
,
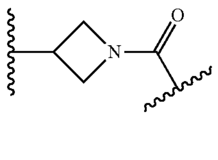
,

-continued

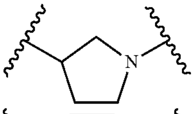,
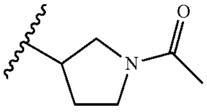,

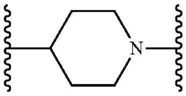,

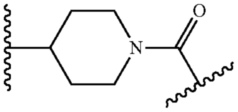, or

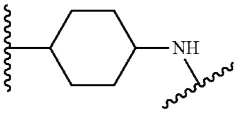;

$L_2$ is absent or is $-(CH_2)_m-$, $-NR^1(CH_2)_m-$, $-(CH_2)_mNR^1C(=O)(CH_2)_m-$, $-X_4$, $-(CH_2)_mNR^1C(=O)X_4$, $-(CH_2)_mNR^1C(=O)-$, $-((CH_2)_mO)_n(CH_2)_m-$, $-((CH_2)_mO)_n(CH_2)_mX_3(CH_2)_m-$, $-NR^1((CH_2)_mO)_nX3(CH_2)_m-$, $-NR^1((CH_2)_mO)_n(CH_2)_mX_3(CH_2)_m-$, $-X_1X2C(=O)(CH_2)_m-$, $-(CH_2)_m(O(CH_2)_m)_n-$, $-(CH_2)_mNR^1(CH_2)_m-$, $-(CH_2)_mNR^1C(=O)(CH_2)_mX_3(CH_2)_m-$, $-(CH_2)_mC(=O)NR^1(CH_2)_mNR^1C(=O)(CH_2)_m-$, $-(CH_2)_mC(=O)-$, $-(CH_2)_mNR^1(CH_2)_mC(=O)X_2XC(=O)-$, $-(CH_2)_mX_3(CH_2)_mC(=O)X_2XC(=O)-$, $-(CH_2)_mC(=O)NR^1(CH_2)_m-$, $-(CH_2)_mC(=O)NR^1(CH_2)_mX_3(CH_2)_m-$, $-(CH_2)_mX_3(CH_2)_mNR^1C(=O)(CH_2)_m-$, $-(CH_2)_mX_3(CH_2)_mC(=O)NR^1(CH_2)_m-$, $-(CH_2)_mO)_n(CH_2)_mNR^1C(=O)(CH_2)_m-$, $-(CH_2)_mC(=O)NR^1(CH_2)_m(O(CH_2)_m)_n-$, $-(CH_2)_m(O(CH_2)_m)_nC(=O)-$, $-(CH_2)_mNR^1(CH_2)_mC(=O)-$, $-(CH_2)_mC(=O)NR^1(CH_2)_mNR^1C(=O)-$, $-(CH_2)_m(O(CH_2)_m)_nX_3(CH_2)_m-$, $-(CH_2)_mX_3((CH_2)_mO)_n(CH_2)_m-$, $-(CH_2)_mX_3(CH_2)_mC(=O)-$, $-(CH_2)_mC(=O)NR^1(CH_2)_mO)_n(CH_2)_mX_3(CH_2)_m-$, $-(CH_2)_mX_3(CH_2)_m(O(CH_2)_m)_nNR^1C(=O)(CH_2)_m-$, $-(CH_2)_mX_3(CH_2)_m(O(CH_2)_m)_nC(=O)-$, $-(CH_2)_mX_3(CH_2)_m(O(CH_2)_m)_n-$, $-(CH_2)_mC(=O)NR^1(CH_2)_mC(=O)-$, $-(CH_2)_mC(=O)NR^1(CH_2)_m(O(CH_2)_m)_nC(=O)-$, $-((CH_2)_mO)_n(CH_2)_mNR^1C(=O)(CH_2)_m-$, $-(CH_2)_mC(=O)NR^1(CH_2)_mC(=O)NR^1(CH_2)_m-$, $-(CH_2)_mNR^1C(=O)(CH_2)_mNR^1C(=O)(CH_2)-(CH_2)_mX_3(CH_2)_mC(=O)NR^1-$, $-(CH_2)_mC(=O)NR^1-$, $-(CH_2)_mX_3-$, $-C(R^1)_2(CH_2)_m-$, $-(CH_2)_mC(R^1)_2NR^1-$, $-(CH_2)_mC(=O)NR^1(CH_2)_mNR^1-$, $-(CH_2)_mC(=O)NR^1(CH_2)_mNR^1C(=O)NR^1-$, $-(CH_2)_mC(=O)X_2X_1C(=O)-$, $-C(R^1)_2(CH_2)_mNR^1C(=O)(CH_2)_m-$, $-(CH_2)_mC(=O)NR^1(CH_2)_mC(R^1)_2NR^1-$, $-C(R^1)_2(CH_2)_mX_3(CH_2)_m-$, $-(CH_2)_mX_3(CH_2)_mC(R^1)_2NR^1-$, $-C(R^1)_2(CH_2)_mOC(=O)NR^1(CH_2)_m-$, $-(CH_2)_mNR^1C(=O)O(CH_2)_mC(R^1)_2NR^1-$, $-(CH_2)_mX_3(CH_2)_mNR^1-$, $-(CH_2)_mX_3(CH_2)_m(O(CH_2)_m)_nNR^1-$, $-(CH_2)_mNR^1-$, $-(CH_2)_mC(=O)NR^1(CH_2)_m(O(CH_2)_m)_nNR^1-$, $-(CH_2)_m(O(CH_2)_m)_nNR^1-$, $-(CH_2CH_2O)_n(CH_2)_m-$, $-(CH_2)_m(OCH_2CH_2)_n$; $-(CH_2)_mO(CH_2)_m-$, $-(CH_2)_mS(=O)_2-$, $-(CH_2)_mC(=O)NR^1(CH_2)_mS(=O)_2-$, $-(CH_2)_mX_3(CH_2)_mS(=O)_2-$, $-(CH_2)_mX_2X_1C(=O)-$, $-(CH_2)_m(O(CH_2)_m)_nC(=O)X_2XC(=O)-$, $-(CH_2)_m(O(CH_2)_m)_nX_2XC(=O)-$, $-(CH_2)_mX_3(CH_2)_mX_2XC(=O)-$, $-(CH_2)_mX_3(CH_2)_m(O(CH_2)_m)_nX_2X$, $C(=O)-$, $-(CH_2)_mX_3(CH_2)_mC(=O)NR^1(CH_2)_mNR^1C(=O)-$, $-(CH_2)_mX_3(CH_2)_mC(=O)NR^1(CH_2)_mC(=O)-$, $-(CH_2)_mX_3(CH_2)_mC(=O)NR^1(CH_2)_m(O(CH_2)_m)_nC(=O)-$, $-(CH_2)_mC(=O)X_2X_1C(=O)NR^1(CH_2)_m-$, $-(CH_2)_mX_3(O(CH_2)_m)_nC(=O)-$, $-(CH_2)_mNR^1C(=O)((CH_2)_mO)_n(CH_2)_m-$, $-(CH_2)_m(O(CH_2)_m)_nC(=O)NR^1(CH_2)_m-$, $-(CH_2)_mNR^1C(=O)NR^1(CH_2)_m-$ or $-(CH_2)_mX_3(CH_2)_mNR^1C(=O)-$;

wherein $X_1$ is

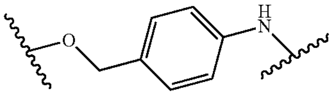,

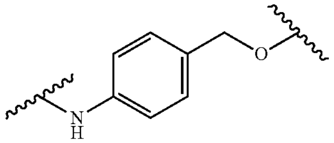,

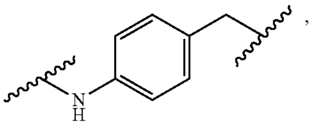,

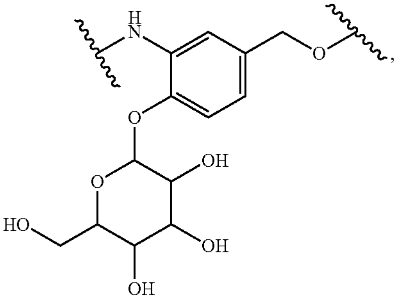, or

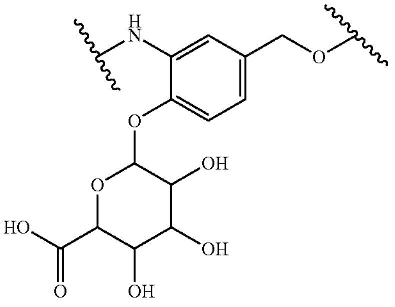;

$X_2$ is

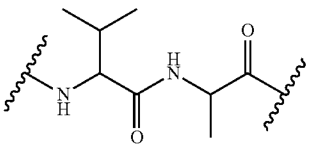,

-continued

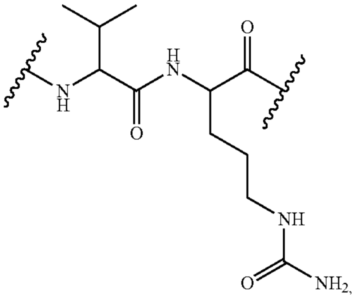

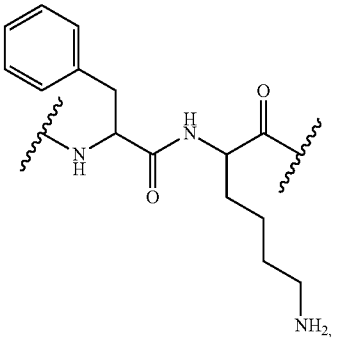

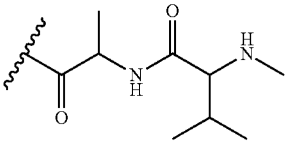

, or

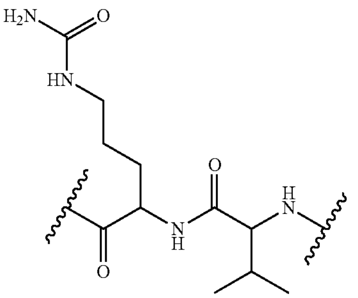

;

$X_3$ is

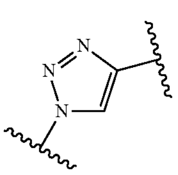

or

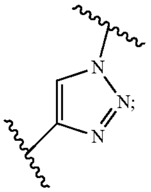

and $X_4$ is

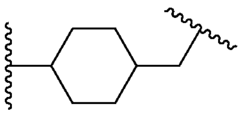

;

wherein $R^1$ is independently selected for each occasion from H and $C_1$-$C_6$ alkyl;

m is independently selected for each occasion from 1, 2, 3, 4, 5, 6, 7, 8, 9 and 10;

n is independently selected for each occasion from 1, 2, 3, 4, 5, 6, 7, 8, 9, 10, 11, 12, 13 and 14; and wherein the single asterisk (*) indicates the attachment point to the cytotoxin (e.g., a PBD), and the double asterisk (**) indicates the attachment point to the reactive substituent Z' or chemical moiety Z, with the proviso that $L_1$ and $L_2$ are not both absent.

In some embodiments, the linker includes a p-aminobenzyl group (PAB). In one embodiment, the p-aminobenzyl group is disposed between the cytotoxic drug and a protease cleavage site in the linker. In one embodiment, the p-aminobenzyl group is part of a p-aminobenzyloxycarbonyl unit. In one embodiment, the p-aminobenzyl group is part of a p-aminobenzylamido unit.

In some embodiments, the linker comprises a peptide selected from the group consisting of Phe-Lys, Val-Lys, Phe-Ala, Phe-Cit, Val-Ala, Val-Cit, and Val-Arg. In some embodiments, the linker comprises one or more of PAB, Val-Cit-PAB, Val-Ala-PAB, Val-Lys(Ac)-PAB, Phe-Lys-PAB, Phe-Lys(Ac)-PAB, D-Val-Leu-Lys, Gly-Gly-Arg, Ala-Ala-Asn-PAB, or Ala-PAB.

In some embodiments, the linker comprises one or more of a peptide, oligosaccharide, $-(CH_2)_p-$, $-(CH_2CH_2O)_q-$, $-(C{=}O)(CH_2)_r-$, $-(C{=}O)(CH_2CH_2O)_t-$, $-(NHCH_2CH_2)_u-$, -PAB, Val-Cit-PAB, Val-Ala-PAB, Val-Lys(Ac)-PAB, Phe-Lys-PAB, Phe-Lys(Ac)-PAB, D-Val-Leu-Lys, Gly-Gly-Arg, Ala-Ala-Asn-PAB, or Ala-PAB, wherein each of p, q, r, t, and u are integers from 1-12, selected independently for each occurrence.

In some embodiments, the linker comprises

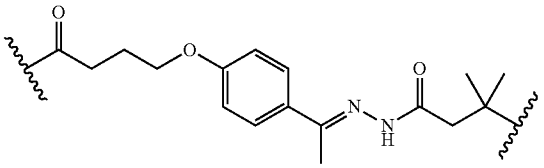

.

In some embodiments, the linker comprises MCC (4-[N-maleimidomethyl]cyclohexane-1-carboxylate).

In some embodiments, the linker comprises PAB-Ala-Val- or PAB-Cit-Val-, a $-(C{=}O)(CH_2)_r-$ unit, a $-(C{=}O)(CH_2CH_2O)_t-$ unit, and a $-(NHCH_2CH_2)_u-$ unit, wherein r, t, and u are integers from 1 to 12, selected independently from each occasion.

In some embodiments, the linker comprises PAB-Ala-Val- or PAB-Cit-Val-, a $-(C{=}O)(CH_2)_r-$ unit, a $-(C{=}O)(CH_2CH_2O)_t-$ unit, and a $-(NHCH_2CH_2)_u-$ unit, wherein r=2, t=8, and u=1. In particular embodiments, the linker may be represented by formula (II):

(II)

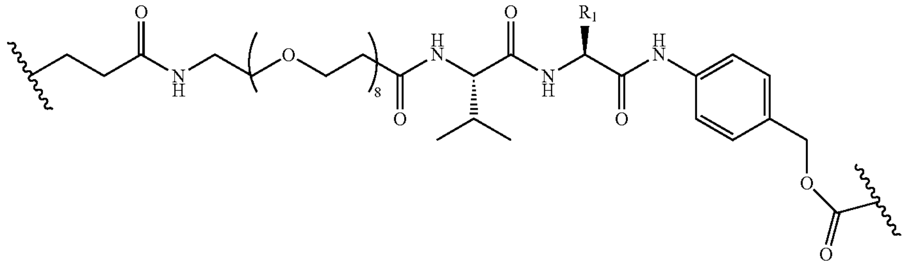

where $R_1$ is $CH_3$ (Ala) or $(CH_2)_3NH(CO)NH_2$ (Cit).

It will be recognized by one of skill in the art that any one or more of the chemical groups, moieties, and features disclosed herein may be combined in multiple ways to form linkers useful for conjugation of the antibodies and cytotoxins as disclosed herein.

Linker-Cytotoxin and Linker-Antibody Conjugation

In certain embodiments, the linker is reacted with the cytotoxin under appropriate conditions to form a linker-cytotoxin conjugate. In certain embodiments, reactive groups are used on the cytotoxin or linker to form a covalent attachment.

In some embodiments, the cytotoxin is a PBD or derivative thereof according to formula (I). The cytotoxin-linker conjugate is subsequently reacted with the antibody, derivatized antibody, or antigen-binding fragment thereof that binds CD45, under appropriate conditions to form the ADC. Alternatively, the linker may first be reacted with the antibody, derivatized antibody or antigen-binding fragment thereof that binds CD45, to form a linker-antibody conjugate, and then reacted with the cytotoxin to form the ADC. Such conjugation reactions will now be described more fully.

A number of different reactions are available for covalent attachment of linkers or cytotoxin-linker conjugates to the antibody or antigen-binding fragment thereof. Suitable attachment points on the antibody molecule include, but are not limited to, the amine groups of lysine, the free carboxylic acid groups of glutamic acid and aspartic acid, the sulfhydryl groups of cysteine, and the various moieties of aromatic amino acids. For instance, non-specific covalent attachment may be undertaken using a carbodiimide reaction to link a carboxy (or amino) group on a linker to an amino (or carboxy) group on an antibody moiety. Additionally, bifunctional agents such as dialdehydes or imidoesters may also be used to link the amino group on a linker to an amino group on an antibody moiety. Also available for attachment of cytotoxins to antibody moieties is the Schiff base reaction. This method involves the periodate oxidation of a glycol or hydroxy group on either the antibody or linker, thus forming an aldehyde which is then reacted with the linker or antibody, respectively. Covalent bond formation occurs via formation of a Schiff base between the aldehyde and an amino group. Isothiocyanates may also be used as coupling agents for covalently attaching cytotoxins or antibody moieties to linkers. Other techniques are known to the skilled artisan and within the scope of the present disclosure.

Linkers useful in for conjugation to the antibodies or antigen-binding fragments as described herein include, without limitation, linkers containing a chemical moiety Z formed by a coupling reaction between the antibody and a reactive chemical moiety (referred to herein as a reactive substituent, Z') on the linker as depicted in Table 2, below. Wavy lines designate points of attachment to the antibody or antigen-binding fragment, and the cytotoxic molecule.

TABLE 2

Exemplary chemical moieties Z formed by coupling reactions in the formation of antibody-drug conjugates.

| Exemplary Coupling Reactions | Chemical Moiety Z Formed by Coupling Reactions |
|---|---|
| [3 + 2] Cycloaddition | 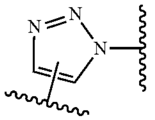 |
| [3 + 2] Cycloaddition | 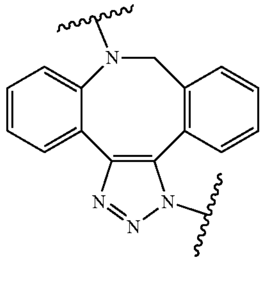 [SMILES: *N1Cc2ccccc2-c2c(nnn2*)-c2ccccc21] |

TABLE 2-continued

| Exemplary Coupling Reactions | Chemical Moiety Z Formed by Coupling Reactions |
| --- | --- |
| [3 + 2] Cycloaddition, Esterification | 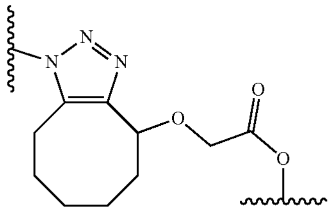 [SMILES: *OC(=O)COC1CCCCCc2c1nnn2*] |
| [3 + 2] Cycloaddition, Esterification | 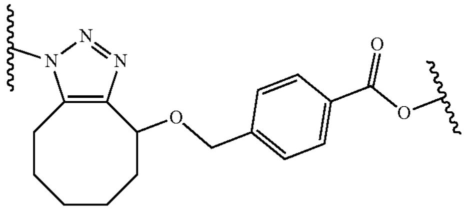 [SMILES: *OC(=O)c1ccc(COC2CCCCCc3c2nnn3*)cc1] |
| [3 + 2] Cycloaddition, Esterification | 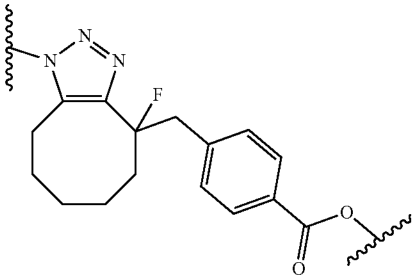 [SMILES: *OC(=O)c1ccc(CC2(F)CCCCCc3c2nnn3*)cc1] |
| [3 + 2] Cycloaddition, Esterification | 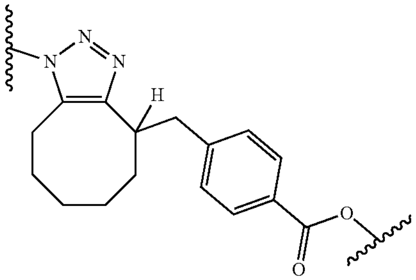 |
| [3 + 2] Cycloaddition, Esterification | 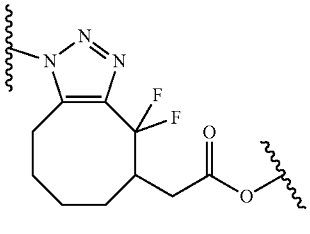 [SMILES: *OC(=O)CC1CCCCc2c(nnn2*)C1(F)F] |
| [3 + 2] Cycloaddition, Esterification | 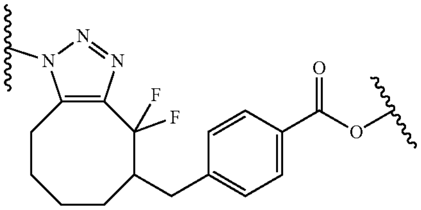 [SMILES: *OC(=O)c1ccc(CC2CCCCc3c(nnn3*)C2(F)F)cc1] |

Exemplary chemical moieties Z formed by coupling reactions in the formation of antibody-drug conjugates.

TABLE 2-continued
Exemplary chemical moieties Z formed by coupling reactions in the formation of antibody-drug conjugates.
| Exemplary Coupling Reactions | Chemical Moiety Z Formed by Coupling Reactions |
|---|---|
| [3 + 2] Cycloaddition, Esterification | 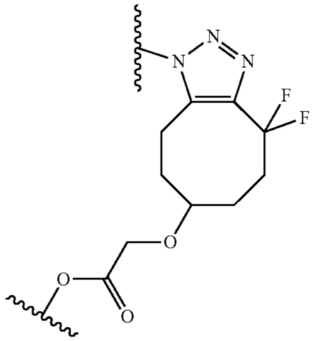 [SMILES: *OC(=O)COC1CCc2c(nnn2*)C(F)(F)CC1] |
| [3 + 2] Cycloaddition, Esterification | 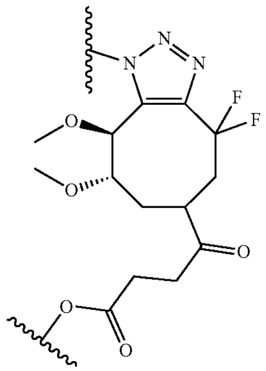 [SMILES: *OC(=O)CCC(=O)C1C[C@H](OC)[C@@H](OC)c2c(nnn2*)C(F)(F)C1] |
| [3 + 2] Cycloaddition, Esterification | 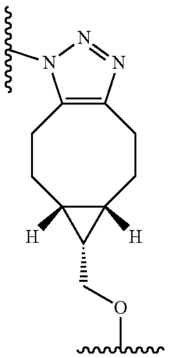 [SMILES: *OC[C@@H]1[C@@H]2CCc3c(nnn3*)CC[C@@H]21] |
| [3 + 2] Cycloaddition, Esterification | 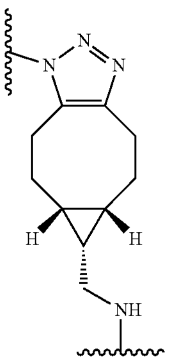 [SMILES: *NC[C@@H]1[C@@H]2CCc3c(nnn3*)CC[C@@H]21] |

TABLE 2-continued

Exemplary chemical moieties Z formed by coupling reactions in the formation of antibody-drug conjugates.

| Exemplary Coupling Reactions | Chemical Moiety Z Formed by Coupling Reactions |
|---|---|
| [3 + 2] Cycloaddition, Esterification | 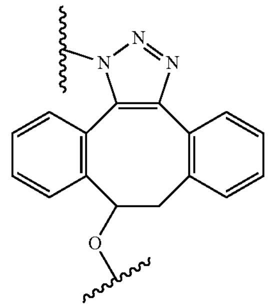 [SMILES: *OC1Cc2ccccc2-c2nnn(*)c2-c2ccccc21] |
| [3 + 2] Cycloaddition, Esterification | 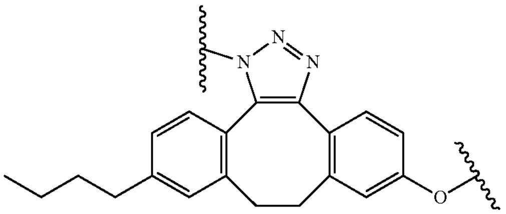 [SMILES: *Oc1ccc2c(c1)CCc1cc(CCCC)ccc1-c1c-2nnn1*] |
| [3 + 2] Cycloaddition | 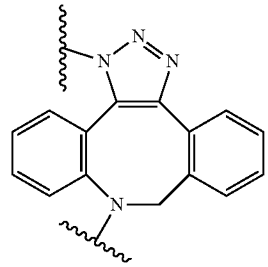 [SMILES: *N1Cc2ccccc2-c2nnn(*)c2-c2ccccc21] |
| Michael addition | 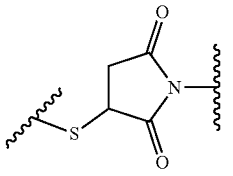 [SMILES: *SC1CC(=O)N(*)C1=O] |
| Michael addition | 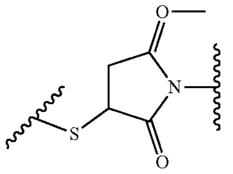 |
| Imine condensation, Amidation | 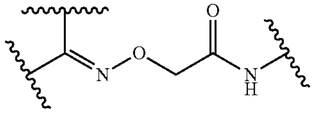 [SMILES: *NC(=O)CON=C(*)*] |
| Imine condensation | 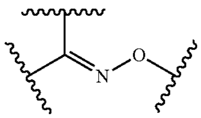 [SMILES: *ON=C(*)*] |
| Disulfide formation | 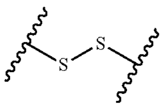 [SMILES: *SS*] |

TABLE 2-continued

| Exemplary chemical moieties Z formed by coupling reactions in the formation of antibody-drug conjugates. | |
|---|---|
| Exemplary Coupling Reactions | Chemical Moiety Z Formed by Coupling Reactions |
| Thiol alkylation | 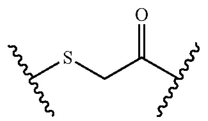 [SMILES: *SCC(*)=O] |
| Condensation, Michael addition | 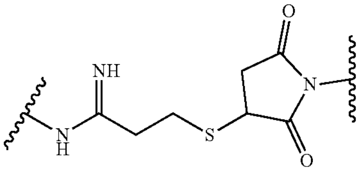 [SMILES: *NC(=N)CCSC1CC(=O)N(*)C1=O] |

One of skill in the art will recognize that a reactive substituent Z' attached to the linker and a reactive substituent on the antibody or antigen-binding fragment thereof, are engaged in the covalent coupling reaction to produce the chemical moiety Z, and will recognize the reactive substituent Z'. Therefore, antibody-drug conjugates useful in conjunction with the methods described herein may be formed by the reaction of an antibody, or antigen-binding fragment thereof, with a linker or cytotoxin-linker conjugate, as described herein, the linker or cytotoxin-linker conjugate including a reactive substituent Z', suitable for reaction with a reactive substituent on the antibody, or antigen-binding fragment thereof, to form the chemical moiety Z.

In some embodiments, Z' is —$NR^1C(=O)CH=CH_2$, —$N_3$, —SH, —$S(=O)_2(CH=CH_2)$, —$(CH_2)_2S(=O)_2(CH=CH_2)$, —$NR^1S(=O)_2(CH=CH_2)$, —$NR^1C(=O)CH_2R^2$, —$NR^1C(=O)CH_2Br$, —$NR^1C(=O)CH_2I$, —$NHC(=O)CH_2Br$, —$NHC(=O)CH_2I$, —$ONH_2$, —$C(O)NHNH_2$, —$CO_2H$, —$NH_2$, —NH(C=O), —NC(=S),

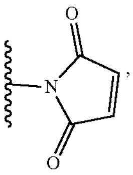 ,
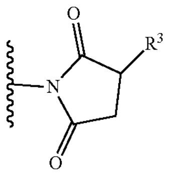 ,
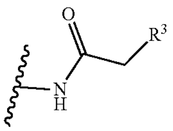 ,
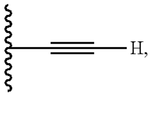
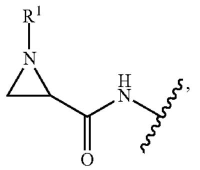

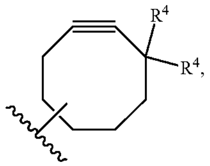
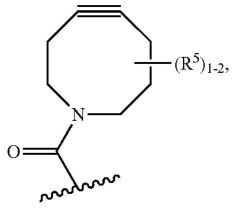
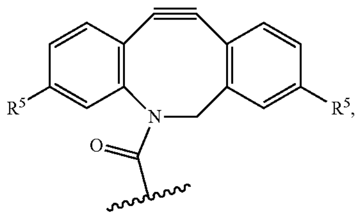

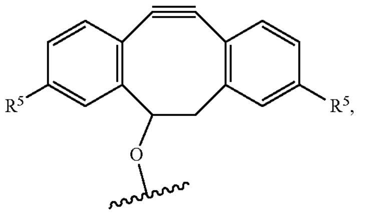
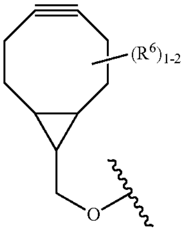 ,
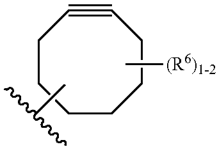 ,

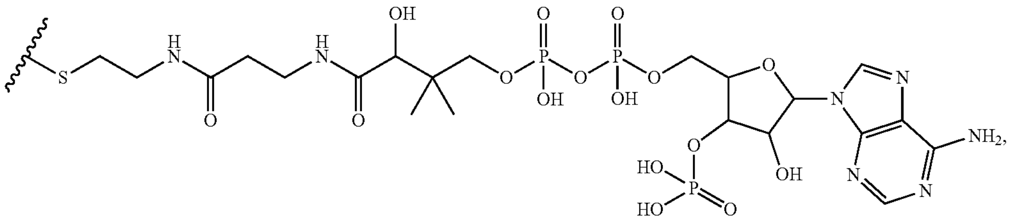

-continued
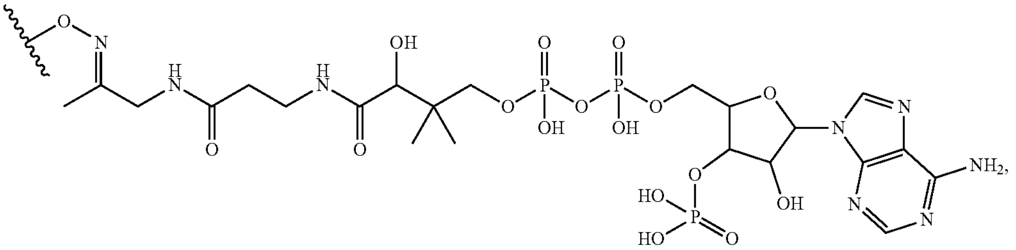
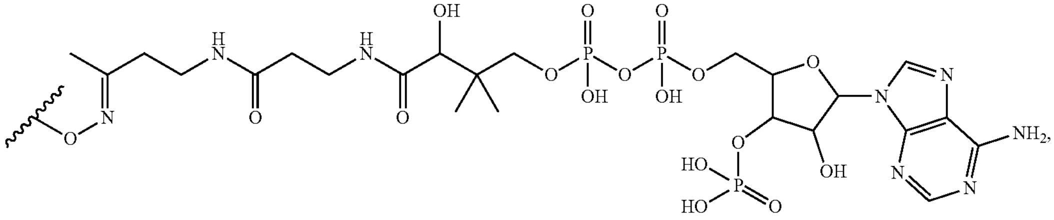
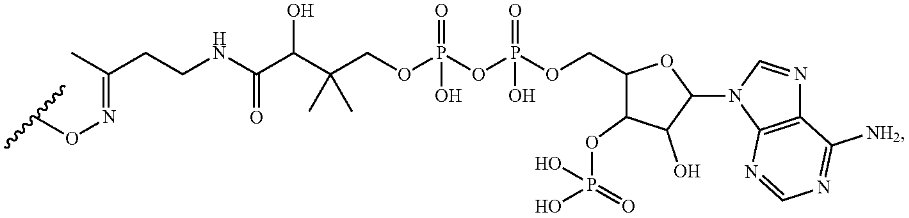
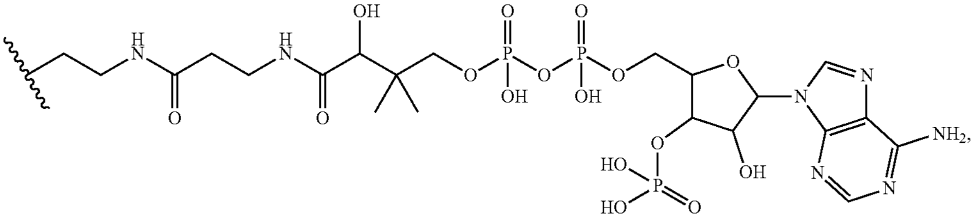
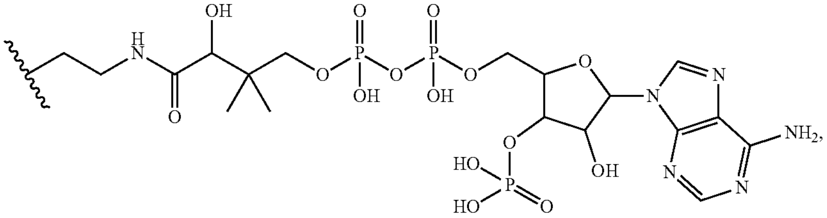
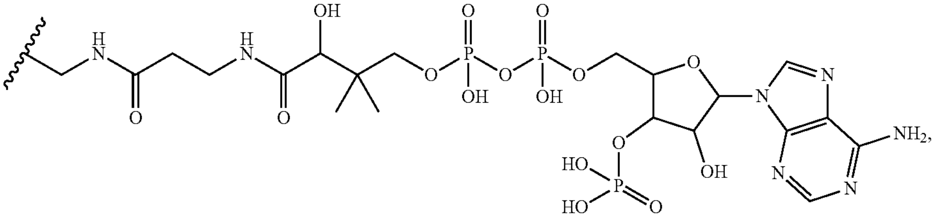
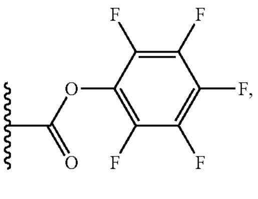
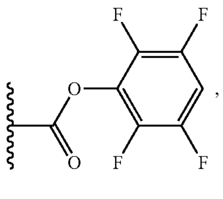
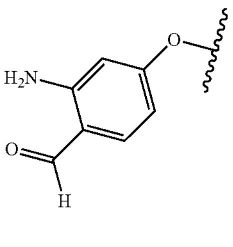
, -continued

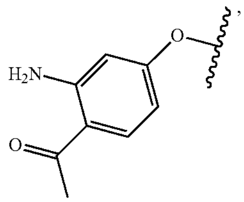 , 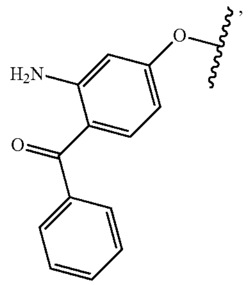 , 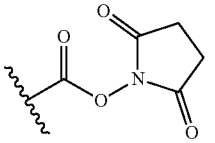 , or 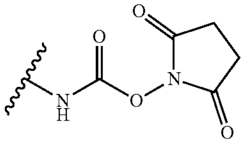 ;

wherein $R^1$ is independently selected for each occasion from H and $C_1$-$C_6$ alkyl;

$R^2$ is —$S(CH_2)_nCHR^3NHC(=O)R^1$;

$R^3$ is $R^1$ or —$C(=O)OR^1$;

$R^4$ is independently selected for each occasion from H, $C_1$-$C_6$ alkyl, F, Cl, and —OH;

$R^5$ is independently selected for each occasion from H, $C_1$-$C_6$ alkyl, F, Cl, —$NH_2$, —$OCH_3$, —$OCH_2CH_3$, —$N(CH_3)_2$, —CN, —$NO_2$ and —OH; and $R^6$ is independently selected for each occasion from H, $C_1$-$C_6$ alkyl, F, benzyloxy substituted with —C(=O)OH, benzyl substituted with —C(=O)OH, $C_1$-$C_4$ alkoxy substituted with —C(=O)OH, and $C_1$-$C_4$ alkyl substituted with —C(=O)OH.

As depicted in Table 2, examples of suitably reactive substituents Z' on the linker and reactive substituents on the antibody or antigen-binding fragment thereof include a nucleophile/electrophile pair (e.g., a thiol/haloalkyl pair, an amine/carbonyl pair, or a thiol/α,β-unsaturated carbonyl pair, and the like), a diene/dienophile pair (e.g., an azide/alkyne pair, or a diene/α,β-unsaturated carbonyl pair, among others), and the like. Coupling reactions between the reactive substituents to form the chemical moiety Z include, without limitation, thiol alkylation, hydroxyl alkylation, amine alkylation, amine or hydroxylamine condensation, hydrazine formation, amidation, esterification, disulfide formation, cycloaddition (e.g., [4+2] Diels-Alder cycloaddition, [3+2] Huisgen cycloaddition, among others), nucleophilic aromatic substitution, electrophilic aromatic substitution, and other reactive modalities known in the art or described herein. In some embodiments, the reactive substituent Z' is an electrophilic functional group suitable for reaction with a nucleophilic functional group on the antibody, or antigen-binding fragment thereof.

Reactive substituents that may be present within an antibody, or antigen-binding fragment thereof, as disclosed herein include, without limitation, nucleophilic groups such as (i)N-terminal amine groups, (ii) side chain amine groups, e.g. lysine, (iii) side chain thiol groups, e.g. cysteine, and (iv) sugar hydroxyl or amino groups where the antibody is glycosylated. Reactive substituents that may be present within an antibody, or antigen-binding fragment thereof, as disclosed herein include, without limitation, hydroxyl moieties of serine, threonine, and tyrosine residues; amino moieties of lysine residues; carboxyl moieties of aspartic acid and glutamic acid residues; and thiol moieties of cysteine residues, as well as propargyl, azido, haloaryl (e.g., fluoroaryl), haloheteroaryl (e.g., fluoroheteroaryl), haloalkyl, and haloheteroalkyl moieties of non-naturally occurring amino acids. In some embodiments, the reactive substituents present within an antibody, or antigen-binding fragment thereof as disclosed herein include, are amine or thiol moieties. Certain antibodies have reducible interchain disulfides, i.e. cysteine bridges. Antibodies may be made reactive for conjugation with linker reagents by treatment with a reducing agent such as DTT (dithiothreitol). Each cysteine bridge will thus form, theoretically, two reactive thiol nucleophiles. Additional nucleophilic groups can be introduced into antibodies through the reaction of lysines with 2-iminothiolane (Traut's reagent) resulting in conversion of an amine into a thiol. Reactive thiol groups may be introduced into the antibody (or fragment thereof) by introducing one, two, three, four, or more cysteine residues (e.g., preparing mutant antibodies comprising one or more non-native cysteine amino acid residues). U.S. Pat. No. 7,521,541 teaches engineering antibodies by introduction of reactive cysteine amino acids.

In some embodiments, the reactive substituent Z' attached to the linker is a nucleophilic group which is reactive with an electrophilic group present on an antibody. Useful electrophilic groups on an antibody include, but are not limited to, aldehyde and ketone carbonyl groups. A nucleophilic group (e.g., a) heteroatom of can react with an electrophilic group on an antibody and form a covalent bond to the antibody. Useful nucleophilic groups include, but are not limited to, hydrazide, oxime, amino, hydroxyl, hydrazine, thiosemicarbazone, hydrazine carboxylate, and arylhydrazide.

In some embodiments, chemical moiety Z is the product of a reaction between reactive nucleophilic substituents present within the antibodies, or antigen-binding fragments thereof, such as amine and thiol moieties, and a reactive electrophilic substituent Z' attached to the linker. For instance, Z' may be a Michael acceptor (e.g., maleimide), activated ester, electron-deficient carbonyl compound, or an aldehyde, among others.

Several representative and non-limiting examples of reactive substituents Z' and the resulting chemical moieties Z are provided in Table 3.

TABLE 3

Complementary reactive substituents and chemical moieties

| | Functional Group Antibody | Z' group | Z group |
|---|---|---|---|
| Naturally Occurring | 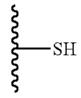 | 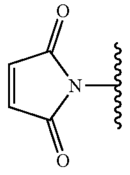 [SMILES: *N1C(=O)C=CC1=O] | 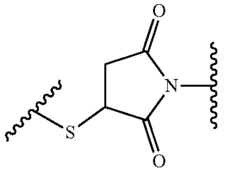 [SMILES: *SC1CC(=O)N(*)C1=O] |

TABLE 3-continued

| Complementary reactive substituents and chemical moieties | | |
|---|---|---|
| Functional Group Antibody | Z' group | Z group |
| | 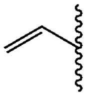 [SMILES: *C=C] | 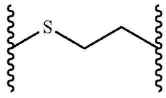 |
| 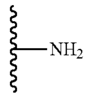 | 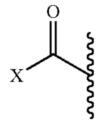 | 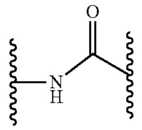 |
| Synthetically Introduced 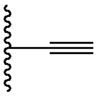 [SMILES: *C#C] | 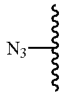 | 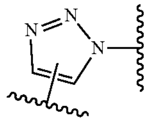 |
| 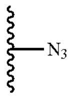 | 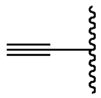 | 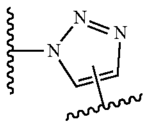 |
| | 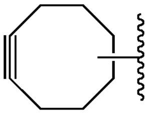 | 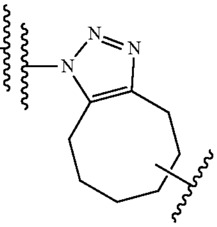 |
| 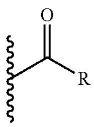 R = H or alkyl | 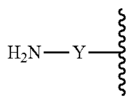 (Y = O or NH) | 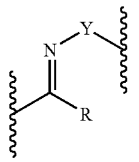 |

For instance, linkers suitable for the synthesis of linker-antibody conjugates and ADCs include, without limitation, reactive substituents Z' attached to the linker, such as a maleimide or haloalkyl group. These may be attached to the linker by, for example, reagents such as succinimidyl 4-(N-maleimidomethyl)-cyclohexane-L-carboxylate (SMCC), N-succinimidyl iodoacetate (SIA), sulfo-SMCC, m-maleimidobenzoyl-N-hydroxysuccinimidyl ester (MBS), sulfo-MBS, and succinimidyl iodoacetate, among others described, in for instance, Liu et al., 18:690-697, 1979, the disclosure of which is incorporated herein by reference as it pertains to linkers for chemical conjugation.

In some embodiments, the reactive substituent Z' attached to linker L is a maleimide, azide, or alkyne. An example of a maleimide-containing linker is the non-cleavable maleimidocaproyl-based linker, which is particularly useful for the conjugation of microtubule-disrupting agents such as auristatins. Such linkers are described by Doronina et al., Bioconjugate Chem. 17:14-24, 2006, the disclosure of which is incorporated herein by reference as it pertains to linkers for chemical conjugation.

In some embodiments, the reactive substituent Z' is —(C═O)— or —NH(C═O)—, such that the linker may be joined to the antibody, or antigen-binding fragment thereof, by an amide or urea moiety, respectively, resulting from reaction of the —(C═O)— or —NH(C═O)— group with an amino group of the antibody or antigen-binding fragment thereof.

In some embodiments, the reactive substituent Z' is an N-maleimidyl group, halogenated N-alkylamido group, sulfonyloxy N-alkylamido group, carbonate group, sulfonyl halide group, thiol group or derivative thereof, alkynyl group comprising an internal carbon-carbon triple bond, (hetero)cycloalkynyl group, bicyclo[6.1.0]non-4-yn-9-yl group, alkenyl group comprising an internal carbon-carbon double bond, cycloalkenyl group, tetrazinyl group, azido group, phosphine group, nitrile oxide group, nitrone group, nitrile imine group, diazo group, ketone group, (O-alkyl) hydroxylamino group, hydrazine group, halogenated N-maleimidyl group, 1,1-bis (sulfonylmethyl)methylcarbonyl group or elimination derivatives thereof, carbonyl halide group, or an allenamide group, each of which may be optionally substituted. In some embodiments, the reactive substituent comprises a cycloalkene group, a cycloalkyne group, or an optionally substituted (hetero)cycloalkynyl group.

In some embodiments, the chemical moiety Z is selected from Table 3. In some embodiments, the chemical moiety Z is:

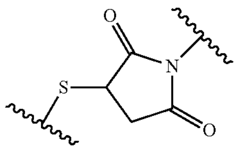 , where S is a sulfur atom which represents the reactive substituent present within an antibody, or antigen-binding fragment thereof, that specifically binds to an antigen expressed on the cell surface of a human stem cell or a T cell (e.g., from the —SH group of a cysteine residue).

In some embodiments, wherein the linker is of formula (II), the linker-reactive substituent group, taken together as L-Z', prior to conjugation with the antibody or antigen binding fragment thereof, has the structure:

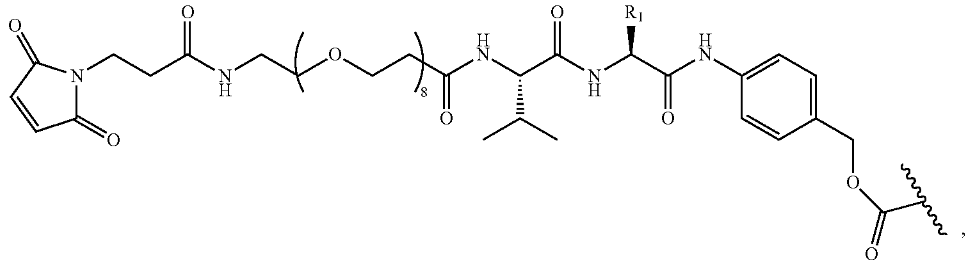

where the wavy line indicates the point of attachment to a substituent on the cytotoxin (e.g., a PBD or derivative thereof). The wavy line at the linker terminus indicates the point of attachment to the cytotoxin, e.g., a PBD. In some embodiments, the linker L and the chemical moiety Z, after conjugation to the antibody, taken together as L-Z-Ab, has the structure:

heterocyclic self-immolative group, $C_1$-$C_{12}$alkyl, $C_1$-$C_{12}$ heteroalkyl, $C_2$-$C_{12}$ alkenyl, $C_2$-$C_{12}$ heteroalkenyl, $C_2$-$C_{12}$ alkynyl, $C_2$-$C_{12}$ heteroalkynyl, $C_3$-$C_{12}$ cycloalkyl, heterocycloalkyl, aryl, heteroaryl, a —(C═O)— group, a —C(O)NH— group, an —OC(O)NH— group, a —$(CH_2CH_2O)_q$— group where p is an integer from 1-12, or a solubility enhancing group;

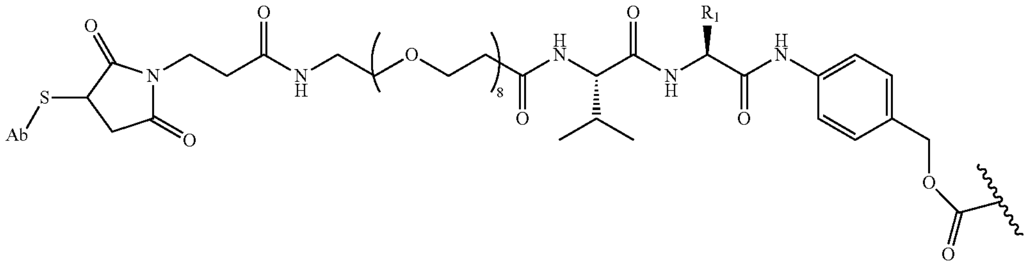

where S is a sulfur atom which represents the reactive substituent present within an antibody, or antigen-binding fragment thereof, that specifically binds to an antigen expressed on the cell surface of a human stem cell or a T cell (e.g., from the —SH group of a cysteine residue. The wavy line at the linker terminus indicates the point of attachment to the cytotoxin, e.g., PBD or derivative thereof.

In some embodiments, the cytotoxin is a pyrrolobenzodiazepine represented by the structural formula (I), and the linker is attached by a bond to the diazepine amino group. In such embodiments, the ADO may be represented by formula (III):

wherein each $C_1$-$C_{12}$ alkyl, $C_1$-$C_{12}$ heteroalkyl, $C_2$-$C_{12}$ alkenyl, $C_2$-$C_{12}$ heteroalkenyl, $C_2$-$C_{12}$alkynyl, $C_2$-$C_{12}$ heteroalkynyl, $C_3$-$C_{12}$ cycloalkyl, heterocycloalkyl, aryl, or heteroaryl group may be optionally substituted with from 1 to 5 substituents independently selected for each occasion from the group consisting of alkyl, alkenyl, alkynyl, cycloalkyl, heterocycloalkyl, alkaryl, alkyl heteroaryl, amino, ammonium, acyl, acyloxy, acylamino, aminocarbonyl, alkoxycarbonyl, ureido, carbamate, aryl, heteroaryl, sulfinyl, sulfonyl, hydroxyl, alkoxy, sulfanyl, halogen, carboxy, trihalomethyl, cyano, hydroxy, mercapto, and nitro;

(III)

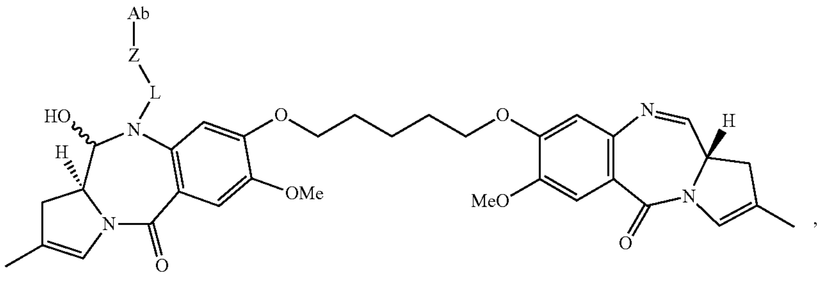

where each of L, Z, and Ab are as described herein.

In some embodiments, the linker L of the ADC of formula (III) is a cleavable linker. In some embodiments, the cleavable linker L comprises one or more of a hydrazine, a disulfide, a thioether, an amino acid, a peptide consisting of up to 10 amino acids, a p-aminobenzyl (PAB) group, a or each $C_1$-$C_{12}$ alkyl, $C_1$-$C_{12}$ heteroalkyl, $C_2$-$C_{12}$ alkenyl, $C_2$-$C_{12}$ heteroalkenyl, $C_2$-$C_{12}$ alkynyl, $C_2$-$C_{12}$ heteroalkynyl, $C_3$-$C_{12}$ cycloalkyl, heterocycloalkyl, aryl, or heteroaryl group may optionally be interrupted by one or more heteroatoms selected from O, S and N.

In some embodiments, the linker comprises one or more of a peptide, oligosaccharide, $-(CH_2)_p-$, $-(CH_2CH_2O)_q-$, $-(C{=}O)(CH_2)_r-$, $-(C{=}O)(CH_2CH_2O)_t-$, $-(NHCH_2CH_2)_u-$, -PAB, Val-Cit-PAB, Val-Ala-PAB, Val-Lys(Ac)-PAB, Phe-Lys-PAB, Phe-Lys(Ac)-PAB, D-Val-Leu-Lys, Gly-Gly-Arg, Ala-Ala-Asn-PAB, or Ala-PAB, wherein each of p, q, r, t, and u are integers from 1-12, selected independently for each occurrence.

In some embodiments, the linker comprises PAB-Ala-Val- or PAB-Cit-Val-, a $-(C{=}O)(CH_2)_r$ unit, a $-(C{=}O)(CH_2CH_2O)_t-$ unit, and a $-(NHCH_2CH_2)_u-$ unit, wherein r=2, t=8, and u=1. In particular embodiments, the linker may be represented by formula (II):

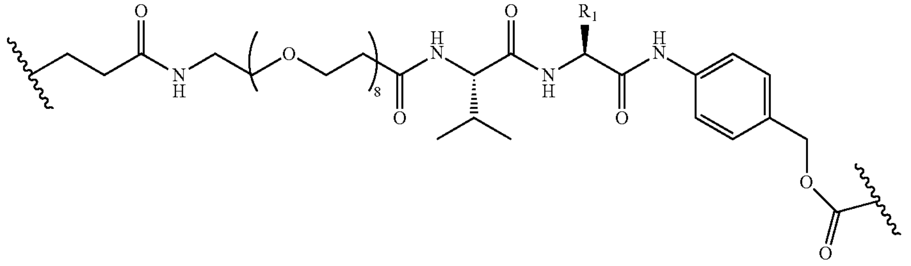

where $R_1$ is $CH_3$ (Ala) or $(CH_2)_3NH(CO)NH_2$ (Cit).

In specific embodiments, wherein the cytotoxin is of formula (I) and the linker is of formula (II) where $R_1$ is $CH_3$, the cytotoxin-linker conjugate, prior to conjugation to the antibody and including the reactive substituent Z', taken together as Cy-L-Z', may be represented by the formula (IV):

(IV)

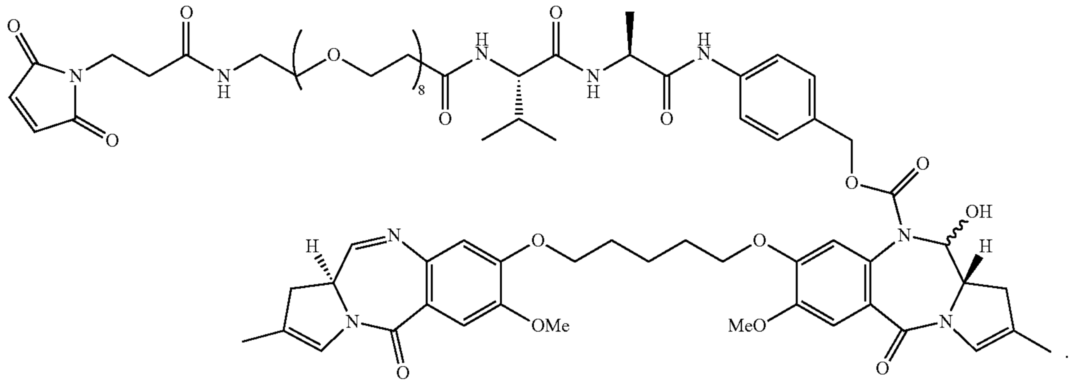

This particular cytotoxin-linker conjugate is known as tesirine (SG3249), and has been described in, for example, Howard et al., ACS Med. Chem. Lett. 2016, 7(11), 983-987, the disclosure of which is incorporated by reference herein in its entirety. A compound of formula (IV), when conjugated to an anti-CD45 antibody as disclosed herein, may be represented by formula (V):

(V)

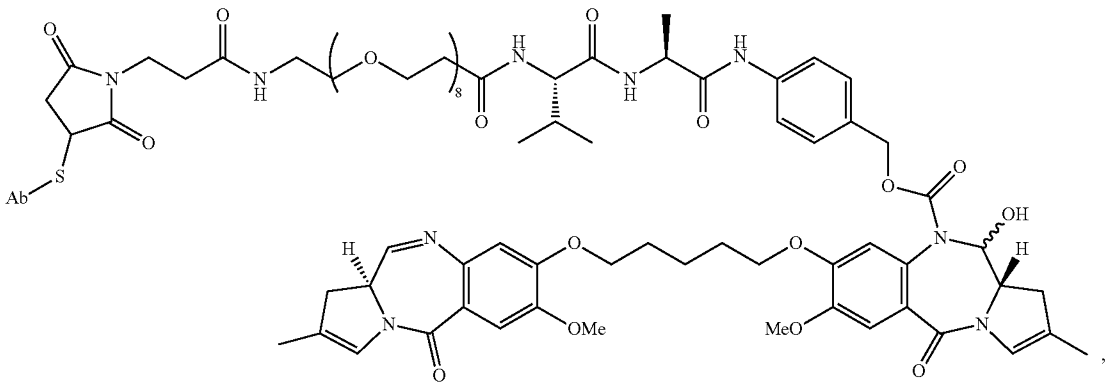

where Ab is the anti-CD45 antibody or antigen binding fragment thereof as disclosed herein, and S represents a sulfur atom (e.g., a cysteine residue thiol) present in or introduced into the antibody.

In some embodiments, the cytotoxin is a pyrrolobenzodiazepine dimer represented by the formula:

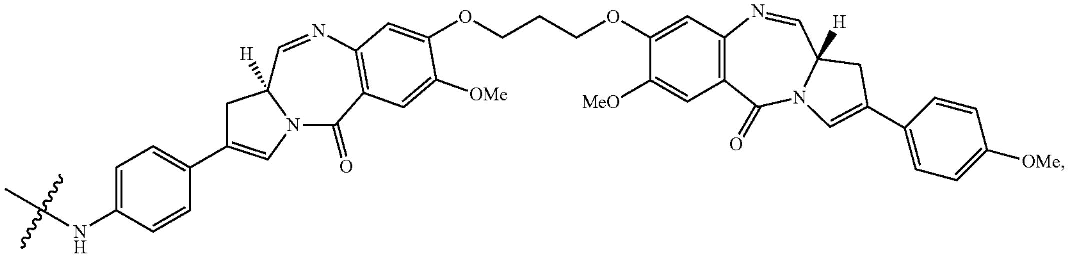 [SMILES: *Nc1ccc(C2=CN3C(=O)c4cc(OC)c(OCCCOc5cc6c(cc5OC)C(=O)N5C=C(c7ccc(OC)cc7)C[C@H]5C=N6)cc4N=C[C@@H]3C2)cc1]

wherein the wavy line indicates the attachment point of the linker.

In some embodiments, the cytotoxin-linker conjugate, prior to conjugation to the antibody and including the reactive substituent Z', taken together as Cy-L-Z', has the structure:

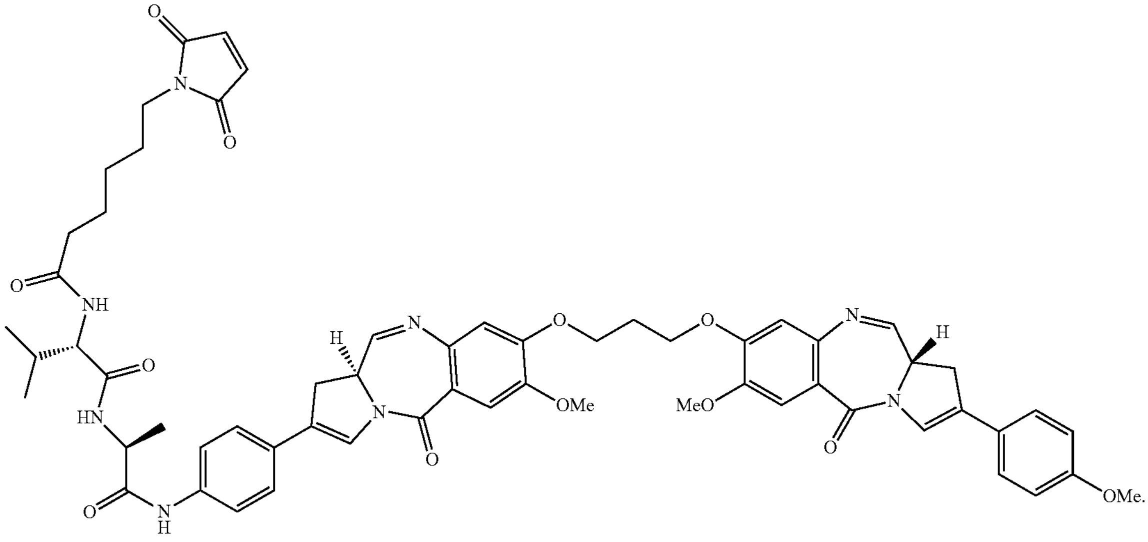 [SMILES: COc1ccc(C2=CN3C(=O)c4cc(OC)c(OCCCOc5cc6c(cc5OC)C(=O)N5C=C(c7ccc(NC(=O)[C@H](C)NC(=O)[C@@H](NC(=O)CCCCCN8C(=O)C=CC8=O)C(C)C)cc7)C[C@H]5C=N6)cc4N=C[C@@H]3C2)cc1]

This particular cytotoxin-linker conjugate is known as talirine, and has been described, for example, in connection with the ADC Vadastuximab talirine (SGN-CD33A), Mantaj et al., Angewandte Chemie International Edition English 2017, 56, 462-488, the disclosure of which is incorporated by reference herein in its entirety.

Preparation of Antibody-Drug Conjugates

In the ADCs of formula Ab-(Z-L-Cy)$_n$ as disclosed herein, such as an ADC of formula (V), an anti-CD45 antibody or antigen binding fragment thereof (Ab) is conjugated to one or more cytotoxic drug moieties (Cy; e.g., a PBD), for example, from about 1 to about 20 cytotoxic moieties per antibody, through a linker L and a chemical moiety Z as disclosed herein. Any number of cytotoxins can be conjugated to the anti-CD45 antibody, e.g., 1, 2, 3, 4, 5, 6, 7, or 8. In some embodiments, n is from about 1 to about 5, about 1 to about 4, about 1 to about 3, or about 2 to about 5, or about 3 to about 5. In some embodiments, n is about 1, about 2, about 3, or about 4.

The ADCs of the present disclosure may be prepared by several routes, employing organic chemistry reactions, conditions, and reagents known to those skilled in the art, including: (1) reaction of a reactive substituent of an antibody or antigen binding fragment thereof with a bivalent linker reagent to form Ab-Z-L as described herein above, followed by reaction with a cytotoxic moiety Cy; or (2) reaction of a reactive substituent of a cytotoxic moiety with a bivalent linker reagent to form Cy-L-Z', followed by reaction with a reactive substituent of an antibody or antigen binding fragment thereof as described herein above, to form an ADC of formula Ab-(Z-L-Cy)$_n$. Additional methods for preparing ADC are described herein.

In one embodiment, the antibody or antigen binding fragment thereof can have one or more carbohydrate groups that can be chemically modified to have one or more sulfhydryl groups. The ADC is then formed by conjugation through the sulfhydryl group's sulfur atom as described herein above.

In another embodiment, the antibody can have one or more carbohydrate groups that can be oxidized to provide an aldehyde (—CHO) group (see, for e.g., Laguzza, et al., J. Med. Chem. 1989, 32(3), 548-55). The ADC is then formed by conjugation through the corresponding aldehyde as described herein above. Other protocols for the modification of proteins for the attachment or association of cytotoxins are described in Coligan et al., Current Protocols in Protein Science, vol. 2, John Wiley & Sons (2002), incorporated herein by reference.

Methods for the conjugation of linker-drug moieties to cell-targeted proteins such as antibodies, immunoglobulins or fragments thereof are found, for example, in U.S. Pat. Nos. 5,208,020; 6,441,163; WO2005037992; WO2005081711; and WO2006/034488, all of which are hereby expressly incorporated by reference in their entirety.

Alternatively, a fusion protein comprising the antibody and cytotoxic agent may be made, e.g., by recombinant techniques or peptide synthesis. The length of DNA may comprise respective regions encoding the two portions of the conjugate either adjacent one another or separated by a region encoding a linker peptide which does not destroy the desired properties of the conjugate.

Pharmaceutical Compositions

ADCs described herein can be administered to a patient (e.g., a human patient suffering from an immune disease or cancer) in a variety of dosage forms. For instance, ADCs described herein can be administered to a patient suffering from an immune disease or cancer in the form of an aqueous solution, such as an aqueous solution containing one or more pharmaceutically acceptable excipients. Suitable pharmaceutically acceptable excipients for use with the compositions and methods described herein include viscosity-modifying agents. The aqueous solution may be sterilized using techniques known in the art.

Pharmaceutical formulations comprising ADCs as described herein are prepared by mixing such ADC with one or more optional pharmaceutically acceptable carriers (Remington's Pharmaceutical Sciences 16th edition, Osol, A. Ed. (1980)), in the form of lyophilized formulations or aqueous solutions. Pharmaceutically acceptable carriers are generally nontoxic to recipients at the dosages and concentrations employed, and include, but are not limited to: buffers such as phosphate, citrate, and other organic acids; antioxidants including ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as polyethylene glycol (PEG).

Administration

The ADCs described herein may be administered by a variety of routes, such as orally, transdermally, subcutaneously, intranasally, intravenously, intramuscularly, intraocularly, or parenterally. The most suitable route for administration in any given case will depend on the particular antibody, or antigen-binding fragment, administered, the patient, pharmaceutical formulation methods, administration methods (e.g., administration time and administration route), the patient's age, body weight, sex, severity of the diseases being treated, the patient's diet, and the patient's excretion rate.

The effective dose of an ADC, antibody, or antigen-binding fragment thereof, described herein can range, for example from about 0.001 to about 100 mg/kg of body weight per single (e.g., bolus) administration, multiple administrations, or continuous administration, or to achieve an optimal serum concentration (e.g., a serum concentration of about 0.0001-about 5000 μg/mL) of the antibody, antigen-binding fragment thereof. The dose may be administered one or more times (e.g., 2-10 times) per day, week, or month to a subject (e.g., a human) suffering from cancer, an autoimmune disease, or undergoing conditioning therapy in preparation for receipt of a hematopoietic stem cell transplant. In the case of a conditioning procedure prior to hematopoietic stem cell transplantation, the ADC, antibody, or antigen-binding fragment thereof, can be administered to the patient at a time that optimally promotes engraftment of the exogenous hematopoietic stem cells, for instance, from 1 hour to 1 week (e.g., about 1 hour, about 2 hours, about 3 hours, about 4 hours, about 5 hours, about 6 hours, about 7 hours, about 8 hours, about 9 hours, about 10 hours, about 11 hours, about 12 hours, about 13 hours, about 14 hours, about 15 hours, about 16 hours, about 17 hours, about 18 hours, about 19 hours, about 20 hours, about 21 hours, about 22 hours, about 23 hours, about 24 hours, about 2 days, about 3 days, about 4 days, about 5 days, about 6 days, or about 7 days) or more prior to administration of the exogenous hematopoietic stem cell transplant.

In one embodiment, the dose of the anti-CD45 antibody conjugated via a linker to a cytotoxin administered to the human patient is about 0.1 mg/kg to about 0.3 mg/kg.

In one embodiment, the dose of the anti-CD45 antibody conjugated via a linker to a cytotoxin administered to the human patient is about 0.15 mg/kg to about 0.3 mg/kg.

In one embodiment, the dose of the anti-CD45 antibody conjugated via a linker to a cytotoxin administered to the human patient is about 0.15 mg/kg to about 0.25 mg/kg.

In one embodiment, the dose of the anti-CD45 antibody conjugated via a linker to a cytotoxin administered to the human patient is about 0.2 mg/kg to about 0.3 mg/kg.

In one embodiment, the dose of the anti-CD45 antibody conjugated via a linker to a cytotoxin administered to the human patient is about 0.25 mg/kg to about 0.3 mg/kg.

In one embodiment, the dose of the anti-CD45 antibody conjugated via a linker to a cytotoxin administered to the human patient is about 0.1 mg/kg.

In one embodiment, the dose of the anti-CD45 antibody conjugated via a linker to a cytotoxin administered to the human patient is about 0.2 mg/kg.

In one embodiment, the dose of the anti-CD45 antibody conjugated via a linker to a cytotoxin administered to the human patient is about 0.3 mg/kg.

In one embodiment, the dose of the anti-CD45 ADC described herein administered to the human patient is about 0.001 mg/kg to 10 mg/kg, about 0.01 mg/kg to 9.5 mg/kg, about 0.1 mg/kg to 9 mg/kg, about 0.1 mg/kg to 8.5 mg/kg, about 0.1 mg/kg to 8 mg/kg, about 0.1 mg/kg to 7.5 mg/kg, about 0.1 mg/kg to 7 mg/kg, about 0.1 mg/kg to 6.5 mg/kg, about 0.1 mg/kg to 6 mg/kg, about 0.1 mg/kg to 5.5 mg/kg, about 0.1 mg/kg to 5 mg/kg, about 0.1 mg/kg to 4.5 mg/kg, about 0.1 mg/kg to 4 mg/kg, about 0.5 mg/kg to 3.5 mg/kg, about 0.5 mg/kg to 3 mg/kg, about 1 mg/kg to 10 mg/kg, about 1 mg/kg to 9 mg/kg, about 1 mg/kg to 8 mg/kg, about 1 mg/kg to 7 mg/kg, about 1 mg/kg to 6 mg/kg, about 1 mg/kg to 5 mg/kg, about 1 mg/kg to 4 mg/kg, or about 1 mg/kg to 3 mg/kg.

In one embodiment, the anti-CD45 ADC described herein that is administered to a human patient for treatment or conditioning has a half-life of equal to or less than 24 hours, equal to or less than 22 hours, equal to or less than 20 hours, equal to or less than 18 hours, equal to or less than 16 hours, equal to or less than 14 hours, equal to or less than 13 hours, equal to or less than 12 hours, equal to or less than 11 hours, equal to or less than 10 hours, equal to or less than 9 hours, equal to or less than 8 hours, equal to or less than 7 hours, equal to or less than 6 hours, or equal to or less than 5 hours. In one embodiment, the half-life of the anti-HC ADC is 5 hours to 7 hours; is 5 hours to 9 hours; is 15 hours to 11 hours; is 5 hours to 13 hours; is 5 hours to 15 hours; is 5 hours to 20 hours; is 5 hours to 24 hours; is 7 hours to 24 hours; is 9 hours to 24 hours; is 11 hours to 24 hours; 12 hours to 22 hours; 10 hours to 20 hours; 8 hours to 18 hours; or 14 hours to 24 hours.

In one embodiment, the methods disclosed herein minimize liver toxicity in the patient receiving the ADC for conditioning. For example, in certain embodiments, the methods disclosed herein result in a liver marker level remaining below a known toxic level in the patient for more than about 24 hours, about 48 hours, about 72 hours, or about 96 hours. In other embodiments, the methods disclosed herein result in a liver marker level remaining within a reference range in the patient for more than about 24 hours, about 48 hours, about 72 hours, or about 96 hours. In certain embodiments, the methods disclosed herein result in a liver marker level rising not more than about 1.5-fold above a reference range, not more than about 3-fold above a reference range, not more than about 5-fold above a reference range, or not more than about 10-fold above a reference range for more than about 24 hours, about 48 hours, about 72 hours, or about 96 hours. Examples of liver markers that can be used to test for toxicity include alanine aminotransaminase (ALT), lactate dehydrogenase (LDH), and aspartate aminotransaminase (AST). In certain embodiments, administration of an ADC as described herein, i.e., where two doses are administered instead of a single dose, results in a transient increase in a liver marker, e.g., AST, LDH, and/or ALT. In some instances, an elevated level of a liver marker indicating toxicity may be reached, but within a certain time period, e.g., about 12 hours, about 18 hours, about 24 hours, about 36 hours, about 48 hours, about 72 hours, about 3 days, about 3.5 days, about 4 days, about 4.5 days, about 5 days, about 5.5 days, about 6 days, about 6.5 days, about 7 days, about 7.5 days, or less than a week, the liver marker level returns to a normal level not associated with liver toxicity. For example, in a human (average adult male), a normal, non-toxic level of ALT is 7 to 55 units per liter (U/L); and a normal, non-toxic level of AST is 8 to 48 U/L. In certain embodiments, at least one of the patient's blood AST, ALT, or LDH levels does not reach a toxic level between administration of a first dose of the ADC and 14 days after administration of the first dose to the patient. For example, the patient may be administered a first dose and subsequently a second dose, a third dose, a fourth dose, or more doses within, e.g., 5, 10, or 14 days of being administered the first dose, yet at least one of the patient's blood AST, ALT, or LDH levels does not reach a toxic level between administration of a first dose of the ADC and 14 days after administration of the first dose to the patient.

In certain embodiments, at least one of the patient's blood AST, ALT, or LDH levels does not rise above normal levels, does not rise more than 1.5-fold above normal levels, does not rise more than 3-fold above normal levels, does not rise more than 5-fold above normal levels, or does not rise more than 10-fold above normal levels.

As described herein, hematopoietic stem cell transplant therapy can be administered to a subject in need of treatment so as to populate or re-populate one or more blood cell types. Hematopoietic stem cells generally exhibit multi-potency, and can thus differentiate into multiple different blood lineages including, but not limited to, granulocytes (e.g., promyelocytes, neutrophils, eosinophils, basophils), erythrocytes (e.g., reticulocytes, erythrocytes), thrombocytes (e.g., megakaryoblasts, platelet producing megakaryocytes, platelets), monocytes (e.g., monocytes, macrophages), dendritic cells, microglia, osteoclasts, and lymphocytes (e.g., NK cells, B-cells and T-cells). Hematopoietic stem cells are additionally capable of self-renewal, and can thus give rise to daughter cells that have equivalent potential as the mother cell, and also feature the capacity to be reintroduced into a transplant recipient whereupon they home to the hematopoietic stem cell niche and re-establish productive and sustained hematopoiesis.

Hematopoietic stem cells can thus be administered to a patient defective or deficient in one or more cell types of the hematopoietic lineage in order to re-constitute the defective or deficient population of cells in vivo, thereby treating the pathology associated with the defect or depletion in the endogenous blood cell population. The compositions and methods described herein can thus be used to treat a non-malignant hemoglobinopathy (e.g., a hemoglobinopathy selected from the group consisting of sickle cell anemia, thalassemia, Fanconi anemia, aplastic anemia, and Wiskott-Aldrich syndrome). Additionally or alternatively, the compositions and methods described herein can be used to treat an immunodeficiency, such as a congenital immunodeficiency. Additionally or alternatively, the compositions and methods described herein can be used to treat an acquired immunodeficiency (e.g., an acquired immunodeficiency selected from the group consisting of HIV and AIDS). The compositions and methods described herein can be used to treat a metabolic disorder (e.g., a metabolic disorder selected from the group consisting of glycogen storage diseases, mucopolysaccharidoses, Gaucher's Disease, Hurlers Disease, sphingolipidoses, and metachromatic leukodystrophy).

Additionally or alternatively, the compositions and methods described herein can be used to treat a malignancy or proliferative disorder, such as a hematologic cancer, myeloproliferative disease. In the case of cancer treatment, the compositions and methods described herein may be administered to a patient so as to deplete a population of endogenous hematopoietic stem cells prior to hematopoietic stem cell transplantation therapy, in which case the transplanted cells can home to a niche created by the endogenous cell depletion step and establish productive hematopoiesis. This, in turn, can re-constitute a population of cells depleted during cancer cell eradication, such as during systemic chemotherapy. Exemplary hematological cancers that can be treated using the compositions and methods described herein include, without limitation, acute myeloid leukemia, acute lymphoid leukemia, chronic myeloid leukemia, chronic lymphoid leukemia, multiple myeloma, diffuse large B-cell lymphoma, and non-Hodgkin's lymphoma, as well as other cancerous conditions, including neuroblastoma.

Additional diseases that can be treated with the compositions and methods described herein include, without limitation, adenosine deaminase deficiency and severe combined immunodeficiency, hyper immunoglobulin M syndrome, Chediak-Higashi disease, hereditary lymphohistiocytosis, osteopetrosis, osteogenesis imperfecta, storage diseases, thalassemia major, systemic sclerosis, systemic lupus erythematosus, multiple sclerosis, and juvenile rheumatoid arthritis.

The antibodies, antigen-binding fragments thereof, ligands, and conjugates described herein may be used to induce solid organ transplant tolerance. For instance, the compositions and methods described herein may be used to deplete or ablate a population of cells from a target tissue (e.g., to deplete hematopoietic stem cells from the bone marrow stem cell niche). Following such depletion of cells from the target tissues, a population of stem or progenitor cells from an organ donor (e.g., hematopoietic stem cells from the organ donor) may be administered to the transplant recipient, and following the engraftment of such stem or progenitor cells, a temporary or stable mixed chimerism may be achieved, thereby enabling long-term transplant organ tolerance without the need for further immunosuppressive agents. For example, the compositions and methods described herein may be used to induce transplant tolerance in a solid organ transplant recipient (e.g., a kidney transplant, lung transplant, liver transplant, and heart transplant, among others). The compositions and methods described herein are well-suited for use in connection the induction of solid organ transplant tolerance, for instance, because a low percentage temporary or stable donor engraftment is sufficient to induce long-term tolerance of the transplanted organ.

In addition, the compositions and methods described herein can be used to treat cancers directly, such as cancers characterized by cells that are CD45+. For instance, the compositions and methods described herein can be used to treat leukemia, particularly in patients that exhibit CD45+ leukemic cells. By depleting CD45+ cancerous cells, such as leukemic cells, the compositions and methods described herein can be used to treat various cancers directly. Exemplary cancers that may be treated in this fashion include hematological cancers, such as acute myeloid leukemia, acute lymphoid leukemia, chronic myeloid leukemia, chronic lymphoid leukemia, multiple myeloma, diffuse large B-cell lymphoma, and non-Hodgkin's lymphoma, In addition, the compositions and methods described herein can be used to treat autoimmune disorders. For instance, an antibody, antigen-binding fragment thereof, or ligand can be administered to a subject, such as a human patient suffering from an autoimmune disorder, so as to kill a CD45+ immune cell. The CD45+ immune cell may be an autoreactive lymphocyte, such as a T-cell that expresses a T-cell receptor that specifically binds, and mounts an immune response against, a self antigen. By depleting self-reactive CD45+ cells, the compositions and methods described herein can be used to treat autoimmune pathologies, such as those described below. Additionally or alternatively, the compositions and methods described herein can be used to treat an autoimmune disease by depleting a population of endogenous hematopoietic stem cells prior to hematopoietic stem cell transplantation therapy, in which case the transplanted cells can home to a niche created by the endogenous cell depletion step and establish productive hematopoiesis. This, in turn, can re-constitute a population of cells depleted during autoimmune cell eradication.

Autoimmune diseases that can be treated using the compositions and methods described herein include, without limitation, psoriasis, psoriatic arthritis, Type 1 diabetes mellitus (Type 1 diabetes), rheumatoid arthritis (RA), human systemic lupus (SLE), multiple sclerosis (MS), inflammatory bowel disease (IBD), lymphocytic colitis, acute disseminated encephalomyelitis (ADEM), Addison's disease, alopecia universalis, ankylosing spondylitis, antiphospholipid antibody syndrome (APS), aplastic anemia, autoimmune hemolytic anemia, autoimmune hepatitis, autoimmune inner ear disease (AIED), autoimmune lymphoproliferative syndrome (ALPS), autoimmune oophoritis, Balo disease, Behcet's disease, bullous pemphigoid, cardiomyopathy, Chagas' disease, chronic fatigue immune dysfunction syndrome (CFIDS), chronic inflammatory demyelinating polyneuropathy, Crohn's disease, cicatrical pemphigoid, coeliac sprue-dermatitis herpetiformis, cold agglutinin disease, CREST syndrome, Degos disease, discoid lupus, dysautonomia, endometriosis, essential mixed cryoglobulinemia, fibromyalgia-fibromyositis, Goodpasture's syndrome, Grave's disease, Guillain-Barre syndrome (GBS), Hashimoto's thyroiditis, Hidradenitis suppurativa, idiopathic and/or acute thrombocytopenic purpura, idiopathic pulmonary fibrosis, IgA neuropathy, interstitial cystitis, juvenile arthritis, Kawasaki's disease, lichen planus, Lyme disease, Meniere disease, mixed connective tissue disease (MCTD), myasthenia gravis, neuromyotonia, opsoclonus myoclonus syndrome (OMS), optic neuritis, Ord's thyroiditis, pemphigus vulgaris, pernicious anemia, polychondritis, polymyositis and dermatomyositis, primary biliary cirrhosis, polyarteritis nodosa, polyglandular syndromes, polymyalgia rheumatica, primary agammaglobulinemia, Raynaud phenomenon, Reiter's syndrome, rheumatic fever, sarcoidosis, scleroderma, Sjögren's syndrome, stiff person syndrome, Takayasu's arteritis, temporal arteritis (also known as "giant cell arteritis"), ulcerative colitis, collagenous colitis, uveitis, vasculitis, vitiligo, vulvodynia ("vulvar vestibulitis"), and Wegener's granulomatosis.

EXAMPLES

Example 1: Anti-CD45-ADC (104-PBD) Kills T Cells In Vitro

The anti-CD45-ADC, 104-PBD, was assessed for T cell killing activity in an in vitro T cell killing assay. 104-PBD contains the variable regions of monoclonal antibody 104, a commercially available anti-CD45 antibody that binds the CD45.2 isoform (BioLegend, San Diego, CA), and is also known as mAb Ly-5.2. The variable regions of mAb 104 were coupled to a human IgG constant region containing S239C and N297A Fc substitutions for conjugation to tesirine via the cysteine residue. PBMC were cultured under a variety of conditions to promote survival and expansion of murine T cells. 25,000 T cells were seeded per well and ADCs were added to the wells at various concentrations before being placed in an incubator at 37° C. and 5% $CO_2$. Following 3 days of culture, each sample were analyzed by flow cytometry. T cell number (FIG. 2A) was determined by enumerating the number of live, CD3+ T cells recovered from each well by flow cytometric analysis. The percentage of Ki-67+ T cells was measured by determining the number of live, CD3+ T cells expressing Ki-67 divided by the total number of live, CD3+ T cells within the sample. A non-specific human IgG conjugated to PDB ("Iso PBD") served as a negative control.

Figure 2B:
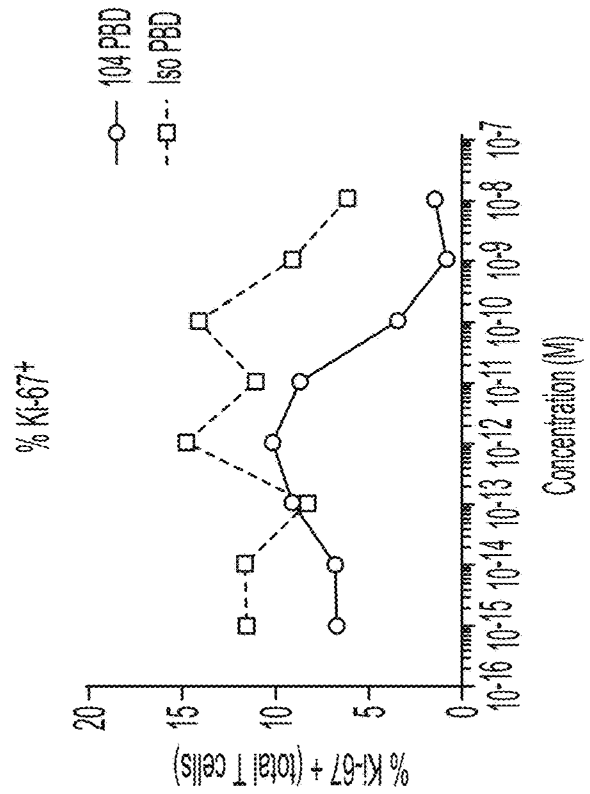
FIGS. 2A and 2B graphically depict the results of an in vitro T cell killing assay including an anti-CD45-PBD ADC (i.e., "104 PBD") in comparison to a negative control (i.e., "Iso PBD"). The results show the total number of T cells (FIG. 2A) or percentage of KI-67+ cells (FIG. 2B) (y-axis) as a function of ADC concentration (x-axis).
Figure 2A:
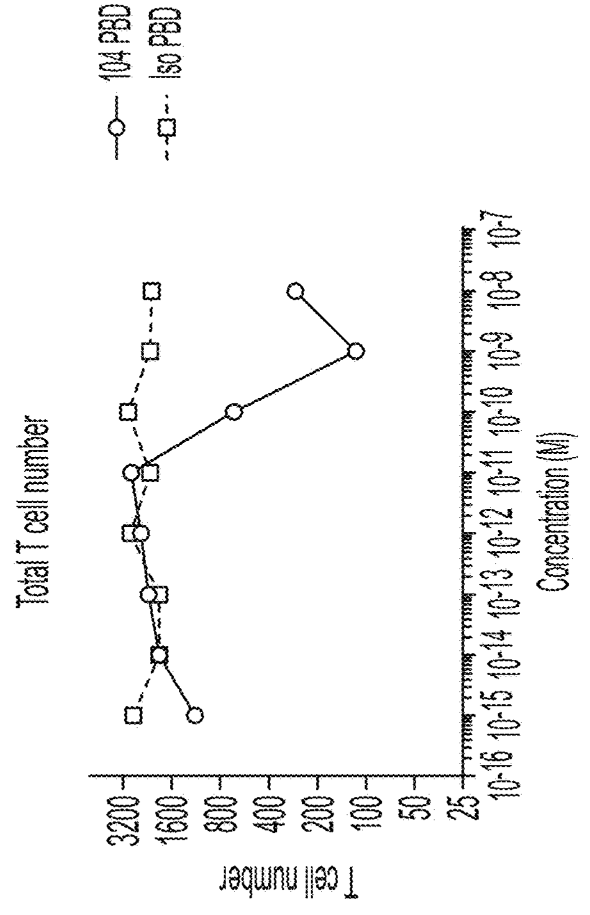

Ki-67+ T cells did not accumulate in vitro after treatment with 104-PBD. As shown in FIG. 2A, T cell death was observed with increasing doses of 104-PBD in vitro. Further, the representation of divided cells decreased with increasing doses of 104-PBD in vitro (FIG. 2B).

Example 2: In Vivo Efficacy of Anti-CD45-ADC (104-PBD) in a Mouse Model of Alloreactive T Cell Activation Treatment with the anti-CD45-ADC, 104-PBD, was assessed in vivo in a mouse model of alloreactivity (see Table 4 for study design). In brief, total B10.D2 splenocytes were transferred into Balb/c (CD45.2) hosts (minor HA mismatch) 24 hours after pre-transplant conditioning with 650 cGy Total Body Irradiation (TBI). After 7 days, 1 mg/kg or 3 mg/kg of anti-CD45-ADC (104-PBD; n=5 mice/treatment group/inoculum) or 3 mg/kg of a negative (isotype) control ("Iso-PBD") were administered. Peripheral blood and spleen were collected from mice and assessed by flow cytometry five days after ADC administration.

Figure 3A:
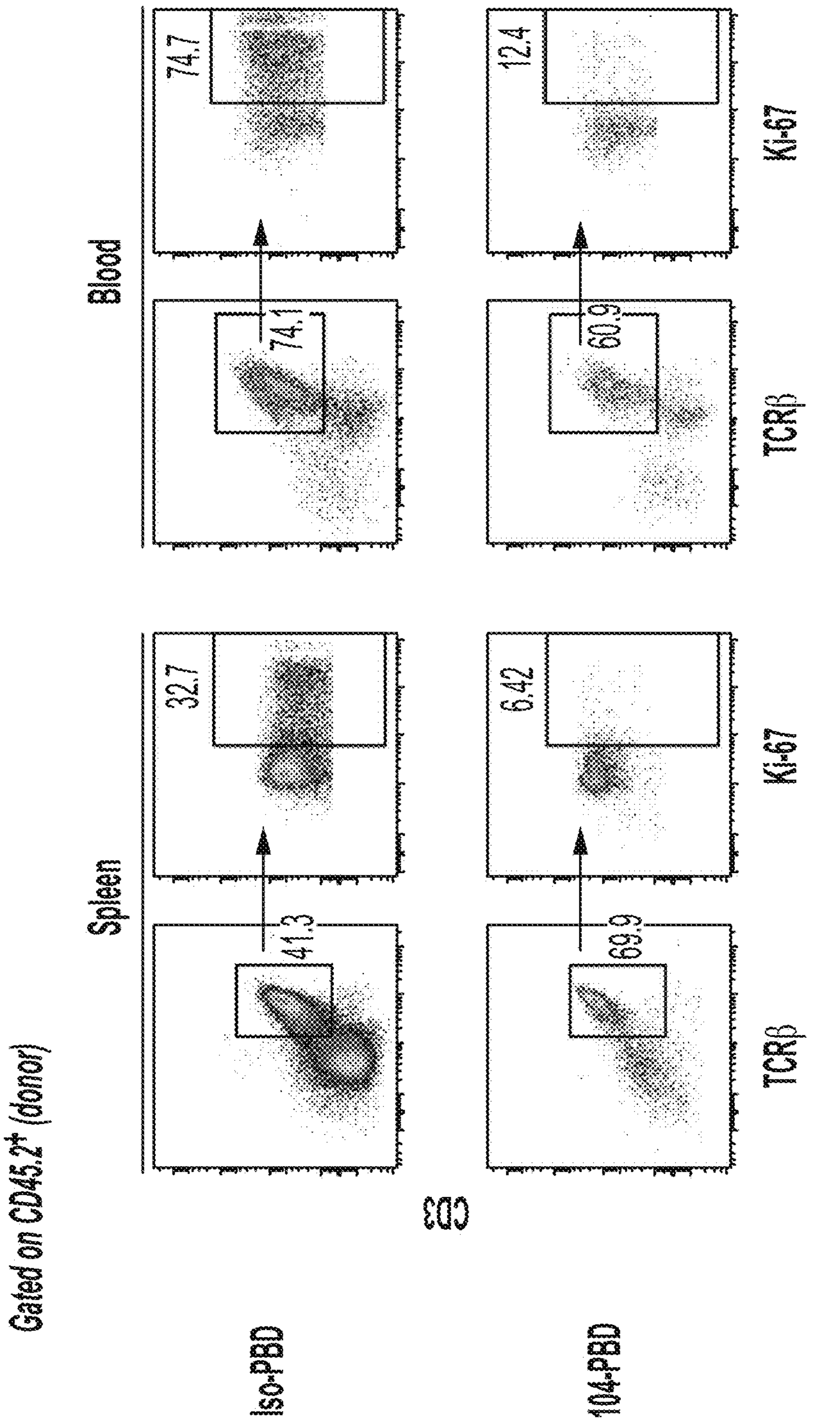
FIGS. 3A and 3B graphically depict the results of an in vivo depletion assay in a mouse model of alloreactive T cell activation, treated with an anti-CD45-ADC (i.e., "104 PBD").
Figure 3B:
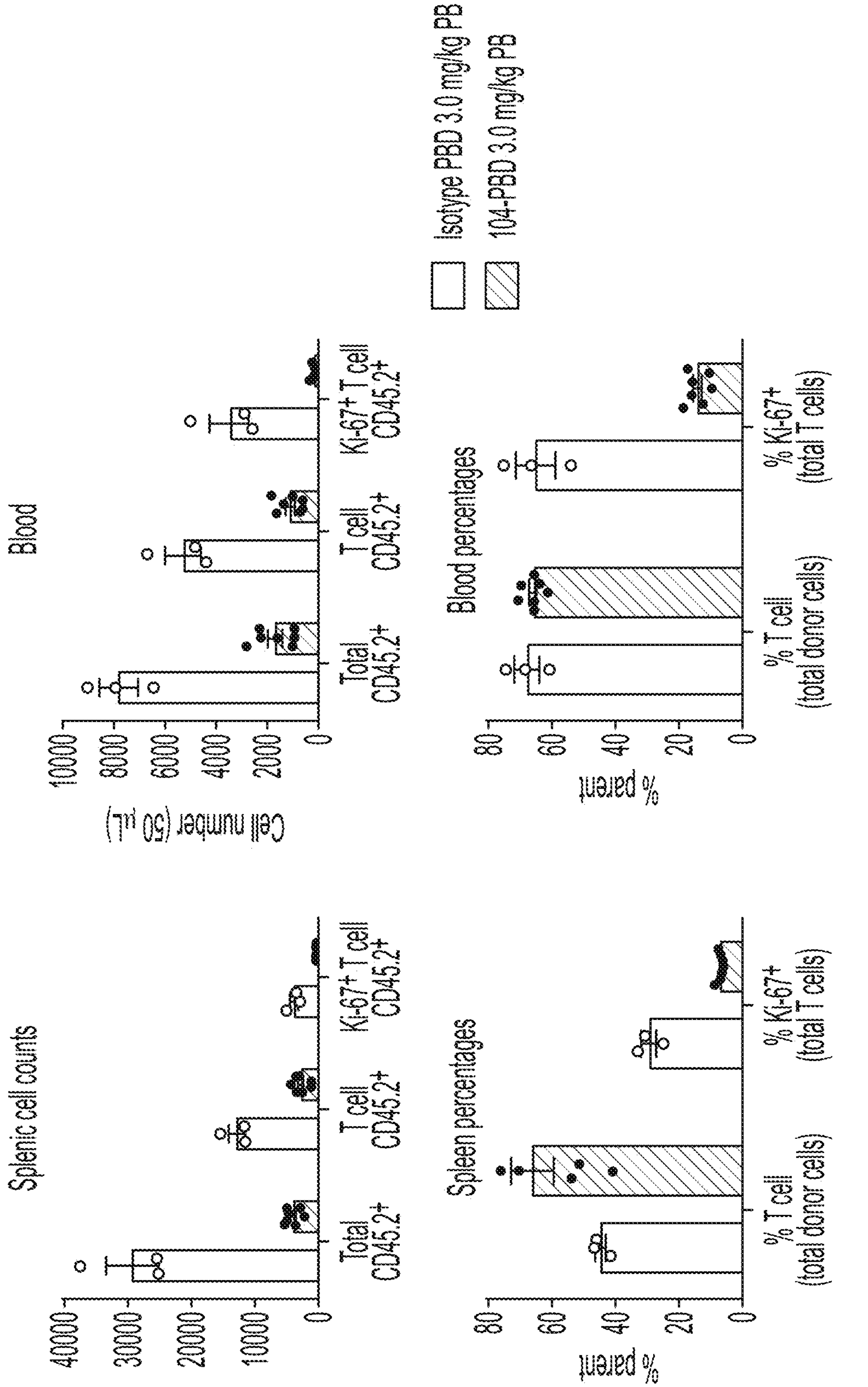

As shown in FIGS. 3A and 3B, dosing with anti-CD45-ADC (i.e., 104-PBD) as compared to Isotype-PBD substantially reduced the number of donor T cells in the mouse model of alloreactive T cell activation. Further, the proportion of divided cells decreased following treatment with anti-CD45-ADC (i.e., 104-PBD) in comparison to treatment with Isotype PBD. These results indicate that in vivo exposure to anti-CD45-ADC (i.e., 104-PBD) results in preferential killing of activated/dividing T cells. This confirms that, as observed in vivo and in vitro, 104-PBD is effective at killing autoreactive or allo-rejecting T-cells.

TABLE 4

| scGVHD Mouse Model Study | | | | |
|---|---|---|---|---|
| Splenocytes/ mouse | IRR Dose | Treatment | Tx Day (post inoculation) | N |
| 1 × $10^8$ | 650 cGy | — | 7 | 5 |
| | 650 cGy | Isotype-PBD | | 5 |
| | | (3 mg/kg) | | 5 |
| | 650 cGy | 1 mg/kg | | 5 |
| | | 104 S239C IHH-PBD | | |
| | 650 cGy | 3 mg/kg | | 5 |
| | | 104 S239C IHH-PBD | | 5 |
| | 650 cGy | 3 mg/kg | | 5 |
| | | 104 S239C IHH-PBD | | 5 |
| | 650 cGy | 3 mg/kg | | 5 |
| | | 104 S239C IHH-PBD | | |

Example 3: In Vivo Efficacy of an Anti-CD45-PBD ADC in a Humanized NSG Mouse Model An anti-CD45 antibody drug conjugate (ADC) comprising an antibody capable of specifically binding human CD45 conjugated to a PBD cytotoxin (teserine) was assessed in this Example ("CD45-PBD"). The anti-CD45 antibody of the ADC included the amino acid substitutions L234A L235A D265C and H435A in the Fc region.

Figure 4:
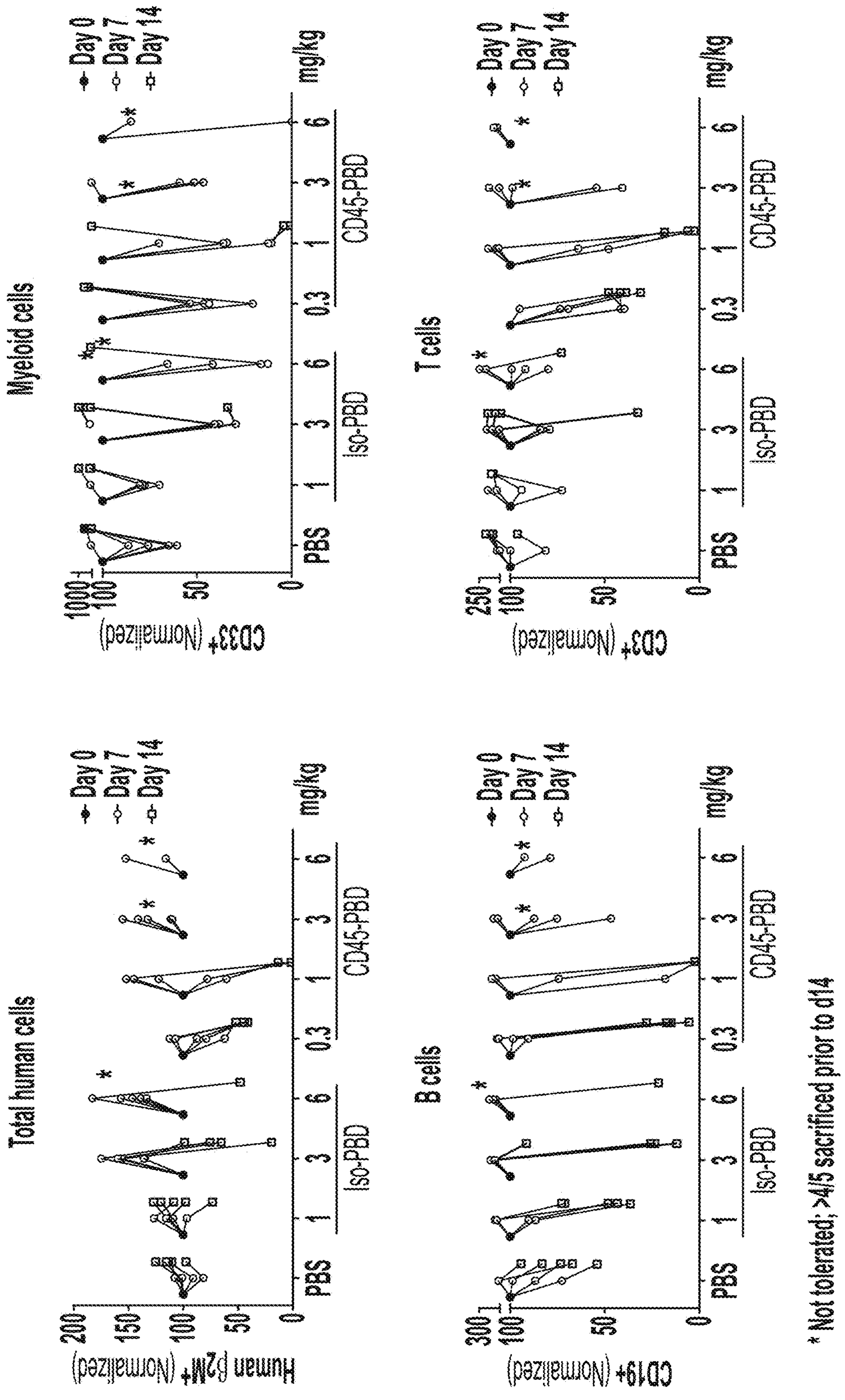
FIG. 4 graphically depicts the results of an in vivo depletion assay in humanized NSG mice treated with an anti-CD45 antibody drug conjugate (CD45-PBD), in which depletion of human cells in peripheral blood was assessed. hNSG mice were administered the indicated single doses of either vehicle (PBS), Isotype control-PBD ("Iso-PBD"), or CD45-PBD. Peripheral blood was collected at the indicated time points and evaluated for total human hematopoietic cell content ($h\beta_2M^+$), myeloid cell content ($CD33^+$), B cell content ($CD19^+$), and T cell content ($CD3^+$). The results are presented as percent depletion normalized to baseline.

CD45-PBD was assessed for its ability to deplete peripheral blood lymphocytes, bone marrow (BM) HSCs, or mature single positive (SP) thymocytes in humanized NSG mice (FIG. 4). hNSG mice were administered the indicated single doses of either vehicle (PBS), an isotype control antibody conjugated to PBD ("Iso-PBD"), or CD45-PBD. CD45-PBD was administered to mice at a single dose of 0.3 mg/kg, 1 mg/kg, 3 mg/kg, or 6 mg/kg ADC. Iso-PBD was administered to mice at a single dose of 1 mg/kg, 3 mg/kg, or 6 mg/kg ADC.

Peripheral blood was collected at Day 0, Day 7, and Day 14 and evaluated for total human hematopoietic cell content ($h\beta_2M^+$), myeloid cell content ($CD33^+$), B cell content ($CD19^+$), and T cell content ($CD3^+$). The results from the peripheral blood studies are presented in FIG. 4. These results indicate that dose-dependent depletion of human cells was achieved in peripheral blood at tolerated doses of CD45-PBD. CD45-PBD doses greater than or equal to 3 mg/kg were not tolerated.

Figure 5:
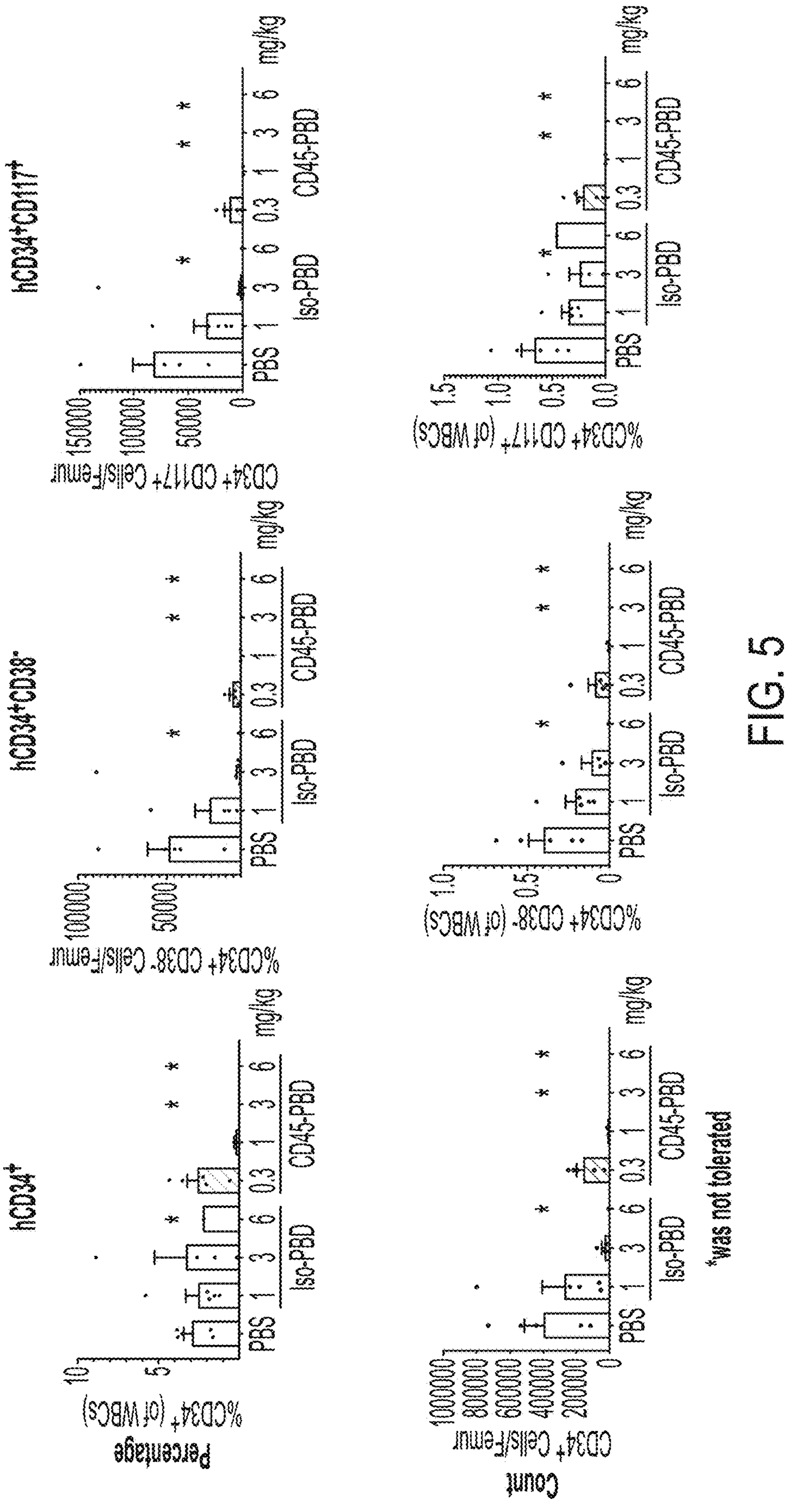
FIG. 5 graphically depicts the results of an in vivo depletion assay in humanized NSG mice treated with an anti-CD45-ADC (CD45-PBD), in which depletion of human cells in bone marrow was assessed. hNSG mice were administered the indicated single doses of either vehicle (PBS), Isotype-PBD, or CD45-PBD. BM samples were collected at Day 14 post treatment and evaluated for human progenitor cell/HSC content. The results are presented as percentage of human cells and absolute number/femur.
Figure 6A:
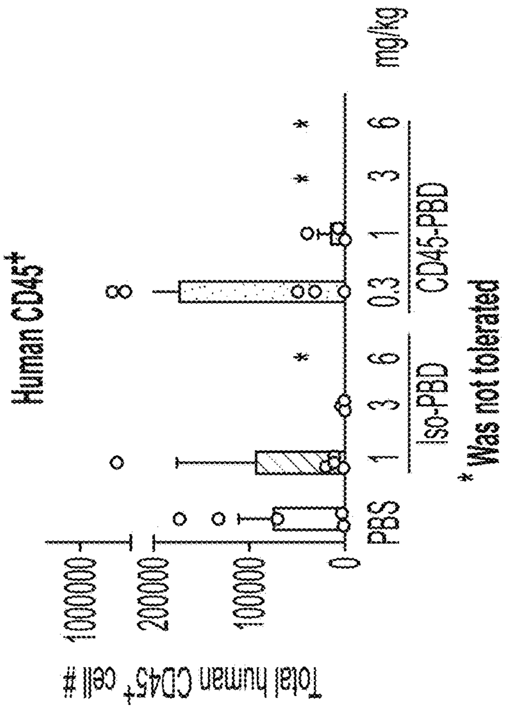
FIG. 6 graphically depicts the results of an in vivo depletion assay in humanized NSG mice treated with an anti-CD45-ADC (CD45-PBD), in which depletion of human CD45+ cells, double-positive (DP) thymocytes, mature $CD4^+$ single-positive (SP) thymocytes, or mature $CD8^+$ single-positive (SP) thymocytes was assessed 14 days post-treatment. hNSG mice were administered the indicated single doses of either vehicle (PBS), Isotype-PBD, or CD45-PBD.
Figure 6B:
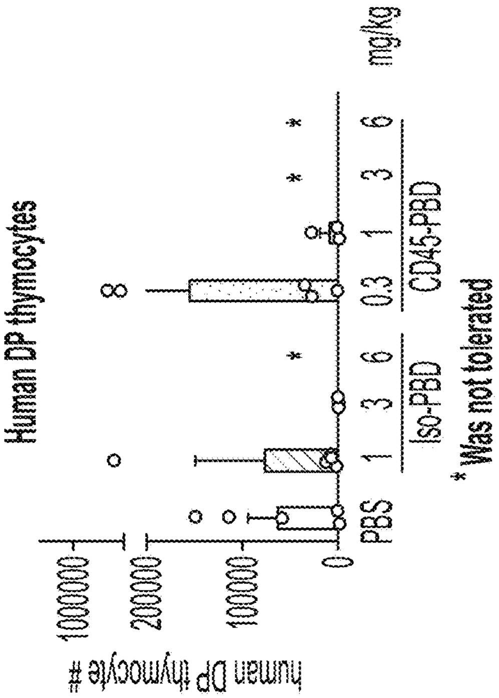
Figure 6C:
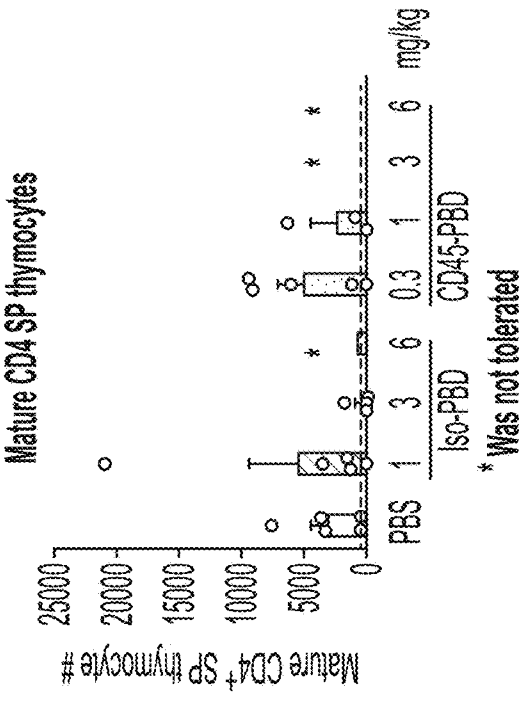
Figure 6D:
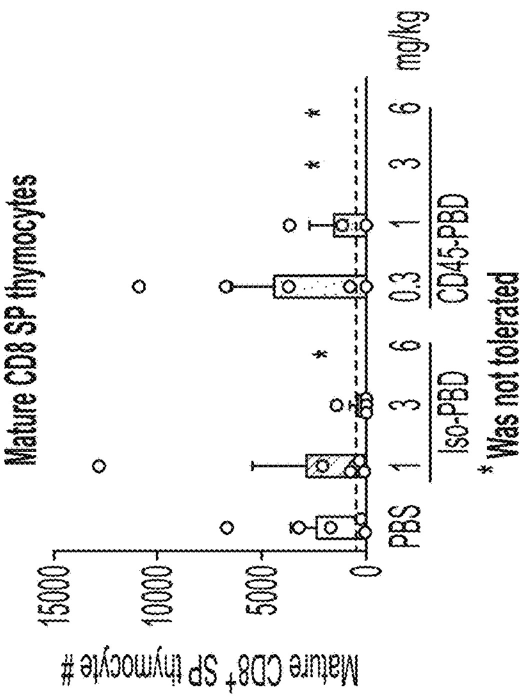

To assess bone marrow depletion, bone marrow samples were collected from mice at Day 14 post-treatment and evaluated for human progenitor cell/HSC content. The results from the bone marrow studies are described in FIG. 5, and are presented as the percentage of human cells ("Percentage") or absolute number of cells per femur ("Count"). These results indicated that CD45-PBD mediated targeted, dose-dependent and deep depletion of human progenitor cells and HSCs in the bone marrow after CD45-PBD treatment. Isotype-PBD had significant platform toxicity in bone marrow at elevated doses of 3 mg/kg and 6 mg/kg.

Next, depletion of double positive (DP) thymocytes and mature single positive (SP) thymocytes by CD45-PBD was assessed. hNSG mice were randomized and treated with increasing doses of Isotype-PBD, CD45-PBD, or vehicle (PBS). The results of the thymocyte depletion study are shown in FIG. 6. A dose-dependent depletion of human CD45+ cells and human double positive (DP) thymocytes was observed in animals treated with CD45-PBD. Incomplete targeted depletion of mature CD4 and CD8 SP thymocytes was observed at tolerated doses of CD45-PBD. Depletion of double positive (DP) thymocytes observed at elevated doses of isotype-PBD is consistent with the known platform toxicity of PBD.

Example 4: In Vivo Efficacy of an Anti-CD45-IGN ADC in a Humanized NSG Mouse Model An anti-CD45 antibody drug conjugate (ADC) comprising an antibody capable of specifically binding human CD45 conjugated to an IGN cytotoxin (DGN549) was assessed in this Example ("CD45-IGN"). The anti-CD45 antibody of the ADC included the amino acid substitutions L234A L235A D265C and H435A in the Fc region.

hNSG mice were administered single doses of either vehicle (PBS), an isotype control antibody conjugated to IGN ("Iso-IGN"), or CD45-IGN. CD45-IGN was administered to mice at a single dose of 0.3 mg/kg, 1 mg/kg, 3 mg/kg, or 6 mg/kg ADC. Iso-IGN was administered to mice at a single dose of 1 mg/kg, 3 mg/kg, or 6 mg/kg ADC.

Figure 7:
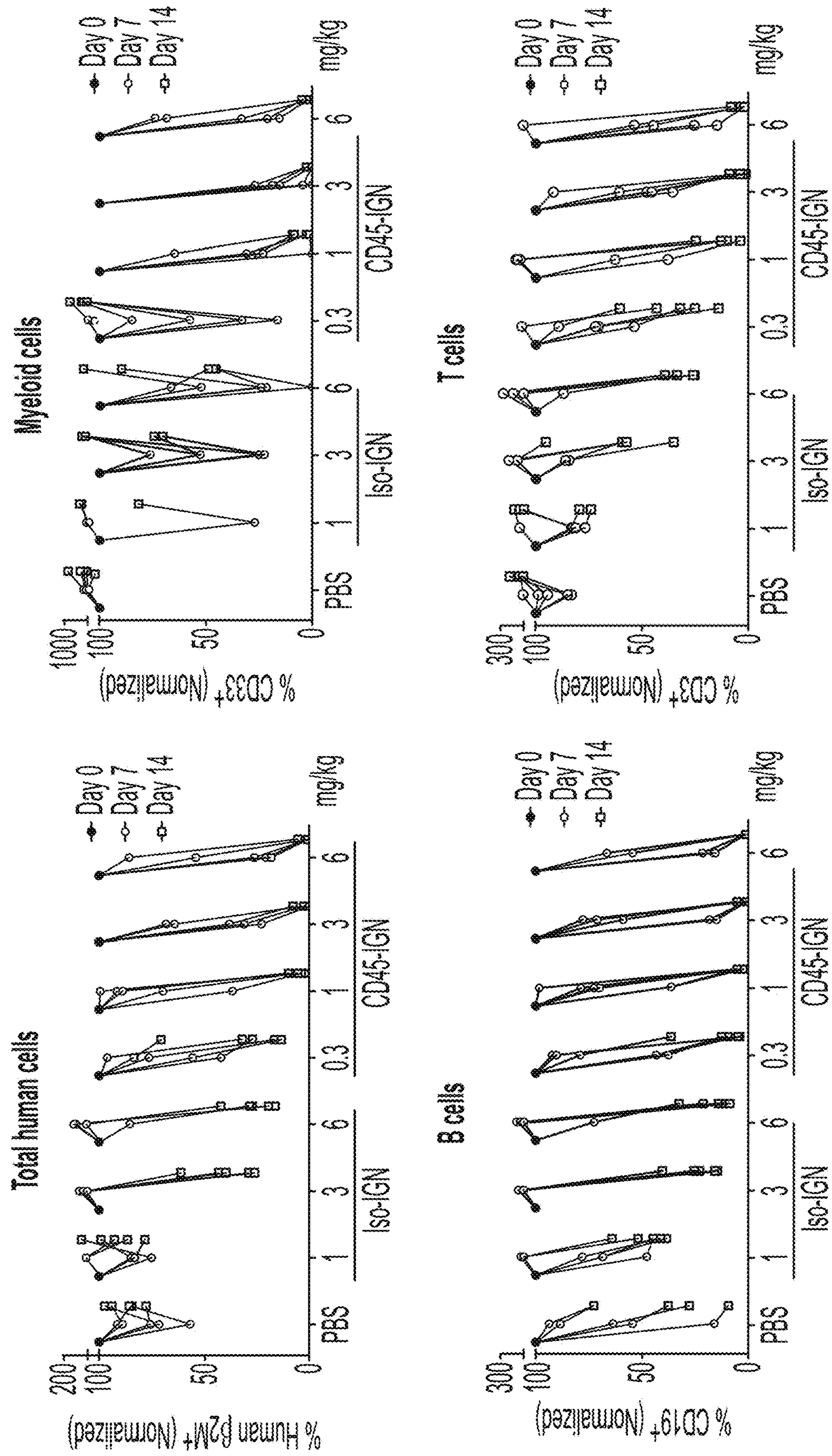
FIG. 7 graphically depicts the results of an in vivo depletion assay in humanized NSG mice treated with an anti-CD45 antibody drug conjugate (CD45-IGN), in which depletion of human cells in peripheral blood was assessed. hNSG mice were administered the indicated single doses of either vehicle (PBS), Isotype control-IGN ("Iso-IGN"), or CD45-IGN. Peripheral blood was collected at the indicated time points and evaluated for total human hematopoietic cell content ($h\beta_2M^+$), myeloid cell content ($CD33^+$), B cell content ($CD19^+$), and T cell content ($CD3^+$). The results are presented as percent depletion normalized to baseline.

Peripheral blood was collected at Day 0, Day 7, and Day 14 and evaluated for total human hematopoietic cell content ($h\beta_2M^+$), myeloid cell content ($CD33^+$), B cell content ($CD19^+$), and T cell content ($CD3^+$). The results from the peripheral blood studies are presented in FIG. 7. These results indicate that dose-dependent depletion of human cells was achieved in peripheral blood following administration of a single dose of CD45-IGN. CD45-IGN was well-tolerated at all tested doses.

Figure 8:
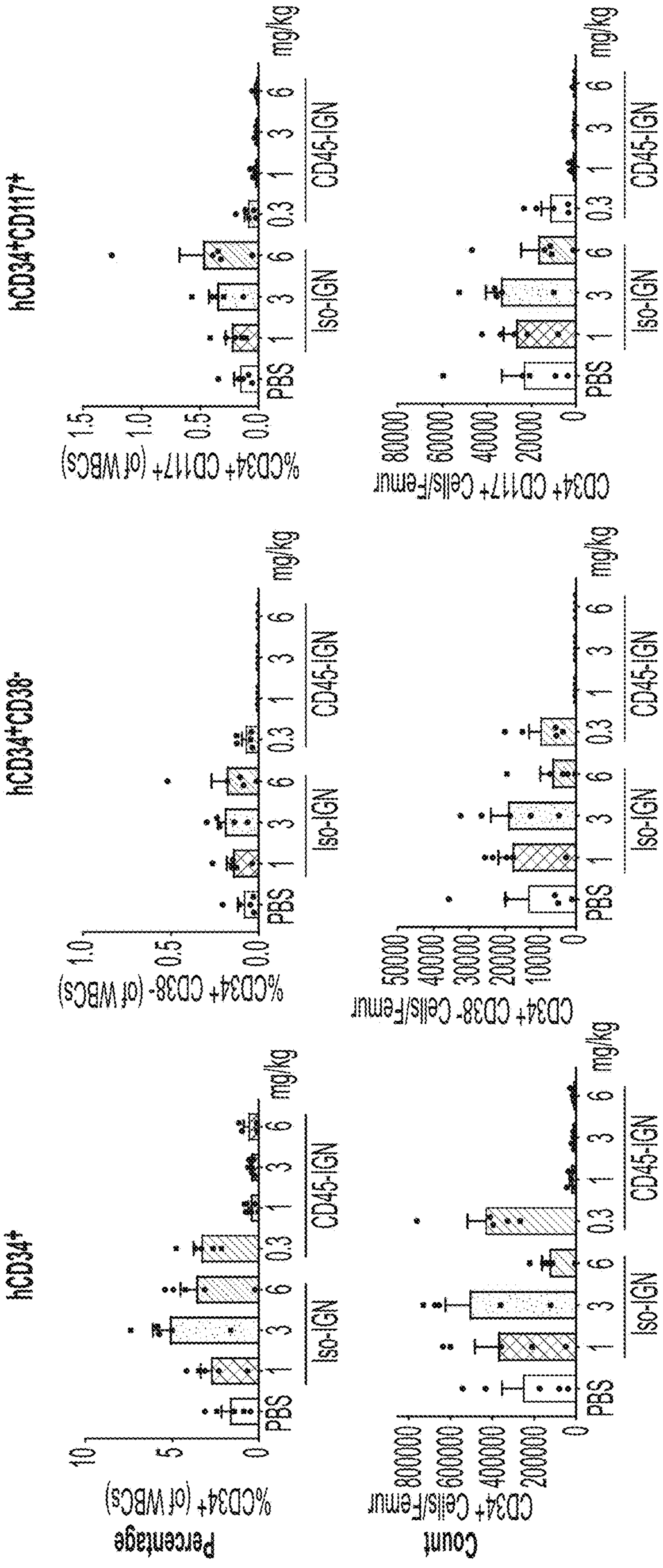
FIG. 8 graphically depicts the results of an in vivo depletion assay in humanized NSG mice treated with CD45-IGN, in which depletion of human cells in bone marrow was assessed. hNSG mice were administered the indicated single doses of either vehicle (PBS), Isotype-IGN, or CD45-IGN. BM samples were collected at Day 14 post treatment and evaluated for human progenitor cell/HSC content. The results are presented as percentage of human cells and absolute number/femur.

Bone marrow depletion was assessed by collection of bone marrow samples from mice at Day 14 post-treatment. Samples were evaluated for human progenitor cell/HSC content. The results from the bone marrow studies are described in FIG. 8, and are presented as the percentage of human cells ("Percentage") or absolute number of cells per femur ("Count"). These results indicated that CD45-IGN mediated targeted, dose-dependent and deep depletion of human progenitor cells and HSCs in the bone marrow after CD45-IGN treatment. Isotype-IGN had no significant effect at any tested dose.

Figure 9:
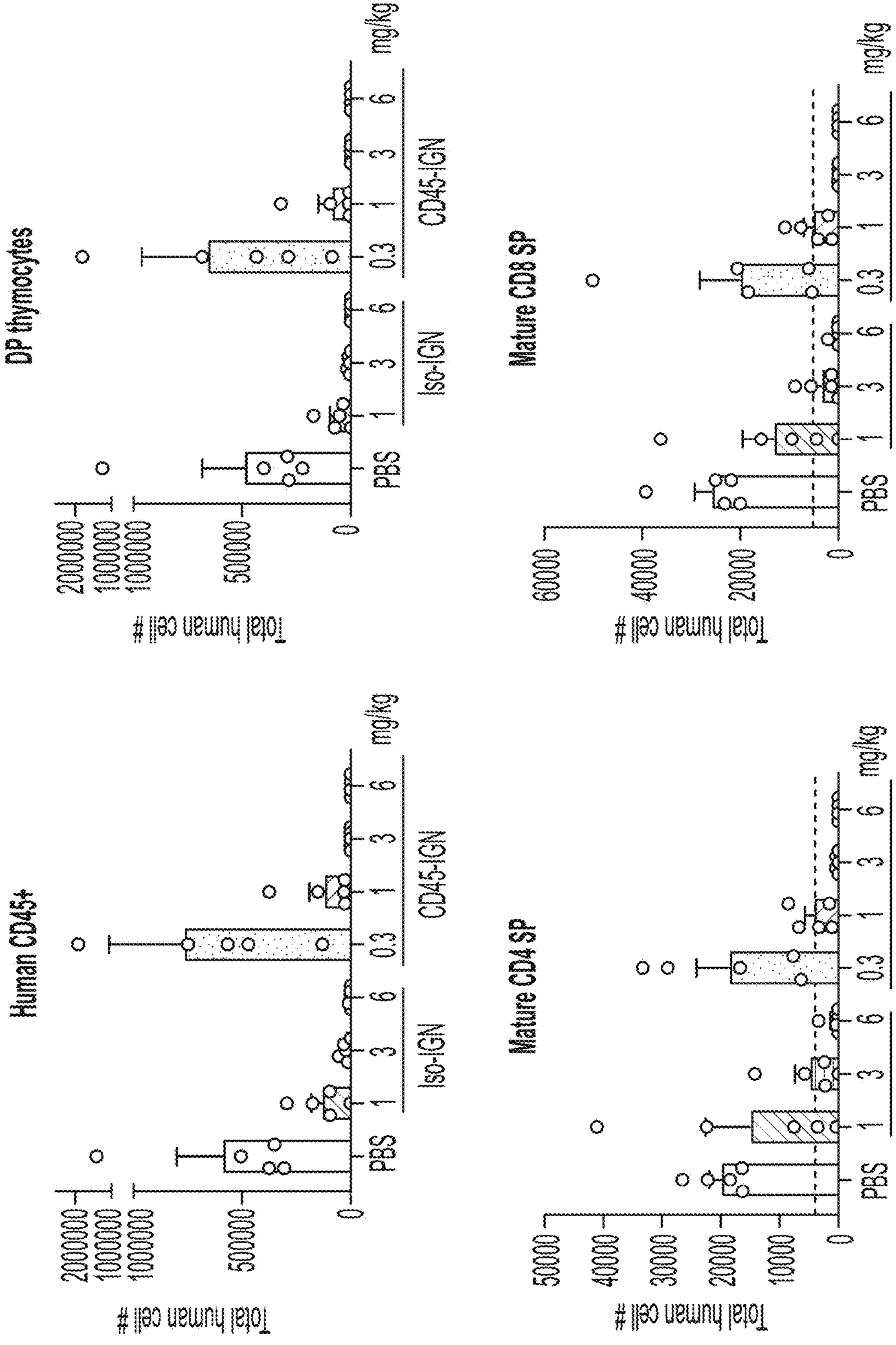
FIG. 9 graphically depicts the results of an in vivo depletion assay in humanized NSG mice treated with CD45-IGN, in which depletion of human CD45+ cells, double-positive (DP) thymocytes, mature $CD4^+$ single-positive (SP) thymocytes, or mature $CD8^+$ single-positive (SP) thymocytes was assessed. hNSG mice were administered the indicated single doses of either vehicle (PBS), Isotype-IGN, or CD45-IGN.

Depletion of double positive (DP) thymocytes and mature single positive (SP) thymocytes by CD45-IGN was also assessed. hNSG mice were randomized and treated with increasing doses of Isotype-IGN, CD45-IGN, or vehicle control (PBS). The results of the thymocyte depletion study are shown in FIG. 9. A dose-dependent depletion of human 0045+ cells and human double positive (DP) thymocytes was observed in animals treated with CD45-IGN. In addition, targeting via CD45-IGN resulted in deeper depletion of 004 and 008 SP thymocytes as compared with Isotype-IGN at matched doses, demonstrating that CD45-IGN ADCs achieve robust and targeted depletion of human thymocytes.

TABLE 5

SEQUENCE LISTING TABLE

| SEQUENCE IDENTIFIER | DESCRIPTION | SEQUENCE |
|---|---|---|
| SEQ ID NO: 1 | CD45RO (Human CD45 Isoform) | MTMYLWLKLLAFGFAFLDTEVFVTGQSPTPSPTDAY LNASETTTLSPSGSAVISTTTIATTPSKPTCDEKYA NITVDYLYNKETKLFTAKLNVNENVECGNNTCTNNE VHNLTECKNASVSISHNSCTAPDKTLILDVPPGVEK FQLHDCTQVEKADTTICLKWKNIETFTCDTQNITYR FQCGNMIFDNKEIKLENLEPEHEYKCDSEILYNNHK FTNASKIIKTDFGSPGEPQIIFCRSEAAHQGVITWN PPQRSFHNFTLCYIKETEKDCLNLDKNLIKYDLQNL KPYTKYVLSLHAYIIAKVQRNGSAAMCHFTTKSAPP SQVWNMTVSMTSDNSMHVKCRPPRDRNGPHERYHLE VEAGNTLVRNESHKNCDFRVKDLQYSTDYTFKAYFH NGDYPGEPFILHHSTSYNSKALIAFLAFLIIVTSIA LLVVLYKIYDLHKKRSCNLDEQQELVERDDEKQLMN VEPIHADILLETYKRKIADEGRLFLAEFQSIPRVFS KFPIKEARKPFNQNKNRYVDILPYDYNRVELSEING DAGSNYINASYIDGFKEPRKYIAAQGPRDETVDDFW RMIWEQKATVIVMVTRCEEGNRNKCAEYWPSMEEGT RAFGDVVVKINQHKRCPDYIIQKLNIVNKKEKATGR EVTHIQFTSWPDHGVPEDPHLLLKLRRRVNAFSNFF SGPIVVHCSAGVGRTGTYIGIDAMLEGLEAENKVDV YGYVVKLRRQRCLMVQVEAQYILIHQALVEYNQFGE TEVNLSELHPYLHNMKKRDPPSEPSPLEAEFQRLPS YRSWRTQHIGNQEENKSKNRNSNVIPYDYNRVPLKH ELEMSKESEHDSDESSDDDSDSEEPSKYINASFIMS YWKPEVMIAAQGPLKETIGDFWQMIFQRKVKVIVML TELKHGDQEICAQYWGEGKQTYGDIEVDLKDTDKSS TYTLRVFELRHSKRKDSRTVYQYQYTNWSVEQLPAE PKELISMIQVVKQKLPQKNSSEGNKHHKSTPLLIHC RDGSQQTGIFCALLNLLESAETEEVVDIFQVVKALR KARPGMVSTFEQYQFLYDVIASTYPAQNGQVKKNNH QEDKIEFDNEVDKVKQDANCVNPLGAPEKLPEAKEQ AEGSEPTSGTEGPEHSVNGPASPALNQGS |
| SEQ ID NO: 2 | CD45RA (Human CD45 Isoform) | MTMYLWLKLLAFGFAFLDTEVFVTGQSPTPSPTGLT TAKMPSVPLSSDPLPTHTTAFSPASTFERENDFSET TTSLSPDNTSTQVSPDSLDNASAFNTTDAYLNASET TTLSPSGSAVISTTTIATTPSKPTCDEKYANITVDY LYNKETKLFTAKLNVNENVECGNNTCTNNEVHNLTE CKNASVSISHNSCTAPDKTLILDVPPGVEKFQLHDC TQVEKADTTICLKWKNIETFTCDTQNITYRFQCGNM |

TABLE 5-continued

SEQUENCE LISTING TABLE

| SEQUENCE IDENTIFIER | DESCRIPTION | SEQUENCE |
|---|---|---|
| | | IFDNKEIKLENLEPEHEYKCDSEILYNNHKFTNASK IIKTDFGSPGEPQIIFCRSEAAHQGVITWNPPQRSF HNFTLCYIKETEKDCLNLDKNLIKYDLQNLKPYTKY VLSLHAYIIAKVQRNGSAAMCHFTTKSAPPSQVWNM TVSMTSDNSMHVKCRPPRDRNGPHERYHLEVEAGNT LVRNESHKNCDFRVKDLQYSTDYTFKAYFHNGDYPG EPFILHHSTSYNSKALIAFLAFLIIVTSIALLVVLY KIYDLHKKRSCNLDEQQELVERDDEKQLMNVEPIHA DILLETYKRKIADEGRLFLAEFQSIPRVFSKFPIKE ARKPFNQNKNRYVDILPYDYNRVELSEINGDAGSNY INASYIDGFKEPRKYIAAQGPRDETVDDFWRMIWEQ KATVIVMVTRCEEGNRNKCAEYWPSMEEGTRAFGDV VVKINQHKRCPDYIIQKLNIVNKKEKATGREVTHIQ FTSWPDHGVPEDPHLLLKLRRRVNAFSNFFSGPIW HCSAGVGRTGTYIGIDAMLEGLEAENKVDVYGYVVK LRRQRCLMVQVEAQYILIHQALVEYNQFGETEVNLS ELHPYLHNMKKRDPPSEPSPLEAEFQRLPSYRSWRT QHIGNQEENKSKNRNSNVIPYDYNRVPLKHELEMSK ESEHDSDESSDDDSDSEEPSKYINASFIMSYWKPEV MIAAQGPLKETIGDFWQMIFQRKVKVIVMLTELKHG DQEICAQYWGEGKQTYGDIEVDLKDTDKSSTYTLRV FELRHSKRKDSRTVYQYQYTNWSVEQLPAEPKELIS MIQVVKQKLPQKNSSEGNKHHKSTPLLIHCRDGSQQ TGIFCALLNLLESAETEEVVDIFQVVKALRKARPGM VSTFEQYQFLYDVIASTYPAQNGQVKKNNHQEDKIE FDNEVDKVKQDANCVNPLGAPEKLPEAKEQAEGSEP TSGTEGPEHSVNGPASPALNQGS |
| SEQ ID NO: 3 | CD45RB (Human CD45 Isoform) | MTMYLWLKLLAFGFAFLDTEVFVTGQSPTPSPTGVS SVQTPHLPTHADSQTPSAGTDTQTFSGSAANAKLNP TPGSNAISDAYLNASETTTLSPSGSAVISTTTIATT PSKPTCDEKYANITVDYLYNKETKLFTAKLNVNENV ECGNNTCTNNEVHNLTECKNASVSISHNSCTAPDKT LILDVPPGVEKFQLHDCTQVEKADTTICLKWKNIET FTCDTQNITYRFQCGNMIFDNKEIKLENLEPEHEYK CDSEILYNNHKFTNASKIIKTDFGSPGEPQIIFCRS EAAHQGVITWNPPQRSFHNFTLCYIKETEKDCLNLD KNLIKYDLQNLKPYTKYVLSLHAYIIAKVQRNGSAA MCHFTTKSAPPSQVWNMTVSMTSDNSMHVKCRPPRD RNGPHERYHLEVEAGNTLVRNESHKNCDFRVKDLQY STDYTFKAYFHNGDYPGEPFILHHSTSYNSKALIAF LAFLIIVTSIALLVVLYKIYDLHKKRSCNLDEQQEL VERDDEKQLMNVEPIHADILLETYKRKIADEGRLFL AEFQSIPRVFSKFPIKEARKPFNQNKNRYVDILPYD YNRVELSEINGDAGSNYINASYIDGFKEPRKYIAAQ GPRDETVDDFWRMIWEQKATVIVMVTRCEEGNRNKC AEYWPSMEEGTRAFGDVVVKINQHKRCPDYIIQKLN IVNKKEKATGREVTHIQFTSWPDHGVPEDPHLLLKL RRRVNAFSNFFSGPIVVHCSAGVGRTGTYIGIDAML EGLEAENKVDVYGYVVKLRRQRCLMVQVEAQYILIH QALVEYNQFGETEVNLSELHPYLHNMKKRDPPSEPS PLEAEFQRLPSYRSWRTQHIGNQEENKSKNRNSNVI PYDYNRVPLKHELEMSKESEHDSDESSDDDSDSEEP SKYINASFIMSYWKPEVMIAAQGPLKETIGDFWQMI FQRKVKVIVMLTELKHGDQEICAQYWGEGKQTYGDI EVDLKDTDKSSTYTLRVFELRHSKRKDSRTVYQYQY TNWSVEQLPAEPKELISMIQVVKQKLPQKNSSEGNK HHKSTPLLIHCRDGSQQTGIFCALLNLLESAETEEV VDIFQVVKALRKARPGMVSTFEQYQFLYDVIASTYP AQNGQVKKNNHQEDKIEFDNEVDKVKQDANCVNPLG APEKLPEAKEQAEGSEPTSGTEGPEHSVNGPASPAL NQGS |
| SEQ ID NO: 4 | CD45RC (Human CD45 Isoform) | MTMYLWLKLLAFGFAFLDTEVFVTGQSPTPSPTDVP GERSTASTFPTDPVSPLTTTLSLAHHSSAALPARTS NTTITANTSDAYLNASETTTLSPSGSAVISTTTIAT TPSKPTCDEKYANITVDYLYNKETKLFTAKLNVNEN VECGNNTCTNNEVHNLTECKNASVSISHNSCTAPDK TLILDVPPGVEKFQLHDCTQVEKADTTICLKWKNIE TFTCDTQNITYRFQCGNMIFDNKEIKLENLEPEHEY KCDSEILYNNHKFTNASKIIKTDFGSPGEPQIIFCR SEAAHQGVITWNPPQRSFHNFTLCYIKETEKDCLNL DKNLIKYDLQNLKPYTKYVLSLHAYIIAKVQRNGSA AMCHFTTKSAPPSQVWNMTVSMTSDNSMHVKCRPPR DRNGPHERYHLEVEAGNTLVRNESHKNCDFRVKDLQ |

TABLE 5-continued

SEQUENCE LISTING TABLE

| SEQUENCE IDENTIFIER | DESCRIPTION | SEQUENCE |
|---|---|---|
| | | YSTDYTFKAYFHNGDYPGEPFILHHSTSYNSKALIA FLAFLIIVTSIALLVVLYKIYDLHKKRSCNLDEQQE LVERDDEKQLMNVEPIHADILLETYKRKIADEGRLF LAEFQSIPRVFSKFPIKEARKPFNQNKNRYVDILPY DYNRVELSEINGDAGSNYINASYIDGFKEPRKYIAA QGPRDETVDDFWRMIWEQKATVIVMVTRCEEGNRNK CAEYWPSMEEGTRAFGDVVVKINQHKRCPDYIIQKL NIVNKKEKATGREVTHIQFTSWPDHGVPEDPHLLLK LRRRVNAFSNFFSGPIVVHCSAGVGRTGTYIGIDAM LEGLEAENKVDVYGYVVKLRRQRCLMVQVEAQYILI HQALVEYNQFGETEVNLSELHPYLHNMKKRDPPSEP SPLEAEFQRLPSYRSWRTQHIGNQEENKSKNRNSNV IPYDYNRVPLKHELEMSKESEHDSDESSDDDSDSEE PSKYINASFIMSYWKPEVMIAAQGPLKETIGDFWQM IFQRKVKVIVMLTELKHGDQEICAQYWGEGKQTYGD IEVDLKDTDKSSTYTLRVFELRHSKRKDSRTVYQYQ YTNWSVEQLPAEPKELISMIQVVKQKLPQKNSSEGN KHHKSTPLLIHCRDGSQQTGIFCALLNLLESAETEE VVDIFQVVKALRKARPGMVSTFEQYQFLYDVIASTY PAQNGQVKKNNHQEDKIEFDNEVDKVKQDANCVNPL GAPEKLPEAKEQAEGSEPTSGTEGPEHSVNGPASPA LNQGS |
| SEQ ID NO: 5 | CD45RAB (Human CD45 Isoform) | MTMYLWLKLLAFGFAFLDTEVFVTGQSPTPSPTGLT TAKMPSVPLSSDPLPTHTTAFSPASTFERENDFSET TTSLSPDNTSTQVSPDSLDNASAFNTTGVSSVQTPH LPTHADSQTPSAGTDTQTFSGSAANAKLNPTPGSNA ISDAYLNASETTTLSPSGSAVISTTTIATTPSKPTC DEKYANITVDYLYNKETKLFTAKLNVNENVECGNNT CTNNEVHNLTECKNASVSISHNSCTAPDKTLILDVP PGVEKFQLHDCTQVEKADTTICLKWKNIETFTCDTQ NITYRFQCGNMIFDNKEIKLENLEPEHEYKCDSEIL YNNHKFTNASKIIKTDFGSPGEPQIIFCRSEAAHQG VITWNPPQRSFHNFTLCYIKETEKDCLNLDKNLIKY DLQNLKPYTKYVLSLHAYIIAKVQRNGSAAMCHFTT KSAPPSQVWNMTVSMTSDNSMHVKCRPPRDRNGPHE RYHLEVEAGNTLVRNESHKNCDFRVKDLQYSTDYTF KAYFHNGDYPGEPFILHHSTSYNSKALIAFLAFLII VTSIALLVVLYKIYDLHKKRSCNLDEQQELVERDDE KQLMNVEPIHADILLETYKRKIADEGRLFLAEFQSI PRVFSKFPIKEARKPFNQNKNRYVDILPYDYNRVEL SEINGDAGSNYINASYIDGFKEPRKYIAAQGPRDET VDDFWRMIWEQKATVIVMVTRCEEGNRNKCAEYWPS MEEGTRAFGDVVVKINQHKRCPDYIIQKLNIVNKKE KATGREVTHIQFTSWPDHGVPEDPHLLLKLRRRVNA FSNFFSGPIVVHCSAGVGRTGTYIGIDAMLEGLEAE NKVDVYGYVVKLRRQRCLMVQVEAQYILIHQALVEY NQFGETEVNLSELHPYLHNMKKRDPPSEPSPLEAEF QRLPSYRSWRTQHIGNQEENKSKNRNSNVIPYDYNR VPLKHELEMSKESEHDSDESSDDDSDSEEPSKYINA SFIMSYWKPEVMIAAQGPLKETIGDFWQMIFQRKVK VIVMLTELKHGDQEICAQYWGEGKQTYGDIEVDLKD TDKSSTYTLRVFELRHSKRKDSRTVYQYQYTNWSVE QLPAEPKELISMIQVVKQKLPQKNSSEGNKHHKSTP LLIHCRDGSQQTGIFCALLNLLESAETEEVVDIFQV VKALRKARPGMVSTFEQYQFLYDVIASTYPAQNGQV KKNNHQEDKIEFDNEVDKVKQDANCVNPLGAPEKLP EAKEQAEGSEPTSGTEGPEHSVNGPASPALNQGS |
| SEQ ID NO: 6 | CD45RBC (Human CD45 Isoform) | MTMYLWLKLLAFGFAFLDTEVFVTGQSPTPSPTGVS SVQTPHLPTHADSQTPSAGTDTQTFSGSAANAKLNP TPGSNAISDVPGERSTASTFPTDPVSPLTTTLSLAH HSSAALPARTSNTTITANTSDAYLNASETTTLSPSG SAVISTTTIATTPSKPTCDEKYANITVDYLYNKETK LFTAKLNVNENVECGNNTCTNNEVHNLTECKNASVS ISHNSCTAPDKTLILDVPPGVEKFQLHDCTQVEKAD TTICLKWKNIETFTCDTQNITYRFQCGNMIFDNKEI KLENLEPEHEYKCDSEILYNNHKFTNASKIIKTDFG SPGEPQIIFCRSEAAHQGVITWNPPQRSFHNFTLCY IKETEKDCLNLDKNLIKYDLQNLKPYTKYVLSLHAY IIAKVQRNGSAAMCHFTTKSAPPSQVWNMTVSMTSD NSMHVKCRPPRDRNGPHERYHLEVEAGNTLVRNESH KNCDFRVKDLQYSTDYTFKAYFHNGDYPGEPFILHH STSYNSKALIAFLAFLIIVTSIALLVVLYKIYDLHK KRSCNLDEQQELVERDDEKQLMNVEPIHADILLETY |

TABLE 5-continued

SEQUENCE LISTING TABLE

| SEQUENCE IDENTIFIER | DESCRIPTION | SEQUENCE |
|---|---|---|
| | | KRKIADEGRLFLAEFQSIPRVFSKFPIKEARKPFNQ NKNRYVDILPYDYNRVELSEINGDAGSNYINASYID GFKEPRKYIAAQGPRDETVDDFWRMIWEQKATVIVM VTRCEEGNRNKCAEYWPSMEEGTRAFGDVVVKINQH KRCPDYIIQKLNIVNKKEKATGREVTHIQFTSWPDH GVPEDPHLLLKLRRRVNAFSNFFSGPIVVHCSAGVG RTGTYIGIDAMLEGLEAENKVDVYGYVVKLRRQRCL MVQVEAQYILIHQALVEYNQFGETEVNLSELHPYLH NMKKRDPPSEPSPLEAEFQRLPSYRSWRTQHIGNQE ENKSKNRNSNVIPYDYNRVPLKHELEMSKESEHDSD ESSDDDSDSEEPSKYINASFIMSYWKPEVMIAAQGP LKETIGDFWQMIFQRKVKVIVMLTELKHGDQEICAQ YWGEGKQTYGDIEVDLKDTDKSSTYTLRVFELRHSK RKDSRTVYQYQYTNWSVEQLPAEPKELISMIQVVKQ KLPQKNSSEGNKHHKSTPLLIHCRDGSQQTGIFCAL LNLLESAETEEVVDIFQVVKALRKARPGMVSTFEQY QFLYDVIASTYPAQNGQVKKNNHQEDKIEFDNEVDK VKQDANCVNPLGAPEKLPEAKEQAEGSEPTSGTEGP EHSVNGPASPALNQGS |
| SEQ ID NO: 7 | CD45RABC (Human CD45 Isoform) | MTMYLWLKLLAFGFAFLDTEVFVTGQSPTPSPTGLT TAKMPSVPLSSDPLPTHTTAFSPASTFERENDFSET TTSLSPDNTSTQVSPDSLDNASAFNTTGVSSVQTPH LPTHADSQTPSAGTDTQTFSGSAANAKLNPTPGSNA ISDVPGERSTASTFPTDPVSPLTTTLSLAHHSSAAL PARTSNTTITANTSDAYLNASETTTLSPSGSAVIST TTIATTPSKPTCDEKYANITVDYLYNKETKLFTAKL NVNENVECGNNTCTNNEVHNLTECKNASVSISHNSC TAPDKTLILDVPPGVEKFQLHDCTQVEKADTTICLK WKNIETFTCDTQNITYRFQCGNMIFDNKEIKLENLE PEHEYKCDSEILYNNHKFTNASKIIKTDFGSPGEPQ IIFCRSEAAHQGVITWNPPQRSFHNFTLCYIKETEK DCLNLDKNLIKYDLQNLKPYTKYVLSLHAYIIAKVQ RNGSAAMCHFTTKSAPPSQVWNMTVSMTSDNSMHVK CRPPRDRNGPHERYHLEVEAGNTLVRNESHKNCDFR VKDLQYSTDYTFKAYFHNGDYPGEPFILHHSTSYNS KALIAFLAFLIIVTSIALLVVLYKIYDLHKKRSCNL DEQQELVERDDEKQLMNVEPIHADILLETYKRKIAD EGRLFLAEFQSIPRVFSKFPIKEARKPFNQNKNRYV DILPYDYNRVELSEINGDAGSNYINASYIDGFKEPR KYIAAQGPRDETVDDFWRMIWEQKATVIVMVTRCEE GNRNKCAEYWPSMEEGTRAFGDVVVKINQHKRCPDY IIQKLNIVNKKEKATGREVTHIQFTSWPDHGVPEDP HLLLKLRRRVNAFSNFFSGPIVVHCSAGVGRTGTYI GIDAMLEGLEAENKVDVYGYVVKLRRQRCLMVQVEA QYILIHQALVEYNQFGETEVNLSELHPYLHNMKKRD PPSEPSPLEAEFQRLPSYRSWRTQHIGNQEENKSKN RNSNVIPYDYNRVPLKHELEMSKESEHDSDESSDDD SDSEEPSKYINASFIMSYWKPEVMIAAQGPLKETIG DFWQMIFQRKVKVIVMLTELKHGDQEICAQYWGEGK QTYGDIEVDLKDTDKSSTYTLRVFELRHSKRKDSRT VYQYQYTNWSVEQLPAEPKELISMIQVVKQKLPQKN SSEGNKHHKSTPLLIHCRDGSQQTGIFCALLNLLES AETEEVVDIFQVVKALRKARPGMVSTFEQYQFLYDV IASTYPAQNGQVKKNNHQEDKIEFDNEVDKVKQDAN CVNPLGAPEKLPEAKEQAEGSEPTSGTEGPEHSVNG PASPALNQGS |
| SEQ ID NO: 8 | Apamistamab Heavy Chain | EVKLLESGGGLVQPGGSLKLSCAASGFDFSRYWMSW VRQAPGKGLEWIGEINPTSSTINFTPSLKDKVFISR DNAKNTLYLQMSKVRSEDTALYYCARGNYYRYGDAM DYWGQGTSVTVSSAKTTPPSVYPLAPGSAAQTNSMV TLGCLVKGYFPEPVTVTWNSGSLSSGVHTFPAVLQS DLYTLSSSVTVPSSTWPSETVTCNVAHPASSTKVDK KIVPRDCGCKPCICTVPEVSSVFIFPPKPKDVLTIT LTPKVTCVVVDISKDDPEVQFSWFVDDVEVHTAQTQ PREEQFNSTERSVSELPIMHQDWLNGKEFKCRVNSA AFPAPIEKTISKTKGRPKAPQVYTIPPPKEQMAKDK VSLTCMITDFFPEDITVEWQWNGQPAENYKNTQPIM DTDGSYFVYSKLNVQKSNWEAGNTFTCSVLHEGLHN HHTEKSLSHSPGK |

TABLE 5-continued

SEQUENCE LISTING TABLE

| SEQUENCE IDENTIFIER | DESCRIPTION | SEQUENCE |
|---|---|---|
| SEQ ID NO: 9 | Apamistamab Light Chain | DIALTQSPASLAVSLGQRATISCRASKSVSTSGYSY LHWYQQKPGQPPKLLIYLASNLESGVPARFSGSGSG TDFTLNIHPVEEEDAATYYCQHSRELPFTFGSGTKL EIKRADAAPTVSIFPPSSEQLTSGGASVVCFLNNEY PKDINVKWKIDGSERQNGVLNSWTDQDSKDSTYSMS STLTLTKDEYERHNSYTCEATHKTSTSPIVKSFNRN EC |
| SEQ ID NO: 10 | Apamistamab Heavy Chain Variable Region | EVKLLESGGGLVQPGGSLKLSCAASGFDFSRYWMSW VRQAPGKGLEWIGEINPTSSTINFTPSLKDKVFISR DNAKNTLYLQMSKVRSEDTALYYCARGNYYRYGDAM DYWGQGTSVTVSSA |
| SEQ ID NO: 11 | Apamistamab Light Chain Variable Region | DIALTQSPASLAVSLGQRATISCRASKSVSTSGYSY LHWYQQKPGQPPKLLIYLASNLESGVPARFSGSGSG TDFTLNIHPVEEEDAATYYCQHSRELPFTFGSGTKL EIKR |
| SEQ ID NO: 12 | 104 S239C/IHH Heavy Chain | EVQLVESGGDLVQPGGSLKLSCTASGFTFSNYGMSW IRQTPDKRLEWVATIVGGGSYTYFPDSMKGRFTVSR DNAKSILYLQMNSLASADTAMYYCTRHDWVFDYWGQ GTPLTVSSASTKGPSVFPLAPSSKSTSGGTAALGCL VKDYFPEPVTVSWNSGALTSGVHTFPAVLQSSGLYS LSSVVTVPSSSLGTQTYICNVNHKPSNTKVDKKVEP KSCDKTHTCPPCPAPELLGGPCVFLFPPKPKDTLMA SRTPEVTCVVVDVSHEDPEVKFNWYVDGVEVHNAKT KPREEQYNSTYRVVSVLTVLAQDWLNGKEYKCKVSN KALPAPIEKTISKAKGQPREPQVYTLPPSRDELTKN QVSLTCLVKGFYPSDIAVEWESNGQPENNYKTTPPV LDSDGSFFLYSKLTVDKSRWQQGNVFSCSVMHEALH NAYTQKSLSLSPGK |
| SEQ ID NO: 13 | 104 S2390/IHH Light Chain | DIVLTQSPASLAVSLGQRAIISCKASQSVSFAGSSL MHWYQQKPGQQPKLLIYRASDLETGIPTRFSGGGSG TDFTLNIHPVEEDDAATYYCQQSREYPYTFGGGTRL EIKRTVAAPSVFIFPPSDEQLKSGTASVVCLLNNFY PREAKVQWKVDNALQSGNSQESVTEQDSKDSTYSLS STLTLSKADYEKHKVYACEVTHQGLSSPVTKSFNRG EC |
| SEQ ID NO: 14 | AbA heavy chain (HC) variable region (CDRs underlined) | EVQLVESGGDRVQPGRSLTLSCVTSGFTFNNYWMTW IRQVPGKGLEWVASISSSGGSIYYPDSVKGRFTISR DNAKNTLYLQMNSLRSEDTATYYCARDERWAGAMDA WGQGTSVTVSS |
| SEQ ID NO: 15 | AbA HC CDR1 | FTFNNYWMT |
| SEQ ID NO: 16 | AbA HC CDR2 | SISSSGGSIYYPDSVKG |
| SEQ ID NO: 17 | AbA HC CDR3 | ARDERWAGAMDA |
| SEQ ID NO: 18 | AbA light chain (LC) variable region (CDRs underlined) | DIQMTQSPPVLSASVGDRVTLSCKASQNINKNLDWY QQKHGEAPKLLIYETNNLQTGIPSRFSGSGSGTDYT LTISSLQPEDVATYYCYQHNSRFTFGSGTKLEIK |
| SEQ ID NO: 19 | AbA LC CDR1 | KASQNINKNLD |
| SEQ ID NO: 20 | AbA LC CDR2 | ETNNLQT |
| SEQ ID NO: 21 | AbA LC CDR3 | YQHNSRFT |
| SEQ ID NO: 22 | AbB heavy chain (HC) variable region (CDRs underlined) | EVQLVESGGDLVQPGRSLKLSCIASGFTFTNFWMTW IRQVSGKGLEWVASISSSGGSIYYPDSVKDRFTISR DNAKNTLYLQMNSLRSEDTATYYCVKLHYYSGGGDA WGQGTSVTVSS |
| SEQ ID NO: 23 | AbB HC CDR1 | FTFTNFWMT |
| SEQ ID NO: 24 | AbB HC CDR2 | SISSSGGSIYYPDSVKD |
| SEQ ID NO: 25 | AbB HC CDR3 | VKLHYYSGGGDA |

TABLE 5-continued

SEQUENCE LISTING TABLE

| SEQUENCE IDENTIFIER | DESCRIPTION | SEQUENCE |
|---|---|---|
| SEQ ID NO: 26 | AbB light chain (LC) variable region (CDRs underlined) | DIQMTQSPSFLSASVGDRVTINCKASQNINKYLDWY QQKHGEAPKLLIHYTNNLHTGIPSRFSGSGSGTDYT LTISSLQPEDVATYFCLQHSSRWTFGGGTKLELK |
| SEQ ID NO: 27 | AbB LC CDR1 | KASQNINKYLD |
| SEQ ID NO: 28 | AbB LC CDR2 | YTNNLHT |
| SEQ ID NO: 29 | AbB LC CDR3 | LQHSSRWT |
| SEQ ID NO: 30 | AbC heavy chain (HC) variable region | EVQLVESGGDLVQPGRSLKLSCVASGFTFNNYWMTW IRQVPGKGLEWVASISSSGGSIYYPDSVKDRFTISR DNAKNTLFLQMNSLRSEDTATYYCARLYYYSGGGDA WGQGTSVTVSS |
| SEQ ID NO: 31 | AbC HC CDR1 | FTFNNYWMT |
| SEQ ID NO: 32 | AbC HC CDR2 | SISSSGGSIYYPDSVKD |
| SEQ ID NO: 33 | AbC HC CDR3 | ARLYYYSGGGDA |
| SEQ ID NO: 34 | AbC light chain (LC) variable region (CDRs underlined) | DIQMTQSPSFLSASVGDRVTIICKASQDINKYLDWY QQKLGEAPKLLIYNTNNLHTGIPSRFSGSGSGTDYT LTISSLQPEDVATYFCLQHISRWTFGGGTKLELK |
| SEQ ID NO: 35 | AbC LC CDR1 | KASQDINKYLD |
| SEQ ID NO: 36 | AbC LC CDR2 | NTNNLHT |
| SEQ ID NO: 37 | AbC LC CDR3 | LQHISRWT |

OTHER EMBODIMENTS

All publications, patents, and patent applications mentioned in this specification are incorporated herein by reference to the same extent as if each independent publication or patent application was specifically and individually indicated to be incorporated by reference.

While the invention has been described in connection with specific embodiments thereof, it will be understood that it is capable of further modifications and this application is intended to cover any variations, uses, or adaptations of the invention following, in general, the principles of the invention and including such departures from the invention that come within known or customary practice within the art to which the invention pertains and may be applied to the essential features hereinbefore set forth, and follows in the scope of the claims.

Other embodiments are within the claims.

What is claimed is:

1. A method of depleting a population of CD45+ cells in a human patient in need of a hematopoietic stem cell (HSC) transplant, the method comprising administering to the human patient an effective amount of an antibody-drug conjugate (ADC), such that a population of CD45+ cells are depleted, wherein the ADC comprises an anti-CD45 antibody or antigen binding portion thereof conjugated to a cytotoxin (Cy) via a linker (L), wherein the cytotoxin comprises an indolinobenzodiazepine (IGN) pseudodimer, and wherein the anti-CD45 antibody is an IgG isotype, wherein the cytotoxin-linker conjugate, prior to conjugation to the antibody or antigen binding portion thereof, and including the reactive substituent Z', taken together as Cy-L-Z', wherein the linker has a structure of formula:

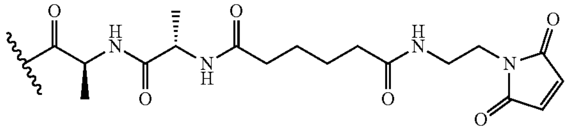 [SMILES: *C(=O)[C@H](C)NC(=O)[C@H](C)NC(=O)CCCCC(=O)NCCN1C(=O)C=CC1=O]

(VII).

2. The method of claim 1, wherein the cytotoxin is an IGN pseudodimer represented by Formula (VI):

(VI)

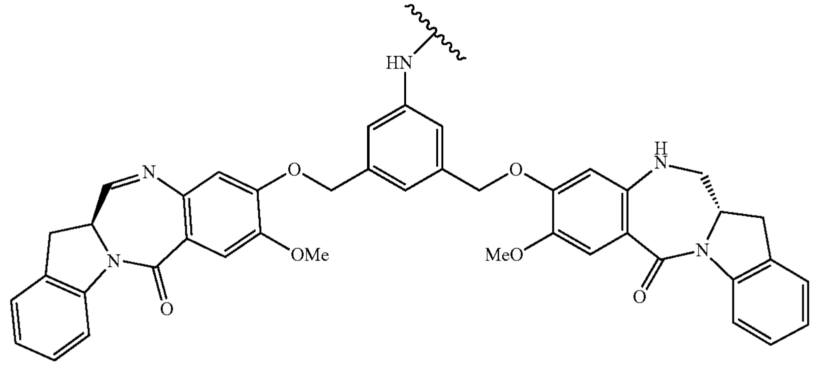

, wherein the wavy line indicates the point of covalent attachment to the linker of the ADC.

3. The ADC of claim 1, wherein the cytotoxin is an IGN and the cytotoxin-linker conjugate, prior to conjugation to the antibody or antigen binding portion thereof, and including the reactive substituent Z', taken together as Cy-L-Z', has a structure of Formula (VII):

(VII)

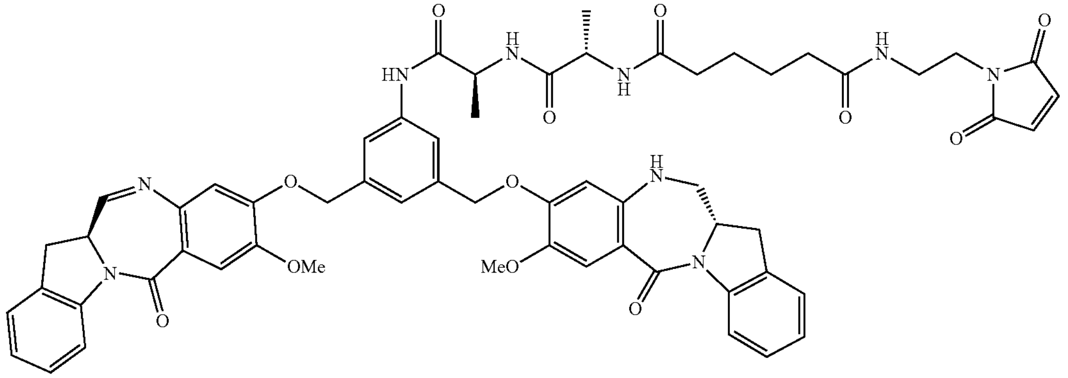

.

4. The method of claim 1, wherein the antibody is a chimeric antibody, a humanized antibody, or a human antibody.

5. The method of claim 1, wherein the antibody or antigen binding portion thereof comprises an Fc domain and is internalized by a CD45+ cell and/or wherein the antibody, or antigen binding portion thereof, is conjugated to the cytotoxin by way of a cysteine residue in the Fc domain.

6. The method of claim 1, wherein the method further comprising administering a hematopoietic stem cell transplant to the patient, or comprises administering the ADC to the patient prior to the patient receiving a transplant comprising hematopoietic stem cells.

7. The method of claim 1, wherein the patient has a blood disease, a metabolic disorder, a cancer, an autoimmune disease, a stem cell disorder, or severe combined immunodeficiency disease (SCID).

8. The method of claim 7, wherein the autoimmune disease is multiple sclerosis or scleroderma.

9. The method of claim 7, wherein the cancer is a hematological cancer.

10. The method of claim 9, wherein the hematological cancer is leukemia or lymphoma.

11. The method of claim 1, wherein a population of endogenous CD45+ HSCs are depleted in the human patient following administration of the ADC.

12. A method of conditioning a human patient for receiving a hematopoietic stem cell (HSC) transplant, the method comprising administering to the human patient an antibody-drug conjugate (ADC), wherein the ADC comprises an anti-CD45 antibody or antigen binding portion thereof conjugated to a cytotoxin (Cy) via a linker (L), wherein the cytotoxin comprises an indolinobenzodiazepine (IGN) pseudodimer, and wherein the anti-CD45 antibody is an IgG isotype, wherein the cytotoxin-linker conjugate, prior to conjugation to the antibody or antigen binding portion thereof, and including the reactive substituent Z', taken together as Cy-L-Z' wherein the linker has a structure of formula:

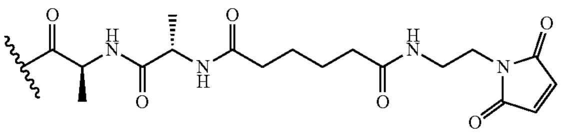

.

* * * * *

SEQUENCE LISTING

<160> NUMBER OF SEQ ID NOS: 37

<210> SEQ ID NO 1
<211> LENGTH: 1145
<212> TYPE: PRT
<213> ORGANISM: Homo sapiens

<400> SEQUENCE: 1

Met Thr Met Tyr Leu Trp Leu Lys Leu Leu Ala Phe Gly Phe Ala Phe
1 5 10 15

Leu Asp Thr Glu Val Phe Val Thr Gly Gln Ser Pro Thr Pro Ser Pro
20 25 30

Thr Asp Ala Tyr Leu Asn Ala Ser Glu Thr Thr Thr Leu Ser Pro Ser
35 40 45

Gly Ser Ala Val Ile Ser Thr Thr Thr Ile Ala Thr Thr Pro Ser Lys
50 55 60

Pro Thr Cys Asp Glu Lys Tyr Ala Asn Ile Thr Val Asp Tyr Leu Tyr
65 70 75 80

Asn Lys Glu Thr Lys Leu Phe Thr Ala Lys Leu Asn Val Asn Glu Asn

-continued

```
                85                  90                  95

Val Glu Cys Gly Asn Asn Thr Cys Thr Asn Asn Glu Val His Asn Leu
            100                 105                 110

Thr Glu Cys Lys Asn Ala Ser Val Ser Ile Ser His Asn Ser Cys Thr
        115                 120                 125

Ala Pro Asp Lys Thr Leu Ile Leu Asp Val Pro Pro Gly Val Glu Lys
    130                 135                 140

Phe Gln Leu His Asp Cys Thr Gln Val Glu Lys Ala Asp Thr Thr Ile
145                 150                 155                 160

Cys Leu Lys Trp Lys Asn Ile Glu Thr Phe Thr Cys Asp Thr Gln Asn
                165                 170                 175

Ile Thr Tyr Arg Phe Gln Cys Gly Asn Met Ile Phe Asp Asn Lys Glu
            180                 185                 190

Ile Lys Leu Glu Asn Leu Glu Pro Glu His Glu Tyr Lys Cys Asp Ser
        195                 200                 205

Glu Ile Leu Tyr Asn Asn His Lys Phe Thr Asn Ala Ser Lys Ile Ile
    210                 215                 220

Lys Thr Asp Phe Gly Ser Pro Gly Glu Pro Gln Ile Ile Phe Cys Arg
225                 230                 235                 240

Ser Glu Ala Ala His Gln Gly Val Ile Thr Trp Asn Pro Pro Gln Arg
                245                 250                 255

Ser Phe His Asn Phe Thr Leu Cys Tyr Ile Lys Glu Thr Glu Lys Asp
            260                 265                 270

Cys Leu Asn Leu Asp Lys Asn Leu Ile Lys Tyr Asp Leu Gln Asn Leu
        275                 280                 285

Lys Pro Tyr Thr Lys Tyr Val Leu Ser Leu His Ala Tyr Ile Ile Ala
    290                 295                 300

Lys Val Gln Arg Asn Gly Ser Ala Ala Met Cys His Phe Thr Thr Lys
305                 310                 315                 320

Ser Ala Pro Pro Ser Gln Val Trp Asn Met Thr Val Ser Met Thr Ser
                325                 330                 335

Asp Asn Ser Met His Val Lys Cys Arg Pro Pro Arg Asp Arg Asn Gly
            340                 345                 350

Pro His Glu Arg Tyr His Leu Glu Val Glu Ala Gly Asn Thr Leu Val
        355                 360                 365

Arg Asn Glu Ser His Lys Asn Cys Asp Phe Arg Val Lys Asp Leu Gln
    370                 375                 380

Tyr Ser Thr Asp Tyr Thr Phe Lys Ala Tyr Phe His Asn Gly Asp Tyr
385                 390                 395                 400

Pro Gly Glu Pro Phe Ile Leu His His Ser Thr Ser Tyr Asn Ser Lys
                405                 410                 415

Ala Leu Ile Ala Phe Leu Ala Phe Leu Ile Ile Val Thr Ser Ile Ala
            420                 425                 430

Leu Leu Val Val Leu Tyr Lys Ile Tyr Asp Leu His Lys Lys Arg Ser
        435                 440                 445

Cys Asn Leu Asp Glu Gln Gln Glu Leu Val Glu Arg Asp Asp Glu Lys
    450                 455                 460

Gln Leu Met Asn Val Glu Pro Ile His Ala Asp Ile Leu Leu Glu Thr
465                 470                 475                 480

Tyr Lys Arg Lys Ile Ala Asp Glu Gly Arg Leu Phe Leu Ala Glu Phe
                485                 490                 495

Gln Ser Ile Pro Arg Val Phe Ser Lys Phe Pro Ile Lys Glu Ala Arg
            500                 505                 510
```

-continued

```
Lys Pro Phe Asn Gln Asn Lys Asn Arg Tyr Val Asp Ile Leu Pro Tyr
        515                 520                 525

Asp Tyr Asn Arg Val Glu Leu Ser Glu Ile Asn Gly Asp Ala Gly Ser
    530                 535                 540

Asn Tyr Ile Asn Ala Ser Tyr Ile Asp Gly Phe Lys Glu Pro Arg Lys
545                 550                 555                 560

Tyr Ile Ala Ala Gln Gly Pro Arg Asp Glu Thr Val Asp Asp Phe Trp
                565                 570                 575

Arg Met Ile Trp Glu Gln Lys Ala Thr Val Ile Val Met Val Thr Arg
            580                 585                 590

Cys Glu Glu Gly Asn Arg Asn Lys Cys Ala Glu Tyr Trp Pro Ser Met
        595                 600                 605

Glu Glu Gly Thr Arg Ala Phe Gly Asp Val Val Val Lys Ile Asn Gln
    610                 615                 620

His Lys Arg Cys Pro Asp Tyr Ile Ile Gln Lys Leu Asn Ile Val Asn
625                 630                 635                 640

Lys Lys Glu Lys Ala Thr Gly Arg Glu Val Thr His Ile Gln Phe Thr
                645                 650                 655

Ser Trp Pro Asp His Gly Val Pro Glu Asp Pro His Leu Leu Leu Lys
            660                 665                 670

Leu Arg Arg Arg Val Asn Ala Phe Ser Asn Phe Phe Ser Gly Pro Ile
        675                 680                 685

Val Val His Cys Ser Ala Gly Val Gly Arg Thr Gly Thr Tyr Ile Gly
    690                 695                 700

Ile Asp Ala Met Leu Glu Gly Leu Glu Ala Glu Asn Lys Val Asp Val
705                 710                 715                 720

Tyr Gly Tyr Val Val Lys Leu Arg Arg Gln Arg Cys Leu Met Val Gln
                725                 730                 735

Val Glu Ala Gln Tyr Ile Leu Ile His Gln Ala Leu Val Glu Tyr Asn
            740                 745                 750

Gln Phe Gly Glu Thr Glu Val Asn Leu Ser Glu Leu His Pro Tyr Leu
        755                 760                 765

His Asn Met Lys Lys Arg Asp Pro Pro Ser Glu Pro Ser Pro Leu Glu
    770                 775                 780

Ala Glu Phe Gln Arg Leu Pro Ser Tyr Arg Ser Trp Arg Thr Gln His
785                 790                 795                 800

Ile Gly Asn Gln Glu Glu Asn Lys Ser Lys Asn Arg Asn Ser Asn Val
                805                 810                 815

Ile Pro Tyr Asp Tyr Asn Arg Val Pro Leu Lys His Glu Leu Glu Met
            820                 825                 830

Ser Lys Glu Ser Glu His Asp Ser Asp Glu Ser Ser Asp Asp Asp Ser
        835                 840                 845

Asp Ser Glu Glu Pro Ser Lys Tyr Ile Asn Ala Ser Phe Ile Met Ser
    850                 855                 860

Tyr Trp Lys Pro Glu Val Met Ile Ala Ala Gln Gly Pro Leu Lys Glu
865                 870                 875                 880

Thr Ile Gly Asp Phe Trp Gln Met Ile Phe Gln Arg Lys Val Lys Val
                885                 890                 895

Ile Val Met Leu Thr Glu Leu Lys His Gly Asp Gln Glu Ile Cys Ala
            900                 905                 910

Gln Tyr Trp Gly Glu Gly Lys Gln Thr Tyr Gly Asp Ile Glu Val Asp
        915                 920                 925
```

```
Leu Lys Asp Thr Asp Lys Ser Ser Thr Tyr Thr Leu Arg Val Phe Glu
    930                 935                 940

Leu Arg His Ser Lys Arg Lys Asp Ser Arg Thr Val Tyr Gln Tyr Gln
945                 950                 955                 960

Tyr Thr Asn Trp Ser Val Glu Gln Leu Pro Ala Glu Pro Lys Glu Leu
                965                 970                 975

Ile Ser Met Ile Gln Val Val Lys Gln Lys Leu Pro Gln Lys Asn Ser
            980                 985                 990

Ser Glu Gly Asn Lys His His Lys  Ser Thr Pro Leu Leu  Ile His Cys
        995                 1000                1005

Arg Asp  Gly Ser Gln Gln Thr  Gly Ile Phe Cys Ala  Leu Leu Asn
    1010                 1015                 1020

Leu Leu  Glu Ser Ala Glu Thr  Glu Glu Val Val Asp  Ile Phe Gln
    1025                 1030                 1035

Val Val  Lys Ala Leu Arg Lys  Ala Arg Pro Gly Met  Val Ser Thr
    1040                 1045                 1050

Phe Glu  Gln Tyr Gln Phe Leu  Tyr Asp Val Ile Ala  Ser Thr Tyr
    1055                 1060                 1065

Pro Ala  Gln Asn Gly Gln Val  Lys Lys Asn Asn His  Gln Glu Asp
    1070                 1075                 1080

Lys Ile  Glu Phe Asp Asn Glu  Val Asp Lys Val Lys  Gln Asp Ala
    1085                 1090                 1095

Asn Cys  Val Asn Pro Leu Gly  Ala Pro Glu Lys Leu  Pro Glu Ala
    1100                 1105                 1110

Lys Glu  Gln Ala Glu Gly Ser  Glu Pro Thr Ser Gly  Thr Glu Gly
    1115                 1120                 1125

Pro Glu  His Ser Val Asn Gly  Pro Ala Ser Pro Ala  Leu Asn Gln
    1130                 1135                 1140

Gly Ser
    1145


<210> SEQ ID NO 2
<211> LENGTH: 1211
<212> TYPE: PRT
<213> ORGANISM: Homo sapiens

<400> SEQUENCE: 2

Met Thr Met Tyr Leu Trp Leu Lys Leu Leu Ala Phe Gly Phe Ala Phe
1               5                   10                  15

Leu Asp Thr Glu Val Phe Val Thr Gly Gln Ser Pro Thr Pro Ser Pro
            20                  25                  30

Thr Gly Leu Thr Thr Ala Lys Met Pro Ser Val Pro Leu Ser Ser Asp
        35                  40                  45

Pro Leu Pro Thr His Thr Thr Ala Phe Ser Pro Ala Ser Thr Phe Glu
    50                  55                  60

Arg Glu Asn Asp Phe Ser Glu Thr Thr Thr Ser Leu Ser Pro Asp Asn
65                  70                  75                  80

Thr Ser Thr Gln Val Ser Pro Asp Ser Leu Asp Asn Ala Ser Ala Phe
                85                  90                  95

Asn Thr Thr Asp Ala Tyr Leu Asn Ala Ser Glu Thr Thr Thr Leu Ser
            100                 105                 110

Pro Ser Gly Ser Ala Val Ile Ser Thr Thr Thr Ile Ala Thr Thr Pro
        115                 120                 125

Ser Lys Pro Thr Cys Asp Glu Lys Tyr Ala Asn Ile Thr Val Asp Tyr
    130                 135                 140
```

```
Leu Tyr Asn Lys Glu Thr Lys Leu Phe Thr Ala Lys Leu Asn Val Asn
145                 150                 155                 160

Glu Asn Val Glu Cys Gly Asn Asn Thr Cys Thr Asn Asn Glu Val His
                165                 170                 175

Asn Leu Thr Glu Cys Lys Asn Ala Ser Val Ser Ile Ser His Asn Ser
            180                 185                 190

Cys Thr Ala Pro Asp Lys Thr Leu Ile Leu Asp Val Pro Pro Gly Val
        195                 200                 205

Glu Lys Phe Gln Leu His Asp Cys Thr Gln Val Glu Lys Ala Asp Thr
    210                 215                 220

Thr Ile Cys Leu Lys Trp Lys Asn Ile Glu Thr Phe Thr Cys Asp Thr
225                 230                 235                 240

Gln Asn Ile Thr Tyr Arg Phe Gln Cys Gly Asn Met Ile Phe Asp Asn
                245                 250                 255

Lys Glu Ile Lys Leu Glu Asn Leu Glu Pro Glu His Glu Tyr Lys Cys
            260                 265                 270

Asp Ser Glu Ile Leu Tyr Asn Asn His Lys Phe Thr Asn Ala Ser Lys
        275                 280                 285

Ile Ile Lys Thr Asp Phe Gly Ser Pro Gly Glu Pro Gln Ile Ile Phe
    290                 295                 300

Cys Arg Ser Glu Ala Ala His Gln Gly Val Ile Thr Trp Asn Pro Pro
305                 310                 315                 320

Gln Arg Ser Phe His Asn Phe Thr Leu Cys Tyr Ile Lys Glu Thr Glu
                325                 330                 335

Lys Asp Cys Leu Asn Leu Asp Lys Asn Leu Ile Lys Tyr Asp Leu Gln
            340                 345                 350

Asn Leu Lys Pro Tyr Thr Lys Tyr Val Leu Ser Leu His Ala Tyr Ile
        355                 360                 365

Ile Ala Lys Val Gln Arg Asn Gly Ser Ala Ala Met Cys His Phe Thr
    370                 375                 380

Thr Lys Ser Ala Pro Pro Ser Gln Val Trp Asn Met Thr Val Ser Met
385                 390                 395                 400

Thr Ser Asp Asn Ser Met His Val Lys Cys Arg Pro Pro Arg Asp Arg
                405                 410                 415

Asn Gly Pro His Glu Arg Tyr His Leu Glu Val Glu Ala Gly Asn Thr
            420                 425                 430

Leu Val Arg Asn Glu Ser His Lys Asn Cys Asp Phe Arg Val Lys Asp
        435                 440                 445

Leu Gln Tyr Ser Thr Asp Tyr Thr Phe Lys Ala Tyr Phe His Asn Gly
    450                 455                 460

Asp Tyr Pro Gly Glu Pro Phe Ile Leu His His Ser Thr Ser Tyr Asn
465                 470                 475                 480

Ser Lys Ala Leu Ile Ala Phe Leu Ala Phe Leu Ile Ile Val Thr Ser
                485                 490                 495

Ile Ala Leu Leu Val Val Leu Tyr Lys Ile Tyr Asp Leu His Lys Lys
            500                 505                 510

Arg Ser Cys Asn Leu Asp Glu Gln Gln Glu Leu Val Glu Arg Asp Asp
        515                 520                 525

Glu Lys Gln Leu Met Asn Val Glu Pro Ile His Ala Asp Ile Leu Leu
    530                 535                 540

Glu Thr Tyr Lys Arg Lys Ile Ala Asp Glu Gly Arg Leu Phe Leu Ala
545                 550                 555                 560
```

-continued

```
Glu Phe Gln Ser Ile Pro Arg Val Phe Ser Lys Phe Pro Ile Lys Glu
                565                 570                 575

Ala Arg Lys Pro Phe Asn Gln Asn Lys Asn Arg Tyr Val Asp Ile Leu
            580                 585                 590

Pro Tyr Asp Tyr Asn Arg Val Glu Leu Ser Glu Ile Asn Gly Asp Ala
        595                 600                 605

Gly Ser Asn Tyr Ile Asn Ala Ser Tyr Ile Asp Gly Phe Lys Glu Pro
    610                 615                 620

Arg Lys Tyr Ile Ala Ala Gln Gly Pro Arg Asp Glu Thr Val Asp Asp
625                 630                 635                 640

Phe Trp Arg Met Ile Trp Glu Gln Lys Ala Thr Val Ile Val Met Val
                645                 650                 655

Thr Arg Cys Glu Glu Gly Asn Arg Asn Lys Cys Ala Glu Tyr Trp Pro
            660                 665                 670

Ser Met Glu Glu Gly Thr Arg Ala Phe Gly Asp Val Val Val Lys Ile
        675                 680                 685

Asn Gln His Lys Arg Cys Pro Asp Tyr Ile Ile Gln Lys Leu Asn Ile
    690                 695                 700

Val Asn Lys Lys Glu Lys Ala Thr Gly Arg Glu Val Thr His Ile Gln
705                 710                 715                 720

Phe Thr Ser Trp Pro Asp His Gly Val Pro Glu Asp Pro His Leu Leu
                725                 730                 735

Leu Lys Leu Arg Arg Arg Val Asn Ala Phe Ser Asn Phe Phe Ser Gly
            740                 745                 750

Pro Ile Val Val His Cys Ser Ala Gly Val Gly Arg Thr Gly Thr Tyr
        755                 760                 765

Ile Gly Ile Asp Ala Met Leu Glu Gly Leu Glu Ala Glu Asn Lys Val
    770                 775                 780

Asp Val Tyr Gly Tyr Val Val Lys Leu Arg Arg Gln Arg Cys Leu Met
785                 790                 795                 800

Val Gln Val Glu Ala Gln Tyr Ile Leu Ile His Gln Ala Leu Val Glu
                805                 810                 815

Tyr Asn Gln Phe Gly Glu Thr Glu Val Asn Leu Ser Glu Leu His Pro
            820                 825                 830

Tyr Leu His Asn Met Lys Lys Arg Asp Pro Pro Ser Glu Pro Ser Pro
        835                 840                 845

Leu Glu Ala Glu Phe Gln Arg Leu Pro Ser Tyr Arg Ser Trp Arg Thr
    850                 855                 860

Gln His Ile Gly Asn Gln Glu Glu Asn Lys Ser Lys Asn Arg Asn Ser
865                 870                 875                 880

Asn Val Ile Pro Tyr Asp Tyr Asn Arg Val Pro Leu Lys His Glu Leu
                885                 890                 895

Glu Met Ser Lys Glu Ser Glu His Asp Ser Asp Glu Ser Ser Asp Asp
            900                 905                 910

Asp Ser Asp Ser Glu Glu Pro Ser Lys Tyr Ile Asn Ala Ser Phe Ile
        915                 920                 925

Met Ser Tyr Trp Lys Pro Glu Val Met Ile Ala Ala Gln Gly Pro Leu
    930                 935                 940

Lys Glu Thr Ile Gly Asp Phe Trp Gln Met Ile Phe Gln Arg Lys Val
945                 950                 955                 960

Lys Val Ile Val Met Leu Thr Glu Leu Lys His Gly Asp Gln Glu Ile
                965                 970                 975

Cys Ala Gln Tyr Trp Gly Glu Gly Lys Gln Thr Tyr Gly Asp Ile Glu
```

980 985 990

Val Asp Leu Lys Asp Thr Asp Lys Ser Ser Thr Tyr Thr Leu Arg Val
995 1000 1005

Phe Glu Leu Arg His Ser Lys Arg Lys Asp Ser Arg Thr Val Tyr
1010 1015 1020

Gln Tyr Gln Tyr Thr Asn Trp Ser Val Glu Gln Leu Pro Ala Glu
1025 1030 1035

Pro Lys Glu Leu Ile Ser Met Ile Gln Val Val Lys Gln Lys Leu
1040 1045 1050

Pro Gln Lys Asn Ser Ser Glu Gly Asn Lys His His Lys Ser Thr
1055 1060 1065

Pro Leu Leu Ile His Cys Arg Asp Gly Ser Gln Gln Thr Gly Ile
1070 1075 1080

Phe Cys Ala Leu Leu Asn Leu Leu Glu Ser Ala Glu Thr Glu Glu
1085 1090 1095

Val Val Asp Ile Phe Gln Val Val Lys Ala Leu Arg Lys Ala Arg
1100 1105 1110

Pro Gly Met Val Ser Thr Phe Glu Gln Tyr Gln Phe Leu Tyr Asp
1115 1120 1125

Val Ile Ala Ser Thr Tyr Pro Ala Gln Asn Gly Gln Val Lys Lys
1130 1135 1140

Asn Asn His Gln Glu Asp Lys Ile Glu Phe Asp Asn Glu Val Asp
1145 1150 1155

Lys Val Lys Gln Asp Ala Asn Cys Val Asn Pro Leu Gly Ala Pro
1160 1165 1170

Glu Lys Leu Pro Glu Ala Lys Glu Gln Ala Glu Gly Ser Glu Pro
1175 1180 1185

Thr Ser Gly Thr Glu Gly Pro Glu His Ser Val Asn Gly Pro Ala
1190 1195 1200

Ser Pro Ala Leu Asn Gln Gly Ser
1205 1210

<210> SEQ ID NO 3
<211> LENGTH: 1192
<212> TYPE: PRT
<213> ORGANISM: Homo sapiens

<400> SEQUENCE: 3

Met Thr Met Tyr Leu Trp Leu Lys Leu Leu Ala Phe Gly Phe Ala Phe
1 5 10 15

Leu Asp Thr Glu Val Phe Val Thr Gly Gln Ser Pro Thr Pro Ser Pro
20 25 30

Thr Gly Val Ser Ser Val Gln Thr Pro His Leu Pro Thr His Ala Asp
35 40 45

Ser Gln Thr Pro Ser Ala Gly Thr Asp Thr Gln Thr Phe Ser Gly Ser
50 55 60

Ala Ala Asn Ala Lys Leu Asn Pro Thr Pro Gly Ser Asn Ala Ile Ser
65 70 75 80

Asp Ala Tyr Leu Asn Ala Ser Glu Thr Thr Thr Leu Ser Pro Ser Gly
85 90 95

Ser Ala Val Ile Ser Thr Thr Thr Ile Ala Thr Thr Pro Ser Lys Pro
100 105 110

Thr Cys Asp Glu Lys Tyr Ala Asn Ile Thr Val Asp Tyr Leu Tyr Asn
115 120 125

-continued

```
Lys Glu Thr Lys Leu Phe Thr Ala Lys Leu Asn Val Asn Glu Asn Val
    130                 135                 140

Glu Cys Gly Asn Asn Thr Cys Thr Asn Asn Glu Val His Asn Leu Thr
145                 150                 155                 160

Glu Cys Lys Asn Ala Ser Val Ser Ile Ser His Asn Ser Cys Thr Ala
                165                 170                 175

Pro Asp Lys Thr Leu Ile Leu Asp Val Pro Pro Gly Val Glu Lys Phe
            180                 185                 190

Gln Leu His Asp Cys Thr Gln Val Glu Lys Ala Asp Thr Thr Ile Cys
        195                 200                 205

Leu Lys Trp Lys Asn Ile Glu Thr Phe Thr Cys Asp Thr Gln Asn Ile
    210                 215                 220

Thr Tyr Arg Phe Gln Cys Gly Asn Met Ile Phe Asp Asn Lys Glu Ile
225                 230                 235                 240

Lys Leu Glu Asn Leu Glu Pro Glu His Glu Tyr Lys Cys Asp Ser Glu
                245                 250                 255

Ile Leu Tyr Asn Asn His Lys Phe Thr Asn Ala Ser Lys Ile Ile Lys
            260                 265                 270

Thr Asp Phe Gly Ser Pro Gly Glu Pro Gln Ile Ile Phe Cys Arg Ser
        275                 280                 285

Glu Ala Ala His Gln Gly Val Ile Thr Trp Asn Pro Pro Gln Arg Ser
    290                 295                 300

Phe His Asn Phe Thr Leu Cys Tyr Ile Lys Glu Thr Glu Lys Asp Cys
305                 310                 315                 320

Leu Asn Leu Asp Lys Asn Leu Ile Lys Tyr Asp Leu Gln Asn Leu Lys
                325                 330                 335

Pro Tyr Thr Lys Tyr Val Leu Ser Leu His Ala Tyr Ile Ile Ala Lys
            340                 345                 350

Val Gln Arg Asn Gly Ser Ala Ala Met Cys His Phe Thr Thr Lys Ser
        355                 360                 365

Ala Pro Pro Ser Gln Val Trp Asn Met Thr Val Ser Met Thr Ser Asp
    370                 375                 380

Asn Ser Met His Val Lys Cys Arg Pro Pro Arg Asp Arg Asn Gly Pro
385                 390                 395                 400

His Glu Arg Tyr His Leu Glu Val Glu Ala Gly Asn Thr Leu Val Arg
                405                 410                 415

Asn Glu Ser His Lys Asn Cys Asp Phe Arg Val Lys Asp Leu Gln Tyr
            420                 425                 430

Ser Thr Asp Tyr Thr Phe Lys Ala Tyr Phe His Asn Gly Asp Tyr Pro
        435                 440                 445

Gly Glu Pro Phe Ile Leu His His Ser Thr Ser Tyr Asn Ser Lys Ala
    450                 455                 460

Leu Ile Ala Phe Leu Ala Phe Leu Ile Ile Val Thr Ser Ile Ala Leu
465                 470                 475                 480

Leu Val Val Leu Tyr Lys Ile Tyr Asp Leu His Lys Lys Arg Ser Cys
                485                 490                 495

Asn Leu Asp Glu Gln Gln Glu Leu Val Glu Arg Asp Asp Glu Lys Gln
            500                 505                 510

Leu Met Asn Val Glu Pro Ile His Ala Asp Ile Leu Leu Glu Thr Tyr
        515                 520                 525

Lys Arg Lys Ile Ala Asp Glu Gly Arg Leu Phe Leu Ala Glu Phe Gln
    530                 535                 540

Ser Ile Pro Arg Val Phe Ser Lys Phe Pro Ile Lys Glu Ala Arg Lys
```

-continued

```
545                 550                 555                 560

Pro Phe Asn Gln Asn Lys Asn Arg Tyr Val Asp Ile Leu Pro Tyr Asp
                565                 570                 575

Tyr Asn Arg Val Glu Leu Ser Glu Ile Asn Gly Asp Ala Gly Ser Asn
            580                 585                 590

Tyr Ile Asn Ala Ser Tyr Ile Asp Gly Phe Lys Glu Pro Arg Lys Tyr
        595                 600                 605

Ile Ala Ala Gln Gly Pro Arg Asp Glu Thr Val Asp Asp Phe Trp Arg
    610                 615                 620

Met Ile Trp Glu Gln Lys Ala Thr Val Ile Val Met Val Thr Arg Cys
625                 630                 635                 640

Glu Glu Gly Asn Arg Asn Lys Cys Ala Glu Tyr Trp Pro Ser Met Glu
                645                 650                 655

Glu Gly Thr Arg Ala Phe Gly Asp Val Val Val Lys Ile Asn Gln His
            660                 665                 670

Lys Arg Cys Pro Asp Tyr Ile Ile Gln Lys Leu Asn Ile Val Asn Lys
        675                 680                 685

Lys Glu Lys Ala Thr Gly Arg Glu Val Thr His Ile Gln Phe Thr Ser
    690                 695                 700

Trp Pro Asp His Gly Val Pro Glu Asp Pro His Leu Leu Leu Lys Leu
705                 710                 715                 720

Arg Arg Arg Val Asn Ala Phe Ser Asn Phe Phe Ser Gly Pro Ile Val
                725                 730                 735

Val His Cys Ser Ala Gly Val Gly Arg Thr Gly Thr Tyr Ile Gly Ile
            740                 745                 750

Asp Ala Met Leu Glu Gly Leu Glu Ala Glu Asn Lys Val Asp Val Tyr
        755                 760                 765

Gly Tyr Val Val Lys Leu Arg Arg Gln Arg Cys Leu Met Val Gln Val
    770                 775                 780

Glu Ala Gln Tyr Ile Leu Ile His Gln Ala Leu Val Glu Tyr Asn Gln
785                 790                 795                 800

Phe Gly Glu Thr Glu Val Asn Leu Ser Glu Leu His Pro Tyr Leu His
                805                 810                 815

Asn Met Lys Lys Arg Asp Pro Pro Ser Glu Pro Ser Pro Leu Glu Ala
            820                 825                 830

Glu Phe Gln Arg Leu Pro Ser Tyr Arg Ser Trp Arg Thr Gln His Ile
        835                 840                 845

Gly Asn Gln Glu Glu Asn Lys Ser Lys Asn Arg Asn Ser Asn Val Ile
    850                 855                 860

Pro Tyr Asp Tyr Asn Arg Val Pro Leu Lys His Glu Leu Glu Met Ser
865                 870                 875                 880

Lys Glu Ser Glu His Asp Ser Asp Glu Ser Ser Asp Asp Asp Ser Asp
                885                 890                 895

Ser Glu Glu Pro Ser Lys Tyr Ile Asn Ala Ser Phe Ile Met Ser Tyr
            900                 905                 910

Trp Lys Pro Glu Val Met Ile Ala Ala Gln Gly Pro Leu Lys Glu Thr
        915                 920                 925

Ile Gly Asp Phe Trp Gln Met Ile Phe Gln Arg Lys Val Lys Val Ile
    930                 935                 940

Val Met Leu Thr Glu Leu Lys His Gly Asp Gln Glu Ile Cys Ala Gln
945                 950                 955                 960

Tyr Trp Gly Glu Gly Lys Gln Thr Tyr Gly Asp Ile Glu Val Asp Leu
                965                 970                 975
```

Lys Asp Thr Asp Lys Ser Ser Thr Tyr Thr Leu Arg Val Phe Glu Leu
980 985 990

Arg His Ser Lys Arg Lys Asp Ser Arg Thr Val Tyr Gln Tyr Gln Tyr
995 1000 1005

Thr Asn Trp Ser Val Glu Gln Leu Pro Ala Glu Pro Lys Glu Leu
1010 1015 1020

Ile Ser Met Ile Gln Val Val Lys Gln Lys Leu Pro Gln Lys Asn
1025 1030 1035

Ser Ser Glu Gly Asn Lys His His Lys Ser Thr Pro Leu Leu Ile
1040 1045 1050

His Cys Arg Asp Gly Ser Gln Gln Thr Gly Ile Phe Cys Ala Leu
1055 1060 1065

Leu Asn Leu Leu Glu Ser Ala Glu Thr Glu Glu Val Val Asp Ile
1070 1075 1080

Phe Gln Val Val Lys Ala Leu Arg Lys Ala Arg Pro Gly Met Val
1085 1090 1095

Ser Thr Phe Glu Gln Tyr Gln Phe Leu Tyr Asp Val Ile Ala Ser
1100 1105 1110

Thr Tyr Pro Ala Gln Asn Gly Gln Val Lys Lys Asn Asn His Gln
1115 1120 1125

Glu Asp Lys Ile Glu Phe Asp Asn Glu Val Asp Lys Val Lys Gln
1130 1135 1140

Asp Ala Asn Cys Val Asn Pro Leu Gly Ala Pro Glu Lys Leu Pro
1145 1150 1155

Glu Ala Lys Glu Gln Ala Glu Gly Ser Glu Pro Thr Ser Gly Thr
1160 1165 1170

Glu Gly Pro Glu His Ser Val Asn Gly Pro Ala Ser Pro Ala Leu
1175 1180 1185

Asn Gln Gly Ser
1190

<210> SEQ ID NO 4
<211> LENGTH: 1193
<212> TYPE: PRT
<213> ORGANISM: Homo sapiens

<400> SEQUENCE: 4

Met Thr Met Tyr Leu Trp Leu Lys Leu Leu Ala Phe Gly Phe Ala Phe
1 5 10 15

Leu Asp Thr Glu Val Phe Val Thr Gly Gln Ser Pro Thr Pro Ser Pro
20 25 30

Thr Asp Val Pro Gly Glu Arg Ser Thr Ala Ser Thr Phe Pro Thr Asp
35 40 45

Pro Val Ser Pro Leu Thr Thr Thr Leu Ser Leu Ala His His Ser Ser
50 55 60

Ala Ala Leu Pro Ala Arg Thr Ser Asn Thr Thr Ile Thr Ala Asn Thr
65 70 75 80

Ser Asp Ala Tyr Leu Asn Ala Ser Glu Thr Thr Thr Leu Ser Pro Ser
85 90 95

Gly Ser Ala Val Ile Ser Thr Thr Thr Ile Ala Thr Thr Pro Ser Lys
100 105 110

Pro Thr Cys Asp Glu Lys Tyr Ala Asn Ile Thr Val Asp Tyr Leu Tyr
115 120 125

Asn Lys Glu Thr Lys Leu Phe Thr Ala Lys Leu Asn Val Asn Glu Asn

-continued

```
    130                 135                 140

Val Glu Cys Gly Asn Asn Thr Cys Thr Asn Asn Glu Val His Asn Leu
145                 150                 155                 160

Thr Glu Cys Lys Asn Ala Ser Val Ser Ile Ser His Asn Ser Cys Thr
                165                 170                 175

Ala Pro Asp Lys Thr Leu Ile Leu Asp Val Pro Pro Gly Val Glu Lys
            180                 185                 190

Phe Gln Leu His Asp Cys Thr Gln Val Glu Lys Ala Asp Thr Thr Ile
        195                 200                 205

Cys Leu Lys Trp Lys Asn Ile Glu Thr Phe Thr Cys Asp Thr Gln Asn
    210                 215                 220

Ile Thr Tyr Arg Phe Gln Cys Gly Asn Met Ile Phe Asp Asn Lys Glu
225                 230                 235                 240

Ile Lys Leu Glu Asn Leu Glu Pro Glu His Glu Tyr Lys Cys Asp Ser
                245                 250                 255

Glu Ile Leu Tyr Asn Asn His Lys Phe Thr Asn Ala Ser Lys Ile Ile
            260                 265                 270

Lys Thr Asp Phe Gly Ser Pro Gly Glu Pro Gln Ile Ile Phe Cys Arg
        275                 280                 285

Ser Glu Ala Ala His Gln Gly Val Ile Thr Trp Asn Pro Pro Gln Arg
    290                 295                 300

Ser Phe His Asn Phe Thr Leu Cys Tyr Ile Lys Glu Thr Glu Lys Asp
305                 310                 315                 320

Cys Leu Asn Leu Asp Lys Asn Leu Ile Lys Tyr Asp Leu Gln Asn Leu
                325                 330                 335

Lys Pro Tyr Thr Lys Tyr Val Leu Ser Leu His Ala Tyr Ile Ile Ala
            340                 345                 350

Lys Val Gln Arg Asn Gly Ser Ala Ala Met Cys His Phe Thr Thr Lys
        355                 360                 365

Ser Ala Pro Pro Ser Gln Val Trp Asn Met Thr Val Ser Met Thr Ser
    370                 375                 380

Asp Asn Ser Met His Val Lys Cys Arg Pro Pro Arg Asp Arg Asn Gly
385                 390                 395                 400

Pro His Glu Arg Tyr His Leu Glu Val Glu Ala Gly Asn Thr Leu Val
                405                 410                 415

Arg Asn Glu Ser His Lys Asn Cys Asp Phe Arg Val Lys Asp Leu Gln
            420                 425                 430

Tyr Ser Thr Asp Tyr Thr Phe Lys Ala Tyr Phe His Asn Gly Asp Tyr
        435                 440                 445

Pro Gly Glu Pro Phe Ile Leu His His Ser Thr Ser Tyr Asn Ser Lys
    450                 455                 460

Ala Leu Ile Ala Phe Leu Ala Phe Leu Ile Ile Val Thr Ser Ile Ala
465                 470                 475                 480

Leu Leu Val Val Leu Tyr Lys Ile Tyr Asp Leu His Lys Lys Arg Ser
                485                 490                 495

Cys Asn Leu Asp Glu Gln Gln Glu Leu Val Glu Arg Asp Asp Glu Lys
            500                 505                 510

Gln Leu Met Asn Val Glu Pro Ile His Ala Asp Ile Leu Leu Glu Thr
        515                 520                 525

Tyr Lys Arg Lys Ile Ala Asp Glu Gly Arg Leu Phe Leu Ala Glu Phe
    530                 535                 540

Gln Ser Ile Pro Arg Val Phe Ser Lys Phe Pro Ile Lys Glu Ala Arg
545                 550                 555                 560
```

```
Lys Pro Phe Asn Gln Asn Lys Asn Arg Tyr Val Asp Ile Leu Pro Tyr
                565                 570                 575

Asp Tyr Asn Arg Val Glu Leu Ser Glu Ile Asn Gly Asp Ala Gly Ser
            580                 585                 590

Asn Tyr Ile Asn Ala Ser Tyr Ile Asp Gly Phe Lys Glu Pro Arg Lys
        595                 600                 605

Tyr Ile Ala Ala Gln Gly Pro Arg Asp Glu Thr Val Asp Asp Phe Trp
    610                 615                 620

Arg Met Ile Trp Glu Gln Lys Ala Thr Val Ile Val Met Val Thr Arg
625                 630                 635                 640

Cys Glu Glu Gly Asn Arg Asn Lys Cys Ala Glu Tyr Trp Pro Ser Met
                645                 650                 655

Glu Glu Gly Thr Arg Ala Phe Gly Asp Val Val Val Lys Ile Asn Gln
            660                 665                 670

His Lys Arg Cys Pro Asp Tyr Ile Ile Gln Lys Leu Asn Ile Val Asn
        675                 680                 685

Lys Lys Glu Lys Ala Thr Gly Arg Glu Val Thr His Ile Gln Phe Thr
    690                 695                 700

Ser Trp Pro Asp His Gly Val Pro Glu Asp Pro His Leu Leu Leu Lys
705                 710                 715                 720

Leu Arg Arg Arg Val Asn Ala Phe Ser Asn Phe Phe Ser Gly Pro Ile
                725                 730                 735

Val Val His Cys Ser Ala Gly Val Gly Arg Thr Gly Thr Tyr Ile Gly
            740                 745                 750

Ile Asp Ala Met Leu Glu Gly Leu Glu Ala Glu Asn Lys Val Asp Val
        755                 760                 765

Tyr Gly Tyr Val Val Lys Leu Arg Arg Gln Arg Cys Leu Met Val Gln
    770                 775                 780

Val Glu Ala Gln Tyr Ile Leu Ile His Gln Ala Leu Val Glu Tyr Asn
785                 790                 795                 800

Gln Phe Gly Glu Thr Glu Val Asn Leu Ser Glu Leu His Pro Tyr Leu
                805                 810                 815

His Asn Met Lys Lys Arg Asp Pro Pro Ser Glu Pro Ser Pro Leu Glu
            820                 825                 830

Ala Glu Phe Gln Arg Leu Pro Ser Tyr Arg Ser Trp Arg Thr Gln His
        835                 840                 845

Ile Gly Asn Gln Glu Glu Asn Lys Ser Lys Asn Arg Asn Ser Asn Val
    850                 855                 860

Ile Pro Tyr Asp Tyr Asn Arg Val Pro Leu Lys His Glu Leu Glu Met
865                 870                 875                 880

Ser Lys Glu Ser Glu His Asp Ser Asp Glu Ser Ser Asp Asp Asp Ser
                885                 890                 895

Asp Ser Glu Glu Pro Ser Lys Tyr Ile Asn Ala Ser Phe Ile Met Ser
            900                 905                 910

Tyr Trp Lys Pro Glu Val Met Ile Ala Ala Gln Gly Pro Leu Lys Glu
        915                 920                 925

Thr Ile Gly Asp Phe Trp Gln Met Ile Phe Gln Arg Lys Val Lys Val
    930                 935                 940

Ile Val Met Leu Thr Glu Leu Lys His Gly Asp Gln Glu Ile Cys Ala
945                 950                 955                 960

Gln Tyr Trp Gly Glu Gly Lys Gln Thr Tyr Gly Asp Ile Glu Val Asp
                965                 970                 975
```

-continued

```
Leu Lys Asp Thr Asp Lys Ser Ser Thr Tyr Thr Leu Arg Val Phe Glu
            980                 985                 990

Leu Arg His Ser Lys Arg Lys Asp  Ser Arg Thr Val Tyr  Gln Tyr Gln
        995                 1000                 1005

Tyr Thr  Asn Trp Ser Val Glu  Gln Leu Pro Ala Glu  Pro Lys Glu
    1010                 1015                 1020

Leu Ile  Ser Met Ile Gln Val  Val Lys Gln Lys Leu  Pro Gln Lys
    1025                 1030                 1035

Asn Ser  Ser Glu Gly Asn Lys  His His Lys Ser Thr  Pro Leu Leu
    1040                 1045                 1050

Ile His  Cys Arg Asp Gly Ser  Gln Gln Thr Gly Ile  Phe Cys Ala
    1055                 1060                 1065

Leu Leu  Asn Leu Leu Glu Ser  Ala Glu Thr Glu Glu  Val Val Asp
    1070                 1075                 1080

Ile Phe  Gln Val Val Lys Ala  Leu Arg Lys Ala Arg  Pro Gly Met
    1085                 1090                 1095

Val Ser  Thr Phe Glu Gln Tyr  Gln Phe Leu Tyr Asp  Val Ile Ala
    1100                 1105                 1110

Ser Thr  Tyr Pro Ala Gln Asn  Gly Gln Val Lys Lys  Asn Asn His
    1115                 1120                 1125

Gln Glu  Asp Lys Ile Glu Phe  Asp Asn Glu Val Asp  Lys Val Lys
    1130                 1135                 1140

Gln Asp  Ala Asn Cys Val Asn  Pro Leu Gly Ala Pro  Glu Lys Leu
    1145                 1150                 1155

Pro Glu  Ala Lys Glu Gln Ala  Glu Gly Ser Glu Pro  Thr Ser Gly
    1160                 1165                 1170

Thr Glu  Gly Pro Glu His Ser  Val Asn Gly Pro Ala  Ser Pro Ala
    1175                 1180                 1185

Leu Asn  Gln Gly Ser
    1190


<210> SEQ ID NO 5
<211> LENGTH: 1258
<212> TYPE: PRT
<213> ORGANISM: Homo sapiens

<400> SEQUENCE: 5

Met Thr Met Tyr Leu Trp Leu Lys Leu Leu Ala Phe Gly Phe Ala Phe
1               5                   10                  15

Leu Asp Thr Glu Val Phe Val Thr Gly Gln Ser Pro Thr Pro Ser Pro
            20                  25                  30

Thr Gly Leu Thr Thr Ala Lys Met Pro Ser Val Pro Leu Ser Ser Asp
        35                  40                  45

Pro Leu Pro Thr His Thr Thr Ala Phe Ser Pro Ala Ser Thr Phe Glu
    50                  55                  60

Arg Glu Asn Asp Phe Ser Glu Thr Thr Thr Ser Leu Ser Pro Asp Asn
65                  70                  75                  80

Thr Ser Thr Gln Val Ser Pro Asp Ser Leu Asp Asn Ala Ser Ala Phe
                85                  90                  95

Asn Thr Thr Gly Val Ser Ser Val Gln Thr Pro His Leu Pro Thr His
            100                 105                 110

Ala Asp Ser Gln Thr Pro Ser Ala Gly Thr Asp Thr Gln Thr Phe Ser
        115                 120                 125

Gly Ser Ala Ala Asn Ala Lys Leu Asn Pro Thr Pro Gly Ser Asn Ala
    130                 135                 140
```

-continued

```
Ile Ser Asp Ala Tyr Leu Asn Ala Ser Glu Thr Thr Thr Leu Ser Pro
145                 150                 155                 160

Ser Gly Ser Ala Val Ile Ser Thr Thr Thr Ile Ala Thr Thr Pro Ser
                165                 170                 175

Lys Pro Thr Cys Asp Glu Lys Tyr Ala Asn Ile Thr Val Asp Tyr Leu
            180                 185                 190

Tyr Asn Lys Glu Thr Lys Leu Phe Thr Ala Lys Leu Asn Val Asn Glu
        195                 200                 205

Asn Val Glu Cys Gly Asn Asn Thr Cys Thr Asn Asn Glu Val His Asn
    210                 215                 220

Leu Thr Glu Cys Lys Asn Ala Ser Val Ser Ile Ser His Asn Ser Cys
225                 230                 235                 240

Thr Ala Pro Asp Lys Thr Leu Ile Leu Asp Val Pro Pro Gly Val Glu
                245                 250                 255

Lys Phe Gln Leu His Asp Cys Thr Gln Val Glu Lys Ala Asp Thr Thr
            260                 265                 270

Ile Cys Leu Lys Trp Lys Asn Ile Glu Thr Phe Thr Cys Asp Thr Gln
        275                 280                 285

Asn Ile Thr Tyr Arg Phe Gln Cys Gly Asn Met Ile Phe Asp Asn Lys
    290                 295                 300

Glu Ile Lys Leu Glu Asn Leu Glu Pro Glu His Glu Tyr Lys Cys Asp
305                 310                 315                 320

Ser Glu Ile Leu Tyr Asn Asn His Lys Phe Thr Asn Ala Ser Lys Ile
                325                 330                 335

Ile Lys Thr Asp Phe Gly Ser Pro Gly Glu Pro Gln Ile Ile Phe Cys
            340                 345                 350

Arg Ser Glu Ala Ala His Gln Gly Val Ile Thr Trp Asn Pro Pro Gln
        355                 360                 365

Arg Ser Phe His Asn Phe Thr Leu Cys Tyr Ile Lys Glu Thr Glu Lys
    370                 375                 380

Asp Cys Leu Asn Leu Asp Lys Asn Leu Ile Lys Tyr Asp Leu Gln Asn
385                 390                 395                 400

Leu Lys Pro Tyr Thr Lys Tyr Val Leu Ser Leu His Ala Tyr Ile Ile
                405                 410                 415

Ala Lys Val Gln Arg Asn Gly Ser Ala Ala Met Cys His Phe Thr Thr
            420                 425                 430

Lys Ser Ala Pro Pro Ser Gln Val Trp Asn Met Thr Val Ser Met Thr
        435                 440                 445

Ser Asp Asn Ser Met His Val Lys Cys Arg Pro Pro Arg Asp Arg Asn
    450                 455                 460

Gly Pro His Glu Arg Tyr His Leu Glu Val Glu Ala Gly Asn Thr Leu
465                 470                 475                 480

Val Arg Asn Glu Ser His Lys Asn Cys Asp Phe Arg Val Lys Asp Leu
                485                 490                 495

Gln Tyr Ser Thr Asp Tyr Thr Phe Lys Ala Tyr Phe His Asn Gly Asp
            500                 505                 510

Tyr Pro Gly Glu Pro Phe Ile Leu His His Ser Thr Ser Tyr Asn Ser
        515                 520                 525

Lys Ala Leu Ile Ala Phe Leu Ala Phe Leu Ile Ile Val Thr Ser Ile
    530                 535                 540

Ala Leu Leu Val Val Leu Tyr Lys Ile Tyr Asp Leu His Lys Lys Arg
545                 550                 555                 560
```

```
Ser Cys Asn Leu Asp Glu Gln Gln Glu Leu Val Glu Arg Asp Asp Glu
                565                 570                 575

Lys Gln Leu Met Asn Val Glu Pro Ile His Ala Asp Ile Leu Leu Glu
            580                 585                 590

Thr Tyr Lys Arg Lys Ile Ala Asp Glu Gly Arg Leu Phe Leu Ala Glu
        595                 600                 605

Phe Gln Ser Ile Pro Arg Val Phe Ser Lys Phe Pro Ile Lys Glu Ala
    610                 615                 620

Arg Lys Pro Phe Asn Gln Asn Lys Asn Arg Tyr Val Asp Ile Leu Pro
625                 630                 635                 640

Tyr Asp Tyr Asn Arg Val Glu Leu Ser Glu Ile Asn Gly Asp Ala Gly
                645                 650                 655

Ser Asn Tyr Ile Asn Ala Ser Tyr Ile Asp Gly Phe Lys Glu Pro Arg
            660                 665                 670

Lys Tyr Ile Ala Ala Gln Gly Pro Arg Asp Glu Thr Val Asp Asp Phe
        675                 680                 685

Trp Arg Met Ile Trp Glu Gln Lys Ala Thr Val Ile Val Met Val Thr
    690                 695                 700

Arg Cys Glu Glu Gly Asn Arg Asn Lys Cys Ala Glu Tyr Trp Pro Ser
705                 710                 715                 720

Met Glu Glu Gly Thr Arg Ala Phe Gly Asp Val Val Val Lys Ile Asn
                725                 730                 735

Gln His Lys Arg Cys Pro Asp Tyr Ile Ile Gln Lys Leu Asn Ile Val
            740                 745                 750

Asn Lys Lys Glu Lys Ala Thr Gly Arg Glu Val Thr His Ile Gln Phe
        755                 760                 765

Thr Ser Trp Pro Asp His Gly Val Pro Glu Asp Pro His Leu Leu Leu
    770                 775                 780

Lys Leu Arg Arg Arg Val Asn Ala Phe Ser Asn Phe Phe Ser Gly Pro
785                 790                 795                 800

Ile Val Val His Cys Ser Ala Gly Val Gly Arg Thr Gly Thr Tyr Ile
                805                 810                 815

Gly Ile Asp Ala Met Leu Glu Gly Leu Glu Ala Glu Asn Lys Val Asp
            820                 825                 830

Val Tyr Gly Tyr Val Val Lys Leu Arg Arg Gln Arg Cys Leu Met Val
        835                 840                 845

Gln Val Glu Ala Gln Tyr Ile Leu Ile His Gln Ala Leu Val Glu Tyr
    850                 855                 860

Asn Gln Phe Gly Glu Thr Glu Val Asn Leu Ser Glu Leu His Pro Tyr
865                 870                 875                 880

Leu His Asn Met Lys Lys Arg Asp Pro Pro Ser Glu Pro Ser Pro Leu
                885                 890                 895

Glu Ala Glu Phe Gln Arg Leu Pro Ser Tyr Arg Ser Trp Arg Thr Gln
            900                 905                 910

His Ile Gly Asn Gln Glu Glu Asn Lys Ser Lys Asn Arg Asn Ser Asn
        915                 920                 925

Val Ile Pro Tyr Asp Tyr Asn Arg Val Pro Leu Lys His Glu Leu Glu
    930                 935                 940

Met Ser Lys Glu Ser Glu His Asp Ser Asp Glu Ser Ser Asp Asp Asp
945                 950                 955                 960

Ser Asp Ser Glu Glu Pro Ser Lys Tyr Ile Asn Ala Ser Phe Ile Met
                965                 970                 975

Ser Tyr Trp Lys Pro Glu Val Met Ile Ala Ala Gln Gly Pro Leu Lys
```

-continued

```
            980                   985                   990

Glu Thr Ile Gly Asp Phe Trp Gln  Met Ile Phe Gln Arg  Lys Val Lys
        995                  1000                 1005

Val Ile  Val Met Leu Thr Glu  Leu Lys His Gly Asp  Gln Glu Ile
    1010                 1015                 1020

Cys Ala  Gln Tyr Trp Gly Glu  Gly Lys Gln Thr Tyr  Gly Asp Ile
    1025                 1030                 1035

Glu Val  Asp Leu Lys Asp Thr  Asp Lys Ser Ser Thr  Tyr Thr Leu
    1040                 1045                 1050

Arg Val  Phe Glu Leu Arg His  Ser Lys Arg Lys Asp  Ser Arg Thr
    1055                 1060                 1065

Val Tyr  Gln Tyr Gln Tyr Thr  Asn Trp Ser Val Glu  Gln Leu Pro
    1070                 1075                 1080

Ala Glu  Pro Lys Glu Leu Ile  Ser Met Ile Gln Val  Val Lys Gln
    1085                 1090                 1095

Lys Leu  Pro Gln Lys Asn Ser  Ser Glu Gly Asn Lys  His His Lys
    1100                 1105                 1110

Ser Thr  Pro Leu Leu Ile His  Cys Arg Asp Gly Ser  Gln Gln Thr
    1115                 1120                 1125

Gly Ile  Phe Cys Ala Leu Leu  Asn Leu Leu Glu Ser  Ala Glu Thr
    1130                 1135                 1140

Glu Glu  Val Val Asp Ile Phe  Gln Val Val Lys Ala  Leu Arg Lys
    1145                 1150                 1155

Ala Arg  Pro Gly Met Val Ser  Thr Phe Glu Gln Tyr  Gln Phe Leu
    1160                 1165                 1170

Tyr Asp  Val Ile Ala Ser Thr  Tyr Pro Ala Gln Asn  Gly Gln Val
    1175                 1180                 1185

Lys Lys  Asn Asn His Gln Glu  Asp Lys Ile Glu Phe  Asp Asn Glu
    1190                 1195                 1200

Val Asp  Lys Val Lys Gln Asp  Ala Asn Cys Val Asn  Pro Leu Gly
    1205                 1210                 1215

Ala Pro  Glu Lys Leu Pro Glu  Ala Lys Glu Gln Ala  Glu Gly Ser
    1220                 1225                 1230

Glu Pro  Thr Ser Gly Thr Glu  Gly Pro Glu His Ser  Val Asn Gly
    1235                 1240                 1245

Pro Ala  Ser Pro Ala Leu Asn  Gln Gly Ser
    1250                 1255


<210> SEQ ID NO 6
<211> LENGTH: 1240
<212> TYPE: PRT
<213> ORGANISM: Homo sapiens

<400> SEQUENCE: 6

Met Thr Met Tyr Leu Trp Leu Lys Leu Leu Ala Phe Gly Phe Ala Phe
1               5                   10                  15

Leu Asp Thr Glu Val Phe Val Thr Gly Gln Ser Pro Thr Pro Ser Pro
            20                  25                  30

Thr Gly Val Ser Ser Val Gln Thr Pro His Leu Pro Thr His Ala Asp
        35                  40                  45

Ser Gln Thr Pro Ser Ala Gly Thr Asp Thr Gln Thr Phe Ser Gly Ser
    50                  55                  60

Ala Ala Asn Ala Lys Leu Asn Pro Thr Pro Gly Ser Asn Ala Ile Ser
65                  70                  75                  80
```

```
Asp Val Pro Gly Glu Arg Ser Thr Ala Ser Thr Phe Pro Thr Asp Pro
                85                  90                  95

Val Ser Pro Leu Thr Thr Thr Leu Ser Leu Ala His His Ser Ser Ala
            100                 105                 110

Ala Leu Pro Ala Arg Thr Ser Asn Thr Thr Ile Thr Ala Asn Thr Ser
        115                 120                 125

Asp Ala Tyr Leu Asn Ala Ser Glu Thr Thr Thr Leu Ser Pro Ser Gly
    130                 135                 140

Ser Ala Val Ile Ser Thr Thr Thr Ile Ala Thr Thr Pro Ser Lys Pro
145                 150                 155                 160

Thr Cys Asp Glu Lys Tyr Ala Asn Ile Thr Val Asp Tyr Leu Tyr Asn
                165                 170                 175

Lys Glu Thr Lys Leu Phe Thr Ala Lys Leu Asn Val Asn Glu Asn Val
            180                 185                 190

Glu Cys Gly Asn Asn Thr Cys Thr Asn Asn Glu Val His Asn Leu Thr
        195                 200                 205

Glu Cys Lys Asn Ala Ser Val Ser Ile Ser His Asn Ser Cys Thr Ala
    210                 215                 220

Pro Asp Lys Thr Leu Ile Leu Asp Val Pro Pro Gly Val Glu Lys Phe
225                 230                 235                 240

Gln Leu His Asp Cys Thr Gln Val Glu Lys Ala Asp Thr Thr Ile Cys
                245                 250                 255

Leu Lys Trp Lys Asn Ile Glu Thr Phe Thr Cys Asp Thr Gln Asn Ile
            260                 265                 270

Thr Tyr Arg Phe Gln Cys Gly Asn Met Ile Phe Asp Asn Lys Glu Ile
        275                 280                 285

Lys Leu Glu Asn Leu Glu Pro Glu His Glu Tyr Lys Cys Asp Ser Glu
    290                 295                 300

Ile Leu Tyr Asn Asn His Lys Phe Thr Asn Ala Ser Lys Ile Ile Lys
305                 310                 315                 320

Thr Asp Phe Gly Ser Pro Gly Glu Pro Gln Ile Ile Phe Cys Arg Ser
                325                 330                 335

Glu Ala Ala His Gln Gly Val Ile Thr Trp Asn Pro Pro Gln Arg Ser
            340                 345                 350

Phe His Asn Phe Thr Leu Cys Tyr Ile Lys Glu Thr Glu Lys Asp Cys
        355                 360                 365

Leu Asn Leu Asp Lys Asn Leu Ile Lys Tyr Asp Leu Gln Asn Leu Lys
    370                 375                 380

Pro Tyr Thr Lys Tyr Val Leu Ser Leu His Ala Tyr Ile Ile Ala Lys
385                 390                 395                 400

Val Gln Arg Asn Gly Ser Ala Ala Met Cys His Phe Thr Thr Lys Ser
                405                 410                 415

Ala Pro Pro Ser Gln Val Trp Asn Met Thr Val Ser Met Thr Ser Asp
            420                 425                 430

Asn Ser Met His Val Lys Cys Arg Pro Pro Arg Asp Arg Asn Gly Pro
        435                 440                 445

His Glu Arg Tyr His Leu Glu Val Glu Ala Gly Asn Thr Leu Val Arg
    450                 455                 460

Asn Glu Ser His Lys Asn Cys Asp Phe Arg Val Lys Asp Leu Gln Tyr
465                 470                 475                 480

Ser Thr Asp Tyr Thr Phe Lys Ala Tyr Phe His Asn Gly Asp Tyr Pro
                485                 490                 495

Gly Glu Pro Phe Ile Leu His His Ser Thr Ser Tyr Asn Ser Lys Ala
```

-continued

```
            500                 505                 510

Leu Ile Ala Phe Leu Ala Phe Leu Ile Ile Val Thr Ser Ile Ala Leu
        515                 520                 525

Leu Val Val Leu Tyr Lys Ile Tyr Asp Leu His Lys Lys Arg Ser Cys
    530                 535                 540

Asn Leu Asp Glu Gln Gln Glu Leu Val Glu Arg Asp Asp Glu Lys Gln
545                 550                 555                 560

Leu Met Asn Val Glu Pro Ile His Ala Asp Ile Leu Leu Glu Thr Tyr
                565                 570                 575

Lys Arg Lys Ile Ala Asp Glu Gly Arg Leu Phe Leu Ala Glu Phe Gln
            580                 585                 590

Ser Ile Pro Arg Val Phe Ser Lys Phe Pro Ile Lys Glu Ala Arg Lys
        595                 600                 605

Pro Phe Asn Gln Asn Lys Asn Arg Tyr Val Asp Ile Leu Pro Tyr Asp
    610                 615                 620

Tyr Asn Arg Val Glu Leu Ser Glu Ile Asn Gly Asp Ala Gly Ser Asn
625                 630                 635                 640

Tyr Ile Asn Ala Ser Tyr Ile Asp Gly Phe Lys Glu Pro Arg Lys Tyr
                645                 650                 655

Ile Ala Ala Gln Gly Pro Arg Asp Glu Thr Val Asp Asp Phe Trp Arg
            660                 665                 670

Met Ile Trp Glu Gln Lys Ala Thr Val Ile Val Met Val Thr Arg Cys
        675                 680                 685

Glu Glu Gly Asn Arg Asn Lys Cys Ala Glu Tyr Trp Pro Ser Met Glu
    690                 695                 700

Glu Gly Thr Arg Ala Phe Gly Asp Val Val Val Lys Ile Asn Gln His
705                 710                 715                 720

Lys Arg Cys Pro Asp Tyr Ile Ile Gln Lys Leu Asn Ile Val Asn Lys
                725                 730                 735

Lys Glu Lys Ala Thr Gly Arg Glu Val Thr His Ile Gln Phe Thr Ser
            740                 745                 750

Trp Pro Asp His Gly Val Pro Glu Asp Pro His Leu Leu Leu Lys Leu
        755                 760                 765

Arg Arg Arg Val Asn Ala Phe Ser Asn Phe Phe Ser Gly Pro Ile Val
    770                 775                 780

Val His Cys Ser Ala Gly Val Gly Arg Thr Gly Thr Tyr Ile Gly Ile
785                 790                 795                 800

Asp Ala Met Leu Glu Gly Leu Glu Ala Glu Asn Lys Val Asp Val Tyr
                805                 810                 815

Gly Tyr Val Val Lys Leu Arg Arg Gln Arg Cys Leu Met Val Gln Val
            820                 825                 830

Glu Ala Gln Tyr Ile Leu Ile His Gln Ala Leu Val Glu Tyr Asn Gln
        835                 840                 845

Phe Gly Glu Thr Glu Val Asn Leu Ser Glu Leu His Pro Tyr Leu His
    850                 855                 860

Asn Met Lys Lys Arg Asp Pro Pro Ser Glu Pro Ser Pro Leu Glu Ala
865                 870                 875                 880

Glu Phe Gln Arg Leu Pro Ser Tyr Arg Ser Trp Arg Thr Gln His Ile
                885                 890                 895

Gly Asn Gln Glu Glu Asn Lys Ser Lys Asn Arg Asn Ser Asn Val Ile
            900                 905                 910

Pro Tyr Asp Tyr Asn Arg Val Pro Leu Lys His Glu Leu Glu Met Ser
        915                 920                 925
```

-continued

```
Lys Glu Ser Glu His Asp Ser Asp Glu Ser Ser Asp Asp Asp Ser Asp
    930                 935                 940

Ser Glu Glu Pro Ser Lys Tyr Ile Asn Ala Ser Phe Ile Met Ser Tyr
945                 950                 955                 960

Trp Lys Pro Glu Val Met Ile Ala Ala Gln Gly Pro Leu Lys Glu Thr
                965                 970                 975

Ile Gly Asp Phe Trp Gln Met Ile Phe Gln Arg Lys Val Lys Val Ile
            980                 985                 990

Val Met Leu Thr Glu Leu Lys His  Gly Asp Gln Glu Ile  Cys Ala Gln
        995                 1000                1005

Tyr Trp  Gly Glu Gly Lys Gln  Thr Tyr Gly Asp Ile  Glu Val Asp
    1010                 1015                 1020

Leu Lys  Asp Thr Asp Lys Ser  Ser Thr Tyr Thr Leu  Arg Val Phe
    1025                 1030                 1035

Glu Leu  Arg His Ser Lys Arg  Lys Asp Ser Arg Thr  Val Tyr Gln
    1040                 1045                 1050

Tyr Gln  Tyr Thr Asn Trp Ser  Val Glu Gln Leu Pro  Ala Glu Pro
    1055                 1060                 1065

Lys Glu  Leu Ile Ser Met Ile  Gln Val Val Lys Gln  Lys Leu Pro
    1070                 1075                 1080

Gln Lys  Asn Ser Ser Glu Gly  Asn Lys His His Lys  Ser Thr Pro
    1085                 1090                 1095

Leu Leu  Ile His Cys Arg Asp  Gly Ser Gln Gln Thr  Gly Ile Phe
    1100                 1105                 1110

Cys Ala  Leu Leu Asn Leu Leu  Glu Ser Ala Glu Thr  Glu Glu Val
    1115                 1120                 1125

Val Asp  Ile Phe Gln Val Val  Lys Ala Leu Arg Lys  Ala Arg Pro
    1130                 1135                 1140

Gly Met  Val Ser Thr Phe Glu  Gln Tyr Gln Phe Leu  Tyr Asp Val
    1145                 1150                 1155

Ile Ala  Ser Thr Tyr Pro Ala  Gln Asn Gly Gln Val  Lys Lys Asn
    1160                 1165                 1170

Asn His  Gln Glu Asp Lys Ile  Glu Phe Asp Asn Glu  Val Asp Lys
    1175                 1180                 1185

Val Lys  Gln Asp Ala Asn Cys  Val Asn Pro Leu Gly  Ala Pro Glu
    1190                 1195                 1200

Lys Leu  Pro Glu Ala Lys Glu  Gln Ala Glu Gly Ser  Glu Pro Thr
    1205                 1210                 1215

Ser Gly  Thr Glu Gly Pro Glu  His Ser Val Asn Gly  Pro Ala Ser
    1220                 1225                 1230

Pro Ala  Leu Asn Gln Gly Ser
    1235                 1240
```

<210> SEQ ID NO 7
<211> LENGTH: 1306
<212> TYPE: PRT
<213> ORGANISM: Homo sapiens

<400> SEQUENCE: 7

```
Met Thr Met Tyr Leu Trp Leu Lys Leu Leu Ala Phe Gly Phe Ala Phe
1               5                   10                  15

Leu Asp Thr Glu Val Phe Val Thr Gly Gln Ser Pro Thr Pro Ser Pro
            20                  25                  30

Thr Gly Leu Thr Thr Ala Lys Met Pro Ser Val Pro Leu Ser Ser Asp
```

```
        35                  40                  45

Pro Leu Pro Thr His Thr Thr Ala Phe Ser Pro Ala Ser Thr Phe Glu
    50                  55                  60

Arg Glu Asn Asp Phe Ser Glu Thr Thr Thr Ser Leu Ser Pro Asp Asn
65                  70                  75                  80

Thr Ser Thr Gln Val Ser Pro Asp Ser Leu Asp Asn Ala Ser Ala Phe
                85                  90                  95

Asn Thr Thr Gly Val Ser Ser Val Gln Thr Pro His Leu Pro Thr His
            100                 105                 110

Ala Asp Ser Gln Thr Pro Ser Ala Gly Thr Asp Thr Gln Thr Phe Ser
        115                 120                 125

Gly Ser Ala Ala Asn Ala Lys Leu Asn Pro Thr Pro Gly Ser Asn Ala
    130                 135                 140

Ile Ser Asp Val Pro Gly Glu Arg Ser Thr Ala Ser Thr Phe Pro Thr
145                 150                 155                 160

Asp Pro Val Ser Pro Leu Thr Thr Thr Leu Ser Leu Ala His His Ser
                165                 170                 175

Ser Ala Ala Leu Pro Ala Arg Thr Ser Asn Thr Thr Ile Thr Ala Asn
            180                 185                 190

Thr Ser Asp Ala Tyr Leu Asn Ala Ser Glu Thr Thr Thr Leu Ser Pro
        195                 200                 205

Ser Gly Ser Ala Val Ile Ser Thr Thr Thr Ile Ala Thr Thr Pro Ser
    210                 215                 220

Lys Pro Thr Cys Asp Glu Lys Tyr Ala Asn Ile Thr Val Asp Tyr Leu
225                 230                 235                 240

Tyr Asn Lys Glu Thr Lys Leu Phe Thr Ala Lys Leu Asn Val Asn Glu
                245                 250                 255

Asn Val Glu Cys Gly Asn Asn Thr Cys Thr Asn Asn Glu Val His Asn
            260                 265                 270

Leu Thr Glu Cys Lys Asn Ala Ser Val Ser Ile Ser His Asn Ser Cys
        275                 280                 285

Thr Ala Pro Asp Lys Thr Leu Ile Leu Asp Val Pro Pro Gly Val Glu
    290                 295                 300

Lys Phe Gln Leu His Asp Cys Thr Gln Val Glu Lys Ala Asp Thr Thr
305                 310                 315                 320

Ile Cys Leu Lys Trp Lys Asn Ile Glu Thr Phe Thr Cys Asp Thr Gln
                325                 330                 335

Asn Ile Thr Tyr Arg Phe Gln Cys Gly Asn Met Ile Phe Asp Asn Lys
            340                 345                 350

Glu Ile Lys Leu Glu Asn Leu Glu Pro Glu His Glu Tyr Lys Cys Asp
        355                 360                 365

Ser Glu Ile Leu Tyr Asn Asn His Lys Phe Thr Asn Ala Ser Lys Ile
    370                 375                 380

Ile Lys Thr Asp Phe Gly Ser Pro Gly Glu Pro Gln Ile Ile Phe Cys
385                 390                 395                 400

Arg Ser Glu Ala Ala His Gln Gly Val Ile Thr Trp Asn Pro Pro Gln
                405                 410                 415

Arg Ser Phe His Asn Phe Thr Leu Cys Tyr Ile Lys Glu Thr Glu Lys
            420                 425                 430

Asp Cys Leu Asn Leu Asp Lys Asn Leu Ile Lys Tyr Asp Leu Gln Asn
        435                 440                 445

Leu Lys Pro Tyr Thr Lys Tyr Val Leu Ser Leu His Ala Tyr Ile Ile
    450                 455                 460
```

```
Ala Lys Val Gln Arg Asn Gly Ser Ala Ala Met Cys His Phe Thr Thr
465                 470                 475                 480

Lys Ser Ala Pro Pro Ser Gln Val Trp Asn Met Thr Val Ser Met Thr
                485                 490                 495

Ser Asp Asn Ser Met His Val Lys Cys Arg Pro Pro Arg Asp Arg Asn
            500                 505                 510

Gly Pro His Glu Arg Tyr His Leu Glu Val Glu Ala Gly Asn Thr Leu
        515                 520                 525

Val Arg Asn Glu Ser His Lys Asn Cys Asp Phe Arg Val Lys Asp Leu
    530                 535                 540

Gln Tyr Ser Thr Asp Tyr Thr Phe Lys Ala Tyr Phe His Asn Gly Asp
545                 550                 555                 560

Tyr Pro Gly Glu Pro Phe Ile Leu His His Ser Thr Ser Tyr Asn Ser
                565                 570                 575

Lys Ala Leu Ile Ala Phe Leu Ala Phe Leu Ile Ile Val Thr Ser Ile
            580                 585                 590

Ala Leu Leu Val Val Leu Tyr Lys Ile Tyr Asp Leu His Lys Lys Arg
        595                 600                 605

Ser Cys Asn Leu Asp Glu Gln Gln Glu Leu Val Glu Arg Asp Asp Glu
    610                 615                 620

Lys Gln Leu Met Asn Val Glu Pro Ile His Ala Asp Ile Leu Leu Glu
625                 630                 635                 640

Thr Tyr Lys Arg Lys Ile Ala Asp Glu Gly Arg Leu Phe Leu Ala Glu
                645                 650                 655

Phe Gln Ser Ile Pro Arg Val Phe Ser Lys Phe Pro Ile Lys Glu Ala
            660                 665                 670

Arg Lys Pro Phe Asn Gln Asn Lys Asn Arg Tyr Val Asp Ile Leu Pro
        675                 680                 685

Tyr Asp Tyr Asn Arg Val Glu Leu Ser Glu Ile Asn Gly Asp Ala Gly
    690                 695                 700

Ser Asn Tyr Ile Asn Ala Ser Tyr Ile Asp Gly Phe Lys Glu Pro Arg
705                 710                 715                 720

Lys Tyr Ile Ala Ala Gln Gly Pro Arg Asp Glu Thr Val Asp Asp Phe
                725                 730                 735

Trp Arg Met Ile Trp Glu Gln Lys Ala Thr Val Ile Val Met Val Thr
            740                 745                 750

Arg Cys Glu Glu Gly Asn Arg Asn Lys Cys Ala Glu Tyr Trp Pro Ser
        755                 760                 765

Met Glu Glu Gly Thr Arg Ala Phe Gly Asp Val Val Val Lys Ile Asn
    770                 775                 780

Gln His Lys Arg Cys Pro Asp Tyr Ile Ile Gln Lys Leu Asn Ile Val
785                 790                 795                 800

Asn Lys Lys Glu Lys Ala Thr Gly Arg Glu Val Thr His Ile Gln Phe
                805                 810                 815

Thr Ser Trp Pro Asp His Gly Val Pro Glu Asp Pro His Leu Leu Leu
            820                 825                 830

Lys Leu Arg Arg Arg Val Asn Ala Phe Ser Asn Phe Phe Ser Gly Pro
        835                 840                 845

Ile Val Val His Cys Ser Ala Gly Val Gly Arg Thr Gly Thr Tyr Ile
    850                 855                 860

Gly Ile Asp Ala Met Leu Glu Gly Leu Glu Ala Glu Asn Lys Val Asp
865                 870                 875                 880
```

-continued

```
Val Tyr Gly Tyr Val Val Lys Leu Arg Arg Gln Arg Cys Leu Met Val
                885                 890                 895

Gln Val Glu Ala Gln Tyr Ile Leu Ile His Gln Ala Leu Val Glu Tyr
            900                 905                 910

Asn Gln Phe Gly Glu Thr Glu Val Asn Leu Ser Glu Leu His Pro Tyr
        915                 920                 925

Leu His Asn Met Lys Lys Arg Asp Pro Pro Ser Glu Pro Ser Pro Leu
    930                 935                 940

Glu Ala Glu Phe Gln Arg Leu Pro Ser Tyr Arg Ser Trp Arg Thr Gln
945                 950                 955                 960

His Ile Gly Asn Gln Glu Glu Asn Lys Ser Lys Asn Arg Asn Ser Asn
                965                 970                 975

Val Ile Pro Tyr Asp Tyr Asn Arg Val Pro Leu Lys His Glu Leu Glu
            980                 985                 990

Met Ser Lys Glu Ser Glu His Asp  Ser Asp Glu Ser Ser  Asp Asp Asp
        995                 1000                1005

Ser Asp  Ser Glu Glu Pro Ser  Lys Tyr Ile Asn Ala  Ser Phe Ile
    1010                1015                1020

Met Ser  Tyr Trp Lys Pro Glu  Val Met Ile Ala Ala  Gln Gly Pro
    1025                1030                1035

Leu Lys  Glu Thr Ile Gly Asp  Phe Trp Gln Met Ile  Phe Gln Arg
    1040                1045                1050

Lys Val  Lys Val Ile Val Met  Leu Thr Glu Leu Lys  His Gly Asp
    1055                1060                1065

Gln Glu  Ile Cys Ala Gln Tyr  Trp Gly Glu Gly Lys  Gln Thr Tyr
    1070                1075                1080

Gly Asp  Ile Glu Val Asp Leu  Lys Asp Thr Asp Lys  Ser Ser Thr
    1085                1090                1095

Tyr Thr  Leu Arg Val Phe Glu  Leu Arg His Ser Lys  Arg Lys Asp
    1100                1105                1110

Ser Arg  Thr Val Tyr Gln Tyr  Gln Tyr Thr Asn Trp  Ser Val Glu
    1115                1120                1125

Gln Leu  Pro Ala Glu Pro Lys  Glu Leu Ile Ser Met  Ile Gln Val
    1130                1135                1140

Val Lys  Gln Lys Leu Pro Gln  Lys Asn Ser Ser Glu  Gly Asn Lys
    1145                1150                1155

His His  Lys Ser Thr Pro Leu  Leu Ile His Cys Arg  Asp Gly Ser
    1160                1165                1170

Gln Gln  Thr Gly Ile Phe Cys  Ala Leu Leu Asn Leu  Leu Glu Ser
    1175                1180                1185

Ala Glu  Thr Glu Glu Val Val  Asp Ile Phe Gln Val  Val Lys Ala
    1190                1195                1200

Leu Arg  Lys Ala Arg Pro Gly  Met Val Ser Thr Phe  Glu Gln Tyr
    1205                1210                1215

Gln Phe  Leu Tyr Asp Val Ile  Ala Ser Thr Tyr Pro  Ala Gln Asn
    1220                1225                1230

Gly Gln  Val Lys Lys Asn Asn  His Gln Glu Asp Lys  Ile Glu Phe
    1235                1240                1245

Asp Asn  Glu Val Asp Lys Val  Lys Gln Asp Ala Asn  Cys Val Asn
    1250                1255                1260

Pro Leu  Gly Ala Pro Glu Lys  Leu Pro Glu Ala Lys  Glu Gln Ala
    1265                1270                1275

Glu Gly  Ser Glu Pro Thr Ser  Gly Thr Glu Gly Pro  Glu His Ser
```

```
    1280                1285                1290

Val Asn  Gly Pro Ala Ser Pro  Ala Leu Asn Gln Gly  Ser
    1295                1300                1305


<210> SEQ ID NO 8
<211> LENGTH: 445
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Glu Val Lys Leu Leu Glu Ser Gly Gly Gly Leu Val Gln Pro Gly Gly
1               5                   10                  15

Ser Leu Lys Leu Ser Cys Ala Ala Ser Gly Phe Asp Phe Ser Arg Tyr
            20                  25                  30

Trp Met Ser Trp Val Arg Gln Ala Pro Gly Lys Gly Leu Glu Trp Ile
        35                  40                  45

Gly Glu Ile Asn Pro Thr Ser Ser Thr Ile Asn Phe Thr Pro Ser Leu
    50                  55                  60

Lys Asp Lys Val Phe Ile Ser Arg Asp Asn Ala Lys Asn Thr Leu Tyr
65                  70                  75                  80

Leu Gln Met Ser Lys Val Arg Ser Glu Asp Thr Ala Leu Tyr Tyr Cys
                85                  90                  95

Ala Arg Gly Asn Tyr Tyr Arg Tyr Gly Asp Ala Met Asp Tyr Trp Gly
            100                 105                 110

Gln Gly Thr Ser Val Thr Val Ser Ser Ala Lys Thr Thr Pro Pro Ser
        115                 120                 125

Val Tyr Pro Leu Ala Pro Gly Ser Ala Ala Gln Thr Asn Ser Met Val
    130                 135                 140

Thr Leu Gly Cys Leu Val Lys Gly Tyr Phe Pro Glu Pro Val Thr Val
145                 150                 155                 160

Thr Trp Asn Ser Gly Ser Leu Ser Ser Gly Val His Thr Phe Pro Ala
                165                 170                 175

Val Leu Gln Ser Asp Leu Tyr Thr Leu Ser Ser Ser Val Thr Val Pro
            180                 185                 190

Ser Ser Thr Trp Pro Ser Glu Thr Val Thr Cys Asn Val Ala His Pro
        195                 200                 205

Ala Ser Ser Thr Lys Val Asp Lys Lys Ile Val Pro Arg Asp Cys Gly
    210                 215                 220

Cys Lys Pro Cys Ile Cys Thr Val Pro Glu Val Ser Ser Val Phe Ile
225                 230                 235                 240

Phe Pro Pro Lys Pro Lys Asp Val Leu Thr Ile Thr Leu Thr Pro Lys
                245                 250                 255

Val Thr Cys Val Val Val Asp Ile Ser Lys Asp Asp Pro Glu Val Gln
            260                 265                 270

Phe Ser Trp Phe Val Asp Asp Val Glu Val His Thr Ala Gln Thr Gln
        275                 280                 285

Pro Arg Glu Glu Gln Phe Asn Ser Thr Glu Arg Ser Val Ser Glu Leu
    290                 295                 300

Pro Ile Met His Gln Asp Trp Leu Asn Gly Lys Glu Phe Lys Cys Arg
305                 310                 315                 320

Val Asn Ser Ala Ala Phe Pro Ala Pro Ile Glu Lys Thr Ile Ser Lys
                325                 330                 335
```

-continued

```
Thr Lys Gly Arg Pro Lys Ala Pro Gln Val Tyr Thr Ile Pro Pro Pro
            340                 345                 350

Lys Glu Gln Met Ala Lys Asp Lys Val Ser Leu Thr Cys Met Ile Thr
        355                 360                 365

Asp Phe Phe Pro Glu Asp Ile Thr Val Glu Trp Gln Trp Asn Gly Gln
    370                 375                 380

Pro Ala Glu Asn Tyr Lys Asn Thr Gln Pro Ile Met Asp Thr Asp Gly
385                 390                 395                 400

Ser Tyr Phe Val Tyr Ser Lys Leu Asn Val Gln Lys Ser Asn Trp Glu
                405                 410                 415

Ala Gly Asn Thr Phe Thr Cys Ser Val Leu His Glu Gly Leu His Asn
            420                 425                 430

His His Thr Glu Lys Ser Leu Ser His Ser Pro Gly Lys
        435                 440                 445


<210> SEQ ID NO 9
<211> LENGTH: 218
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Asp Ile Ala Leu Thr Gln Ser Pro Ala Ser Leu Ala Val Ser Leu Gly
1               5                   10                  15

Gln Arg Ala Thr Ile Ser Cys Arg Ala Ser Lys Ser Val Ser Thr Ser
            20                  25                  30

Gly Tyr Ser Tyr Leu His Trp Tyr Gln Gln Lys Pro Gly Gln Pro Pro
        35                  40                  45

Lys Leu Leu Ile Tyr Leu Ala Ser Asn Leu Glu Ser Gly Val Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Ala Ala Thr Tyr Tyr Cys Gln His Ser Arg
                85                  90                  95

Glu Leu Pro Phe Thr Phe Gly Ser Gly Thr Lys Leu Glu Ile Lys Arg
            100                 105                 110

Ala Asp Ala Ala Pro Thr Val Ser Ile Phe Pro Pro Ser Ser Glu Gln
        115                 120                 125

Leu Thr Ser Gly Gly Ala Ser Val Val Cys Phe Leu Asn Asn Glu Tyr
    130                 135                 140

Pro Lys Asp Ile Asn Val Lys Trp Lys Ile Asp Gly Ser Glu Arg Gln
145                 150                 155                 160

Asn Gly Val Leu Asn Ser Trp Thr Asp Gln Asp Ser Lys Asp Ser Thr
                165                 170                 175

Tyr Ser Met Ser Ser Thr Leu Thr Leu Thr Lys Asp Glu Tyr Glu Arg
            180                 185                 190

His Asn Ser Tyr Thr Cys Glu Ala Thr His Lys Thr Ser Thr Ser Pro
        195                 200                 205

Ile Val Lys Ser Phe Asn Arg Asn Glu Cys
    210                 215


<210> SEQ ID NO 10
<211> LENGTH: 122
<212> TYPE: PRT
<213> ORGANISM: Artificial Sequence
```

```
<220> FEATURE:
<223> OTHER INFORMATION: Description of Artificial Sequence: Synthetic
      polypeptide

<400> SEQUENCE: 10

Glu Val Lys Leu Leu Glu Ser Gly Gly Gly Leu Val Gln Pro Gly Gly
1               5                   10                  15

Ser Leu Lys Leu Ser Cys Ala Ala Ser Gly Phe Asp Phe Ser Arg Tyr
            20                  25                  30

Trp Met Ser Trp Val Arg Gln Ala Pro Gly Lys Gly Leu Glu Trp Ile
        35                  40                  45

Gly Glu Ile Asn Pro Thr Ser Ser Thr Ile Asn Phe Thr Pro Ser Leu
    50                  55                  60

Lys Asp Lys Val Phe Ile Ser Arg Asp Asn Ala Lys Asn Thr Leu Tyr
65                  70                  75                  80

Leu Gln Met Ser Lys Val Arg Ser Glu Asp Thr Ala Leu Tyr Tyr Cys
                85                  90                  95

Ala Arg Gly Asn Tyr Tyr Arg Tyr Gly Asp Ala Met Asp Tyr Trp Gly
            100                 105                 110

Gln Gly Thr Ser Val Thr Val Ser Ser Ala
        115                 120


<210> SEQ ID NO 11
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

Asp Ile Ala Leu Thr Gln Ser Pro Ala Ser Leu Ala Val Ser Leu Gly
1               5                   10                  15

Gln Arg Ala Thr Ile Ser Cys Arg Ala Ser Lys Ser Val Ser Thr Ser
            20                  25                  30

Gly Tyr Ser Tyr Leu His Trp Tyr Gln Gln Lys Pro Gly Gln Pro Pro
        35                  40                  45

Lys Leu Leu Ile Tyr Leu Ala Ser Asn Leu Glu Ser Gly Val Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Ala Ala Thr Tyr Tyr Cys Gln His Ser Arg
                85                  90                  95

Glu Leu Pro Phe Thr Phe Gly Ser Gly Thr Lys Leu Glu Ile Lys Arg
            100                 105                 110


<210> SEQ ID NO 12
<211> LENGTH: 446
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Glu Val Gln Leu Val Glu Ser Gly Gly Asp Leu Val Gln Pro Gly Gly
1               5                   10                  15

Ser Leu Lys Leu Ser Cys Thr Ala Ser Gly Phe Thr Phe Ser Asn Tyr
            20                  25                  30
```

-continued

```
Gly Met Ser Trp Ile Arg Gln Thr Pro Asp Lys Arg Leu Glu Trp Val
        35                  40                  45

Ala Thr Ile Val Gly Gly Gly Ser Tyr Thr Tyr Phe Pro Asp Ser Met
    50                  55                  60

Lys Gly Arg Phe Thr Val Ser Arg Asp Asn Ala Lys Ser Ile Leu Tyr
65                  70                  75                  80

Leu Gln Met Asn Ser Leu Ala Ser Ala Asp Thr Ala Met Tyr Tyr Cys
                85                  90                  95

Thr Arg His Asp Trp Val Phe Asp Tyr Trp Gly Gln Gly Thr Pro Leu
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Leu Leu Gly Gly Pro Cys Val Phe
225                 230                 235                 240

Leu Phe Pro Pro Lys Pro Lys Asp Thr Leu Met Ala Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu Ala Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Asp Glu Leu Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn Ala Tyr Thr Gln Lys Ser Leu Ser Leu Ser Pro Gly Lys
        435                 440                 445
```

<210> SEQ ID NO 13
<211> LENGTH: 218
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 13

```
Asp Ile Val Leu Thr Gln Ser Pro Ala Ser Leu Ala Val Ser Leu Gly
1               5                   10                  15

Gln Arg Ala Ile Ile Ser Cys Lys Ala Ser Gln Ser Val Ser Phe Ala
            20                  25                  30

Gly Ser Ser Leu Met His Trp Tyr Gln Gln Lys Pro Gly Gln Gln Pro
        35                  40                  45

Lys Leu Leu Ile Tyr Arg Ala Ser Asp Leu Glu Thr Gly Ile Pro Thr
    50                  55                  60

Arg Phe Ser Gly Gly Gly Ser Gly Thr Asp Phe Thr Leu Asn Ile His
65                  70                  75                  80

Pro Val Glu Glu Asp Asp Ala Ala Thr Tyr Tyr Cys Gln Gln Ser Arg
                85                  90                  95

Glu Tyr Pro Tyr Thr Phe Gly Gly Gly Thr Arg Leu Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215
```

<210> SEQ ID NO 14
<211> LENGTH: 119
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 14

```
Glu Val Gln Leu Val Glu Ser Gly Gly Asp Arg Val Gln Pro Gly Arg
1               5                   10                  15

Ser Leu Thr Leu Ser Cys Val Thr Ser Gly Phe Thr Phe Asn Asn Tyr
            20                  25                  30

Trp Met Thr Trp Ile Arg Gln Val Pro Gly Lys Gly Leu Glu Trp Val
        35                  40                  45

Ala Ser Ile Ser Ser Ser Gly Gly Ser Ile Tyr Tyr Pro Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ser Glu Asp Thr Ala Thr Tyr Tyr Cys
```

-continued

```
                85                  90                  95

Ala Arg Asp Glu Arg Trp Ala Gly Ala Met Asp Ala Trp Gly Gln Gly
            100                 105                 110

Thr Ser Val Thr Val Ser Ser
        115


<210> SEQ ID NO 15
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Phe Thr Phe Asn Asn Tyr Trp Met Thr
1               5


<210> SEQ ID NO 16
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Ser Ile Ser Ser Ser Gly Gly Ser Ile Tyr Tyr Pro Asp Ser Val Lys
1               5                   10                  15

Gly


<210> SEQ ID NO 17
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Ala Arg Asp Glu Arg Trp Ala Gly Ala Met Asp Ala
1               5                   10


<210> SEQ ID NO 18
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

Asp Ile Gln Met Thr Gln Ser Pro Pro Val Leu Ser Ala Ser Val Gly
1               5                   10                  15

Asp Arg Val Thr Leu Ser Cys Lys Ala Ser Gln Asn Ile Asn Lys Asn
            20                  25                  30

Leu Asp Trp Tyr Gln Gln Lys His Gly Glu Ala Pro Lys Leu Leu Ile
        35                  40                  45

Tyr Glu Thr Asn Asn Leu Gln Thr Gly Ile Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Val Ala Thr Tyr Tyr Cys Tyr Gln His Asn Ser Arg Phe Thr
```

-continued

```
                85                  90                  95

Phe Gly Ser Gly Thr Lys Leu Glu Ile Lys
            100                 105


<210> SEQ ID NO 19
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Lys Ala Ser Gln Asn Ile Asn Lys Asn Leu Asp
1               5                   10


<210> SEQ ID NO 20
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Glu Thr Asn Asn Leu Gln Thr
1               5


<210> SEQ ID NO 21
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Tyr Gln His Asn Ser Arg Phe Thr
1               5


<210> SEQ ID NO 22
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

Glu Val Gln Leu Val Glu Ser Gly Gly Asp Leu Val Gln Pro Gly Arg
1               5                   10                  15

Ser Leu Lys Leu Ser Cys Ile Ala Ser Gly Phe Thr Phe Thr Asn Phe
            20                  25                  30

Trp Met Thr Trp Ile Arg Gln Val Ser Gly Lys Gly Leu Glu Trp Val
        35                  40                  45

Ala Ser Ile Ser Ser Ser Gly Gly Ser Ile Tyr Tyr Pro Asp Ser Val
    50                  55                  60

Lys Asp Arg Phe Thr Ile Ser Arg Asp Asn Ala Lys Asn Thr Leu Tyr
65                  70                  75                  80

Leu Gln Met Asn Ser Leu Arg Ser Glu Asp Thr Ala Thr Tyr Tyr Cys
                85                  90                  95

Val Lys Leu His Tyr Tyr Ser Gly Gly Gly Asp Ala Trp Gly Gln Gly
            100                 105                 110
```

Thr Ser Val Thr Val Ser Ser
115

<210> SEQ ID NO 23
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 23

Phe Thr Phe Thr Asn Phe Trp Met Thr
1 5

<210> SEQ ID NO 24
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 24

Ser Ile Ser Ser Ser Gly Gly Ser Ile Tyr Tyr Pro Asp Ser Val Lys
1 5 10 15

Asp

<210> SEQ ID NO 25
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 25

Val Lys Leu His Tyr Tyr Ser Gly Gly Gly Asp Ala
1 5 10

<210> SEQ ID NO 26
<211> LENGTH: 106
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 26

Asp Ile Gln Met Thr Gln Ser Pro Ser Phe Leu Ser Ala Ser Val Gly
1 5 10 15

Asp Arg Val Thr Ile Asn Cys Lys Ala Ser Gln Asn Ile Asn Lys Tyr
20 25 30

Leu Asp Trp Tyr Gln Gln Lys His Gly Glu Ala Pro Lys Leu Leu Ile
35 40 45

His Tyr Thr Asn Asn Leu His Thr Gly Ile Pro Ser Arg Phe Ser Gly
50 55 60

Ser Gly Ser Gly Thr Asp Tyr Thr Leu Thr Ile Ser Ser Leu Gln Pro
65 70 75 80

Glu Asp Val Ala Thr Tyr Phe Cys Leu Gln His Ser Ser Arg Trp Thr
85 90 95

Phe Gly Gly Gly Thr Lys Leu Glu Leu Lys
100 105

<210> SEQ ID NO 27
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 27

Lys Ala Ser Gln Asn Ile Asn Lys Tyr Leu Asp
1 5 10

<210> SEQ ID NO 28
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 28

Tyr Thr Asn Asn Leu His Thr
1 5

<210> SEQ ID NO 29
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 29

Leu Gln His Ser Ser Arg Trp Thr
1 5

<210> SEQ ID NO 30
<211> LENGTH: 119
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 30

Glu Val Gln Leu Val Glu Ser Gly Gly Asp Leu Val Gln Pro Gly Arg
1 5 10 15

Ser Leu Lys Leu Ser Cys Val Ala Ser Gly Phe Thr Phe Asn Asn Tyr
20 25 30

Trp Met Thr Trp Ile Arg Gln Val Pro Gly Lys Gly Leu Glu Trp Val
35 40 45

Ala Ser Ile Ser Ser Ser Gly Gly Ser Ile Tyr Tyr Pro Asp Ser Val
50 55 60

Lys Asp Arg Phe Thr Ile Ser Arg Asp Asn Ala Lys Asn Thr Leu Phe
65 70 75 80

```
Leu Gln Met Asn Ser Leu Arg Ser Glu Asp Thr Ala Thr Tyr Tyr Cys
                85                  90                  95

Ala Arg Leu Tyr Tyr Tyr Ser Gly Gly Gly Asp Ala Trp Gly Gln Gly
            100                 105                 110

Thr Ser Val Thr Val Ser Ser
        115


<210> SEQ ID NO 31
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Phe Thr Phe Asn Asn Tyr Trp Met Thr
1               5


<210> SEQ ID NO 32
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Ser Ile Ser Ser Ser Gly Gly Ser Ile Tyr Tyr Pro Asp Ser Val Lys
1               5                   10                  15

Asp


<210> SEQ ID NO 33
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Ala Arg Leu Tyr Tyr Tyr Ser Gly Gly Gly Asp Ala
1               5                   10


<210> SEQ ID NO 34
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 34

Asp Ile Gln Met Thr Gln Ser Pro Ser Phe Leu Ser Ala Ser Val Gly
1               5                   10                  15
```

Asp Arg Val Thr Ile Ile Cys Lys Ala Ser Gln Asp Ile Asn Lys Tyr
20 25 30

Leu Asp Trp Tyr Gln Gln Lys Leu Gly Glu Ala Pro Lys Leu Leu Ile
35 40 45

Tyr Asn Thr Asn Asn Leu His Thr Gly Ile Pro Ser Arg Phe Ser Gly
50 55 60

Ser Gly Ser Gly Thr Asp Tyr Thr Leu Thr Ile Ser Ser Leu Gln Pro
65 70 75 80

Glu Asp Val Ala Thr Tyr Phe Cys Leu Gln His Ile Ser Arg Trp Thr
85 90 95

Phe Gly Gly Gly Thr Lys Leu Glu Leu Lys
100 105

<210> SEQ ID NO 35
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 35

Lys Ala Ser Gln Asp Ile Asn Lys Tyr Leu Asp
1 5 10

<210> SEQ ID NO 36
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 36

Asn Thr Asn Asn Leu His Thr
1 5

<210> SEQ ID NO 37
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 37

Leu Gln His Ile Ser Arg Trp Thr
1 5